United States Patent
Seymour et al.

(10) Patent No.: US 11,951,183 B2
(45) Date of Patent: *Apr. 9, 2024

(54) ADENO-ASSOCIATED VIRUS COMPOSITIONS FOR PAH GENE TRANSFER AND METHODS OF USE THEREOF

(71) Applicant: HOMOLOGY MEDICINES, INC., Bedford, MA (US)

(72) Inventors: Albert Barnes Seymour, Westborough, MA (US); Seemin Seher Ahmed, Worcester, MA (US); Jason Boke Wright, Concord, MA (US); Serena Nicole Dollive, Waltham, MA (US); Hillard Rubin, Northborough, MA (US)

(73) Assignee: HOMOLOGY MEDICINES, INC., Bedford, MA (US)

( * ) Notice: Subject to any disclaimer, the term of this patent is extended or adjusted under 35 U.S.C. 154(b) by 886 days.

This patent is subject to a terminal disclaimer.

(21) Appl. No.: 16/824,008

(22) Filed: Mar. 19, 2020

(65) Prior Publication Data

US 2020/0316223 A1  Oct. 8, 2020

Related U.S. Application Data

(60) Division of application No. 16/369,879, filed on Mar. 29, 2019, now Pat. No. 10,610,606, which is a continuation of application No. PCT/US2019/016351, filed on Feb. 1, 2019.

(60) Provisional application No. 62/625,150, filed on Feb. 1, 2018.

(51) Int. Cl.
| | |
|---|---|
| *C12N 15/11* | (2006.01) |
| *A61K 48/00* | (2006.01) |
| *C12N 7/01* | (2006.01) |
| *C12N 15/113* | (2010.01) |
| *C12N 15/12* | (2006.01) |
| *C12N 15/52* | (2006.01) |
| *C12N 15/86* | (2006.01) |

(52) U.S. Cl.
CPC .......... *A61K 48/0066* (2013.01); *C12N 15/86* (2013.01); *C12N 2750/14143* (2013.01); *C12N 2750/14152* (2013.01); *C12N 2750/14171* (2013.01); *C12N 2830/32* (2013.01)

(58) Field of Classification Search
None
See application file for complete search history.

(56) References Cited

U.S. PATENT DOCUMENTS

| | | |
|---|---|---|
| 5,252,479 A | 10/1993 | Srivastava |
| 5,474,935 A | 12/1995 | Chatterjee et al. |
| 5,589,377 A | 12/1996 | Lebkowski et al. |
| 5,622,856 A | 4/1997 | Natsoulis |
| 5,650,309 A | 7/1997 | Wong-Staal et al. |
| 5,753,500 A | 5/1998 | Shenk et al. |
| 5,780,447 A | 7/1998 | Nienhuis |
| 5,895,759 A | 4/1999 | Strauss et al. |
| 6,025,195 A | 2/2000 | Sandig et al. |
| 6,153,436 A | 11/2000 | Hermonat et al. |
| 6,156,303 A | 12/2000 | Russell et al. |
| 6,180,613 B1 | 1/2001 | Kaplitt et al. |
| 6,238,914 B1 | 5/2001 | Boyce |
| 6,268,212 B1 | 7/2001 | Simonet |
| 6,329,181 B1 | 12/2001 | Xiao et al. |
| 6,338,962 B1 | 1/2002 | Boyce |
| 6,387,670 B1 | 5/2002 | Leblois-Prehaud et al. |
| 6,610,906 B1 | 8/2003 | Kurachi et al. |
| 6,759,237 B1 | 7/2004 | Wilson et al. |
| 6,919,209 B1 | 7/2005 | Chatterjee et al. |
| 6,924,128 B2 | 8/2005 | Allen |
| 6,936,243 B2 | 8/2005 | Snyder et al. |
| 6,936,466 B2 | 8/2005 | Feldhaus |
| 6,953,690 B1 | 10/2005 | Gao et al. |
| 6,984,517 B1 | 1/2006 | Chiorini et al. |
| 7,001,764 B2 | 2/2006 | Little et al. |
| 7,022,519 B2 | 4/2006 | Gao et al. |
| 7,056,502 B2 | 6/2006 | Hildinger et al. |
| 7,091,029 B2 | 8/2006 | Hwang |
| 7,094,604 B2 | 8/2006 | Snyder et al. |
| 7,148,341 B2 | 12/2006 | Kleinschmidt et al. |
| 7,157,571 B2 | 1/2007 | Wang et al. |
| 7,172,893 B2 | 2/2007 | Rabinowitz et al. |
| 7,179,903 B2 | 2/2007 | McArthur et al. |
| 7,198,951 B2 | 4/2007 | Gao et al. |

(Continued)

FOREIGN PATENT DOCUMENTS

| | | |
|---|---|---|
| EP | 126544 A2 | 11/1984 |
| EP | 161788 A1 | 11/1985 |

(Continued)

OTHER PUBLICATIONS

Grisch-Chan et al., State-of-the-Art 2019 on Gene Therapy for Phenylketonuria. Human Gene Therapy, 2019, pp. 1274-1283.*
Strisciuglio and Concolino, New Strategies for the Treatment of Phenylketonuria (PKU), Metabolites 2014, 4, 1007-1017.*
Duan, D, Systemic delivery of adeno-associated viral vectors, Curr Opin Virol. Dec. 2016 ; 21: 16-25.*

(Continued)

*Primary Examiner* — Maria Marvich
(74) *Attorney, Agent, or Firm* — Dechert LLP; Andrew T. Wilkins

(57) ABSTRACT

Provided herein are adeno-associated virus (AAV) compositions that can express a phenylalanine hydroxylase (PAH) polypeptide in a cell, thereby restoring the PAH gene function. Also provided are methods of use of the AAV compositions, and packaging systems for making the AAV compositions.

18 Claims, 23 Drawing Sheets

Specification includes a Sequence Listing.

(56) References Cited

U.S. PATENT DOCUMENTS

| | | |
|---|---|---|
| 7,220,577 B2 | 5/2007 | Zolotukhin |
| 7,235,393 B2 | 6/2007 | Gao et al. |
| 7,259,151 B2 | 8/2007 | Arbetman et al. |
| 7,282,199 B2 | 10/2007 | Gao et al. |
| 7,351,813 B2 | 4/2008 | Miao et al. |
| 7,465,583 B2 | 12/2008 | Sumulski et al. |
| 7,482,156 B2 | 1/2009 | Arroyo et al. |
| 7,588,772 B2 | 9/2009 | Kay et al. |
| 7,749,492 B2 | 7/2010 | Bartlett et al. |
| 7,790,154 B2 | 9/2010 | Samulski et al. |
| 7,906,111 B2 | 3/2011 | Wilson et al. |
| 8,030,065 B2 | 10/2011 | Gray |
| 8,067,156 B2 | 11/2011 | Kaplitt et al. |
| 8,163,543 B2 | 4/2012 | Urabe et al. |
| 8,168,425 B2 | 5/2012 | Gray |
| 8,241,622 B2 | 8/2012 | Engelhardt et al. |
| 8,283,151 B2 | 10/2012 | Schmidt et al. |
| 8,298,818 B2 | 10/2012 | Boye et al. |
| 8,476,418 B2 | 7/2013 | Mueller et al. |
| 8,524,446 B2 | 9/2013 | Gao et al. |
| 8,628,966 B2 | 1/2014 | Chatterjee et al. |
| 8,632,764 B2 | 1/2014 | Xiao et al. |
| 8,716,461 B2 | 5/2014 | Delwart et al. |
| 8,846,387 B2 | 9/2014 | Russell et al. |
| 8,846,389 B2 | 9/2014 | Chiorini et al. |
| 8,926,958 B2 | 1/2015 | Shah et al. |
| 8,999,678 B2 | 4/2015 | Vandenberghe et al. |
| 8,999,948 B2 | 4/2015 | Tubert et al. |
| 9,150,882 B2 | 10/2015 | Kay et al. |
| 9,169,299 B2 | 10/2015 | Lisowski et al. |
| 9,169,494 B2 | 10/2015 | Hewitt et al. |
| 9,193,956 B2 | 11/2015 | Schaffer et al. |
| 9,217,155 B2 | 12/2015 | Gao et al. |
| 9,222,105 B2 | 12/2015 | Cost et al. |
| 9,402,919 B2 | 8/2016 | Roeth et al. |
| 9,408,904 B2 | 8/2016 | Wright et al. |
| 9,409,953 B2 | 8/2016 | Asokan et al. |
| 9,441,244 B2 | 9/2016 | Schaffer et al. |
| 9,617,548 B2 | 4/2017 | Chuah et al. |
| 9,764,045 B2 | 9/2017 | Nathwani et al. |
| 9,783,824 B2 | 10/2017 | Kay et al. |
| 9,840,719 B2 | 12/2017 | High et al. |
| 9,890,396 B2 | 2/2018 | Chatterjee et al. |
| 10,610,606 B2 * | 4/2020 | Seymour ............ A61K 48/0066 |
| 2003/0129203 A1 | 7/2003 | Vega et al. |
| 2003/0130221 A1 | 7/2003 | High et al. |
| 2003/0198620 A1 | 10/2003 | Ozawa et al. |
| 2004/0086485 A1 | 5/2004 | Aguilar-Cordova et al. |
| 2004/0142416 A1 | 7/2004 | Laipis et al. |
| 2004/0235174 A1 | 11/2004 | Grimm et al. |
| 2005/0112765 A1 | 5/2005 | Li et al. |
| 2009/0191597 A1 | 7/2009 | Sumulski et al. |
| 2009/0215879 A1 | 8/2009 | Diprimio et al. |
| 2010/0297084 A1 | 11/2010 | Bennett et al. |
| 2010/0316623 A1 | 12/2010 | Turner et al. |
| 2012/0046349 A1 | 2/2012 | Bell et al. |
| 2012/0093772 A1 | 4/2012 | Horsager et al. |
| 2012/0244127 A1 | 9/2012 | Lipschutz et al. |
| 2013/0023033 A1 | 1/2013 | Wilson et al. |
| 2013/0189225 A1 | 7/2013 | Voit et al. |
| 2013/0310443 A1 | 11/2013 | Srivastava et al. |
| 2013/0323226 A1 | 12/2013 | Wilson et al. |
| 2014/0037585 A1 | 2/2014 | Wright et al. |
| 2014/0050701 A1 | 2/2014 | Zhong et al. |
| 2014/0107185 A1 | 4/2014 | Maclaren et al. |
| 2014/0271550 A1 | 9/2014 | Rabinowitz et al. |
| 2014/0336245 A1 | 11/2014 | Mingozzi et al. |
| 2014/0359799 A1 | 12/2014 | Wang et al. |
| 2015/0023924 A1 | 1/2015 | High et al. |
| 2015/0024467 A1 | 1/2015 | Sheldon et al. |
| 2015/0065562 A1 | 3/2015 | Yazicioglu et al. |
| 2015/0079038 A1 | 3/2015 | Deverman et al. |
| 2015/0110762 A1 | 4/2015 | Holmes et al. |
| 2015/0111955 A1 | 4/2015 | High et al. |
| 2015/0184197 A1 | 7/2015 | Davidson et al. |
| 2015/0238550 A1 | 8/2015 | McCown et al. |
| 2015/0315610 A1 | 11/2015 | Nishe et al. |
| 2015/0352228 A1 | 12/2015 | Torbett et al. |
| 2015/0374803 A1 | 12/2015 | Wolfe |
| 2015/0376240 A1 | 12/2015 | Cronin et al. |
| 2016/0000887 A1 | 1/2016 | Wilson et al. |
| 2016/0017295 A1 | 1/2016 | Schaffer et al. |
| 2016/0032319 A1 | 2/2016 | Wright et al. |
| 2016/0123990 A1 | 5/2016 | High et al. |
| 2016/0175365 A1 | 6/2016 | Golden |
| 2016/0229904 A1 | 8/2016 | Xiao et al. |
| 2017/0119906 A1 | 5/2017 | Riley |
| 2017/0211094 A1 | 7/2017 | Chatterjee et al. |
| 2017/0326256 A1 | 11/2017 | Doering et al. |

FOREIGN PATENT DOCUMENTS

| | | |
|---|---|---|
| EP | 1497436 B1 | 1/2005 |
| WO | WO 1996/008560 A1 | 3/1996 |
| WO | WO 1998/009524 A1 | 3/1998 |
| WO | WO 1998/021349 A1 | 5/1998 |
| WO | WO 1998/027207 A1 | 6/1998 |
| WO | WO 1998/028417 A1 | 7/1998 |
| WO | WO 1999/003981 A1 | 1/1999 |
| WO | WO 1999018227 A1 | 4/1999 |
| WO | WO 1999/055564 A1 | 11/1999 |
| WO | WO 1999/064569 A1 | 12/1999 |
| WO | WO 2000/049160 A1 | 8/2000 |
| WO | WO 2001/036620 A2 | 5/2001 |
| WO | WO 2002/066611 A2 | 8/2002 |
| WO | WO 2003/087383 A1 | 10/2003 |
| WO | WO 2003/093436 A2 | 11/2003 |
| WO | WO 2005/111220 A2 | 11/2005 |
| WO | WO 2006/096815 A2 | 9/2006 |
| WO | WO 2007/019646 A1 | 2/2007 |
| WO | WO 2008/021140 A2 | 2/2008 |
| WO | WO 2009/000552 A2 | 12/2008 |
| WO | WO 2009/043936 A1 | 4/2009 |
| WO | WO 2009/130208 A1 | 10/2009 |
| WO | WO 2009/134681 A2 | 11/2009 |
| WO | WO 2010/124180 A1 | 10/2010 |
| WO | WO 2010/129021 A1 | 11/2010 |
| WO | WO 2011/012724 A1 | 2/2011 |
| WO | WO 2011038187 A1 | 3/2011 |
| WO | WO 2014/064277 A1 | 5/2014 |
| WO | WO 2014/089212 A1 | 6/2014 |
| WO | WO 2014/193716 A2 | 12/2014 |
| WO | WO 2015/061491 A1 | 4/2015 |
| WO | WO 2015/143177 A1 | 9/2015 |
| WO | WO 2015/164723 A1 | 10/2015 |
| WO | 2016049230 A1 | 3/2016 |
| WO | WO 2016/097218 A1 | 6/2016 |
| WO | WO 2016/097219 A1 | 6/2016 |
| WO | WO 2016/100575 A1 | 6/2016 |
| WO | WO 2016/146757 A1 | 9/2016 |
| WO | WO 2017/015154 A1 | 1/2017 |
| WO | WO 2017/100551 A1 | 6/2017 |
| WO | WO 2018/046737 A1 | 3/2018 |
| WO | WO 2018/126112 A1 | 7/2018 |
| WO | WO 2018/126116 A1 | 7/2018 |
| WO | WO 2018/129586 A1 | 7/2018 |
| WO | WO 2019/010091 A1 | 1/2019 |

OTHER PUBLICATIONS

BioMarin, U.S. FDA Placed a Clinical Hold on BMN 307 Phearless Phase 1/2 Gene Therapy Study in Adults with PKU Based on Interim Pre-clinical Study Findings, 2021, pp. 1-2.*

Mendell et al, Current Clinical Applications of In Vivo Gene Therapy with AAVs, Molecular Therapy vol. 29 No. 2 Feb. 2021, p. 464-488.*

Hacein-Bey-Abina et al. (2008) "Insertional oncogenesis in 4 patients after retrovirus-mediated gene therapy of SCID-X1," J Clin Invest. 118(9):3132-42.

Kramer et al. (2003) "In vitro and in vivo comparative study of chimeric liver-specific promoters," Mol Therapy. 7:375-385.

(56) References Cited

OTHER PUBLICATIONS

Lu et al. (2013) "A mini-intronic plasmid (MIP): a novel robust transgene expression vector in vivo and in vitro," Mol Ther. 21(5):954-63.
Lu et al. (2017) "A 5' Noncoding Exon Containing Engineered Intron Enhances Transgene Expression from Recombinant AAV Vectors in vivo," Hum Gene Ther. 28(1):125-134.
Savy et al. (2017) "Impact of Inverted Terminal Repeat Integrity on rAAV8 Production Using the Baculovirus/Sf9 Cells System," Human Gene Therapy Methods. 28(5):277-289.
Sibley et al. (2016) "Lessons from non-canonical splicing," Nat Rev Gen. 17:407-21.
Yagi et al. (2011) "Complete restoration of phenylalanine oxidation in phenylketonuria mouse by a self-complementary adeno-associated virus vector," J Gene Med. 13:114-122.
De Sabbata et al., "Development of a novel AAV-based gene therapy in combination with tolerogenic nanoparticles for sustained treatment of ornithine transcarbamylase deficiency," Changing the Face of Modern Medicine: Stem Cell and Gene Therapy. Dec. 13, 2018;29(12):P343.
Grisch-Chan et al., "Low-Dose Gene Therapy for Murine PKU Using Episomal Naked DNA Vectors Expressing PAH from Its Endogenous Liver Promoter," Mol Ther Nucleic Acids. Jun. 16, 2017;7:339-349.
"*Homo sapiens* phenylalanine hydroxylase (PAH) mRNA, complete cds," GenBank U49897.1. Accessed Oct. 28, 2022.
Thöny, "Long-term correction of murine phenylketonuria by viral gene transfer: liver versus muscle," J Inherit Metab Dis. Dec. 2010;33(6):677-80, abstract only.

\* cited by examiner

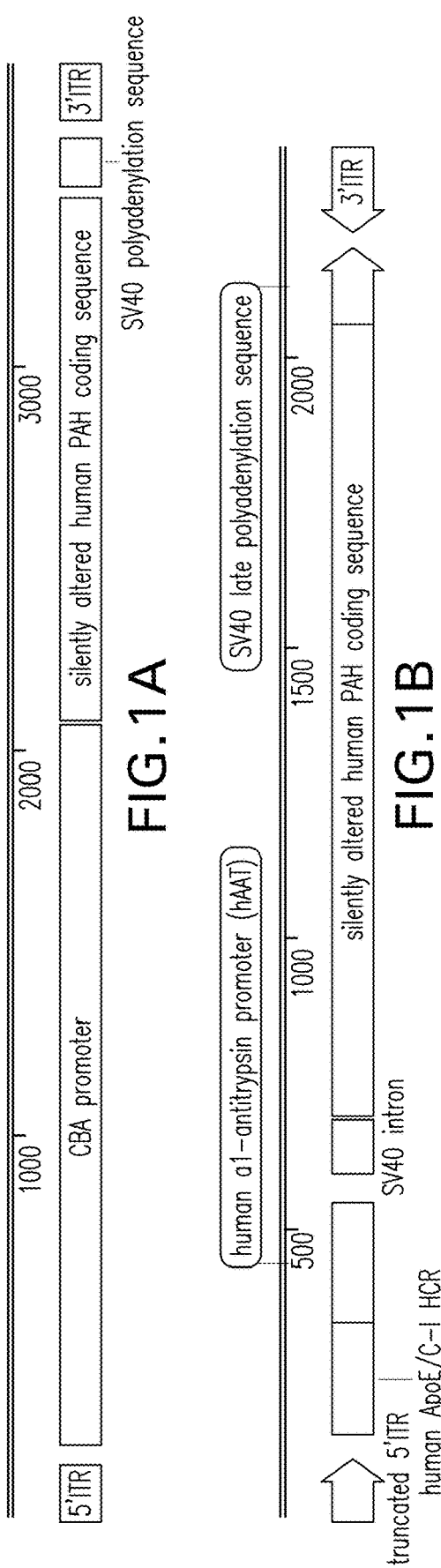
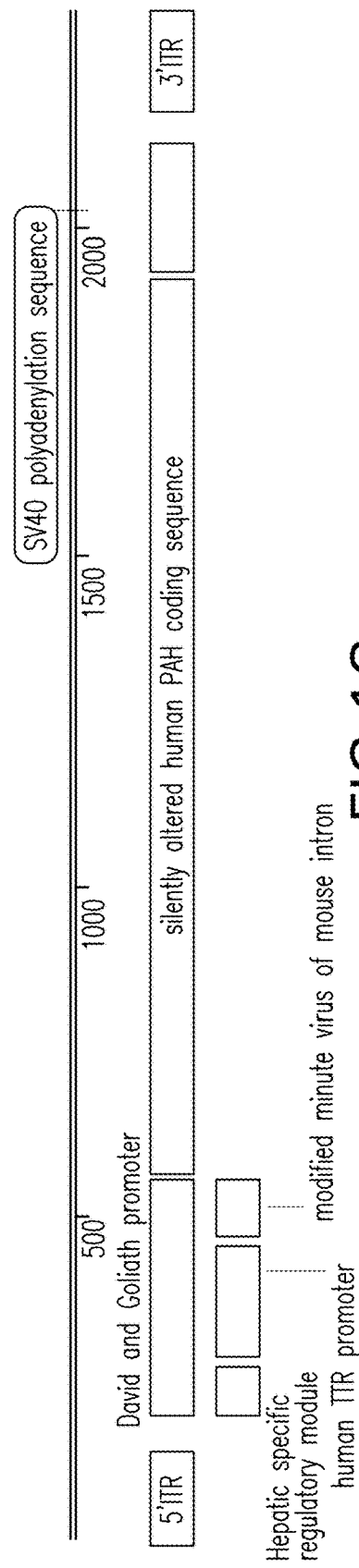
FIG.1A
FIG.1B
FIG.1C

ADENO-ASSOCIATED VIRUS COMPOSITIONS FOR PAH GENE TRANSFER AND METHODS OF USE THEREOF

RELATED APPLICATIONS

This application is a division of U.S. patent application Ser. No. 16/369,879, now U.S. Pat. No. 10,610,606, filed Mar. 29, 2019, which is a continuation of International Patent Application No. PCT/US2019/016351, filed Feb. 1, 2019, which claims priority to U.S. Provisional Patent Application Ser. No. 62/625,150, filed Feb. 1, 2018, the entire disclosures of which are hereby incorporated herein by reference.

BACKGROUND

Phenylketonuria (PKU) is an autosomal recessive genetic disorder where the majority of cases are caused by mutations in the phenylalanine hydroxylase (PAH) gene. The PAH gene encodes a hepatic enzyme that catalyzes the hydroxylation of L-phenylalanine (Phe) to L-tyrosine (Tyr) upon multimerization. Reduction or loss of PAH activity leads to phenylalanine accumulation and its conversion into phenylpyruvate (also known as phenylketone). This abnormality in phenylalanine metabolism impairs neuronal maturation and the synthesis of myelin, resulting in mental retardation, seizures and other serious medical problems.

Currently, there is no cure for PKU. The standard of care is diet management by minimizing foods that contain high amounts of phenylalanine. Dietary management from birth with a low phenylalanine formula largely prevents the development of the intellectual disability of the disorder. However, even on a low-phenylalanine diet, children still suffer from growth retardation, and adults often have osteoporosis and vitamin deficiencies. Moreover, adherence to life-long dietary treatment is difficult, particularly once children reach school age.

New treatment strategies have recently emerged, including large neutral amino acid (LNAA) supplementation, cofactor tetrahydrobiopterin therapy, enzyme replacement therapy, and genetically modified probiotic therapy. However, these strategies suffer from shortcomings. The LNAA supplementation is suitable only for adults not adhering to a low Phe diet. The cofactor tetrahydrobiopterin can only be used in some mild forms of PKU. Enzyme replacement by administration of a substitute for PAH, e.g., phenylalanine ammonia-lyase (PAL), can lead to immune responses that reduce the efficacy and/or cause side effects. As to genetically modified probiotic therapy, the pathogenicity of PAL-expressing *E. coli* has been a concern.

Gene therapy provides a unique opportunity to cure PKU. Retroviral vectors, including lentiviral vectors, are capable of integrating nucleic acids into host cell genomes, raising safety concerns due to their non-targeted insertion into the genome. For example, there is a risk of the vector disrupting a tumor suppressor gene or activating an oncogene, thereby causing a malignancy. Indeed, in a clinical trial for treating X-linked severe combined immunodeficiency (SCID) by transducing CD34+ bone marrow precursors with a gammaretroviral vector, four out of ten patients developed leukemia (Hacein-Bey-Abina et al., J Clin Invest. (2008) 118(9):3132-42). Non-integrating vectors, on the other hand, often suffer insufficient expression level or inadequate duration of expression in vivo.

Accordingly, there is a need in the art for improved gene therapy compositions and methods that can efficiently and safely restore PAH gene function in PKU patients.

SUMMARY

Provided herein are adeno-associated virus (AAV) compositions that can restore PAH gene function in cells, and methods for using the same to treat diseases associated with reduction of PAH gene function (e.g., PKU). Also provided are packaging systems for making the adeno-associated virus compositions.

Accordingly, in one aspect, the instant disclosure provides a method for expressing a PAH polypeptide in a cell, the method comprising transducing the cell with a replication-defective adeno-associated virus (AAV) comprising:
  (a) an AAV capsid comprising an AAV Clade F capsid protein; and
  (b) a transfer genome comprising a transcriptional regulatory element operably linked to a PAH coding sequence.

In certain embodiments, the cell is a hepatocyte, a renal cell, or a cell in the brain, pituitary gland, adrenal gland, pancreas, urinary bladder, gallbladder, colon, small intestine, or breast. In certain embodiments, the cell is in a mammalian subject and the AAV is administered to the subject in an amount effective to transduce the cell in the subject.

In another aspect, the instant disclosure provides a method for treating a subject having a disease or disorder associated with a PAH gene mutation, the method comprising administering to the subject an effective amount of a replication-defective AAV comprising:
  (a) an AAV capsid comprising an AAV Clade F capsid protein; and
  (b) a transfer genome comprising a transcriptional regulatory element operably linked to a PAH coding sequence.

In certain embodiments, the disease or disorder is phenylketonuria. In certain embodiments, the subject is a human subject.

In another aspect, the instant disclosure provides a replication-defective adeno-associated virus (AAV) comprising:
  (a) an AAV capsid comprising an AAV Clade F capsid protein; and
  (b) a transfer genome comprising a transcriptional regulatory element operably linked to a PAH coding sequence.

The following embodiments apply to each of the foregoing aspects.

In certain embodiments, the PAH coding sequence encodes an amino acid sequence set forth in SEQ ID NO: 23. In certain embodiments, the PAH coding sequence comprises the nucleotide sequence set forth in SEQ ID NO: 24. In certain embodiments, the PAH coding sequence is silently altered. In certain embodiments, the PAH coding sequence comprises the nucleotide sequence set forth in SEQ ID NO: 25.

In certain embodiments, the transcriptional regulatory element is capable of mediating transcription in a hepatocyte, a renal cell, or a cell in the brain, pituitary gland, adrenal gland, pancreas, urinary bladder, gallbladder, colon, small intestine, or breast. In certain embodiments, the transcriptional regulatory element is capable of mediating transcription in a hepatocyte or renal cell. In certain embodiments, the transcriptional regulatory element comprises one of the elements selected from the group consisting of a CAG promoter, a human EF-1α promoter, a human hepatic control region 1 (HCR1), a human a1-antitrypsin (hAAT) promoter, a hepatic specific regulatory module of the hAAT promoter, an SV40 intron, and a minute virus of mouse (MVM) intron. In certain embodiments, the transcriptional regulatory element comprises a nucleotide sequence at least 90% identical to a sequence selected from the group consisting of SEQ ID NOs: 28-30 and 32-41. In certain embodiments, the transcriptional regulatory element comprises a nucleotide sequence selected from the group consisting of SEQ ID NOs: 28-30 and 32-41. In certain embodiments, the transcriptional regulatory element comprises from 5' to 3' the nucleotide sequences set forth in SEQ ID NOs: 29, 30, and 31. In certain embodiments, the transcriptional regulatory element comprises the nucleotide sequences set forth in SEQ ID NO: 32.

In certain embodiments, the transfer genome further comprises an intron operably linked to the PAH coding sequence. In certain embodiments, the intron comprises a nucleotide sequence at least 90% identical to the sequence set forth in SEQ ID NO: 31 or 35. In certain embodiments, the intron comprises the nucleotide sequence set forth in SEQ ID NO: 31 or 35. In certain embodiments, the transfer genome comprises from 5' to 3': a non-coding exon, the intron, and the PAH coding sequence.

In certain embodiments, the transfer genome further comprises a polyadenylation sequence 3' to the PAH coding sequence. In certain embodiments, the polyadenylation sequence is an exogenous polyadenylation sequence. In certain embodiments, the exogenous polyadenylation sequence is an SV40 polyadenylation sequence. In certain embodiments, the SV40 polyadenylation sequence comprises a sequence selected from the group consisting of SEQ ID NOs: 42, 43, and 45.

In certain embodiments, the transfer genome comprises a sequence selected from the group consisting of SEQ ID NOs: 46-50, 61, 64, 67, 74, 76, 78, 80, 82, 84, 86, and 89.

In certain embodiments, the transfer genome further comprises a 5' inverted terminal repeat (5' ITR) nucleotide sequence 5' of the genome, and a 3' inverted terminal repeat (3' ITR) nucleotide sequence 3' of the genome. In certain embodiments, the 5' ITR nucleotide sequence has at least 95% sequence identity to SEQ ID NO: 18, and the 3' ITR nucleotide sequence has at least 95% sequence identity to SEQ ID NO: 19. In certain embodiments, the 5' ITR nucleotide sequence has at least 95% sequence identity to SEQ ID NO: 20, and the 3' ITR nucleotide sequence has at least 95% sequence identity to SEQ ID NO: 21. In certain embodiments, the 5' ITR nucleotide sequence has at least 95% sequence identity to SEQ ID NO: 26, and the 3' ITR nucleotide sequence has at least 95% sequence identity to SEQ ID NO: 27.

In certain embodiments, the transfer genome comprises a nucleotide sequence selected from the group consisting of SEQ ID NOs: 51-55, 62, 65, 68, 75, 77, 79, 81, 83, 85, 87, and 90. In certain embodiments, the transfer genome consists of a nucleotide sequence selected from the group consisting of SEQ ID NOs: 51-55, 62, 65, 68, 75, 77, 79, 81, 83, 85, 87, and 90. In certain embodiments, the transfer genome consists of the nucleotide sequence set forth in SEQ ID NO: 52.

In certain embodiments, the AAV Clade F capsid protein comprises an amino acid sequence having at least 95% sequence identity with the amino acid sequence of amino acids 203-736 of SEQ ID NO: 2, 3, 4, 6, 7, 10, 11, 12, 13, 15, 16, or 17. In certain embodiments, the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G;
  (b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
  (c) the amino acid in the capsid protein corresponding to amino acid 505 of SEQ ID NO: 2 is R, and the amino acid in the capsid protein corresponding to amino acid 687 of SEQ ID NO: 2 is R;
  (d) the amino acid in the capsid protein corresponding to amino acid 346 of SEQ ID NO: 2 is A, and the amino acid in the capsid protein corresponding to amino acid 505 of SEQ ID NO: 2 is R; or
  (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 203-736 of SEQ ID NO: 2, 3, 4, 6, 7, 10, 11, 12, 13, 15, 16, or 17.

In certain embodiments, the AAV Clade F capsid protein comprises an amino acid sequence having at least 95% sequence identity with the amino acid sequence of amino acids 138-736 of SEQ ID NO: 2, 3, 4, 5, 6, 7, 9, 10, 11, 12, 13, 15, 16, or 17. In certain embodiments, the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G;
(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(c) the amino acid in the capsid protein corresponding to amino acid 505 of SEQ ID NO: 2 is R, and the amino acid in the capsid protein corresponding to amino acid 687 of SEQ ID NO: 2 is R;
(d) the amino acid in the capsid protein corresponding to amino acid 346 of SEQ ID NO: 2 is A, and the amino acid in the capsid protein corresponding to amino acid 505 of SEQ ID NO: 2 is R; or
(e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 138-736 of SEQ ID NO: 2, 3, 4, 5, 6, 7, 9, 10, 11, 12, 13, 15, 16, or 17.

In certain embodiments, the AAV Clade F capsid protein comprises an amino acid sequence having at least 95% sequence identity with the amino acid sequence of amino acids 1-736 of SEQ ID NO: 2, 3, 4, 5, 6, 7, 8, 9, 10, 11, 12, 13, 15, 16, or 17. In certain embodiments, the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 2 of SEQ ID NO: 2 is T, and the amino acid in the capsid protein corresponding to amino acid 312 of SEQ ID NO: 2 is Q;
(b) the amino acid in the capsid protein corresponding to amino acid 65 of SEQ ID NO: 2 is I, and the amino acid in the capsid protein corresponding to amino acid 626 of SEQ ID NO: 2 is Y;
(c) the amino acid in the capsid protein corresponding to amino acid 77 of SEQ ID NO: 2 is R, and the amino acid in the capsid protein corresponding to amino acid 690 of SEQ ID NO: 2 is K;
(d) the amino acid in the capsid protein corresponding to amino acid 119 of SEQ ID NO: 2 is L, and the amino acid in the capsid protein corresponding to amino acid 468 of SEQ ID NO: 2 is S;
(e) the amino acid in the capsid protein corresponding to amino acid 626 of SEQ ID NO: 2 is G, and the amino acid in the capsid protein corresponding to amino acid 718 of SEQ ID NO: 2 is G;
(f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(g) the amino acid in the capsid protein corresponding to amino acid 505 of SEQ ID NO: 2 is R, and the amino acid in the capsid protein corresponding to amino acid 687 of SEQ ID NO: 2 is R;
(h) the amino acid in the capsid protein corresponding to amino acid 346 of SEQ ID NO: 2 is A, and the amino acid in the capsid protein corresponding to amino acid 505 of SEQ ID NO: 2 is R; or
(i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 1-736 of SEQ ID NO: 2, 3, 4, 5, 6, 7, 8, 9, 10, 11, 12, 13, 15, 16, or 17.

In another aspect, the instant disclosure provides a pharmaceutical composition comprising an AAV disclosed herein.

In another aspect, the instant disclosure provides a packaging system for recombinant preparation of an AAV, wherein the packaging system comprises:
(a) a Rep nucleotide sequence encoding one or more AAV Rep proteins;
(b) a Cap nucleotide sequence encoding one or more AAV Clade F capsid proteins as disclosed herein; and
(c) a transfer genome as disclosed herein, wherein the packaging system is operative in a cell for enclosing the transfer genome in the capsid to form the AAV.

In certain embodiments, the packaging system comprises a first vector comprising the Rep nucleotide sequence and the Cap nucleotide sequence, and a second vector comprising the transfer genome. In certain embodiments, the Rep nucleotide sequence encodes an AAV2 Rep protein. In certain embodiments, the AAV2 Rep protein is 78/68 or Rep 68/52. In certain embodiments, the AAV2 Rep protein comprises an amino acid sequence having a minimum percent sequence identity to the AAV2 Rep amino acid sequence of SEQ ID NO: 22, wherein the minimum percent sequence identity is at least 70% across the length of the amino acid sequence encoding the AAV2 Rep protein.

In certain embodiments, the packaging system further comprises a third vector, wherein the third vector is a helper virus vector. In certain embodiments, the helper virus vector is an independent third vector. In certain embodiments, the helper virus vector is integral with the first vector. In certain embodiments, the helper virus vector is integral with the second vector. In certain embodiments, the third vector comprises genes encoding helper virus proteins.

In certain embodiments, the helper virus is selected from the group consisting of adenovirus, herpes virus, vaccinia virus, and cytomegalovirus (CMV). In certain embodiments, the helper virus is adenovirus. In certain embodiments, the adenovirus genome comprises one or more adenovirus RNA genes selected from the group consisting of E1, E2, E4 and VA. In certain embodiments, the helper virus is herpes simplex virus (HSV). In certain embodiments, the HSV genome comprises one or more of HSV genes selected from the group consisting of UL5/8/52, ICPO, ICP4, ICP22 and UL30/UL42.

In certain embodiments, the first vector and the third vector are contained within a first transfecting plasmid. In certain embodiments, the nucleotides of the second vector and the third vector are contained within a second transfecting plasmid. In certain embodiments, the nucleotides of the first vector and the third vector are cloned into a recombinant helper virus. In certain embodiments, the nucleotides of the second vector and the third vector are cloned into a recombinant helper virus.

In another aspect, the instant disclosure provides a method for recombinant preparation of an AAV, the method comprising introducing a packaging system as described herein into a cell under conditions operative for enclosing the transfer genome or the transfer genome in the capsid to form the AAV.

BRIEF DESCRIPTION OF THE DRAWINGS

FIGS. 1A, 1B, 1C, 1D, and 1E are vector maps of the pHMI-hPAH-TC-004, pHMI-hPAH-TC-025, pHMI-hPAH-TC-010, pHMI-hPAH-TC-011, and pHMI-hPAH-TC-012 vectors, respectively.

FIG. 10A is a graph showing serum Phe levels over time of male Pah$^{-/-}$ PAH$^{emu2}$ mice. FIG. 10B is a graph showing serum Phe levels over time of female Pah$^{-/-}$ PAH$^{emu2}$ mice. FIG. 10C is a graph showing the average baseline serum Phe levels of the male and female mice in the study (55 mice per group; **** indicates p<0.05).

DETAILED DESCRIPTION

Figure 1D:

The instant disclosure provided adeno-associated virus (AAV) compositions that can restore PAH gene function in a cell. Also provide are packaging systems for making the adeno-associated virus compositions.

I. Definitions

As used herein, the term "replication-defective adeno-associated virus" refers to an AAV comprising a genome lacking Rep and Cap genes.

As used herein, the term "PAH gene" refers to the phenylalanine hydroxylase gene. The human PAH gene is identified by Entrez Gene ID 5053. An exemplary nucleotide sequence of a PAH mRNA is provided as SEQ ID NO: 24. An exemplary amino acid sequence of a PAH polypeptide is provided as SEQ ID NO: 23.

As used herein, the term "transfer genome" refers to a recombinant AAV genome comprising a coding sequence operably linked to an exogenous transcriptional regulatory element that mediates expression of the coding sequence when the transfer genome is introduced into a cell. In certain embodiments, the transfer genome does not integrate in the chromosomal DNA of the cell. The skilled artisan will appreciate that the portion of a transfer genome comprising the transcriptional regulatory element operably linked to a PAH coding sequence can be in the sense or antisense orientation relative to direction of transcription of the PAH coding sequence.

As used herein, the term "Clade F capsid protein" refers to an AAV VP1, VP2, or VP3 capsid protein that has at least 90% identity with the VP1, VP2, or VP3 amino acid sequences set forth, respectively, in amino acids 1-736, 138-736, and 203-736 of SEQ ID NO: 1 herein.

As used herein, the identity between two nucleotide sequences or between two amino acid sequences is determined by the number of identical nucleotides or amino acids in alignment divided by the full length of the longer nucleotide or amino acid sequence.

As used herein, the term "a disease or disorder associated with a PAH gene mutation" refers to any disease or disorder caused by, exacerbated by, or genetically linked with mutation of a PAH gene. In certain embodiments, the disease or disorder associated with a PAH gene mutation is phenylketonuria (PKU).

As used herein, the term "coding sequence" refers to the portion of a complementary DNA (cDNA) that encodes a polypeptide, starting at the start codon and ending at the stop codon. A gene may have one or more coding sequences due to alternative splicing, alternative translation initiation, and variation within the population. A coding sequence may either be wild-type or codon-altered. An exemplary wild-type PAH coding sequence is set forth in SEQ ID NO: 24.

As used herein, the term "silently altered" refers to alteration of a coding sequence or a stuffer-inserted coding sequence of a gene (e.g., by nucleotide substitution) without changing the amino acid sequence of the polypeptide encoded by the coding sequence or stuffer-inserted coding sequence. Such silent alteration is advantageous in that it may increase the translation efficiency of a coding sequence.

In the instant disclosure, nucleotide positions in a PAH gene are specified relative to the first nucleotide of the start codon. The first nucleotide of a start codon is position 1; the nucleotides 5' to the first nucleotide of the start codon have negative numbers; the nucleotides 3' to the first nucleotide of the start codon have positive numbers. An exemplary nucleotide 1 of the human PAH gene is nucleotide 5,473 of the NCBI Reference Sequence: NG_008690.1, and an exemplary nucleotide 3 of the human PAH gene is nucleotide 5,475 of the NCBI Reference Sequence: NG_008690.1. The nucleotide adjacently 5' to the start codon is nucleotide −1.

In the instant disclosure, exons and introns in a PAH gene are specified relative to the exon encompassing the first nucleotide of the start codon, which is nucleotide 5473 of the NCBI Reference Sequence: NG_008690.1. The exon encompassing the first nucleotide of the start codon is exon 1. Exons 3' to exon 1 are from 5' to 3': exon 2, exon 3, etc. Introns 3' to exon 1 are from 5' to 3': intron 1, intron 2, etc. Accordingly, the PAH gene comprises from 5' to 3': exon 1, intron 1, exon 2, intron 2, exon 3, etc. An exemplary exon 1 of the human PAH gene is nucleotides 5001-5532 of the NCBI Reference Sequence: NG_008690.1. An exemplary intron 1 of the human PAH gene is nucleotides 5533-9704 of the NCBI Reference Sequence: NG_008690.1.

As used herein, the term "transcriptional regulatory element" or "TRE" refers to a cis-acting nucleotide sequence, for example, a DNA sequence, that regulates (e.g., controls, increases, or reduces) transcription of an operably linked nucleotide sequence by an RNA polymerase to form an RNA molecule. A TRE relies on one or more trans-acting molecules, such as transcription factors, to regulate transcription. Thus, one TRE may regulate transcription in different ways when it is in contact with different trans-acting molecules, for example, when it is in different types of cells. A TRE may comprise one or more promoter elements and/or enhancer elements. A skilled artisan would appreciate that the promoter and enhancer elements in a gene may be close in location, and the term "promoter" may refer to a sequence comprising a promoter element and an enhancer element. Thus, the term "promoter" does not exclude an enhancer element in the sequence. The promoter and enhancer elements do not need to be derived from the same gene or species, and the sequence of each promoter or enhancer element may be either identical or substantially identical to the corresponding endogenous sequence in the genome.

As used herein, the term "operably linked" is used to describe the connection between a TRE and a coding sequence to be transcribed. Typically, gene expression is placed under the control of a TRE comprising one or more promoter and/or enhancer elements. The coding sequence is "operably linked" to the TRE if the transcription of the coding sequence is controlled or influenced by the TRE. The promoter and enhancer elements of the TRE may be in any orientation and/or distance from the coding sequence, as long as the desired transcriptional activity is obtained. In certain embodiments, the TRE is upstream from the coding sequence.

As used herein, the term "polyadenylation sequence" refers to a DNA sequence that when transcribed into RNA constitutes a polyadenylation signal sequence. The polyadenylation sequence can be native (e.g., from the PAH gene) or exogenous. The exogenous polyadenylation sequence can be a mammalian or a viral polyadenylation sequence (e.g., an SV40 polyadenylation sequence).

As used herein, "exogenous polyadenylation sequence" refers to a polyadenylation sequence not identical or substantially identical to the endogenous polyadenylation sequence of a PAH gene (e.g., human PAH gene). In certain embodiments, an exogenous polyadenylation sequence is a polyadenylation sequence of a non-PAH gene in the same species (e.g., human). In certain embodiments, an exogenous polyadenylation sequence is a polyadenylation sequence of a different species (e.g., a virus).

As used herein, the term "effective amount" in the context of the administration of an AAV to a subject refers to the amount of the AAV that achieves a desired prophylactic or therapeutic effect.

II. Adeno-Associated Virus Compositions

In one aspect, provided herein are novel replication-defective AAV compositions useful for expressing PAH polypeptide in cells with reduced or otherwise defective PAH gene function. In certain embodiments, the AAV disclosed herein comprise: an AAV capsid comprising an AAV Clade F capsid protein; and a transfer genome comprising a transcriptional regulatory element operably linked to a PAH coding sequence, allowing for extrachromosomal expression of PAH.

Any AAV Clade F capsid protein or derivative thereof can be used in the AAV compositions disclosed herein. For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 2, 3, 4, 5, 6, 7, 8, 9, 10, 11, 12, 13, 15, 16, or 17, wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 203-736 of SEQ ID NO: 2, 3, 4, 6, 7, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 2, 3, 4, 5, 6, 7, 8, 9, 10, 11, 12, 13, 15, 16, or 17, wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 138-736 of SEQ ID NO: 2, 3, 4, 5, 6, 7, 9, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 2, 3, 4, 5, 6, 7, 8, 9, 10, 11, 12, 13, 15, 16, or 17, wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 2 of SEQ ID NO: 2 is T, and the amino acid in the capsid protein corresponding to amino acid 312 of SEQ ID NO: 2 is Q. In certain embodiments, the amino acid in the capsid protein corresponding to amino acid 65 of SEQ ID NO: 2 is I, and the amino acid in the capsid protein corresponding to amino acid 626 of SEQ ID NO: 2 is Y. In certain embodiments, the amino acid in the capsid protein corresponding to amino acid 77 of SEQ ID NO: 2 is R, and the amino acid in the capsid protein corresponding to amino acid 690 of SEQ ID NO: 2 is K. In certain embodiments, the amino acid in the capsid protein corresponding to amino acid 119 of SEQ ID NO: 2 is L, and the amino acid in the capsid protein corresponding to amino acid 468 of SEQ ID NO: 2 is S. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 1-736 of SEQ ID NO: 2, 3, 4, 5, 6, 7, 8, 9, 10, 11, 12, 13, 15, 16, or 17.

In certain embodiments, the AAV capsid comprises two or more of: (a) a Clade F capsid protein comprising the amino acid sequence of amino acids 203-736 of SEQ ID NO: 2, 3, 4, 6, 7, 10, 11, 12, 13, 15, 16, or 17; (b) a Clade F capsid protein comprising the amino acid sequence of amino acids 138-736 of SEQ ID NO: 2, 3, 4, 5, 6, 7, 9, 10, 11, 12, 13, 15, 16, or 17; and (c) a Clade F capsid protein comprising the amino acid sequence of amino acids 1-736 of SEQ ID NO: 2, 3, 4, 5, 6, 7, 8, 9, 10, 11, 12, 13, 15, 16, or 17. In certain embodiments, the AAV capsid comprises: (a) a Clade F capsid protein having an amino acid sequence consisting of amino acids 203-736 of SEQ ID NO: 2, 3, 4, 6, 7, 10, 11, 12, 13, 15, 16, or 17; (b) a Clade F capsid protein having an amino acid sequence consisting of amino acids 138-736 of SEQ ID NO: 2, 3, 4, 5, 6, 7, 9, 10, 11, 12, 13, 15, 16, or 17; and (c) a Clade F capsid protein having an amino acid sequence consisting of amino acids 1-736 of SEQ ID NO: 2, 3, 4, 5, 6, 7, 8, 9, 10, 11, 12, 13, 15, 16, or 17.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 8; (b) a Clade F capsid protein comprising an amino acid sequence having at least 80%, 81%, 82%, 83%, 84%, 85%, 86%, 8'7%, 88%, 89%, 90%, 91%, 92%, 93%, 94%, 95%, 96%, 97%, 98%, or 99% sequence identity with the sequence of amino acids 138-736 of SEQ ID NO: 8; and (c) a Clade F capsid protein comprising an amino acid sequence having at least 80%, 81%, 82%, 83%, 84%, 85%, 86%, 8'7%, 88%, 89%, 90%, 91%, 92%, 93%, 94%, 95%, 96%, 97%, 98%, or 99% sequence identity with the sequence of amino acids 1-736 of SEQ ID NO: 8. In certain embodiments, the AAV capsid comprises one or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises two or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises: (a) a Clade F capsid protein having an amino acid sequence consisting of amino acids 203-736 of SEQ ID NO: 8; (b) a Clade F capsid protein having an amino acid sequence consisting of amino acids 138-736 of SEQ ID NO: 8; and (c) a Clade F capsid protein having an amino acid sequence consisting of amino acids 1-736 of SEQ ID NO: 8.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 11; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 11; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 11. In certain embodiments, the AAV capsid comprises one or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises two or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises: (a) a Clade F capsid protein having an amino acid sequence consisting of amino acids 203-736 of SEQ ID NO: 11; (b) a Clade F capsid protein having an amino acid sequence consisting of amino acids 138-736 of SEQ ID NO: 11; and (c) a Clade F capsid protein having an amino acid sequence consisting of amino acids 1-736 of SEQ ID NO: 11.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 13; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 13; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 13. In certain embodiments, the AAV capsid comprises one or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises two or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises: (a) a Clade F capsid protein having an amino acid sequence consisting of amino acids 203-736 of SEQ ID NO: 13; (b) a Clade F capsid protein having an amino acid sequence consisting of amino acids 138-736 of SEQ ID NO: 13; and (c) a Clade F capsid protein having an amino acid sequence consisting of amino acids 1-736 of SEQ ID NO: 13.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 16; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 16; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 16. In certain embodiments, the AAV capsid comprises one or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises two or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises: (a) a Clade F capsid protein having an amino acid sequence consisting of amino acids 203-736 of SEQ ID NO: 16; (b) a Clade F capsid protein having an amino acid sequence consisting of amino acids 138-736 of SEQ ID NO: 16; and (c) a Clade F capsid protein having an amino acid sequence consisting of amino acids 1-736 of SEQ ID NO: 16.

Transfer genomes useful in the AAV compositions disclosed herein generally comprise a transcriptional regulatory element (TRE) operably linked to a PAH coding sequence. In certain embodiments, the transfer genome comprises a 5' inverted terminal repeat (5' ITR) nucleotide sequence 5' of the TRE and PAH coding sequence, and a 3' inverted terminal repeat (3' ITR) nucleotide sequence 3' of the TRE and PAH coding sequence.

In certain embodiments, the PAH coding sequence comprises all or substantially all of a coding sequence of a PAH gene. In certain embodiments, the transfer genome comprises a nucleotide sequence encoding SEQ ID NO: 23 and can optionally further comprise an exogenous polyadenylation sequence 3' to the PAH coding sequence. In certain embodiments, the nucleotide sequence encoding SEQ ID NO: 23 is wild-type (e.g., having the sequence set forth in SEQ ID NO: 24). In certain embodiments, the nucleotide sequence encoding SEQ ID NO: 23 is codon-altered (e.g., having the sequence set forth in SEQ ID NO: 25). In certain embodiments, the nucleotide sequence encoding SEQ ID NO: 23 is codon-altered (e.g., having the sequence set forth in SEQ ID NO: 69, 70, 71, 72, or 73).

In certain embodiments, the PAH coding sequence encodes a polypeptide comprising all or substantially all of the amino acids sequence of a PAH protein. In certain embodiments, the PAH coding sequence encodes the amino acid sequence of a wild-type PAH protein (e.g., human PAH protein). In certain embodiments, the PAH coding sequence encodes the amino acid sequence of a mutant PAH protein (e.g., human PAH protein), wherein the mutant PAH polypeptide is a functional equivalent of the wild-type PAH polypeptide, i.e., can function as a wild-type PAH polypeptide. In certain embodiments, the functionally equivalent PAH polypeptide further comprises at least one characteristic not found in the wild-type PAH polypeptide, e.g., the ability to stabilize PAH protein (e.g., dimer or tetramer), or the ability to resist protein degradation.

The transfer genome can be used to express PAH in any mammalian cells (e.g., human cells). Thus, the TRE can be active in any mammalian cells (e.g., human cells). In certain embodiments, the TRE is active in a broad range of human cells. Such TREs may comprise constitutive promoter and/or enhancer elements including cytomegalovirus (CMV) promoter/enhancer (e.g., comprising a nucleotide sequence at least 90%, 91%, 92%, 93%, 94%, 95%, 96%, 97%, 98%, 99%, or 100% identical to SEQ ID NO: 58), SV40 promoter, chicken beta actin (CBA) promoter (e.g., comprising a nucleotide sequence at least 90%, 91%, 92%, 93%, 94%, 95%, 96%, 97%, 98%, 99%, or 100% identical to SEQ ID NO: 59), human elongation factor 1 alpha (EF1α) promoter (e.g., comprising a nucleotide sequence at least 90%, 91%, 92%, 93%, 94%, 95%, 96%, 97%, 98%, 99%, or 100% identical to SEQ ID NO: 40), minute virus of mouse (MVM) intron which comprises transcription factor binding sites (e.g., comprising a nucleotide sequence at least 90%, 91%, 92%, 93%, 94%, 95%, 96%, 97%, 98%, 99%, or 100% identical to SEQ ID NO: 35), human phosphoglycerate kinase (PGK1) promoter, human ubiquitin C (Ubc) promoter, human beta actin promoter, human neuron-specific enolase (ENO2) promoter, human beta-glucuronidase (GUSB) promoter, a rabbit beta-globin element (e.g., comprising a nucleotide sequence at least 90%, 91%, 92%, 93%, 94%, 95%, 96%, 97%, 98%, 99%, or 100% identical to SEQ ID NO: 60), and/or human Methyl-CpG Binding Protein 2 (MeCP2) promoter. Any of these TREs can be combined in any order to drive efficient transcription. For example, a transfer genome may comprise a CMV enhancer, a CBA promoter, and the splice acceptor from exon 3 of the rabbit beta-globin gene, collectively called a CAG promoter (e.g., comprising a nucleotide sequence at least 90%, 91%, 92%, 93%, 94%, 95%, 96%, 97%, 98%, 99%, or 100% identical to SEQ ID NO: 28). For example, a transfer genome may comprise a hybrid of CMV enhancer and CBA promoter followed by a splice donor and splice acceptor, collectively called a CASI promoter region (e.g., comprising a nucleotide sequence at least 90%, 91%, 92%, 93%, 94%, 95%, 96%, 97%, 98%, 99%, or 100% identical to SEQ ID NO: 63).

Alternatively, the TRE may be a tissue-specific TRE, i.e., it is active in specific tissue(s) and/or organ(s). A tissue-specific TRE comprises one or more tissue-specific promoter and/or enhancer elements, and optionally one or more constitutive promoter and/or enhancer elements. A skilled artisan would appreciate that tissue-specific promoter and/or enhancer elements can be isolated from genes specifically expressed in the tissue by methods well known in the art. In certain embodiments, the TRE is liver-specific (e.g., hepatocyte-specific). Exemplary liver-specific TREs may comprise one or more elements selected from the group consisting of human albumin promoter, human transthyretin (TTR) promoter (e.g., comprising a nucleotide sequence at least 90%, 91%, 92%, 93%, 94%, 95%, 96%, 97%, 98%, 99%, or 100% identical to SEQ ID NO: 34), human APOE/C-I hepatic control region (HCR) 1 or 2 (e.g., comprising a nucleotide sequence at least 90%, 91%, 92%, 93%, 94%, 95%, 96%, 97%, 98%, 99%, or 100% identical to SEQ ID NO: 29 or 37), human APOH promoter, and human SERPINA1 (hAAT) promoter (e.g., comprising a nucleotide sequence at least 90%, 91%, 92%, 93%, 94%, 95%, 96%, 97%, 98%, 99%, or 100% identical to SEQ ID NO: 30 or 38) or a hepatic specific regulatory module thereof (e.g., comprising a nucleotide sequence at least 90%, 91%, 92%, 93%, 94%, 95%, 96%, 97%, 98%, 99%, or 100% identical to SEQ ID NO: 33). In certain embodiments, an hAAT promoter region comprises a nucleotide sequence at least 90%, 91%, 92%, 93%, 94%, 95%, 96%, 97%, 98%, 99%, or 100% identical to SEQ ID NO: 66. More liver-specific promoter elements are disclosed in WO 2009/130208 and Kramer et al. (Molecular Therapy (2003) 7, 375-385), which are incorporated by reference herein in their entirety.

In certain embodiments, the TRE is kidney-specific (e.g., renal epithelial cell-specific). Exemplary kidney-specific TREs may comprise one or more elements selected from the group consisting of human nephrin promoter, human parathyroid hormone receptor promoter, human uromodulin promoter, and human SLC12A1 promoter. In certain embodiments, the TRE is brain-specific (e.g., neuron-specific, glial cell-specific, astrocyte-specific, oligodendrocyte-specific, microglia-specific and/or central nervous system-specific). Exemplary brain-specific TREs may comprise one or more elements selected from the group consisting of human glial fibrillary acidic protein (GFAP) promoter and human synapsin 1 (SYN1) promoter. More brain-specific promoter elements are disclosed in WO 2016/100575A1, which is incorporated by reference herein in its entirety.

In certain embodiments, the transfer genome comprises two or more TREs, optionally comprising at least one of the TREs disclosed above. A skilled person in the art would appreciate that any of these TREs can be combined in any order, and combinations of a constitutive TRE and a tissue-specific TRE can drive efficient and tissue-specific transcription. For example, in certain embodiments, the transfer genome comprises a human HCR1 (e.g., comprising a nucleotide sequence at least 90%, 91%, 92%, 93%, 94%, 95%, 96%, 97%, 98%, or 99% identical to SEQ ID NO: 29 or 37) and a human EF-1a promoter (e.g., comprising a nucleotide sequence at least 90%, 91%, 92%, 93%, 94%, 95%, 96%, 97%, 98%, or 99% identical to SEQ ID NO: 40), optionally wherein the human HCR1 is 5' to the human EF-1a promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 41. In certain embodiments, the transfer genome comprises a human HCR1 (e.g., comprising the nucleotide sequence set forth in SEQ ID NO: 29 or 37) and a human EF-1α promoter (e.g., comprising the nucleotide sequence set forth in SEQ ID NO: 40), optionally wherein the human HCR1 is 5' to the human EF-1a promoter. In certain embodiments, the transfer genome comprises the sequence set forth in SEQ ID NO: 41.

Similarly, combinations of two or more tissue-specific TREs can drive efficient and tissue-specific transcription. For example, in certain embodiments, the transfer genome comprises a human HCR1 (e.g., comprising a nucleotide sequence at least 90%, 91%, 92%, 93%, 94%, 95%, 96%, 97%, 98%, or 99% identical to SEQ ID NO: 29) and a hAAT promoter (e.g., comprising a nucleotide sequence at least 90%, 91%, 92%, 93%, 94%, 95%, 96%, 97%, 98%, or 99% identical to SEQ ID NO: 30), optionally wherein the human HCR1 is 5' to the hAAT promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 32. In certain embodiments, the transfer genome comprises a human HCR1 (e.g., comprising the nucleotide sequence set forth in SEQ ID NO: 29) and a hAAT promoter (e.g., comprising the nucleotide sequence set forth in SEQ ID NO: 30), optionally wherein the human HCR1 is 5' to the hAAT promoter. In certain embodiments, the transfer genome comprises the nucleotide sequence set forth in SEQ ID NO: 32.

In certain embodiments, the transfer genome comprises a hepatic specific regulatory module of hAAT promoter (e.g., comprising a nucleotide sequence at least 90%, 91%, 92%, 93%, 94%, 95%, 96%, 97%, 98%, or 99% identical to SEQ ID NO: 33) and a human TTR promoter (e.g., comprising a nucleotide sequence at least 90%, 91%, 92%, 93%, 94%, 95%, 96%, 97%, 98%, or 99% identical to SEQ ID NO: 34), optionally wherein the hepatic specific regulatory module is 5' to the human TTR promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 36. In certain embodiments, the transfer genome comprises a hepatic specific regulatory module of hAAT promoter (e.g., comprising the nucleotide sequence set forth in SEQ ID NO: 33) and a human TTR promoter (e.g., comprising the nucleotide sequence set forth in SEQ ID NO: 34), optionally wherein the hepatic specific regulatory module is 5' to the human TTR promoter. In certain embodiments, the transfer genome comprises the nucleotide sequence set forth in SEQ ID NO: 36.

In certain embodiment, the transfer genome comprises a human HCR1 (e.g., comprising a nucleotide sequence at least 90%, 91%, 92%, 93%, 94%, 95%, 96%, 97%, 98%, or 99% identical to SEQ ID NO: 29 or 37) and a hAAT promoter (e.g., comprising a nucleotide sequence at least 90%, 91%, 92%, 93%, 94%, 95%, 96%, 97%, 98%, or 99% identical to SEQ ID NO: 30 or 38), optionally wherein the human HCR1 is 5' to the hAAT promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 39. In certain embodiment, the transfer genome comprises a human HCR1 (e.g., comprising the nucleotide sequence set forth in SEQ ID NO: 29 or 37) and a hAAT promoter (e.g., comprising the nucleotide sequence set forth in SEQ ID NO: 30 or 38), optionally wherein the human HCR1 is 5' to the hAAT promoter. In certain embodiments, the transfer genome comprises the nucleotide sequence set forth in SEQ ID NO: 39.

In certain embodiments, the transfer vector further comprises an intron 5' to or inserted in the PAH coding sequence. Such introns can increase transgene expression, for example, by reducing transcriptional silencing and enhancing mRNA export from the nucleus to the cytoplasm. In certain embodiments, the transfer genome comprises from 5' to 3': a non-coding exon, an intron, and the PAH coding sequence. In certain embodiments, an intron sequence is inserted in the PAH coding sequence, optionally wherein the intron is inserted at an internucleotide bond that links two native exons. In certain embodiments, the intron is inserted at an internucleotide bond that links native exon 1 and exon 2.

The intron can comprise a native intron sequence of the PAH gene, an intron sequence from a different species or a different gene from the same species, and/or a synthetic intron sequence. A skilled worker will appreciate that synthetic intron sequences can be designed to mediate RNA splicing by introducing any consensus splicing motifs known in the art (e.g., in Sibley et al., (2016) Nature Reviews Genetics, 17, 407-21, which is incorporated by reference herein in its entirety). Exemplary intron sequences are provided in Lu et al. (2013) Molecular Therapy 21(5): 954-63, and Lu et al. (2017) Hum. Gene Ther. 28(1): 125-34, which are incorporated by reference herein in their entirety. In certain embodiments, the transfer genome comprises an SV40 intron (e.g., comprising a nucleotide sequence at least 90%, 91%, 92%, 93%, 94%, 95%, 96%, 97%, 98%, or 99% identical to SEQ ID NO: 31) or a minute virus of mouse (MVM) intron (e.g., comprising a nucleotide sequence at least 90%, 91%, 92%, 93%, 94%, 95%, 96%, 97%, 98%, or 99% identical to SEQ ID NO: 35). In certain embodiments, the transfer genome comprises an SV40 intron (e.g., comprising the nucleotide sequence set forth in SEQ ID NO: 31)

or a minute virus of mouse (MVM) intron (e.g., comprising the nucleotide sequence set forth in SEQ ID NO: 35).

In certain embodiments, the transfer genome disclosed herein further comprises a transcription terminator (e.g., a polyadenylation sequence). In certain embodiments, the transcription terminator is 3' to the PAH coding sequence. The transcription terminator may be any sequence that effectively terminates transcription, and a skilled artisan would appreciate that such sequences can be isolated from any genes that are expressed in the cell in which transcription of the PAH coding sequence is desired. In certain embodiments, the transcription terminator comprises a polyadenylation sequence. In certain embodiments, the polyadenylation sequence is identical or substantially identical to the endogenous polyadenylation sequence of the human PAH gene. In certain embodiments, the polyadenylation sequence is an exogenous polyadenylation sequence. In certain embodiments, the polyadenylation sequence is an SV40 polyadenylation sequence (e.g., comprising the nucleotide sequence set forth in SEQ ID NO: 42, 43, or 45, or a nucleotide sequence complementary thereto). In certain embodiments, the polyadenylation sequence comprises the sequence set forth in SEQ ID NO: 43.

In certain embodiments, the transfer genome comprises from 5' to 3': a TRE, optionally a non-coding exon and an intron, a PAH coding sequence, and a polyadenylation sequence. In certain embodiments, the TRE has at least 90%, 91%, 92%, 93%, 94%, 95%, 96%, 97%, 98%, or 99% sequence identity to any one of SEQ ID NOs: 28-30 and 32-41; the intron has at least 90%, 91%, 92%, 93%, 94%, 95%, 96%, 97%, 98%, or 99% sequence identity to SEQ ID NO: 31 or 35; the PAH coding sequence has at least 90%, 91%, 92%, 93%, 94%, 95%, 96%, 97%, 98%, or 99% sequence identity to SEQ ID NO: 25; and/or the polyadenylation sequence has at least 90%, 91%, 92%, 93%, 94%, 95%, 96%, 97%, 98%, or 99% sequence identity to any one of SEQ ID NOs: 42, 43, and 45. In certain embodiments, the TRE comprises a nucleotide sequence selected from the group consisting of SEQ ID NOs: 28-30 and 32-41; the intron comprises a nucleotide sequence selected from the group consisting of SEQ ID NOs: 31 and 35; the PAH coding sequence comprises the sequence set forth in SEQ ID NO: 25; and/or the polyadenylation sequence comprises a nucleotide sequence selected from the group consisting of SEQ ID NOs: 42, 43, and 45. In certain embodiments, the TRE comprises the sequence set forth in SEQ ID NO: 28; the PAH coding sequence comprises the sequence set forth in SEQ ID NO: 25; and/or the polyadenylation sequence comprises the sequence set forth in SEQ ID NO: 42. In certain embodiments, the TRE comprises from 5' to 3' the sequence set forth in SEQ ID NO: 29, and the sequence set forth in SEQ ID NO: 30 (e.g., the TRE comprises the sequence set forth in SEQ ID NO: 32); the intron comprises the sequence set forth in SEQ ID NO: 31; the PAH coding sequence comprises the sequence set forth in SEQ ID NO: 25; and/or the polyadenylation sequence comprises the sequence set forth in SEQ ID NO: 43. In certain embodiments, the TRE comprises from 5' to 3' the sequence set forth in SEQ ID NO: 33, and the sequence set forth in SEQ ID NO: 34 (e.g., the TRE comprises the sequence set forth in SEQ ID NO: 36); the intron comprises the sequence set forth in SEQ ID NO: 35; the PAH coding sequence comprises the sequence set forth in SEQ ID NO: 25; and/or the polyadenylation sequence comprises the sequence set forth in SEQ ID NO: 45. In certain embodiments, the TRE comprises from 5' to 3' the sequence set forth in SEQ ID NO: 37, and the sequence set forth in SEQ ID NO: 38 (e.g., the TRE comprises the sequence set forth in SEQ ID NO: 39); the intron comprises the sequence set forth in SEQ ID NO: 35; the PAH coding sequence comprises the sequence set forth in SEQ ID NO: 25; and/or the polyadenylation sequence comprises the sequence set forth in SEQ ID NO: 45. In certain embodiments, the TRE comprises from 5' to 3' the sequence set forth in SEQ ID NO: 37, and the sequence set forth in SEQ ID NO: 40 (e.g., the TRE comprises the sequence set forth in SEQ ID NO: 41); and/or the polyadenylation sequence comprises the sequence set forth in SEQ ID NO: 45.

In certain embodiments, the transfer genome comprises a sequence at least 80%, 85%, 90%, 91%, 92%, 93%, 94%, 95%, 96%, 97%, 98%, or 99% identical to SEQ ID NO: 46, 47, 48, 49, 50, 61, 64, 67, 74, 76, 78, 80, 82, 84, 86, or 89. In certain embodiments, the transfer genome comprises the nucleotide sequence set forth in SEQ ID NO: 46, 47, 48, 49, 50, 61, 64, 67, 74, 76, 78, 80, 82, 84, 86, or 89. In certain embodiments, the transfer genome consists of the nucleotide sequence set forth in SEQ ID NO: 46, 47, 48, 49, 50, 61, 64, 67, 74, 76, 78, 80, 82, 84, 86, or 89. In certain embodiments, the transfer genome comprises the nucleotide sequence set forth in SEQ ID NO: 47. In certain embodiments, the transfer genome consists of the nucleotide sequence set forth in SEQ ID NO: 47.

In certain embodiments, the transfer genomes disclosed herein further comprise a 5' inverted terminal repeat (5' ITR) nucleotide sequence 5' of the TRE, and a 3' inverted terminal repeat (3' ITR) nucleotide sequence 3' of the PAH coding sequence. ITR sequences from any AAV serotype or variant thereof can be used in the transfer genomes disclosed herein. The 5' and 3' ITR can be from an AAV of the same serotype or from AAVs of different serotypes. Exemplary ITRs for use in the transfer genomes disclosed herein are set forth in SEQ ID NOs: 18-21, 26, and 27 herein.

In certain embodiments, the 5' ITR or 3' ITR is from AAV2. In certain embodiments, both the 5' ITR and the 3' ITR are from AAV2. In certain embodiments, the 5' ITR nucleotide sequence has at least 90% (e.g., at least 95%, at least 96%, at least 97%, at least 98%, at least 99%, or 100%) sequence identity to SEQ ID NO: 18, or the 3' ITR nucleotide sequence has at least 90% (e.g., at least 95%, at least 96%, at least 97%, at least 98%, at least 99%, or 100%) sequence identity to SEQ ID NO: 19. In certain embodiments, the 5' ITR nucleotide sequence has at least 90% (e.g., at least 95%, at least 96%, at least 97%, at least 98%, at least 99%, or 100%) sequence identity to SEQ ID NO: 18, and the 3' ITR nucleotide sequence has at least 90% (e.g., at least 95%, at least 96%, at least 97%, at least 98%, at least 99%, or 100%) sequence identity to SEQ ID NO: 19. In certain embodiments, the transfer genome comprises a nucleotide sequence set forth in any one of SEQ ID NOs: 46-50, 61, 64, 67, 74, 76, 78, 80, 82, 84, 86, and 89, a 5' ITR nucleotide sequence having the sequence of SEQ ID NO: 18, and a 3' ITR nucleotide sequence having the sequence of SEQ ID NO: 19.

In certain embodiments, the 5' ITR or 3' ITR are from AAV5. In certain embodiments, both the 5' ITR and 3' ITR are from AAV5. In certain embodiments, the 5' ITR nucleotide sequence has at least 90% (e.g., at least 95%, at least 96%, at least 97%, at least 98%, at least 99%, or 100%) sequence identity to SEQ ID NO: 20, or the 3' ITR nucleotide sequence has at least 90% (e.g., at least 95%, at least 96%, at least 97%, at least 98%, at least 99%, or 100%) sequence identity to SEQ ID NO: 21. In certain embodiments, the 5' ITR nucleotide sequence has at least 90% (e.g., at least 95%, at least 96%, at least 97%, at least 98%, at least 99%, or 100%) sequence identity to SEQ ID NO: 20, and the 3' ITR nucleotide sequence has at least 90% (e.g., at least 95%, at least 96%, at least 97%, at least 98%, at least 99%, or 100%) sequence identity to SEQ ID NO: 21. In certain embodiments, the transfer genome comprises a nucleotide sequence set forth in any one of SEQ ID NOs: 46-50, a 5' ITR nucleotide sequence having the sequence of SEQ ID NO: 20, and a 3' ITR nucleotide sequence having the sequence of SEQ ID NO: 21.

In certain embodiments, the 5' ITR nucleotide sequence and the 3' ITR nucleotide sequence are substantially complementary to each other (e.g., are complementary to each other except for mismatch at 1, 2, 3, 4, or 5 nucleotide positions in the 5' or 3' ITR).

In certain embodiments, the 5' ITR or the 3' ITR is modified to reduce or abolish resolution by Rep protein ("non-resolvable ITR"). In certain embodiments, the non-resolvable ITR comprises an insertion, deletion, or substitution in the nucleotide sequence of the terminal resolution site. Such modification allows formation of a self-complementary, double-stranded DNA genome of the AAV after the transfer genome is replicated in an infected cell. Exemplary non-resolvable ITR sequences are known in the art (see e.g., those provided in U.S. Pat. Nos. 7,790,154 and 9,783,824, which are incorporated by reference herein in their entirety). In certain embodiments, the 5' ITR comprises a nucleotide sequence at least 95%, 96%, 97%, 98%, or 99% identical to SEQ ID NO: 26. In certain embodiments, the 5' ITR consists of a nucleotide sequence at least 95%, 96%, 97%, 98%, or 99% identical to SEQ ID NO: 26. In certain embodiments, the 5' ITR consists of the nucleotide sequence set forth in SEQ ID NO: 26. In certain embodiments, the 3' ITR comprises a nucleotide sequence at least 95%, 96%, 97%, 98%, or 99% identical to SEQ ID NO: 27. In certain embodiments, the 5' ITR consists of a nucleotide sequence at least 95%, 96%, 97%, 98%, or 99% identical to SEQ ID NO: 27. In certain embodiments, the 3' ITR consists of the nucleotide sequence set forth in SEQ ID NO: 27. In certain embodiments, the 5' ITR consists of the nucleotide sequence set forth in SEQ ID NO: 26, and the 3' ITR consists of the nucleotide sequence set forth in SEQ ID NO: 27. In certain embodiments, the 5' ITR consists of the nucleotide sequence set forth in SEQ ID NO: 26, and the 3' ITR consists of the nucleotide sequence set forth in SEQ ID NO: 19.

In certain embodiments, the 3' ITR is flanked by an additional nucleotide sequence derived from a wild-type AAV2 genomic sequence. In certain embodiments, the 3' ITR is flanked by an additional 37 bp sequence derived from a wild-type AAV2 sequence that is adjacent to a wild-type AAV2 ITR. See, e.g., Savy et al., *Human Gene Therapy Methods* (2017) 28(5): 277-289 (which is hereby incorporated by reference herein in its entirety). In certain embodiments, the additional 37 bp sequence is internal to the 3' ITR. In certain embodiments, the 37 bp sequence consists of the sequence set forth in SEQ ID NO: 56. In certain embodiments, the 3' ITR comprises a nucleotide sequence at least 95%, 96%, 97%, 98%, or 99% identical to SEQ ID NO: 57. In certain embodiments, the 3' ITR comprises the nucleotide sequence set forth in SEQ ID NO: 57. In certain embodiments, the nucleotide sequence of the 3' ITR consists of a nucleotide sequence at least 95%, 96%, 97%, 98%, or 99% identical to SEQ ID NO: 57. In certain embodiments, the nucleotide sequence of the 3' ITR consists of the nucleotide sequence set forth in SEQ ID NO: 57.

In certain embodiments, the transfer genome comprises from 5' to 3': a 5' ITR; an internal element comprising from 5' to 3': a TRE, optionally a non-coding exon and an intron, a PAH coding sequence, and a polyadenylation sequence, as disclosed herein; a non-resolvable ITR; a nucleotide sequence complementary to the internal element; and a 3' ITR. Such transfer genome can form a self-complementary, double-stranded DNA genome of the AAV after infection and before replication.

In certain embodiments, the transfer genome comprises from 5' to 3': a 5' ITR, a TRE, optionally a non-coding exon and an intron, a PAH coding sequence, a polyadenylation sequence, and a 3' ITR. In certain embodiments, the 5' ITR has at least 90%, 91%, 92%, 93%, 94%, 95%, 96%, 97%, 98%, or 99% sequence identity to SEQ ID: 18, 20, or 26; the TRE has at least 90%, 91%, 92%, 93%, 94%, 95%, 96%, 97%, 98%, or 99% sequence identity to any one of SEQ ID NOs: 28-30 and 32-41; the intron has at least 90%, 91%, 92%, 93%, 94%, 95%, 96%, 97%, 98%, or 99% sequence identity to SEQ ID NO: 31 or 35; the PAH coding sequence has at least 90%, 91%, 92%, 93%, 94%, 95%, 96%, 97%, 98%, or 99% sequence identity to SEQ ID NO: 25; the polyadenylation sequence has at least 90%, 91%, 92%, 93%, 94%, 95%, 96%, 97%, 98%, or 99% sequence identity to any one of SEQ ID NOs: 42, 43, and 45; and/or the 3' ITR has at least 90%, 91%, 92%, 93%, 94%, 95%, 96%, 97%, 98%, or 99% sequence identity to SEQ ID: 19, 21, or 27. In certain embodiments, the 5' ITR comprises or consists of a nucleotide sequence selected from the group consisting of SEQ ID NOs: 18, 20, and 26; the TRE comprises a nucleotide sequence selected from the group consisting of SEQ ID NOs: 28-30 and 32-41; the intron comprises a nucleotide sequence selected from the group consisting of SEQ ID NOs: 31 and 35; the PAH coding sequence comprises the sequence set forth in SEQ ID NO: 25; the polyadenylation sequence comprises a nucleotide sequence selected from the group consisting of SEQ ID NOs: 42, 43, and 45; and/or the 3' ITR comprises or consists of a nucleotide sequence selected from the group consisting of SEQ ID NOs: 19, 21, and 27. In certain embodiments, the 5' ITR comprises or consists of the sequence set forth in SEQ ID NO: 18; the TRE comprises the sequence set forth in SEQ ID NO: 28; the PAH coding sequence comprises the sequence set forth in SEQ ID NO: 25; the polyadenylation sequence comprises the sequence set forth in SEQ ID NO: 42; and/or the 3' ITR comprises or consists of the sequence set forth in SEQ ID NO: 19. In certain embodiments, the 5' ITR comprises or consists of the sequence set forth in SEQ ID NO: 26; the TRE comprises from 5' to 3' the sequence set forth in SEQ ID NO: 29, and the sequence set forth in SEQ ID NO: 30 (e.g., the TRE comprises the sequence set forth in SEQ ID NO: 32); the intron comprises the sequence set forth in SEQ ID NO: 31; the PAH coding sequence comprises the sequence set forth in SEQ ID NO: 25; the polyadenylation sequence comprises the sequence set forth in SEQ ID NO: 43 and/or the 3' ITR comprises or consists of the sequence set forth in SEQ ID NO: 27. In certain embodiments, the 5' ITR comprises or consists of the sequence set forth in SEQ ID NO: 18; the TRE comprises from 5' to 3' the sequence set forth in SEQ ID NO: 33, and the sequence set forth in SEQ ID NO: 34 (e.g., the TRE comprises the sequence set forth in SEQ ID NO: 36); the intron comprises the sequence set forth in SEQ ID NO: 35; the PAH coding sequence comprises the sequence set forth in SEQ ID NO: 25; the polyadenylation sequence comprises the sequence set forth in SEQ ID NO: 45; and/or the 3' ITR comprises or consists of the sequence set forth in SEQ ID NO: 19. In certain embodiments, the 5' ITR comprises or consists of the sequence set forth in SEQ ID NO: 18; the TRE comprises from 5' to 3' the sequence set forth in SEQ ID NO: 37, and the sequence set forth in SEQ ID NO: 38 (e.g., the TRE comprises the sequence set forth in SEQ ID NO: 39); the intron comprises the sequence set forth in SEQ ID NO: 35; the PAH coding sequence comprises the sequence set forth in SEQ ID NO: 25; the polyadenylation sequence comprises the sequence set forth in SEQ ID NO: 45; and/or the 3' ITR comprises or consists of the sequence set forth in SEQ ID NO: 19. In certain embodiments, the 5' ITR comprises or consists of the sequence set forth in SEQ ID NO: 18; the TRE comprises from 5' to 3' the sequence set forth in SEQ ID NO: 37, and the sequence set forth in SEQ ID NO: 40 (e.g., the TRE comprises the sequence set forth in SEQ ID NO: 41); the polyadenylation sequence comprises the sequence set forth in SEQ ID NO: 45; and/or the 3' ITR comprises or consists of the sequence set forth in SEQ ID NO: 19.

In certain embodiments, the transfer genome comprises a sequence at least 80% (e.g., at least 85%, 90%, 91%, 92%, 93%, 94%, 95%, 96%, 97%, 98%, or 99%) identical to the sequence set forth in SEQ ID NO: 51, 52, 53, 54, 55, 62, 65, 68, 75, 77, 79, 81, 83, 85, 87, or 90. In certain embodiments, the transfer genome comprises the sequence set forth in SEQ ID NO: 51, 52, 53, 54, 55, 62, 65, 68, 75, 77, 79, 81, 83, 85, 87, or 90. In certain embodiments, the transfer genome comprises the sequence set forth in SEQ ID NO: 52. In certain embodiments, the transfer genome consists of the sequence set forth in SEQ ID NO: 51, 52, 53, 54, 55, 62, 65, 68, 75, 77, 79, 81, 83, 85, 87, or 90. In certain embodiments, the transfer genome consists of the sequence set forth in SEQ ID NO: 52.

In certain embodiments, the replication-defective AAV comprises: (a) an AAV capsid protein comprising the amino acid sequence of amino acids 203-736 of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27); (b) an AAV capsid protein comprising the amino acid sequence of amino acids 138-736 of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27; and/or (c) an AAV capsid protein comprising the amino acid sequence of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27.

In certain embodiments, the replication-defective AAV comprises: (a) an AAV capsid protein comprising the amino acid sequence of amino acids 203-736 of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90; (b) an AAV capsid protein comprising the amino acid sequence of amino acids 138-736 of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90; and/or (c) an AAV capsid protein comprising the amino acid sequence of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90.

In another aspect, provided herein is a polynucleotide comprising a nucleic acid sequence that is at least 80% (e.g., at least 85%, 90%, 91%, 92%, 93%, 94%, 95%, 96%, 97%, 98%, or 99%) identical to the nucleic acid sequence set forth in SEQ ID NO: 88, 91, or 92. In certain embodiments, the polynucleotide comprises the nucleic acid sequence set forth in SEQ ID NO: 88, 91, or 92. In certain embodiments, the polynucleotide comprises the nucleic acid sequence set forth in SEQ ID NO: 92. In certain embodiments, the polynucleotide consists of the nucleic acid sequence set forth in SEQ ID NO: 88, 91, or 92. In certain embodiments, the polynucleotide consists of the nucleic acid sequence set forth in SEQ ID NO: 92.

In another aspect, the instant disclosure provides pharmaceutical compositions comprising an AAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in Remington's Pharmaceutical Sciences, current Ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al, 7th ed., Lippincott, Williams, & Wilkins; and Handbook of Pharmaceutical Excipients (2000) A. H. Kibbe et al, 3rd ed. Amer. Pharmaceutical Assoc.

In another aspect, the instant disclosure provides a polynucleotide comprising a coding sequence encoding a human PAH protein or a fragment thereof, wherein the coding sequence has been codon-altered to have less than 100% (e.g., less than 95%, 90%, 85%, 80%, 75%, 70%, 65%, 60%, 55%, or 50%) identical to a wild-type human PAH gene. In certain embodiments, the polynucleotide comprises the sequence set forth in SEQ ID NO: 25. In certain embodiments, the polynucleotide comprises nucleotides 4 to 1359 of the sequence set forth in SEQ ID NO: 25. The polynucleotide can comprise DNA, RNA, modified DNA, modified RNA, or a combination thereof. In certain embodiments, the polynucleotide is an expression vector.

III. Method of Use

In another aspect, the instant disclosure provides methods for expressing a PAH polypeptide in a cell. The methods generally comprise transducing the cell with a replication-defective AAV as disclosed herein. Such methods are highly efficient at restoring PAH expression. Accordingly, in certain embodiments, the methods disclosed herein involve transducing the cell with a replication-defective AAV as disclosed herein.

The methods disclosed herein can be applied to any cell harboring a mutation in the PAH gene. The skilled worker will appreciate that cells that are active in Phe metabolism are of particular interest. Accordingly, in certain embodiments, the method is applied to cells in the liver, kidney, brain, pituitary gland, adrenal gland, pancreas, urinary bladder, gallbladder, colon, small intestine, or breast. In certain embodiments, the method is applied to hepatocytes and/or renal cells.

The methods disclosed herein can be performed in vitro for research purposes or can be performed ex vivo or in vivo for therapeutic purposes.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with a PAH gene mutation, the method generally comprising administering to the subject an effective amount of a replication-defective AAV as disclosed herein. The subject can be a human subject, a non-human primate subject (e.g., a cynomolgus), or a rodent subject (e.g., a mouse) with a PAH mutation, or a non-human primate subject (e.g., a cynomolgus) or a rodent subject (e.g., a mouse) containing PAH-mutant human liver cells. Suitable mouse subjects include without limitation, mice into which human liver cells (e.g., human hepatocytes) have been engrafted. Any disease or disorder associated with a PAH gene mutation can be treated using the methods disclosed herein. Suitable diseases or disorders include, without limitation, phenylketonuria.

In certain embodiments, the foregoing methods employ a replication-defective AAV comprising: (a) an AAV capsid protein comprising the amino acid sequence of amino acids 203-736 of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27); (b) an AAV capsid protein comprising the amino acid sequence of amino acids 138-736 of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27; and/or (c) an AAV capsid protein comprising the amino acid sequence of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27.

In certain embodiments, the foregoing methods employ a replication-defective AAV comprising: (a) an AAV capsid protein comprising the amino acid sequence of amino acids 203-736 of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90; (b) an AAV capsid protein comprising the amino acid sequence of amino acids 138-736 of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90; and/or (c) an AAV capsid protein comprising the amino acid sequence of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90.

The methods disclosed herein are particularly advantageous in that they are capable of expressing a PAH protein in a cell with high efficiency both in vivo and in vitro. In certain embodiments, the expression level of the PAH protein is at least 10%, 20%, 30%, 40%, 50%, 60%, 70%, 80%, 90%, or 100% of the expression level of the endogenous PAH protein in a cell of the same type that does not have a mutation in the PAH gene. In certain embodiments, the expression level of the PAH protein is at least 1.1, 1.2, 1.3, 1.4, 1.5, 1.6, 1.7, 1.8, 1.9, 2, 3, 4, 5, 6, 7, 8, 9, or 10 fold higher than the expression level of the endogenous PAH protein in a cell of the same type that does not have a mutation in the PAH gene. Any methods of determining the expression level of the PAH protein can be employed including, without limitation, ELISA, Western blotting, immunostaining, and mass spectrometry.

In certain embodiments, transduction of a cell with an AAV composition disclosed herein can be performed as provided herein or by any method of transduction known to one of ordinary skill in the art. In certain embodiments, the cell may be contacted with the AAV at a multiplicity of infection (MOI) of 50,000; 100,000; 150,000; 200,000; 250,000; 300,000; 350,000; 400,000; 450,000; or 500,000, or at any MOI that provides for optimal transduction of the cell.

An AAV composition disclosed herein can be administered to a subject by any appropriate route including, without limitation, intravenous, intraperitoneal, subcutaneous, intramuscular, intranasal, topical or intradermal routes. In certain embodiments, the composition is formulated for administration via intravenous injection or subcutaneous injection.

IV. AAV Packaging Systems

In another aspect, the instant disclosure provides packaging systems for recombinant preparation of a replication-defective AAV disclosed herein. Such packaging systems generally comprise: a Rep nucleotide sequence encoding one or more AAV Rep proteins; a Cap nucleotide sequence encoding one or more AAV Clade F capsid proteins as disclosed herein; and a transfer genome for expression of the PAH gene as disclosed herein, wherein the packaging system is operative in a cell for enclosing the transfer genome in the capsid to form the AAV.

In certain embodiments, the packaging system comprises a first vector comprising the Rep nucleotide sequence and the Cap nucleotide sequence, and a second vector comprising the transfer genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

Any AAV Rep protein can be employed in the packaging systems disclosed herein. In certain embodiments of the packaging system, the Rep nucleotide sequence encodes an AAV2 Rep protein. Suitable AAV2 Rep proteins include, without limitation, Rep 78/68 or Rep 68/52. In certain embodiments of the packaging system, the nucleotide sequence encoding the AAV2 Rep protein comprises a nucleotide sequence that encodes a protein having a minimum percent sequence identity to the AAV2 Rep amino acid sequence of SEQ ID NO: 22, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein. In certain embodiments of the packaging system, the AAV2 Rep protein has the amino acid sequence set forth in SEQ ID NO: 22.

In certain embodiments of the packaging system, the packaging system further comprises a third vector, e.g., a helper virus vector. The third vector may be an independent third vector, integral with the first vector, or integral with the second vector. In certain embodiments, the third vector comprises genes encoding helper virus proteins.

In certain embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In certain embodiments of the packaging system, where the helper virus is adenovirus, the adenovirus genome comprises one or more adenovirus RNA genes selected from the group consisting of E1, E2, E4 and VA. In certain embodiments of the packaging system, where the helper virus is HSV, the HSV genome comprises one or more of HSV genes selected from the group consisting of UL5/8/52, ICPO, ICP4, ICP22 and UL30/UL42.

In certain embodiments of the packaging system, the first, second, and/or third vector are contained within one or more transfecting plasmids. In certain embodiments, the first vector and the third vector are contained within a first transfecting plasmid. In certain embodiments the second vector and the third vector are contained within a second transfecting plasmid.

In certain embodiments of the packaging system, the first, second, and/or third vector are contained within one or more recombinant helper viruses. In certain embodiments, the first vector and the third vector are contained within a recombinant helper virus. In certain embodiments, the second vector and the third vector are contained within a recombinant helper virus.

In a further aspect, the disclosure provides a method for recombinant preparation of an AAV as described herein, wherein the method comprises transfecting or transducing a cell with a packaging system as described under conditions operative for enclosing the transfer genome in the capsid to form the AAV as described herein. Exemplary methods for recombinant preparation of an AAV include transient transfection (e.g., with one or more transfection plasmids containing a first, and a second, and optionally a third vector as described herein), viral infection (e.g. with one or more recombinant helper viruses, such as a adenovirus, poxvirus (such as vaccinia virus), herpes virus (including HSV, cytomegalovirus, or baculovirus, containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV Clade F capsid proteins as described herein, and with a transfer genome as described herein being delivered in the form of a transfecting plasmid or a recombinant helper virus).

V. Examples

The recombinant AAV vectors disclosed herein mediate highly efficient gene transfer in vitro and in vivo. The following examples demonstrate the efficient restoration of the expression of the PAH gene, which is mutated in certain human diseases, such as phenylketonuria, using an AAV-based vector as disclosed herein. These examples are offered by way of illustration, and not by way of limitation.

Example 1: Human PAH Transfer Vector

This example provides human PAH transfer vectors pHMI-hPAH-TC-004, pHMI-hPAH-TC-025, pHMI-hPAH-TC-010, pHMI-hPAH-TC-011, and pHMI-hPAH-TC-012 for expression of human PAH in a human or mouse cell.

a) pHMI-hPAH-TC-004

PAH transfer vector pHMI-hPAH-TC-004, as shown in FIG. 1A, comprises 5' to 3' the following genetic elements: a 5' ITR element, a CAG promoter, a silently altered human PAH coding sequence, an SV40 polyadenylation sequence, and a 3' ITR element. The sequences of these elements are set forth in Table 1. This vector is capable of expressing a human PAH protein in a cell (e.g., a human cell or a mouse cell) to which the vector is transduced.

TABLE 1

Genetic elements in human PAH transfer vector pHMI-hPAH-TC-004

| Genetic Element | SEQ ID NO |
|---|---|
| 5' ITR element | 18 |
| CAG promoter | 28 |
| codon-altered human PAH coding sequence | 25 |
| SV40 polyadenylation sequence | 42 |
| 3' ITR element | 19 |
| Transfer genome (from promoter to polyadenylation sequence) | 46 |
| Transfer genome (from 5' ITR to 3' ITR) | 51 | b) pHMI-hPAH-TC-025

PAH transfer vector pHMI-hPAH-TC-025, as shown in FIG. 1B, comprises 5' to 3' the following genetic elements: a truncated 5' ITR element, a human hepatic control region 1 (HCR1), a human a1-antitrypsin (hAAT) promoter, an SV40 intron, a silently altered human PAH coding sequence, an SV40 polyadenylation sequence, and a modified 3' ITR element. The sequences of these elements are set forth in Table 2. The truncated 5' ITR allows the vector to form a double-stranded AAV genome after transduction into cells. This vector is capable of expressing a human PAH protein in a human hepatocyte to which the vector is transduced.

TABLE 2

Genetic elements in human PAH transfer vector pHMI-hPAH-TC-025

| Genetic Element | SEQ ID NO |
| --- | --- |
| truncated 5' ITR element | 26 |
| human HCR1 | 29 |
| human α1-antitrypsin (hAAT) promoter | 30 |
| SV40 intron | 31 |
| transcriptional regulatory region comprising the human HCR1 and hAAT promoter | 32 |
| codon-altered human PAH coding sequence | 25 |
| SV40 polyadenylation sequence | 43 |
| modified 3' ITR element | 27 |
| Transfer genome (from HCR1 to polyadenylation sequence) | 47 |
| Transfer genome (from 5' ITR to 3' ITR) | 52 |
| Full sequence of transfer vector | 92 | c) pHMI-hPAH-TC-010

PAH transfer vector pHMI-hPAH-TC-010, as shown in FIG. 1C, comprises 5' to 3' the following genetic elements: a 5' ITR element, a hepatic specific regulatory module of hAAT promoter, a human TTR promoter, a modified minute virus of mouse (MVM) intron, a silently altered human PAH coding sequence, an SV40 polyadenylation sequence, and a 3' ITR element. The sequences of these elements are set forth in Table 3. This vector is capable of expressing a human PAH protein in a cell (e.g., a human cell or a mouse cell) to which the vector is transduced, particularly at a high level in a hepatocyte.

TABLE 3

Genetic elements in human PAH transfer vector pHMI-hPAH-TC-010

| Genetic Element | SEQ ID NO |
| --- | --- |
| 5' ITR element | 18 |
| hepatic specific regulatory module of hAAT promoter | 33 |
| human TTR promoter | 34 |
| modified minute virus of mouse (MVM) intron | 35 |
| transcriptional regulatory region comprising the hepatic specific regulatory module (HSRM) and human TTR promoter | 36 |
| codon-altered human PAH coding sequence | 25 |
| SV40 polyadenylation sequence | 45 |
| 3' ITR element | 19 |
| Transfer genome (from HSRM to polyadenylation sequence) | 48 |
| Transfer genome(from 5' ITR to 3' ITR) | 53 | d) pHMI-hPAH-TC-011

PAH transfer vector pHMI-hPAH-TC-011, as shown in FIG. 1D, comprises 5' to 3' the following genetic elements: a 5' ITR element, a human HCR1, a human al-antitrypsin (hAAT) promoter, an modified MVM intron, a silently altered human PAH coding sequence, an SV40 polyadenylation sequence, and a 3' ITR element. The sequences of these elements are set forth in Table 4. This vector is capable of expressing a human PAH protein in a human hepatocyte to which the vector is transduced.

TABLE 4

Genetic elements in human PAH transfer vector pHMI-hPAH-TC-011

| Genetic Element | SEQ ID NO |
| --- | --- |
| truncated 5' ITR element | 18 |
| human HCR1 | 37 |
| human α1-antitrypsin (hAAT) promoter | 38 |
| modified minute virus of mouse (MVM) intron | 35 |
| transcriptional regulatory region comprising the human HCR1 and hAAT promoter | 39 |
| codon-altered human PAH coding sequence | 25 |
| SV40 polyadenylation sequence | 45 |
| modified 3' ITR element | 19 |
| Transfer genome (from HCR1 to polyadenylation sequence) | 49 |
| Transfer genome(from 5' ITR to 3' ITR) | 54 | e) pHMI-hPAH-TC-012

Figure 1E:
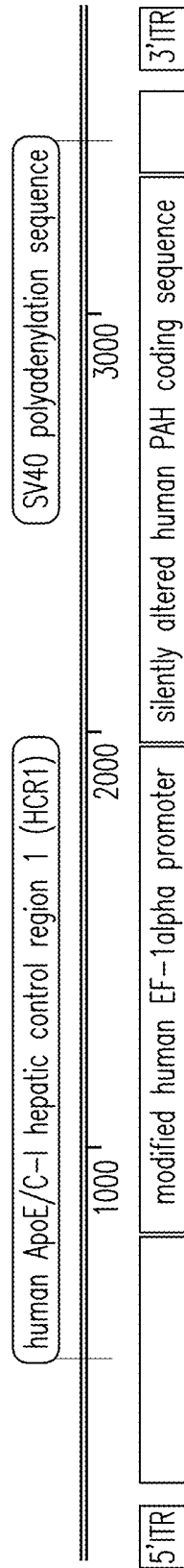

PAH transfer vector pHMI-hPAH-TC-012, as shown in FIG. 1E, comprises 5' to 3' the following genetic elements: a 5' ITR element, a human hepatic control region 1 (HCR1), a modified human EF-1a promoter, a silently altered human PAH coding sequence, an SV40 polyadenylation sequence, and a 3' ITR element. The sequences of these elements are set forth in Table 5. This vector is capable of expressing a human PAH protein in a human hepatocyte to which the vector is transduced.

TABLE 5

Genetic elements in human PAH transfer vector pHMI-hPAH-TC-012

| Genetic Element | SEQ ID NO |
| --- | --- |
| truncated 5' ITR element | 18 |
| human hepatic control region 1 (HCR1) | 37 |
| modified human EF-1α promoter | 40 |
| transcriptional regulatory region comprising the human HCR1 and modified human EF-1α promoter | 41 |
| codon-altered human PAH coding sequence | 25 |
| SV40 polyadenylation sequence | 45 |
| modified 3' ITR element | 19 |
| Transfer genome (from HCR1 to polyadenylation sequence) | 50 |
| Transfer genome (from 5' ITR to 3' ITR) | 55 |

Figure 2:
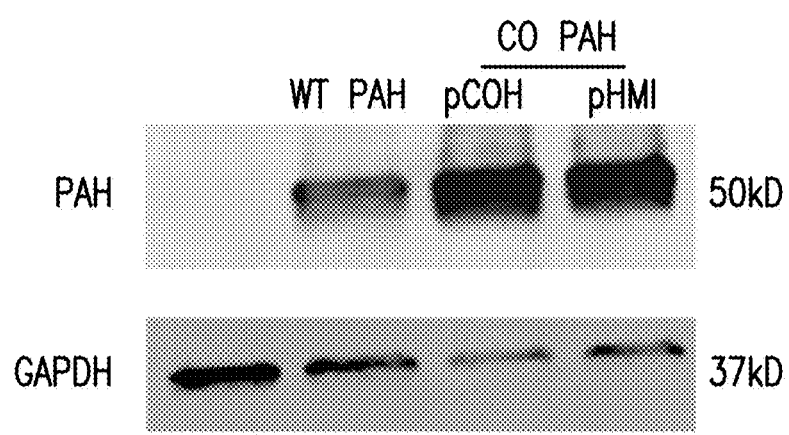
FIG. 2 is an image of Western blot showing the expression of human PAH from the pCOH-WT-PAH ("WT PAH"), pCOH—CO-PAH ("CO PAH pCOH"), and pHMI-CO-PAH ("CO PAH pHMI") vectors. $5\times10^5$ HEK 293 cells were transfected with 1 μg of vector. Lysate of the cells was collected 48 hours after transfection. The expression of human PAH was detected by Western blotting with an anti-PAH antibody (Sigma HPA031642). The amount of GAPDH protein as detected by an anti-GAPDH antibody (Millipore MAB 374) was shown as a loading control.

The silent alteration significantly improves the expression of the PAH protein, as demonstrated by comparison of expression vectors pCOH-WT-PAH, pCOH—CO-PAH, and pHMI-CO-PAH. The pCOH-WT-PAH vector comprises a CAG promoter operably linked to a wild-type PAH coding sequence set forth in SEQ ID NO: 24. The pCOH—CO-PAH and pHMI-CO-PAH vectors each comprise a CAG promoter operably linked to a codon-altered human PAH coding sequence as set forth in SEQ ID NO: 25. The pCOH—CO-PAH and pHMI-CO-PAH vectors are highly similar. Each vector was transfected in HEK 293 cells which is naturally deficient in PAH. As shown in FIG. 2, VG-GT-CO-PAH ("CO-hPAH") gave rise to an expression level of human PAH several fold higher than VG-GT-PAH ("WT-hPAH").

The vectors disclosed herein can be packaged in an AAV clade F capsid, such as an AAVHSC5, AAVHSC7, AAVHSC15 or AAVHSC17 capsid. The packaged viral particles can be administered to a wild-type animal, a PAH deficient animal, or a reconstituted animal having human hepatocytes obtained from a patient with phenylketonuria caused by a PAH mutation. The gene transfer efficiency can be measured by collecting liver samples and quantifying the percentage of PAH-positive cells (e.g., cells that have a unique nucleotide sequence from the vector, cells that express a wild-type PAH protein, or cells with a higher PAH activity than in cells from a control animal not receiving the PAH expression vector). The restoration of phenylalanine metabolism, which indicates the efficacy of the PAH expression vectors, can be assessed by measuring the Phe level in the blood and by observing the coat color of the mouse. Safety of the viral particle administration can be evaluated by measuring the aspartate aminotransferase (AST) and alanine aminotransferase (ALT) levels in serum.

Example 2: Mouse PAH Gene Transfer in a Mouse Model

This example provides a mouse PAH transfer vector rAAV-CBA-mPAH that is similar to the human PAH transfer vector pHMI-hPAH-TC-004 described in Example 1 except that a wild-type mouse PAH coding sequence is substituted for the codon-altered human PAH coding sequence. This vector is capable of expressing a mouse PAH protein in a cell (e.g., a human cell or a mouse cell) to which the vector is transduced.

Briefly, Pah$^{-/-}$ (PAH$^{enu2}$) mice were housed in clear polycarbonate cages with contact bedding in an isolator. Picolab Mouse Diet 5058 was provided to the animals ad libitum. Spring or tap water acidified with 1N HCl to a targeted pH of 2.5-3.0 was provided ad libitum. Vectors packaged in AAVHSC15 capsid were prepared in PBS (with Ca and Mg), supplemented with 35 mM NaCl, 1% sucrose, and 0.05% Pluronic F-68. The formulation was injected intravenously via the tail vein.

Blood samples were collected every week after the administration of the PAH transfer vector (0 week: prior to administration) by facial vein puncture or tail snip. The samples were allowed to clot at room temperature for at least 30 minutes, centrifuged at ambient temperature at minimum 1000×g for 10 minutes and the serum samples were extracted. Serum samples were stored at −70° C. Serum phenylalanine and tyrosine levels were measured by tandem mass spectrometry.

For collection of tissue samples, the animals underwent cardiac perfusion with saline. Liver (caudate lobe), kidney (left), brain, heart, and muscle (quadriceps) tissues were snap frozen in liquid nitrogen and stored at −70° C. The snap frozen tissues were ground into powder in liquid nitrogen in a mortar and pestle and divided in to aliquots to test for PAH expression for vector genome biodistribution by qPCR.

The safety of the rAAV-CBA-mPAH vector was assessed by measuring the aspartate aminotransferase (AST) and alanine aminotransferase (ALT) levels in the treated animals. Serum samples were collected pre-dose and one week after administration of the viral particles. The levels of AST and ALT were measured by the Sigma MAK055 and Sigma MAK052 ELISA kits.

Figure 3A:
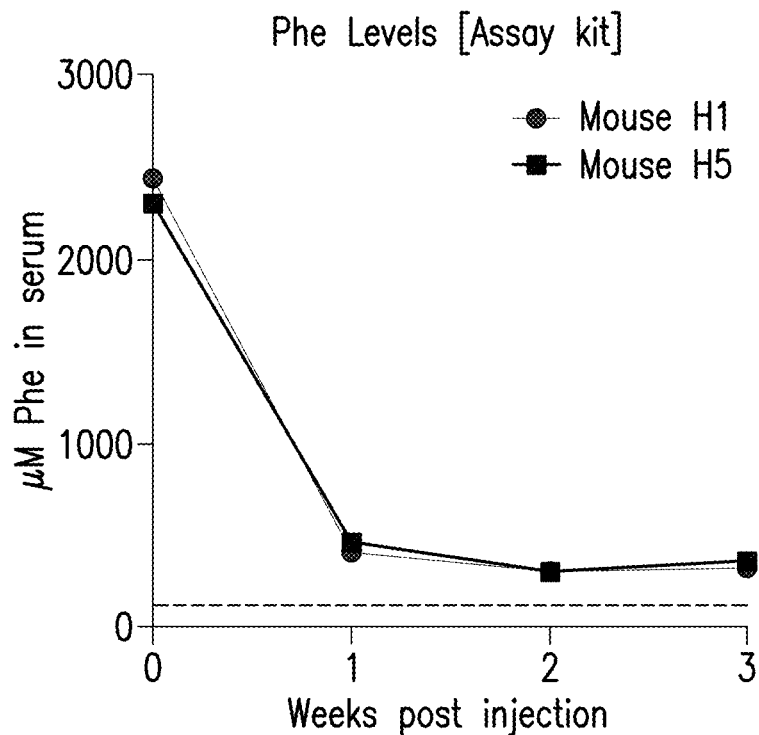
FIGS. 3A and 3B are graphs showing the Phe level in the serum of two pah$^{-/-}$ mice ("Mouse H1" and "Mouse H5") each administered with $5\times10^{13}$ vector genomes of the rAAV-CBA-mPAH vector packaged in an AAVHSC capsid per kg of body weight intravenously via the tail vein. Serum samples were collected in a time course. The Phe levels were measured with a BioAssay Systems ELISA kit EPHE-100 (FIG. 3A) or mass spectrometry (FIG. 3B).
Figure 3B:
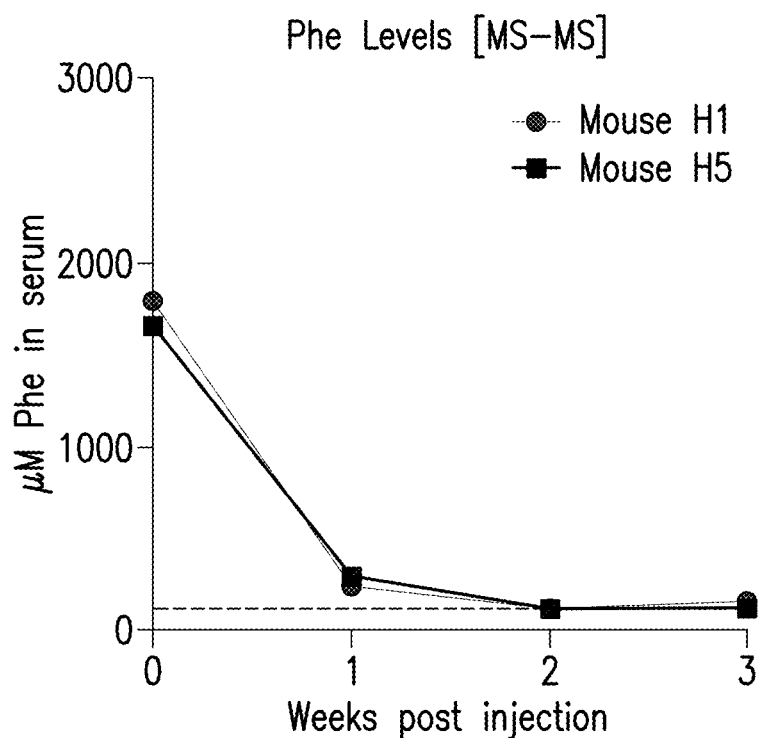

The pah$^{-/-}$ mice manifested phenylketonuria and had lighter coat color than wild-type mice. As shown in FIGS. 3A and 3B, the administration of the rAAV-CBA-mPAH vector lead to significant reduction of Phe levels in the serum within one week, and the Phe levels remained low for four weeks. The coat color also changed from brown to black within one week.

Figure 4:
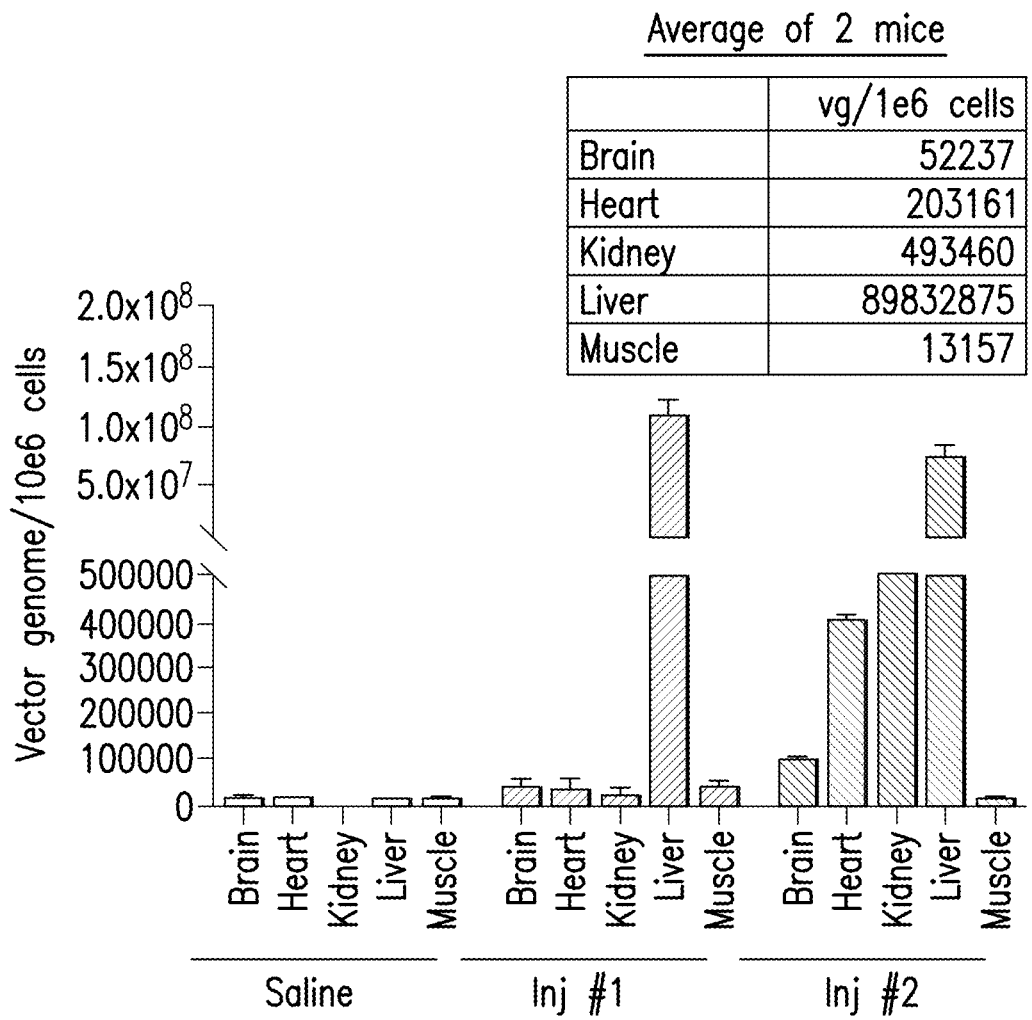
FIG. 4 is a graph and a table showing the numbers of vector genomes per $10^6$ cells detected in major organs. The rAAV-CBA-mPAH vector packaged in an AAVHSC capsid was injected to pah$^{-/-}$ mice intravenously via the tail vein at a dose of $5\times10^{13}$ vector genomes per kg of body weight. Organs of the mice were collected 4 weeks after the administration. The numbers of vector genomes per $10^6$ cells were measured by the following method: (1) the weight/volume concentration of the vector genome in a sample was measured by Taqman PCR using a standard curve generated with serial dilutions of the vector plasmid; (2) the mass of a single vector genome was calculated based on the sequence of the vector; (3) the number/volume concentration of the vector genome in the sample was calculated; (4) the weight/volume concentration of genomic DNA in the same sample was measured by Taqman PCR of the apolipoprotein B gene using a standard curve generated with serial dilutions of calculated amounts of genomic DNA isolated from mouse tissues; (5) the number/volume concentration of cell genome in the sample was calculated based on copies of ApoB; and (6) the number of vector genomes per $10^6$ cells was calculated by dividing the number/volume concentration of the vector genome by the number/volume concentration of the cell genome and multiplying the result by $10^6$.

Expression of mPAH was also observed in tissue samples. As shown in FIG. 4, DNA of the rAAV-CBA-mPAH vector was detectable in many organs, wherein the numbers of viral genomes per 10$^6$ cells was the highest in liver, heart, and kidney.

Figure 5A:
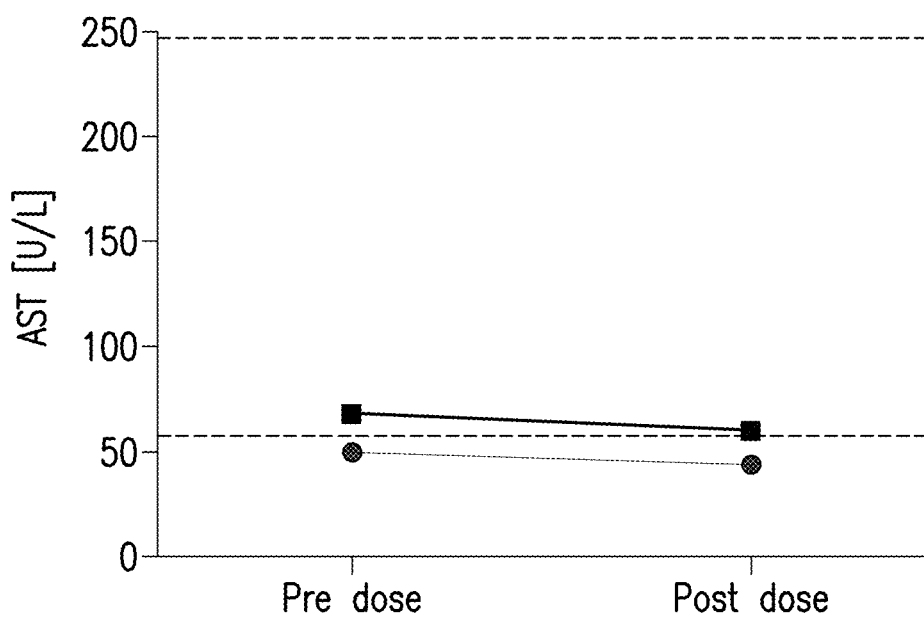
FIGS. 5A and 5B are graphs showing the aspartate aminotransferase (AST) and alanine aminotransferase (ALT) levels in the serum of pah$^{-/-}$ mice administered with the rAAV-CBA-mPAH vector. The rAAV-CBA-mPAH vector packaged in an AAVHSC capsid was injected to pah$^{-/-}$ mice intravenously via the tail vein at a dose of $5\times10^{13}$ vector genomes per kg of body weight. Serum samples were collected 4 weeks after the administration. The levels of AST (FIG. 5A) and ALT (FIG. 5B) were measured by ELISA using the Sigma MAK055 and Sigma MAK052 kits, respectively.
Figure 5B:
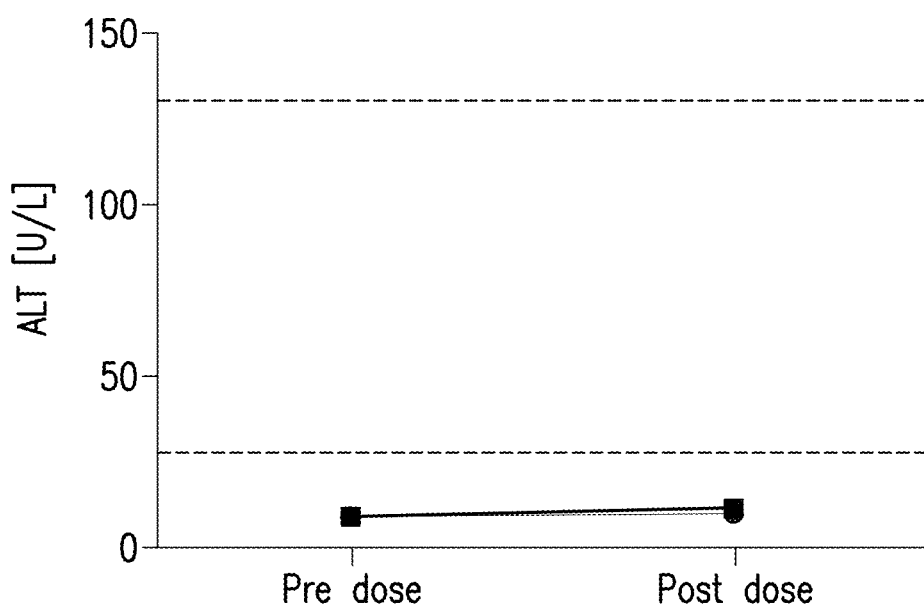

With respect to the safety of the AAV administration, the AST and ALT levels remained low after administration (FIGS. 5A and 5B), suggesting that the rAAV-CBA-mPAH vector was not toxic to the liver.

Example 3: Human PAH Gene Transfer in a Mouse Model

This example demonstrates that the PAH transfer vectors described in Example 1 effectively reversed the phenotype caused by PAH gene deficiency in a mouse model. The mouse model, AAV packaging and formulation, and methods for examining gene transfer efficiency were identical to the ones described in Example 2.

To examine the efficacy of the five PAH transfer vectors in reversing the phenotypes, a single dose of 2.6×10$^{13}$ vector genomes per kg of body weight for male mice, or a dose of 6×10$^{13}$ vector genomes per kg of body weight for female mice. The pah$^{-/-}$ mice manifested increased level of phenylalanine (Phe) and reduced level of tyrosine (Tyr) in the serum. As shown in FIGS. 6A-6H, the administration of any one of the five vectors led to significant reduction of Phe levels and increase of Tyr levels within one week. The efficacy lasted for at least 12 weeks in male mice, and at least 6 weeks in female mice. Other than pHMI-hPAH-TC-004, all the vectors maintained complete reduction of serum Phe levels during the time examined.

Figure 6A:
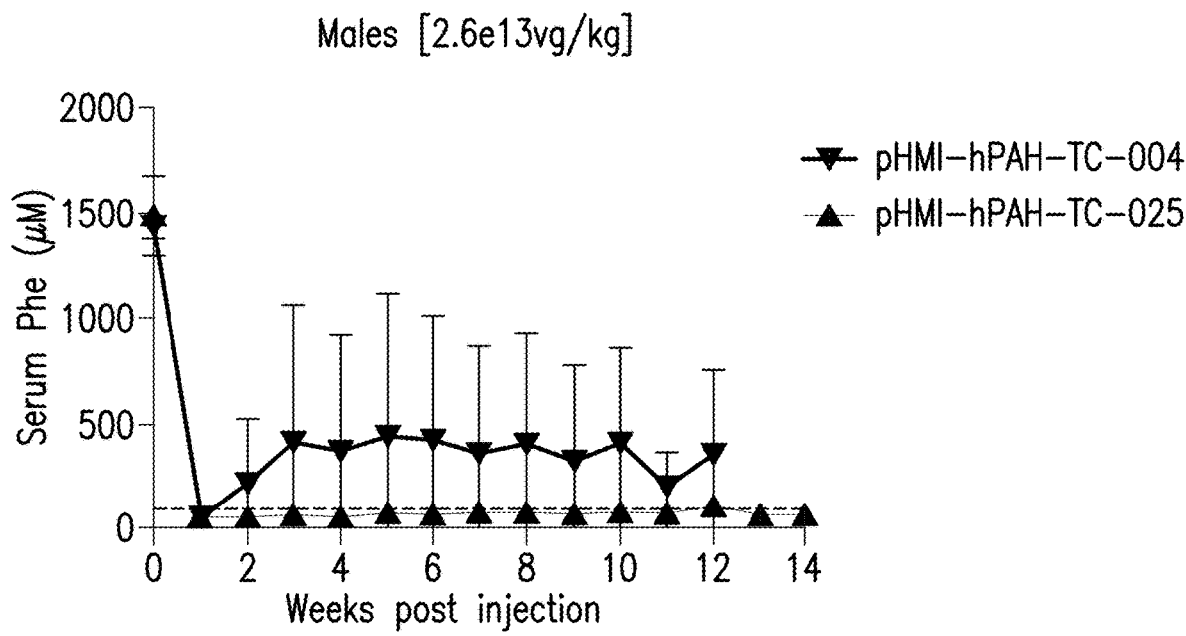
FIGS. 6A-6H are graphs showing the levels of phenylalanine (FIGS. 6A, 6C, 6E, and 6G) or tyrosine (FIGS. 6B, 6D, 6F, and 6H) in the serum of male (FIGS. 6A, 6B, 6E, and 6F) or female (FIGS. 6C, 6D, 6G, and 6H) mice administered with the indicated doses of the pHMI-hPAH-TC-004, pHMI-hPAH-TC-025, pHMI-hPAH-TC-010, pHMI-hPAH-TC-011, or pHMI-hPAH-TC-012 vector.
Figure 6B:
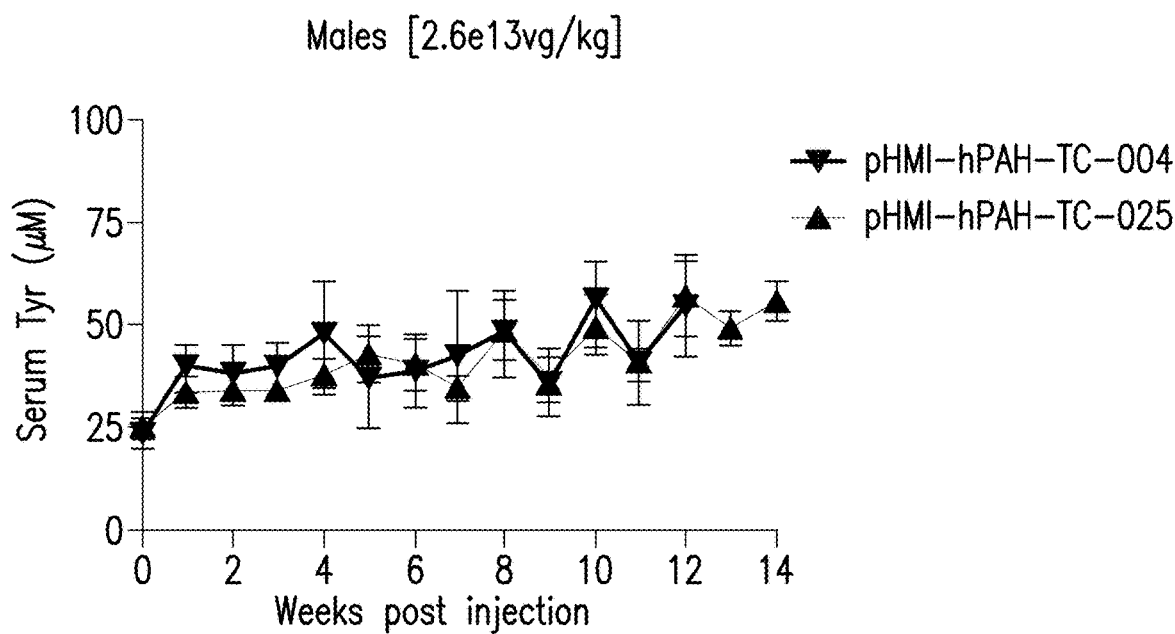
Figure 6C:
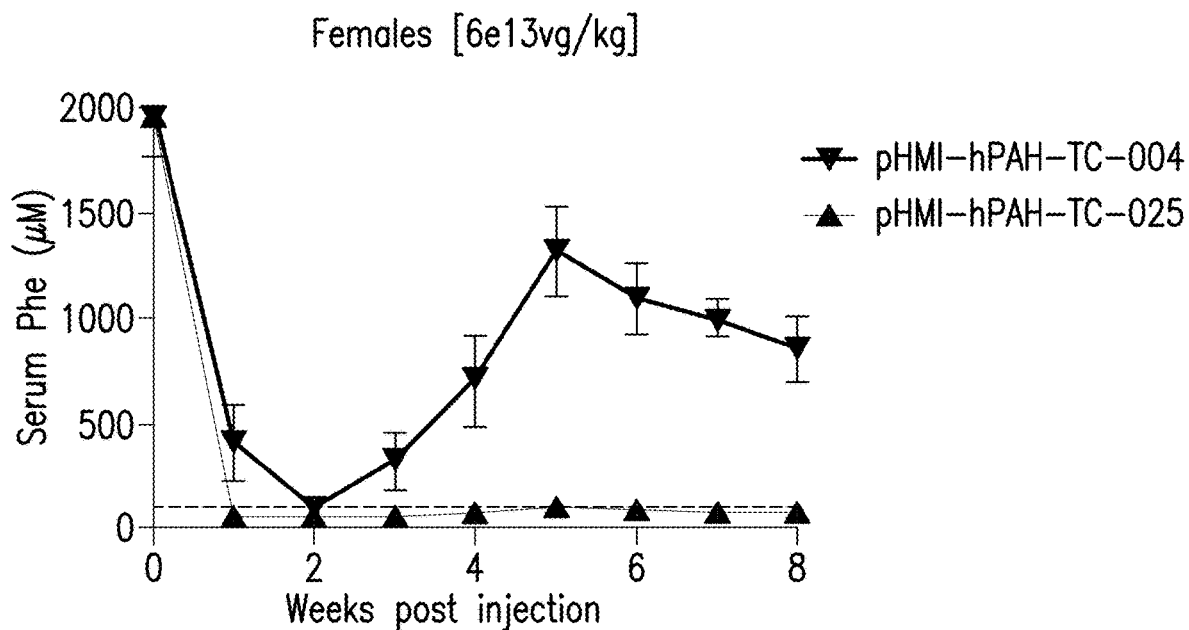
Figure 6D:
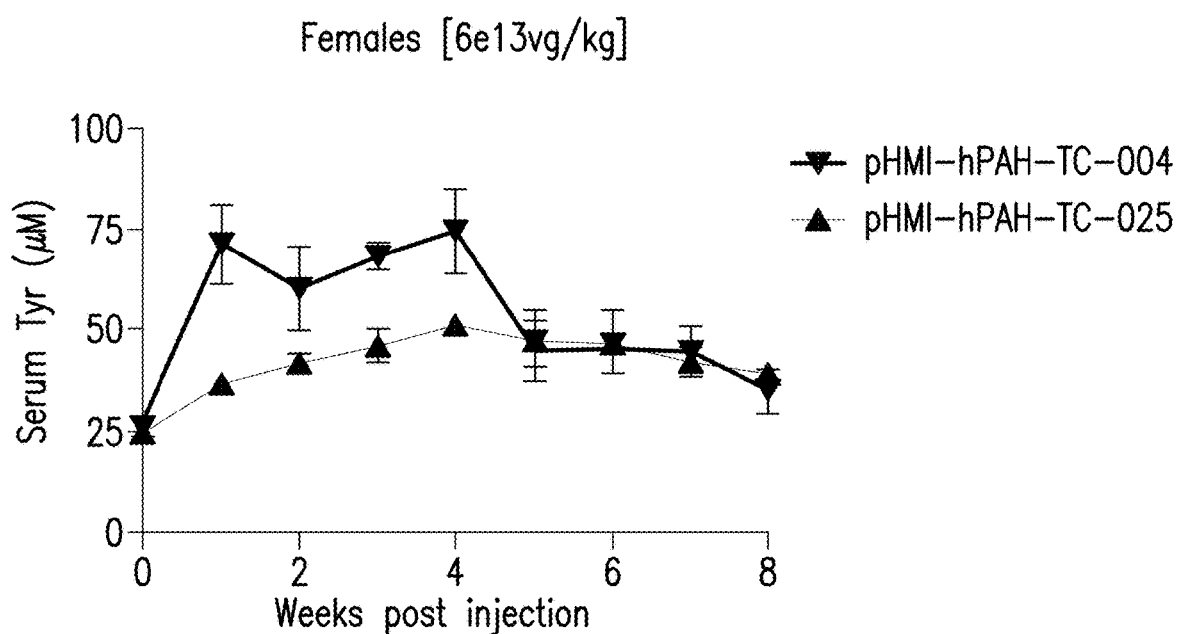
Figure 6E:
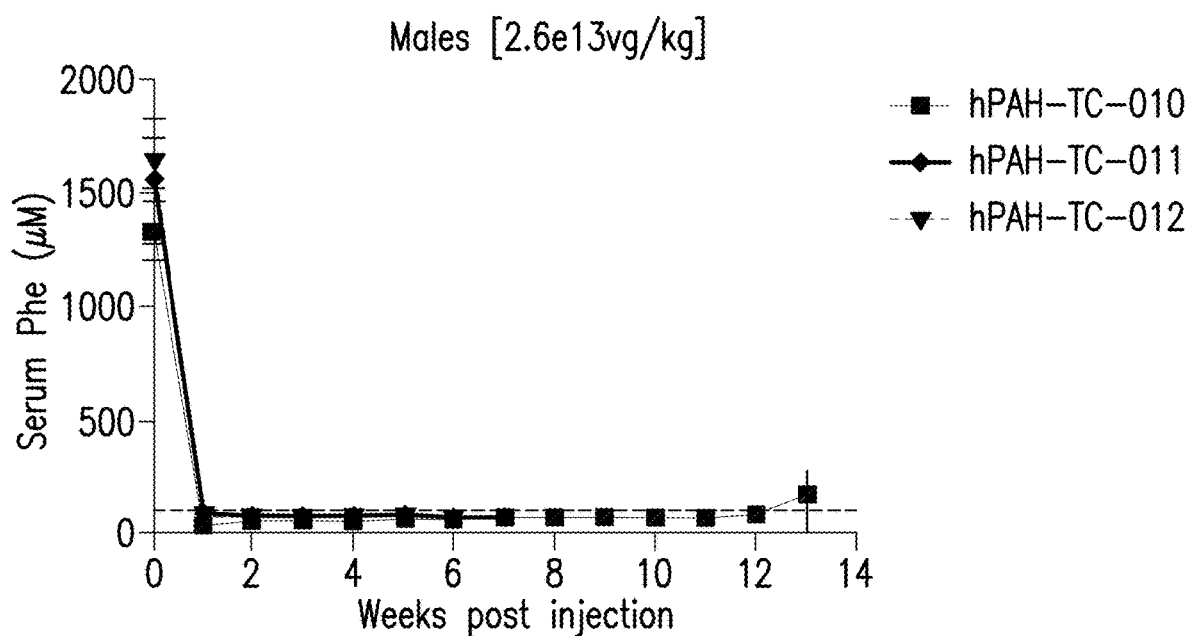
Figure 6F:
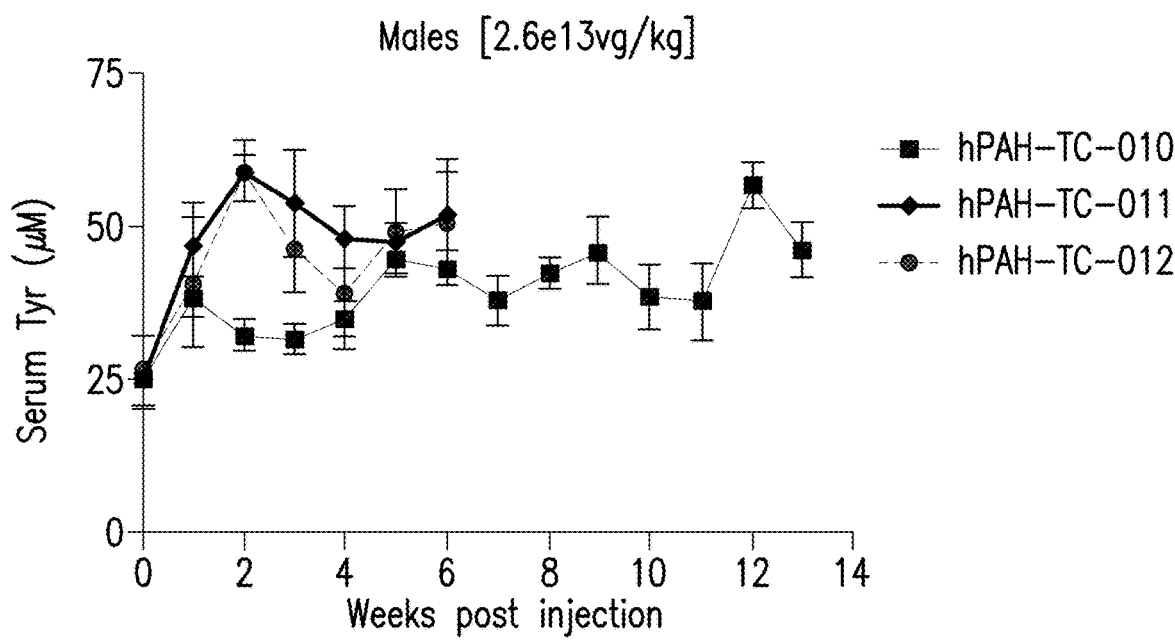
Figure 6G:
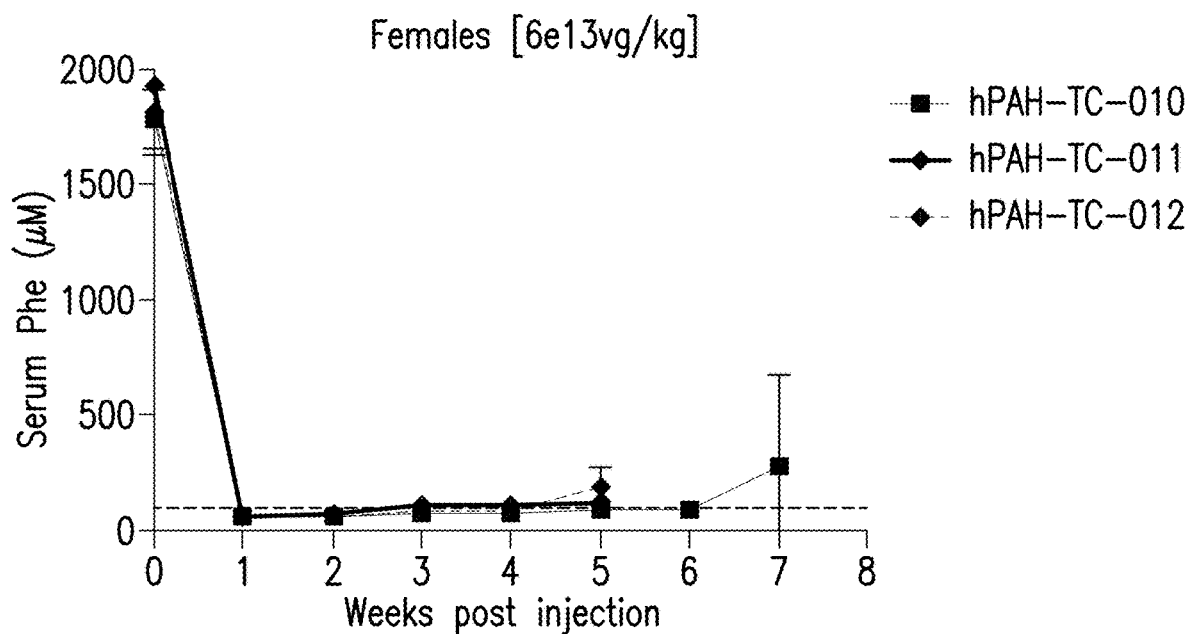
Figure 6H:
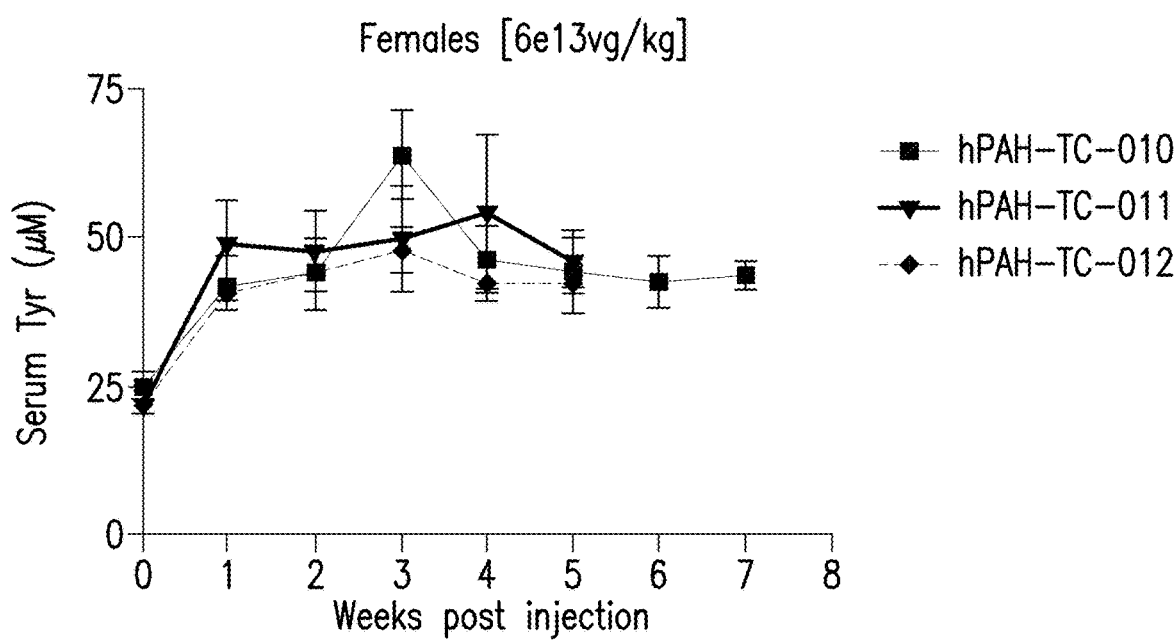
Figure 6I:
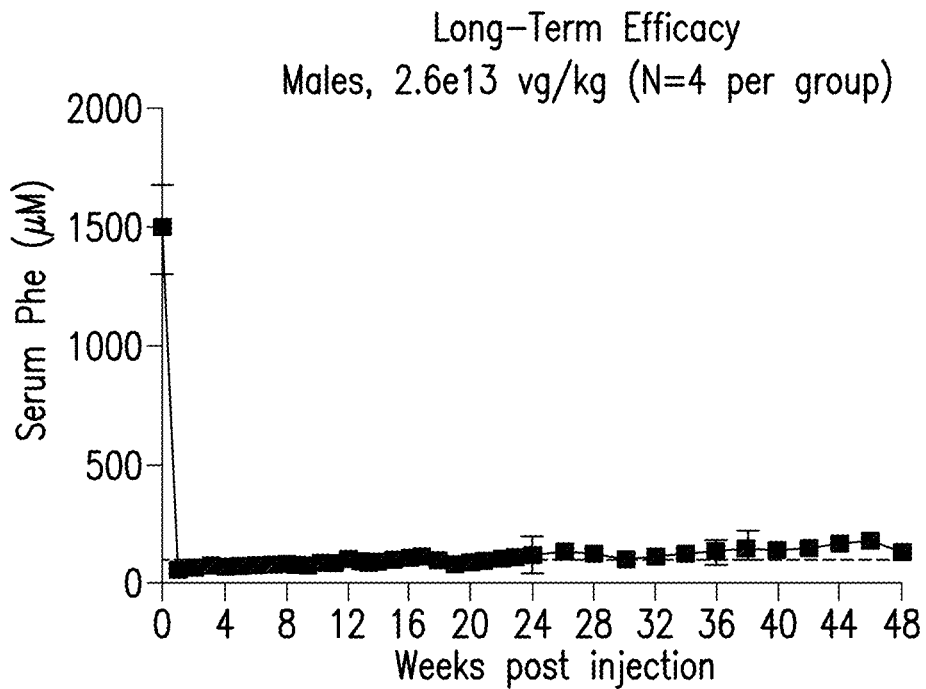
FIGS. 6I-6J are graphs showing the long-term efficacy on levels of phenylalanine in the serum of male (FIG. 6I) or female (FIG. 6J) mice administered the indicated doses of the pHMI-hPAH-TC-025 vector.
Figure 6J:
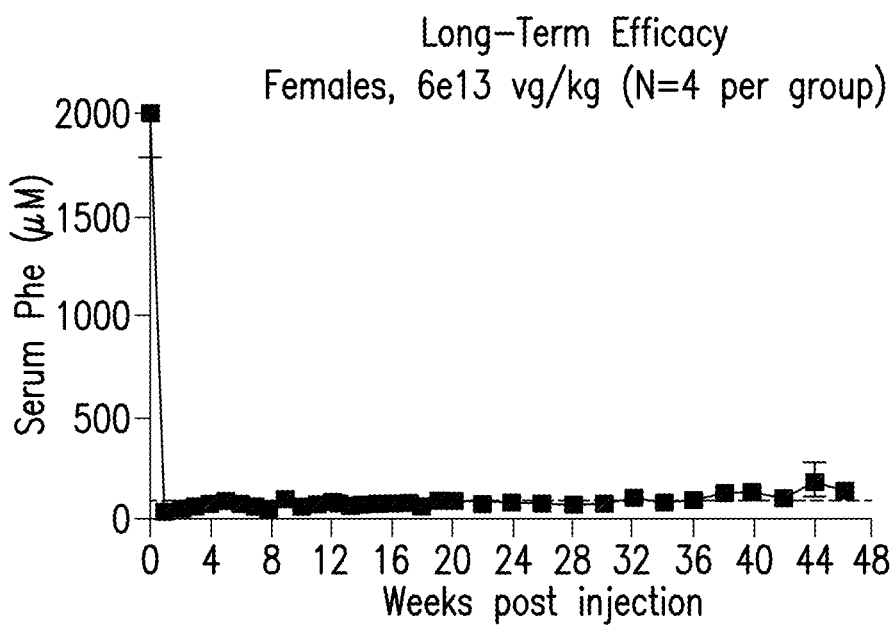
Figure 7A:
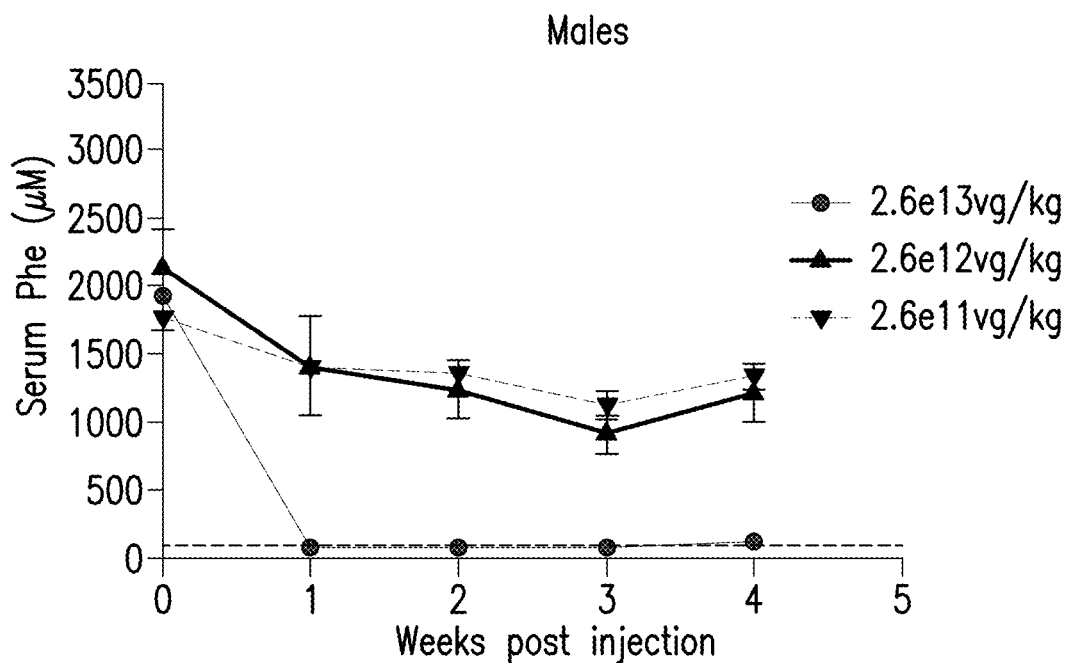
FIGS. 7A-7D are graphs showing the levels of phenylalanine (FIGS. 7A and 7C) or tyrosine (FIGS. 7B and 7D) in the serum of male (FIGS. 7A and 7B) or female (FIGS. 7C and 7D) mice administered with the indicated doses of the pHMI-hPAH-TC-025 vector.
Figure 7B:
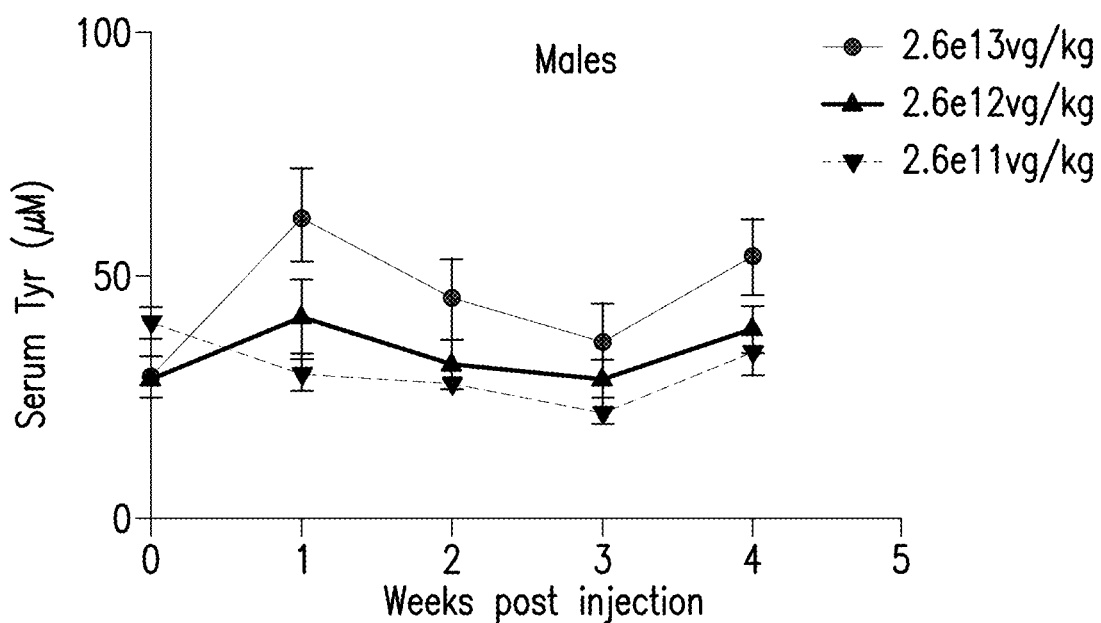
Figure 7C:
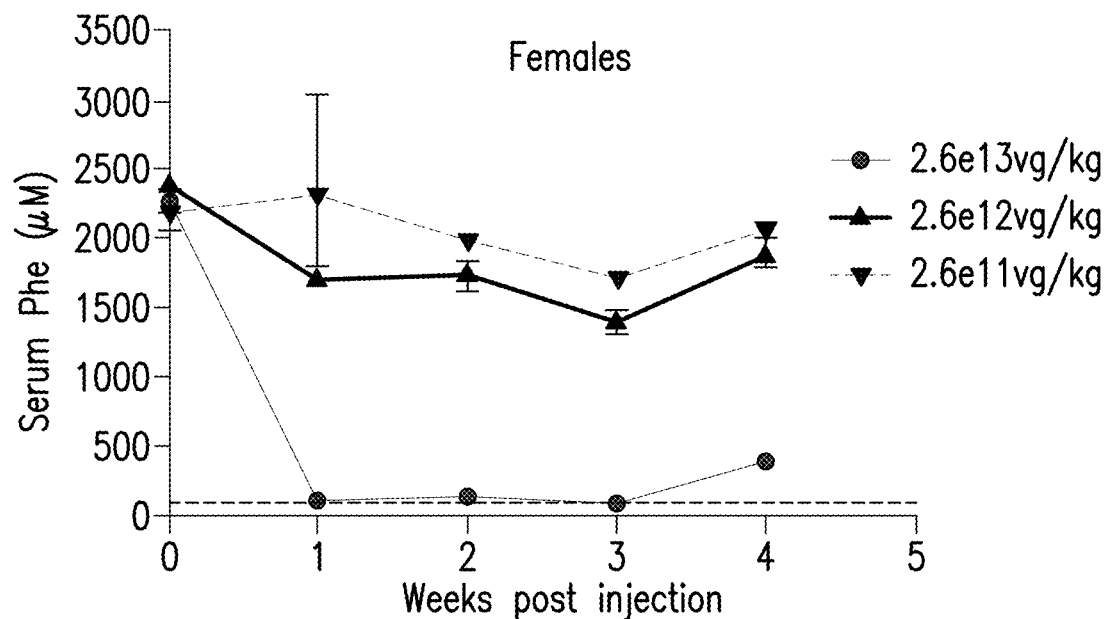
Figure 7D:
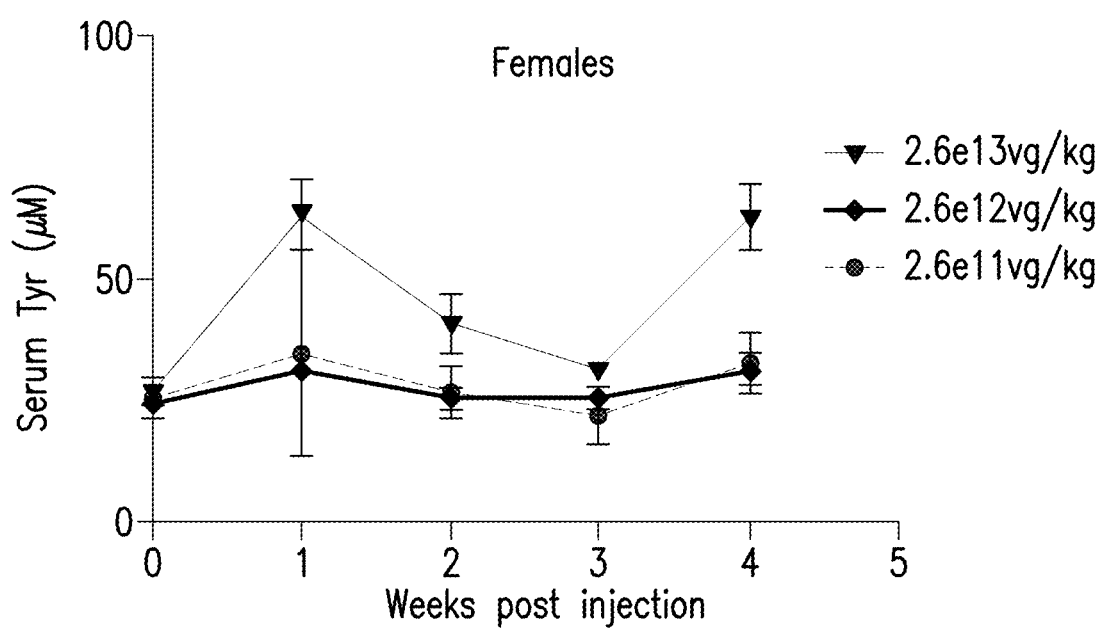

To examine the long-term efficacy of pHMI-hPAH-TC-025 in reversing the phenotype caused by PAH gene deficiency, a single dose of 2.6×10$^{13}$ vector genomes per kg of body weight was administered to male mice, or a single dose of 6×10$^{13}$ vector genomes per kg of body weight was administered to female mice. As shown in FIGS. 6I and 6J, the administration of the pHMI-hPAH-TC-025 vector led to significant reduction of Phe levels within one week. This reduction persisted for at least 48 weeks in male mice, and at least 46 weeks in female mice. Additionally, within two weeks post administration of the AAV, the coat color of the mice administered with pHMI-hPAH-TC-004 changed from brown to black. An increase of PAH mRNA was observed by ddPCR in the liver samples of these mice collected 4 weeks post injection relative to the mice not administered with AAV vectors. An increase of the PAH enzymatic activity was also detected in liver samples by mass spectrometry.

The efficacy of different doses of the pHMI-hPAH-TC-025 vector was further assessed. A single dose of 2.6×10$^{11}$, 2.6×10$^{12}$, or 2.6×10$^{13}$ vector genomes per kg of body weight was administered to male mice and female mice, and the serum levels of Phe and Tyr were measured. As shown in FIGS. 7A-7D, the dose of 2.6×10$^{13}$ vector genomes per kg of body weight reduced the Phe levels and increased the Tyr levels more significantly than the two lower doses, and maintained complete reduction of serum Phe levels during the time examined in both male and female subjects.

Example 3: Additional Human PAH Transfer Vectors

This example provides human PAH transfer vectors pHMI-hPAH-TC-009, pHMI-hPAH-TC-013, and pHMI-hPAH-TC-017 for expression of human PAH in a human or mouse cell. Vector maps are shown in FIGS. 8A, 8B, and 8C, respectively.

a) pHMI-hPAH-TC-009

Figure 8A:
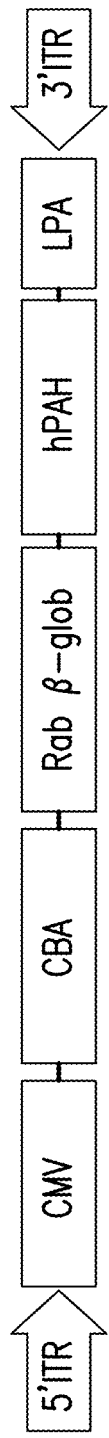
FIG. 8A, 8B, 8C are vector maps of pHMI-hPAH-TC-009, pHMI-hPAH-TC-013 and pHMI-hPAH-TC-017 vectors, respectively.
Figure 8B:
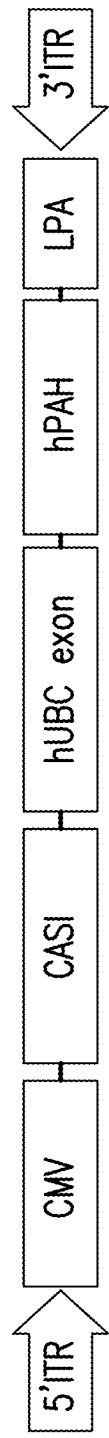
Figure 8C:
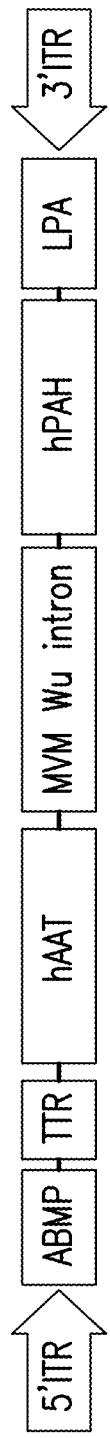

PAH transfer vector pHMI-hPAH-TC-009, as shown in FIG. 8A, comprises 5' to 3' the following genetic elements: a 5' ITR element, a CMV enhancer, a CBA promoter, a rabbit β-globin element, a human PAH coding sequence, a polyadenylation sequence, and a 3' ITR element. The sequences of these elements are set forth in Table 6. This vector is capable of expressing a human PAH protein in a cell (e.g., a human cell or a mouse cell) to which the vector is transduced.

TABLE 6

Genetic elements in human PAH transfer vector pHMI-hPAH-TC-009

| Genetic Element | SEQ ID NO |
|---|---|
| 5' ITR element | 18 |
| CMV enhancer | 58 |
| CBA promoter | 59 |
| Rabbit β-globin element | 60 |
| codon-altered human PAH coding sequence | 25 |
| Polyadenylation sequence | 45 |
| 3' ITR element | 19 |
| Transfer genome (from CMV to polyadenylation sequence) | 61 |
| Transfer genome (from 5' ITR to 3' ITR) | 62 | b) pHMI-hPAH-TC-013

PAH transfer vector pHMI-hPAH-TC-013, as shown in FIG. 8B, comprises 5' to 3' the following genetic elements: a 5' ITR element, a CASI promoter region (comprising a CMV enhancer, a CASI promoter, and a ubiquitin C enhancer element (hUBC exon)), a human PAH coding sequence, a polyadenylation sequence, and a 3' ITR element. The sequences of these elements are set forth in Table 7. This vector is capable of expressing a human PAH protein in a cell (e.g., a human cell or a mouse cell) to which the vector is transduced.

TABLE 7

Genetic elements in human PAH transfer vector pHMI-hPAH-TC-013

| Genetic Element | SEQ ID NO |
|---|---|
| 5' ITR element | 18 |
| CASI promoter region | 63 |
| Human PAH coding sequence | 25 |
| Polyadenylation sequence | 45 |
| 3' ITR element | 19 |
| Transfer genome (from promoter region to polyadenylation sequence) | 64 |
| Transfer genome (from 5' ITR to 3' ITR) | 65 | f) pHMI-hPAH-TC-017

PAH transfer vector pHMI-hPAH-TC-017, as shown in FIG. 8C, comprises 5' to 3' the following genetic elements: a 5' ITR element, an hAAT promoter region (comprising an ABMP enhancer (an enhancer region adjacent to a gene on chromosome 9 that expresses highly in liver, 5' to the ATG), a TTR enhancer, an hAAT promoter, and an MVM intron), a human PAH coding sequence, a polyadenylation sequence, and a 3' ITR element. The sequences of these elements are set forth in Table 8. This vector is capable of expressing a human PAH protein in a cell (e.g., a human cell or a mouse cell) to which the vector is transduced.

TABLE 8

Genetic elements in human PAH transfer vector pHMI-hPAH-TC-017

| Genetic Element | SEQ ID NO |
|---|---|
| 5' ITR element | 18 |
| hAAT promoter region | 66 |
| Human PAH coding sequence | 25 |
| Polyadenylation sequence | 45 |
| 3' ITR element | 19 |
| Transfer genome (from promoter region to polyadenylation sequence) | 67 |
| Transfer genome (from 5' ITR to 3' ITR) | 68 |

Figure 9A:
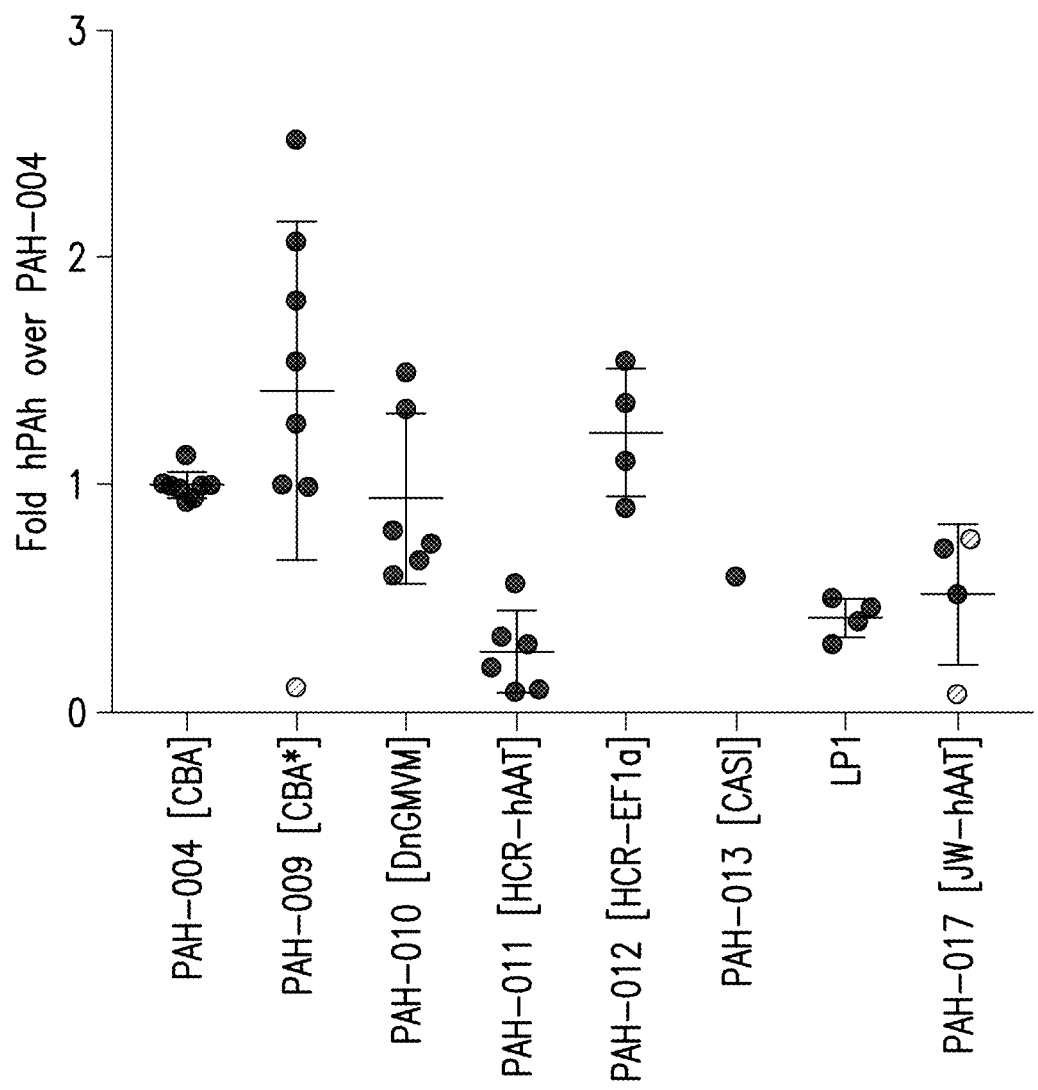
FIG. 9A-9B depict the quantification of Western blots of human PAH expression, from the indicated AAV vectors, in Huh7 cells (FIG. 9A) and HEK293 cells (FIG. 9B).
Figure 9B:
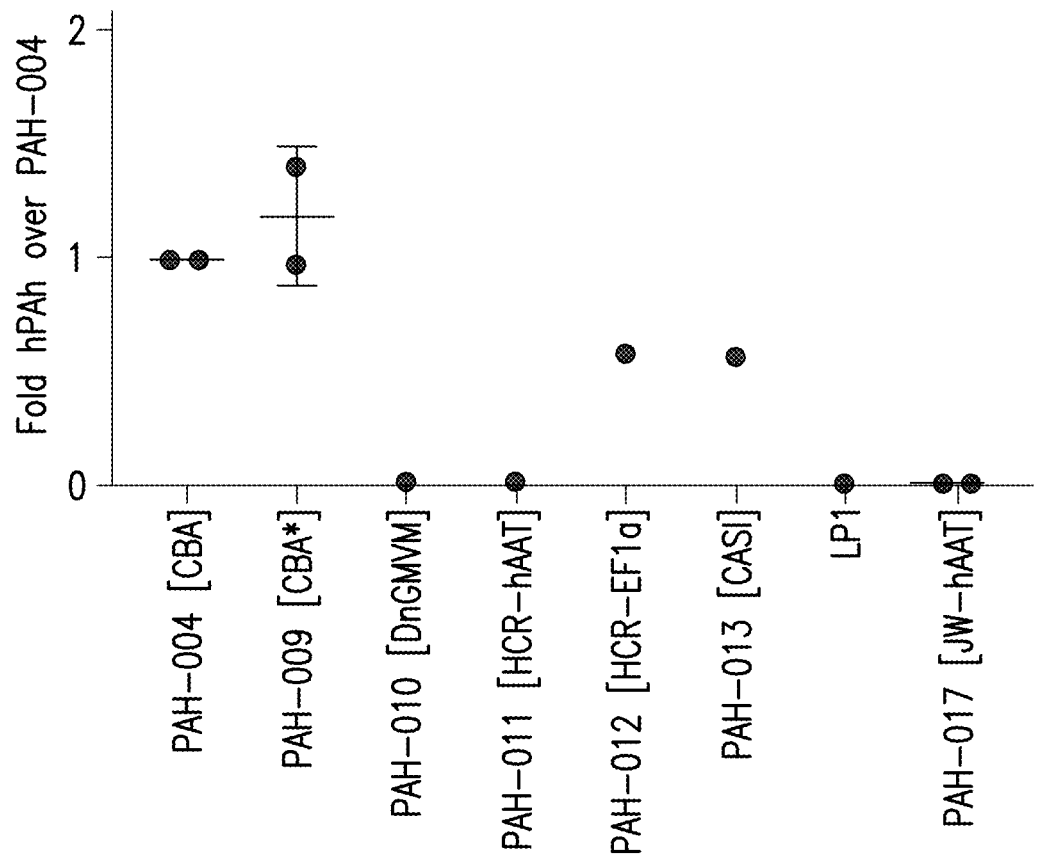

The vectors described in this example were tested for expression in two different cell lines. $5 \times 10^5$ HEK293 cells (kidney; non-liver) and $5 \times 10^5$ Huh7 cells (liver) were transfected with 1 ug each of the following vectors: pHMI-hPAH-TC-004 (PAH-004); pHMI-hPAH-TC-009 (PAH-009); pHMI-hPAH-TC-010 (PAH-010); pHMI-hPAH-TC-011 (PAH-011); pHMI-hPAH-TC-012 (PAH-012); pHMI-hPAH-TC-013 (PAH-013); pHMI-hPAH-TC-025 (LP1); pHMI-hPAH-TC-017 (PAH-017). Lysate of the cells was collected 48 hours after transfection. The expression of human PAH was detected by Western blotting with an anti-PAH antibody (Sigma HPA031642). The amount of GAPDH protein as detected by an anti-GAPDH antibody (Millipore MAB 374) was used as a loading control. PAH expression levels of all vectors were normalized to pHMI-hPAH-TC-004 expression level; data was collected from multiple independent transfections and plotted in FIG. 9. FIG. 9A shows the normalized PAH expression level of the indicated vectors in Huh7 cells. FIG. 9B shows the normalized PAH expression level of the indicated vectors in HEK293 cells.

Figure 10A:
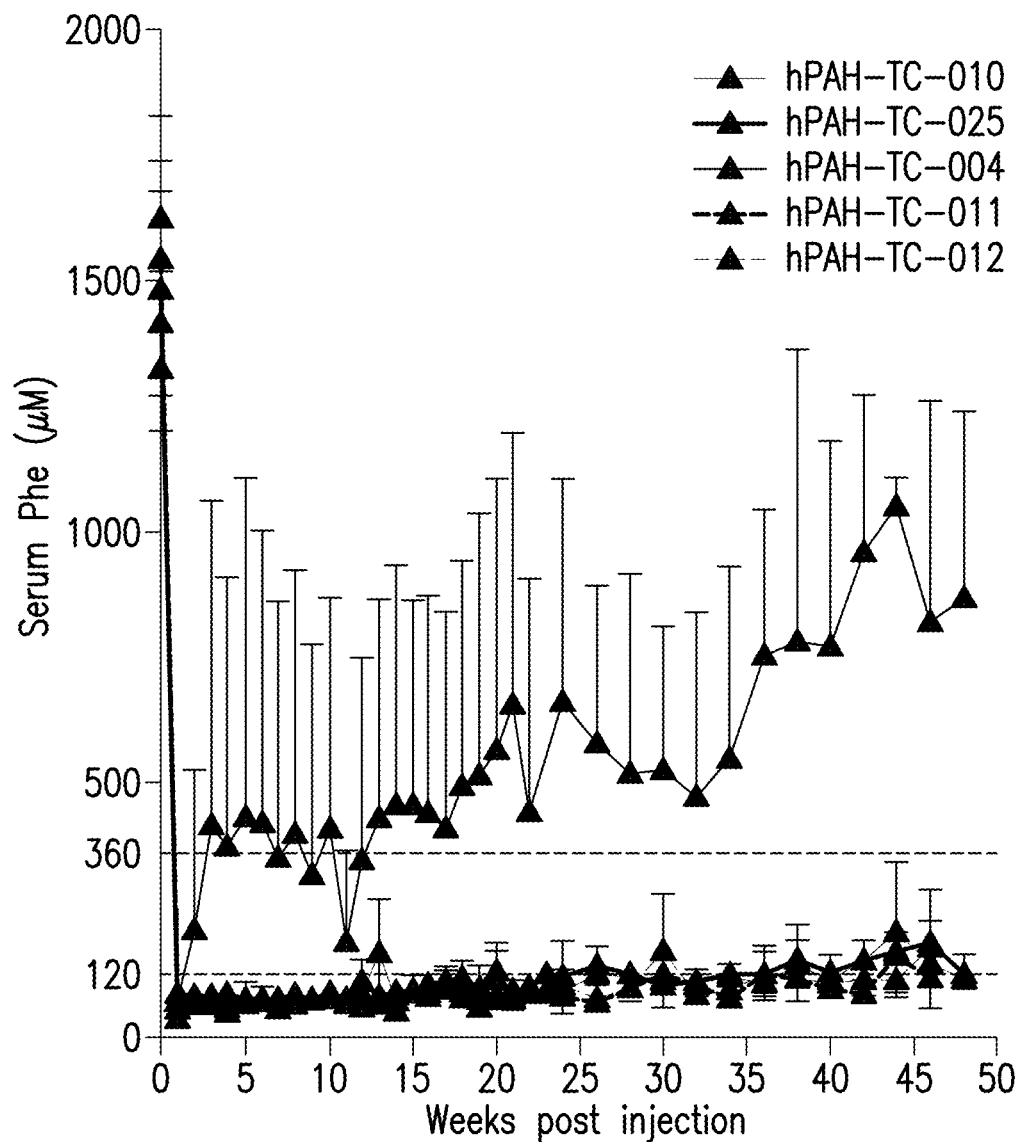
FIG. 10A-10C are graphs showing serum phenylalanine levels in mice that have been administered the indicated AAV vectors.
Figure 10B:
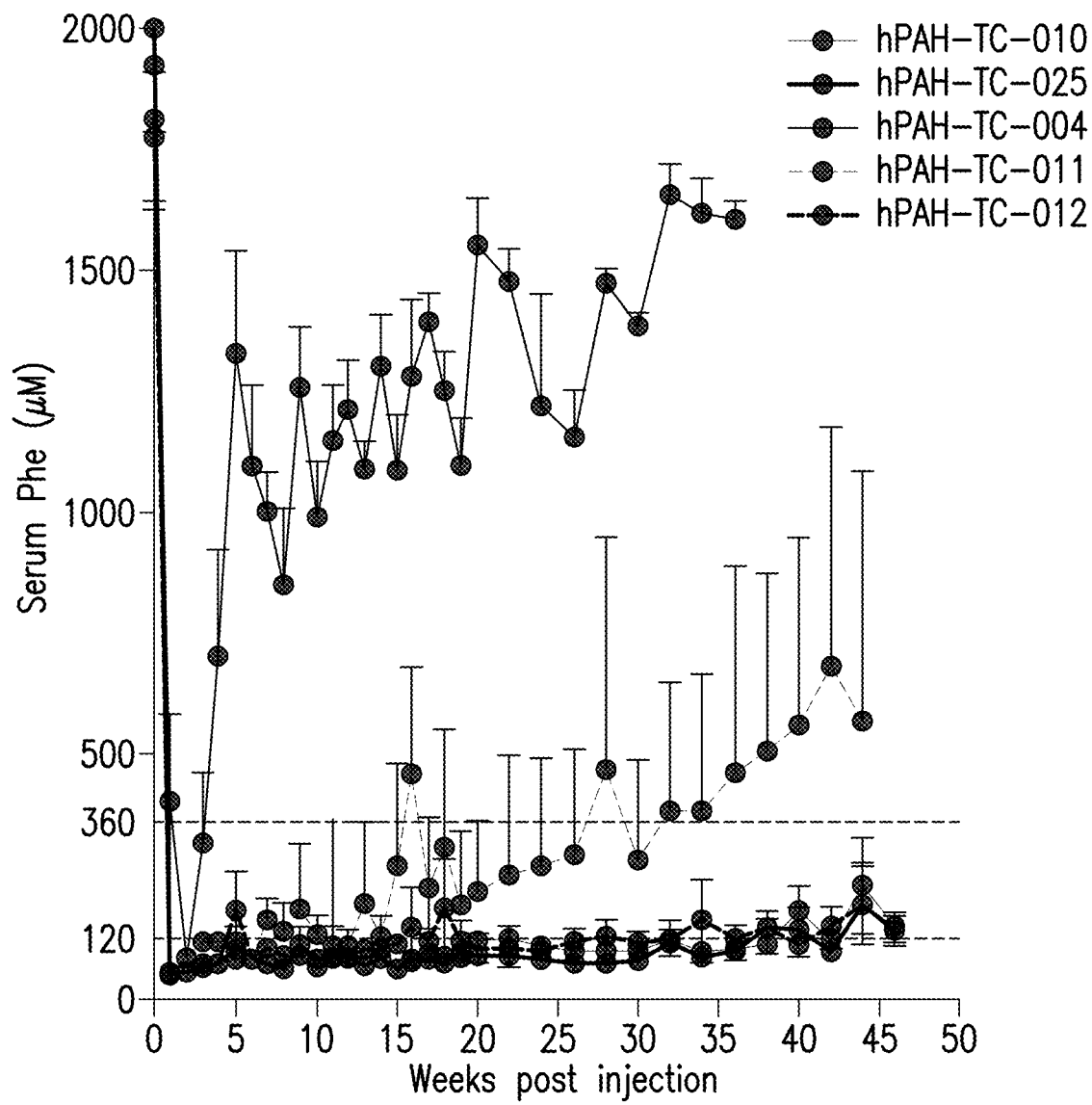
Figure 10C:
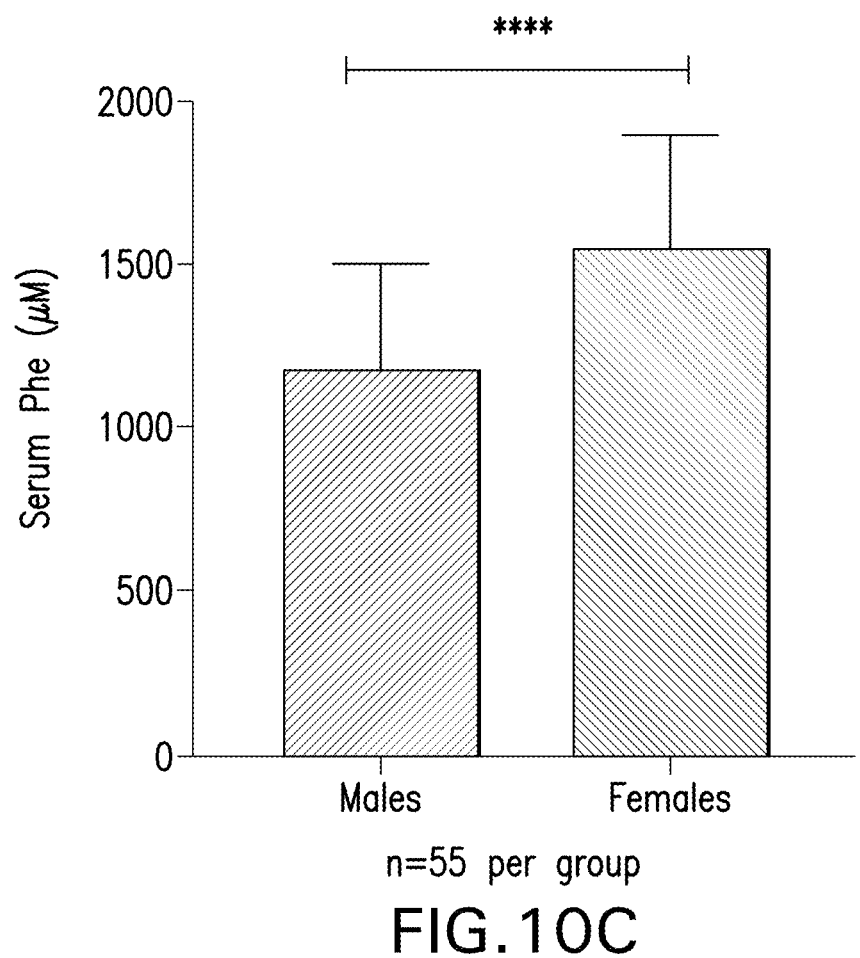
Figure 11A:
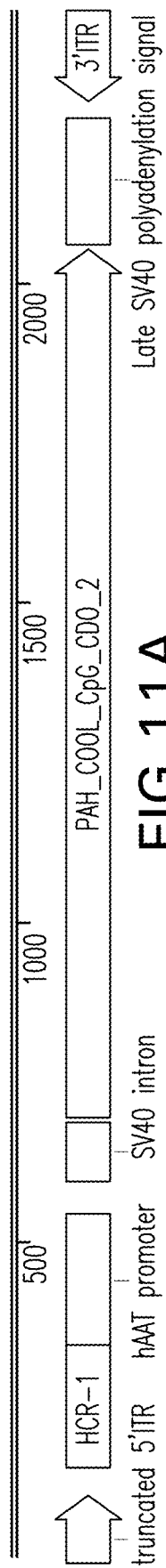
FIGS. 11A, 11B, 11C, 11D, 11E, and 11F are vector maps of pHMI-hPAH-TC-018, pHMI-hPAH-TC-019, pHMI-hPAH-TC-020, pHMI-hPAH-TC-021, pHMI-hPAH-TC-022, and pHMI-hPAH-TC-023 vectors, respectively.
Figure 11B:
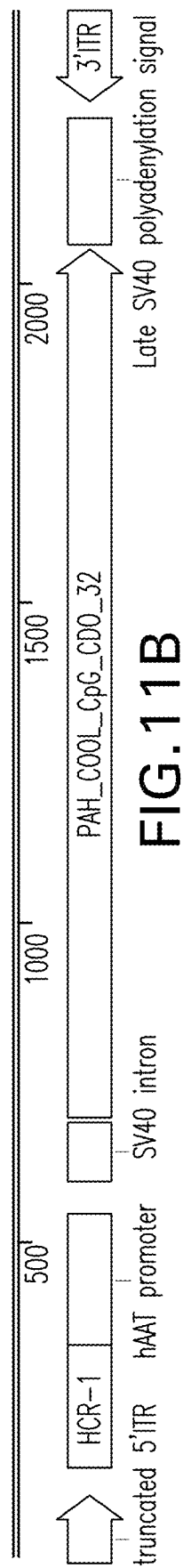
Figure 11C:
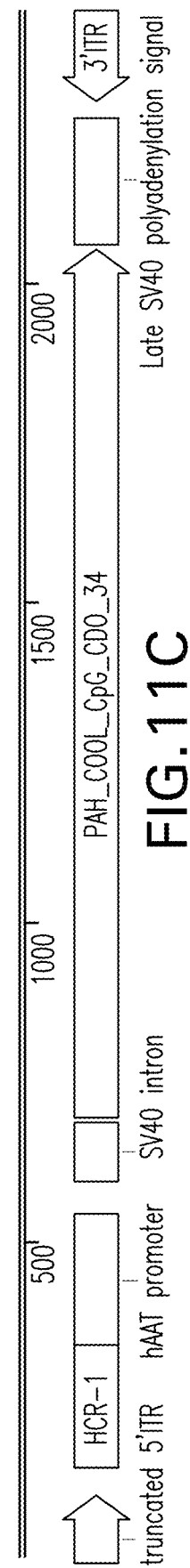
Figure 11D:
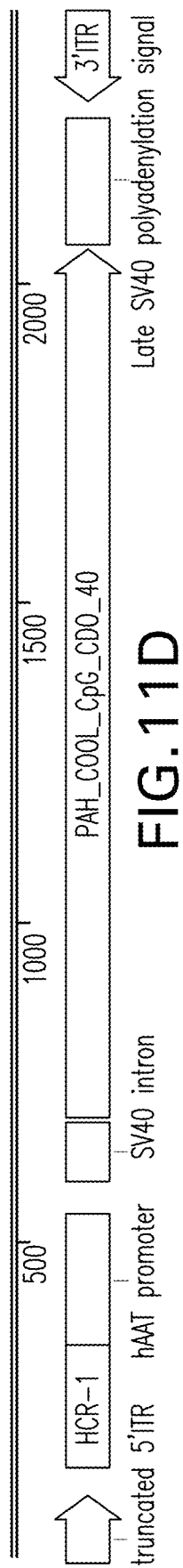
Figure 11E:
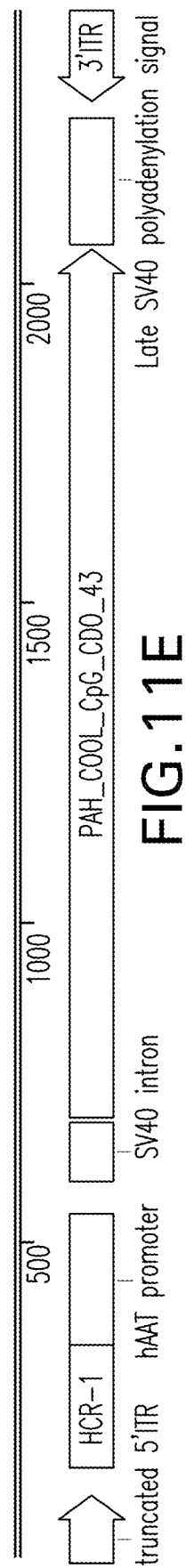
Figure 11F:
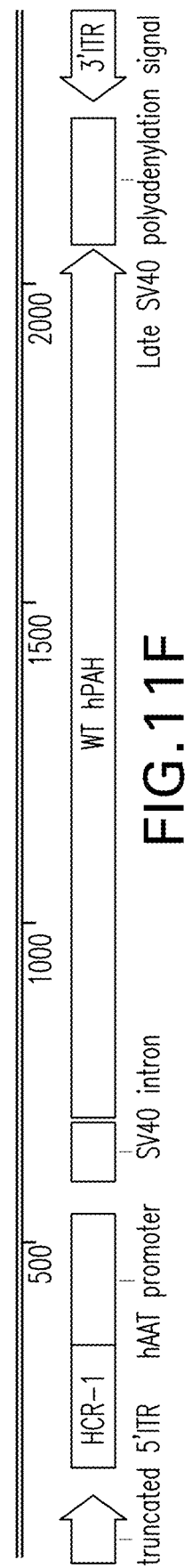

FIGS. 10A and 10B are graphs showing the serum phenylalanine levels over time of male and female homozygous $Pah^{-/-}$ $PAH^{emu2}$ mice respectively. Male and female mice were dosed at 2e13 vg/kg and 6e13 vg/kg respectively with pHMI-hPAH-TC-010 (hPAH-TC-010), pHMI-hPAH-TC-025 (hPAH-TC-025), pHMI-hPAH-TC-004 (hPAH-TC-004), pHMI-hPAH-TC-011 (hPAH-TC-011), or pHMI-hPAH-TC-012 (hPAH-TC-012) vectors packaged in AAVHSC15 capsid. Serum samples were collected weekly then biweekly after the administration. Serum phenylalanine concentrations were assessed by LC-MS/MS. FIG. 10C is a graph showing the average baseline serum phenylalanine level for the male and female homozygous $Pah^{-/-}$ $PAH^{emu2}$ mice in the study. The data represents a total of 55 mice per group.

As shown in FIG. 10, the administration of certain vectors led to significant reduction of Phe levels within one week of administration, and this reduction persisted for at least 45 weeks. FIG. 10 demonstrates that some of the PAH transfer vectors effectively reversed the phenotype caused by PAH gene deficiency in a mouse model. The mouse model, AAV packaging and formulation, and methods for examining gene transfer efficiency were identical to those described in Example 2 herein. The sizes of the AAV vectors were as follows: pHMI-hPAH-TC-010 (hPAH-TC-010): 2391 bp; pHMI-hPAH-TC-025 (hPAH-TC-025): 2351 bp; pHMI-hPAH-TC-004 (hPAH-TC-004): 3781 bp; pHMI-hPAH-TC-011 (hPAH-TC-011): 3158 bp; and pHMI-hPAH-TC-012 (hPAH-TC-012): 3799 bp.

Example 4: Additional Human PAH Transfer Vectors

This example examines the effect of PAH gene CpG content on PAH protein expression, using the PAH transfer vectors pHMI-hPAH-TC-018, pHMI-hPAH-TC-019, pHMI-hPAH-TC-020, pHMI-hPAH-TC-021, pHMI-hPAH-TC-022, and pHMI-hPAH-TC-023. Vector maps are shown in FIGS. 11A, 11B, 11C, 11D, 11E, and 11F, respectively. These PAH transfer vectors comprise the sequences and elements set forth in Table 9.

TABLE 9

Genetic elements in PAH transfer vectors

| Genetic Element | pHMI-hPAH-TC-XXX Vector SEQ ID NO | | | | | |
|---|---|---|---|---|---|---|
| | -018 | -019 | -020 | -021 | -022 | -023 |
| 5' ITR element | 26 | 26 | 26 | 26 | 26 | 26 |
| HCR1 | 29 | 29 | 29 | 29 | 29 | 29 |
| hAAT promoter | 30 | 30 | 30 | 30 | 30 | 30 |
| SV40 intron | 31 | 31 | 31 | 31 | 31 | 31 |
| PAH coding sequence | 69 | 70 | 71 | 72 | 73 | 24 |
| Late SV40 polyadenylation sequence | 45 | 45 | 45 | 45 | 45 | 45 |
| 3' ITR element | 27 | 27 | 27 | 27 | 27 | 27 |
| Transfer genome (from HCR1 to polyadenylation sequence) | 74 | 76 | 78 | 80 | 82 | 84 |
| Transfer genome (from 5' ITR to 3' ITR) | 75 | 77 | 79 | 81 | 83 | 85 |

Figure 12:
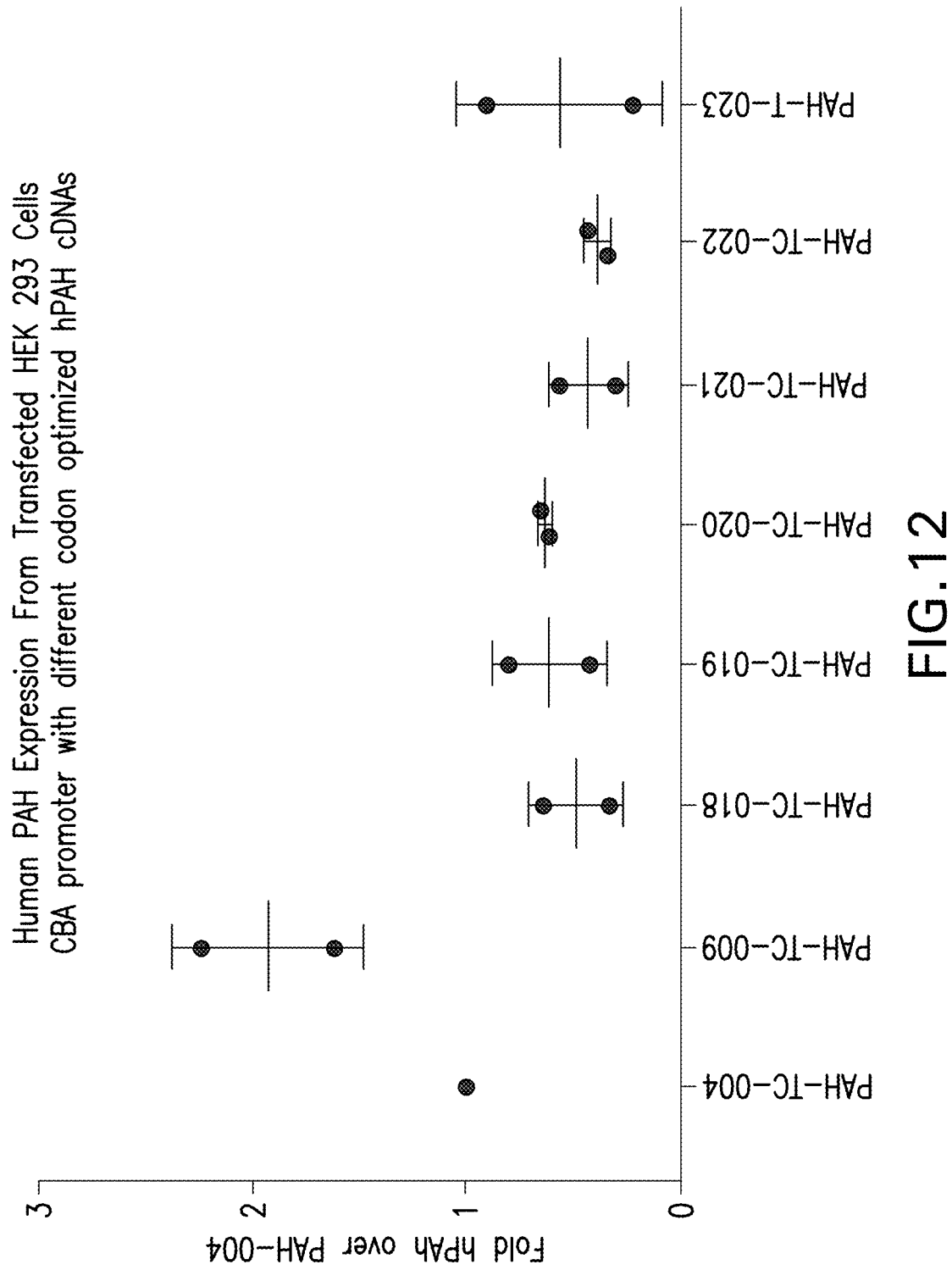
FIG. 12 depicts the quantification of Western blots of human PAH expression from HEK293 cells transfected with the indicated AAV vectors under the control of a CBA promoter.

The vectors described in this example were tested for expression in HEK293 cells but under the control of a CBA promoter. 5×10$^5$ HEK293 cells were transfected with 1 ug each of the following vectors: pHMI-hPAH-TC-004 (PAH-TC-004); pHMI-hPAH-TC-009 (PAH-TC-009); pHMI-hPAH-TC-018 (PAH-TC-018); pHMI-hPAH-TC-019 (PAH-TC-019); pHMI-hPAH-TC-020 (PAH-TC-020); pHMI-hPAH-TC-021 (PAH-TC-021); pHMI-hPAH-TC-022 (PAH-TC-022); pHMI-hPAH-TC-023 (PAH-TC-023). Lysate of the cells was collected 48 hours after transfection. The expression of human PAH was detected by Western blotting with an anti-PAH antibody (Sigma HPA031642). The amount of GAPDH protein as detected by an anti-GAPDH antibody (Millipore MAB 374) was used as a loading control. PAH expression levels of all vectors were normalized to pHMI-hPAH-TC-004 expression level; data was plotted in FIG. 12.

Figure 13:
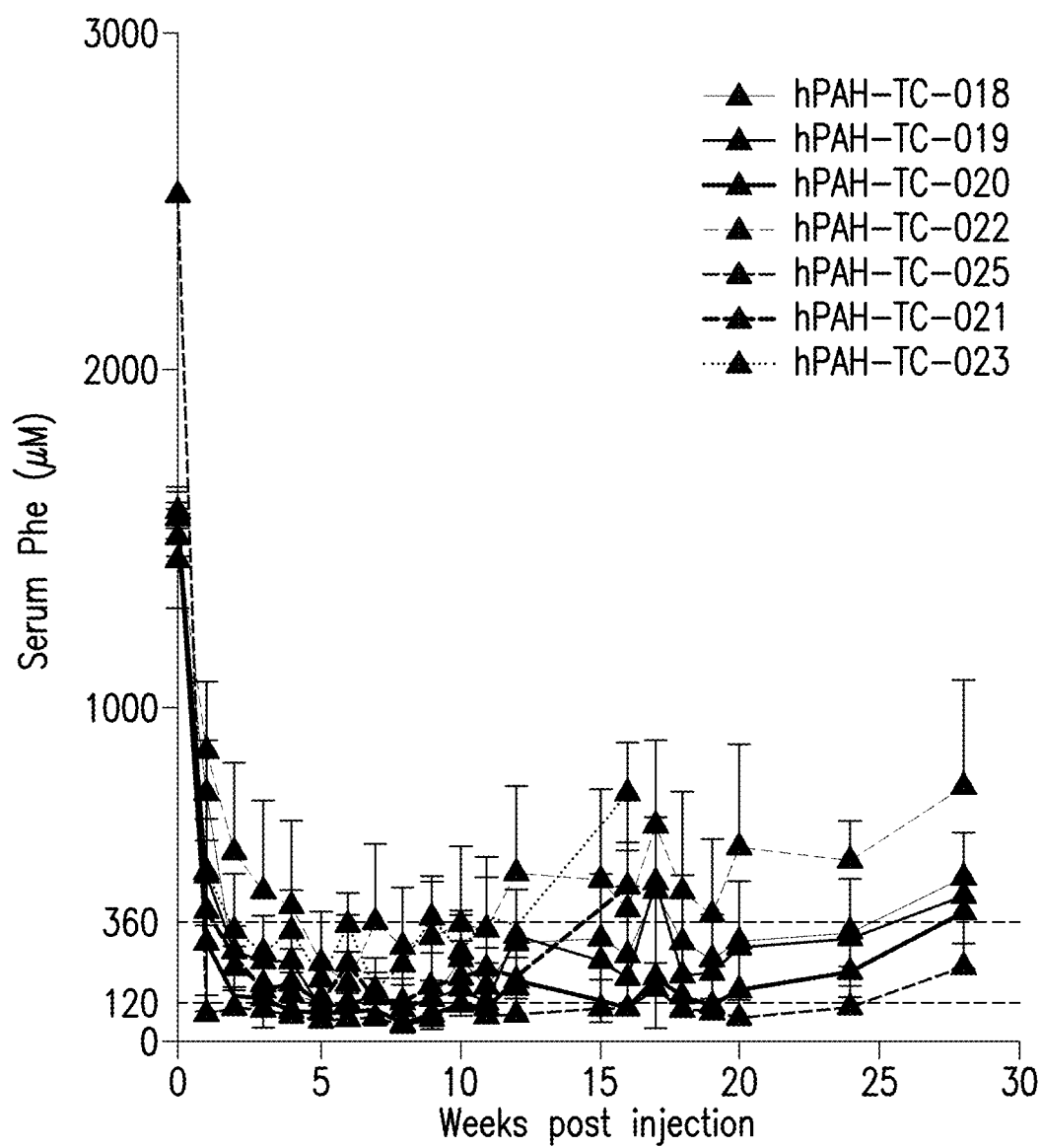
FIG. 13 is a graph showing serum phenylalanine levels over time of male Pah$^{-/-}$ PAH$^{emu2}$ mice administered the indicated AAV vectors.

FIG. 13 is a graph showing the serum phenylalanine levels over time of male homozygous Pah$^{-/-}$ PAH$^{enu2}$ mice. Male mice have been dosed at 2e13 vg/kg with pHMI-hPAH-TC-018 (hPAH-TC-018); pHMI-hPAH-TC-019 (hPAH-TC-019); pHMI-hPAH-TC-020 (hPAH-TC-020); pHMI-hPAH-TC-021 (hPAH-TC-021); pHMI-hPAH-TC-022 (hPAH-TC-022); pHMI-hPAH-TC-023 (hPAH-TC-023); and pHMI-hPAH-TC-025 (hPAH-TC-025) vectors packaged in AAVHSC15 capsid. Serum samples were collected weekly after the administration. Serum phenylalanine concentration was assessed by LC-MS/MS.

As shown in FIG. 13, the administration of certain vectors led to significant reduction of Phe levels within one week of administration, and this reduction persisted for at least 25 weeks. The mouse model, AAV packaging and formulation, and methods for examining gene transfer efficiency were identical to those previously described in Example 2 herein. The CpG content of the vectors were as follows: pHMI-hPAH-TC-018 (hPAH-TC-018): 2; pHMI-hPAH-TC-019 (hPAH-TC-019): 7; pHMI-hPAH-TC-020 (hPAH-TC-020): 22; pHMI-hPAH-TC-021 (hPAH-TC-021): 10; pHMI-hPAH-TC-022 (hPAH-TC-022): 7; pHMI-hPAH-TC-023 (hPAH-TC-023): 23; and pHMI-hPAH-TC-025 (hPAH-TC-025): 60.

Example 5: Alternative ITR Human PAH Transfer Vectors

This example provides human PAH transfer vectors pHMI-01004 and pHMI-01008 for expression of human PAH in a human or mouse cell. Vector maps are shown in FIGS. 14A and 14B, respectively. These PAH transfer vectors comprise the sequences and elements set forth in Table 10.

TABLE 10

Genetic elements in PAH transfer vectors pHMI-01004 and pHMI-01008

| Genetic Element | pHMI-01004 SEQ ID NO | pHMI-01008 SEQ ID NO |
|---|---|---|
| 5' ITR element | 26 | 26 |
| HCR1 | 29 | 29 |
| hAAT promoter region | 30 | 30 |
| SV40 intron | 31 | 31 |
| Human PAH coding sequence | 25 | 25 |
| Polyadenylation sequence | 43 | 43 |
| 3' ITR element | 27 | 57 |
| Transfer genome (from HCR1 to polyadenylation sequence) | 86 | 89 |
| Transfer genome (from 5' ITR to 3' ITR) | 87 | 90 |
| Full sequence of transfer vector | 88 | 91 |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A packaging system for preparation of a replication-defective AAV comprising:
   (a) a first nucleotide sequence comprising a first transcriptional regulatory element operably linked to a nucleotide sequence encoding one or more AAV Rep proteins;
   (b) a second nucleotide sequence comprising a second transcriptional regulatory element operably linked to a nucleotide sequence encoding an AAV capsid protein; and
   (c) a third nucleotide sequence comprising a transfer genome comprising, from 5' to 3':
      (i) an AAV2 5' inverted terminal repeat (ITR) nucleotide sequence;
      (ii) a transcriptional regulatory element comprising, from 5' to 3', a human hepatic control region 1 (HCR1) and a human a1-antitrypsin (hAAT) promoter;
      (iii) a silently altered PAH coding sequence having at least 80% sequence identity to the nucleotide sequence of SEQ ID NO: 71, wherein the silently altered PAH coding sequence encodes the amino acid sequence set forth in SEQ ID NO: 23; and
      (iv) an AAV2 3' ITR nucleotide sequence.

2. A method for producing a replication-defective AAV, the method comprising introducing the packaging system of claim 1 into a cell under conditions operative for producing the AAV.

3. The packaging system of claim 1, wherein the packaging system comprises a first vector comprising the first nucleotide sequence and the second nucleotide sequence, and a second vector comprising the third nucleotide sequence.

4. The packaging system of claim 3, further comprising a third vector, wherein the third vector is a helper virus vector.

5. The packaging system of claim 4, wherein the helper virus vector is an independent third vector.

6. The packaging system of claim 4, wherein the third vector comprises genes encoding helper virus proteins.

7. The packaging system of claim 4, wherein the helper virus is selected from the group consisting of adenovirus, herpes virus, vaccinia virus, and cytomegalovirus (CMV).

8. The packaging system of claim 7, wherein the helper virus is adenovirus.

9. The packaging system of claim 8, wherein the adenovirus genome comprises one or more adenovirus RNA genes selected from the group consisting of E1, E2, E4 and VA.

10. The packaging system of claim 7, wherein the helper virus is herpes simplex virus (HSV).

11. The packaging system of claim 10, wherein the HSV genome comprises one or more HSV genes selected from the group consisting of UL5/8/52, ICP0, 1CP4, ICP22 and UL30/UL42.

12. The packaging system of claim 4, wherein the first vector and the third vector are contained within a first transfecting plasmid.

13. The packaging system of claim 4, wherein the nucleotide sequences of the second vector and the third vector are contained within a second transfecting plasmid.

14. The packaging system of claim 4, wherein the nucleotide sequences of the first vector and the third vector are cloned into a recombinant helper virus.

15. The packaging system of claim 4, wherein the nucleotide sequences of the second vector and the third vector are cloned into a recombinant helper virus.

16. The packaging system of claim 1, wherein the Rep nucleotide sequence encodes an AAV2 Rep protein.

17. The packaging system of claim 16, wherein the AAV2 Rep protein is Rep 78/68 or Rep 68/52.

18. The packaging system of claim 16, wherein the AAV2 Rep protein comprises an amino acid sequence having at least 70% sequence identity to the amino acid sequence of SEQ ID NO: 22.

* * * * *

SEQUENCE LISTING

<160> NUMBER OF SEQ ID NOS: 92

<210> SEQ ID NO 1
<211> LENGTH: 736
<212> TYPE: PRT

<213> ORGANISM: Artificial Sequence
<220> FEATURE:
<223> OTHER INFORMATION: adeno-associated AAV9

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
```

```
              385                 390                 395                 400
        Pro Ser Gln Met Leu Arg Thr Gly Asn Asn Phe Gln Phe Ser Tyr Glu
                        405                 410                 415

Phe Glu Asn Val Pro Phe His Ser Ser Tyr Ala His Ser Gln Ser Leu
                        420                 425                 430

Asp Arg Leu Met Asn Pro Leu Ile Asp Gln Tyr Leu Tyr Tyr Leu Ser
                        435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
        465                 470                 475                 480

Gly Pro Ser Tyr Arg Gln Gln Arg Val Ser Thr Thr Val Thr Gln Asn
                        485                 490                 495

Asn Asn Ser Glu Phe Ala Trp Pro Gly Ala Ser Ser Trp Ala Leu Asn
                        500                 505                 510

Gly Arg Asn Ser Leu Met Asn Pro Gly Pro Ala Met Ala Ser His Lys
                        515                 520                 525

Glu Gly Glu Asp Arg Phe Phe Pro Leu Ser Gly Ser Leu Ile Phe Gly
                        530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                        565                 570                 575

Tyr Gly Gln Val Ala Thr Asn His Gln Ser Ala Gln Ala Gln Ala Gln
                        580                 585                 590

Thr Gly Trp Val Gln Asn Gln Gly Ile Leu Pro Gly Met Val Trp Gln
                        595                 600                 605

Asp Arg Asp Val Tyr Leu Gln Gly Pro Ile Trp Ala Lys Ile Pro His
                        610                 615                 620

Thr Asp Gly Asn Phe His Pro Ser Pro Leu Met Gly Gly Phe Gly Met
        625                 630                 635                 640

Lys His Pro Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                        660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
        705                 710                 715                 720

Tyr Ser Glu Pro Arg Pro Ile Gly Thr Arg Tyr Leu Thr Arg Asn Leu
                        725                 730                 735

<210> SEQ ID NO 2
<211> LENGTH: 736
<212> TYPE: PRT
<213> ORGANISM: Artificial Sequence
<220> FEATURE:
<223> OTHER INFORMATION: novel AAV isolate

<400> SEQUENCE: 2

Met Thr Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
```

```
                20              25              30
Lys Ala Asn Gln Gln His Gln Asp Asn Ala Arg Gly Leu Val Leu Pro
            35              40              45
Gly Tyr Lys Tyr Leu Gly Pro Gly Asn Gly Leu Asp Lys Gly Glu Pro
        50              55              60
Val Asn Ala Ala Asp Ala Ala Leu Glu His Asp Lys Ala Tyr Asp
65              70              75              80
Gln Gln Leu Lys Ala Gly Asp Asn Pro Tyr Leu Lys Tyr Asn His Ala
            85              90              95
Asp Ala Glu Phe Gln Glu Arg Leu Lys Glu Asp Thr Ser Phe Gly Gly
            100             105             110
Asn Leu Gly Arg Ala Val Phe Gln Ala Lys Lys Arg Leu Leu Glu Pro
            115             120             125
Leu Gly Leu Val Glu Glu Ala Ala Lys Thr Ala Pro Gly Lys Lys Arg
            130             135             140
Pro Val Glu Gln Ser Pro Gln Glu Pro Asp Ser Ser Ala Gly Ile Gly
145             150             155             160
Lys Ser Gly Ala Gln Pro Ala Lys Lys Arg Leu Asn Phe Gly Gln Thr
            165             170             175
Gly Asp Thr Glu Ser Val Pro Asp Pro Gln Pro Ile Gly Glu Pro Pro
            180             185             190
Ala Ala Pro Ser Gly Val Gly Ser Leu Thr Met Ala Ser Gly Gly Gly
            195             200             205
Ala Pro Val Ala Asp Asn Asn Glu Gly Ala Asp Gly Val Gly Ser Ser
            210             215             220
Ser Gly Asn Trp His Cys Asp Ser Gln Trp Leu Gly Asp Arg Val Ile
225             230             235             240
Thr Thr Ser Thr Arg Thr Trp Ala Leu Pro Thr Tyr Asn Asn His Leu
            245             250             255
Tyr Lys Gln Ile Ser Asn Ser Thr Ser Gly Gly Ser Ser Asn Asp Asn
            260             265             270
Ala Tyr Phe Gly Tyr Ser Thr Pro Trp Gly Tyr Phe Asp Phe Asn Arg
            275             280             285
Phe His Cys His Phe Ser Pro Arg Asp Trp Gln Arg Leu Ile Asn Asn
            290             295             300
Asn Trp Gly Phe Arg Pro Lys Gln Leu Asn Phe Lys Leu Phe Asn Ile
305             310             315             320
Gln Val Lys Glu Val Thr Asp Asn Asn Gly Val Lys Thr Ile Ala Asn
            325             330             335
Asn Leu Thr Ser Thr Val Gln Val Phe Thr Asp Ser Asp Tyr Gln Leu
            340             345             350
Pro Tyr Val Leu Gly Ser Ala His Glu Gly Cys Leu Pro Pro Phe Pro
            355             360             365
Ala Asp Val Phe Met Ile Pro Gln Tyr Gly Tyr Leu Thr Leu Asn Asp
            370             375             380
Gly Ser Gln Ala Val Gly Arg Ser Ser Phe Tyr Cys Leu Glu Tyr Phe
385             390             395             400
Pro Ser Gln Met Leu Arg Thr Gly Asn Asn Phe Gln Phe Ser Tyr Glu
            405             410             415
Phe Glu Asn Val Pro Phe His Ser Ser Tyr Ala His Ser Gln Ser Leu
            420             425             430
Asp Arg Leu Met Asn Pro Leu Ile Asp Gln Tyr Leu Tyr Tyr Leu Ser
            435             440             445
```

-continued

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Artificial Sequence
<220> FEATURE:
<223> OTHER INFORMATION: novel AAV isolate

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

```
Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

```
Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Gly Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Gly Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: novel AAV isolate

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Ile Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
```

```
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
                610                 615                 620
Thr Tyr Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
                690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 5
<211> LENGTH: 736
<212> TYPE: PRT
<213> ORGANISM: Artificial Sequence
<220> FEATURE:
<223> OTHER INFORMATION: novel AAV isolate

<400> SEQUENCE: 5

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
                20                  25                  30
Lys Ala Asn Gln Gln His Gln Asp Asn Ala Arg Gly Leu Val Leu Pro
                35                  40                  45
Gly Tyr Lys Tyr Leu Gly Pro Gly Asn Gly Leu Asp Lys Gly Glu Pro
                50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
                115                 120                 125
Leu Gly Leu Val Glu Glu Ala Ala Lys Thr Ala Pro Gly Lys Lys Arg
                130                 135                 140
Pro Val Glu Gln Ser Pro Gln Glu Pro Asp Ser Ser Ala Gly Ile Asp
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
```

-continued

```
                180                 185                 190
Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605
```

```
Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 6
<211> LENGTH: 736
<212> TYPE: PRT
<213> ORGANISM: Artificial Sequence
<220> FEATURE:
<223> OTHER INFORMATION: novel AAV isolate

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Leu Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240
```

```
Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
        260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Ser Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655
```

```
Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 736
<212> TYPE: PRT
<213> ORGANISM: Artificial Sequence
<220> FEATURE:
<223> OTHER INFORMATION: novel AAV isolate

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
```

```
                            705                 710                 715                 720
Tyr Ser Glu Pro Arg Pro Ile Gly Thr Arg Tyr Leu Thr Arg Asn Leu
                725                 730                 735

<210> SEQ ID NO 8
<211> LENGTH: 736
<212> TYPE: PRT
<213> ORGANISM: Artificial Sequence
<220> FEATURE:
<223> OTHER INFORMATION: novel AAV isolate

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Val Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
```

```
                    340                 345                 350
Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 9
<211> LENGTH: 736
<212> TYPE: PRT
<213> ORGANISM: Artificial Sequence
```

<220> FEATURE:
<223> OTHER INFORMATION: novel AAV isolate

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Arg Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400
```

```
Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 10
<211> LENGTH: 736
<212> TYPE: PRT
<213> ORGANISM: Artificial Sequence
<220> FEATURE:
<223> OTHER INFORMATION: novel AAV isolate

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30
```

```
Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Cys Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445
```

```
Lys Thr Ile Asn Gly Ser Gly Gln Asn Gln Gln Thr Leu Lys Phe Ser
            450             455                 460

Val Ala Gly Pro Ser Asn Met Ala Val Gln Gly Arg Asn Tyr Ile Pro
465             470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530             535                 540

Lys Gln Gly Thr Gly Arg Asp Asn Val Asp Ala Asp Lys Val Met Ile
545             550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610             615                 620

Thr Asp Gly Asn Phe His Pro Ser Pro Leu Met Gly Gly Phe Gly Met
625             630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690             695                 700

Tyr Tyr Lys Ser Asn Asn Val Glu Phe Ala Val Asn Thr Glu Gly Val
705             710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Arg Ala Tyr Asp
65                  70                  75                  80
```

```
Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
```

```
                 500                 505                 510
Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Lys Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 12
<211> LENGTH: 736
<212> TYPE: PRT
<213> ORGANISM: Artificial Sequence
<220> FEATURE:
<223> OTHER INFORMATION: novel AAV isolate

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
```

-continued

```
            130                 135                 140
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro His Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Asn
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560
```

```
Thr Asn Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Met Glu Ile Glu Trp Glu Leu Gln
                675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 13
<211> LENGTH: 736
<212> TYPE: PRT
<213> ORGANISM: Artificial Sequence
<220> FEATURE:
<223> OTHER INFORMATION: novel AAV isolate

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190
```

```
Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605
```

-continued

```
Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 14
<211> LENGTH: 26
<212> TYPE: DNA
<213> ORGANISM: Artificial Sequence
<220> FEATURE:
<223> OTHER INFORMATION: splice acceptor

<400> SEQUENCE: 14
ctgacctctt ctcttcctcc cacagg                                         26

<210> SEQ ID NO 15
<211> LENGTH: 736
<212> TYPE: PRT
<213> ORGANISM: Artificial Sequence
<220> FEATURE:
<223> OTHER INFORMATION: novel AAV isolate

<400> SEQUENCE: 15

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175
```

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
```

```
            595                 600                 605
Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Phe Gly Met
625                 630                 635                 640

Lys His Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Arg Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735

<210> SEQ ID NO 16
<211> LENGTH: 736
<212> TYPE: PRT
<213> ORGANISM: Artificial Sequence
<220> FEATURE:
<223> OTHER INFORMATION: novel AAV isolate

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
```

-continued

```
            225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Ser Ser Asn Asp Asn
            260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Ala Asp Ser Asp Tyr Gln Leu
            340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
            450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Arg Ala Ser Ser Trp Ala Leu Asn
            500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
            610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
```

```
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 17
<211> LENGTH: 736
<212> TYPE: PRT
<213> ORGANISM: Artificial Sequence
<220> FEATURE:
<223> OTHER INFORMATION: novel AAV isolate

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Ile Ala Trp Pro Arg Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
690                 695                 700
```

```
Tyr Cys Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 18
<211> LENGTH: 145
<212> TYPE: DNA
<213> ORGANISM: Artificial Sequence
<220> FEATURE:
<223> OTHER INFORMATION: AAV2 5' ITR

<400> SEQUENCE: 18
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                         145

<210> SEQ ID NO 19
<211> LENGTH: 145
<212> TYPE: DNA
<213> ORGANISM: Artificial Sequence
<220> FEATURE:
<223> OTHER INFORMATION: AAV2 3' ITR

<400> SEQUENCE: 19
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag agagggagtg gccaa                                         145

<210> SEQ ID NO 20
<211> LENGTH: 167
<212> TYPE: DNA
<213> ORGANISM: Artificial Sequence
<220> FEATURE:
<223> OTHER INFORMATION: AAV5 5' ITR

<400> SEQUENCE: 20
ctctcccccc tgtcgcgttc gctcgctcgc tggctcgttt ggggggggtgg cagctcaaag    60 agctgccaga cgacggccct ctggccgtcg ccccccccaaa cgagccagcg agcgagcgaa   120
cgcgacaggg gggagagtgc cacactctca agcaagggg ttttgta                   167

<210> SEQ ID NO 21
<211> LENGTH: 167
<212> TYPE: DNA
<213> ORGANISM: Artificial Sequence
<220> FEATURE:
<223> OTHER INFORMATION: AAV5 3' ITR

<400> SEQUENCE: 21
tacaaaacct ccttgcttga gagtgtggca ctctcccccc tgtcgcgttc gctcgctcgc    60
tggctcgttt ggggggggtgg cagctcaaag agctgccaga cgacggccct ctggccgtcg   120 ccccccccaaa cgagccagcg agcgagcgaa cgcgacaggg gggagag                 167

<210> SEQ ID NO 22
<211> LENGTH: 621
<212> TYPE: PRT
<213> ORGANISM: Artificial Sequence
<220> FEATURE:
<223> OTHER INFORMATION: AAV2 Rep

<400> SEQUENCE: 22
```

-continued

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
50                      55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
        130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
                260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
        290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415
```

-continued

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Lys Asp His Val Val Glu Val
465                 470                 475                 480

Glu His Glu Phe Tyr Val Lys Lys Gly Ala Lys Lys Arg Pro Ala
                485                 490                 495

Pro Ser Asp Ala Asp Ile Ser Glu Pro Lys Arg Val Arg Glu Ser Val
        500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
        530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
            610                 615                 620

<210> SEQ ID NO 23
<211> LENGTH: 452
<212> TYPE: PRT
<213> ORGANISM: Homo sapiens

<400> SEQUENCE: 23

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

-continued

```
Val Glu Tyr Met Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450

<210> SEQ ID NO 24
<211> LENGTH: 1359
<212> TYPE: DNA
<213> ORGANISM: Homo sapiens

<400> SEQUENCE: 24
atgtccactg cggtcctgga aacccaggc ttgggcagga aactctctga ctttggacag    60
gaaacaagct atattgaaga caactgcaat caaaatggtg ccatatcact gatcttctca   120
ctcaaagaag aagttggtgc attggccaaa gtattgcgct catttgagga gaatgatgta   180
aacctgaccc acattgaatc tagaccttct cgtttaaaga agatgagta tgaattttc    240 acccatttgg ataaacgtag cctgcctgct ctgacaaaca tcatcaagat cttgaggcat   300
gacattggtg ccactgtcca tgagctttca cgagataaga agaaagacac agtgccctgg   360
ttcccaagaa ccattcaaga gctggacaga tttgccaatc agattctcag ctatggagcg   420
gaactggatg ctgaccaccc tggttttaaa gatcctgtgt accgtgcaag acggaagcag   480
```

```
tttgctgaca ttgcctacaa ctaccgccat gggcagccca tccctcgagt ggaatacatg        540
gaggaagaaa agaaaacatg gggcacagtg ttcaagactc tgaagtcctt gtataaaacc        600
catgcttgct atgagtacaa tcacattttt ccacttcttg aaaagtactg tggcttccat        660
gaagataaca ttccccagct ggaagacgtt tctcaattcc tgcagacttg cactggtttc        720
cgcctccgac ctgtggctgg cctgctttcc tctcgggatt tcttgggtgg cctggccttc        780
cgagtcttcc actgcacaca gtacatcaga catggatcca agcccatgta taccccgaa         840 cctgacatct gccatgagct gttgggacat gtgcccttgt tttcagatcg cagctttgcc        900
cagttttccc aggaaattgg ccttgcctct ctgggtgcac ctgatgaata cattgaaaag        960
ctcgccacaa tttactggtt tactgtggag tttgggctct gcaaacaagg agactccata       1020
aaggcatatg gtgctgggct cctgtcatcc tttggtgaat acagtactg cttatcagag        1080 aagccaaagc ttctcccct ggagctggag aagacagcca tccaaaatta cactgtcacg        1140
gagttccagc ccctgtatta cgtggcagag agtttaatg atgccaagga gaaagtaagg        1200
aactttgctg ccacaatacc tcggcccttc tcagttcgct acgacccata cacccaaagg       1260
attgaggtct ggacaataac ccagcagctt aagattttgg ctgattccat taacagtgaa       1320
attggaatcc tttgcagtgc cctccagaaa ataaagtaa                              1359
```

<210> SEQ ID NO 25
<211> LENGTH: 1359
<212> TYPE: DNA
<213> ORGANISM: Artificial Sequence
<220> FEATURE:
<223> OTHER INFORMATION: Silently altered PAH coding sequence

<400> SEQUENCE: 25

```
atgtccaccg ctgtgctgga gaaccctggg ctggggagga aactgtcaga cttcgggcag         60
gagacttcat acattgagga taactgtaac cagaatggcg ccatctctct gatcttcagc        120
ctgaaggagg aagtgggcgc cctggcaaag gtgctgcgcc tgtttgagga gaacgacgtg        180
aatctgaccc acatcgagtc ccggccttct agactgaaga aggacgagta cgagttcttt        240
acccacctgg ataagcggtc cctgccagcc ctgacaaaca tcatcaagat cctgaggcac        300
gacatcggag caaccgtgca cgagctgtct cgggacaaga gaaggatac cgtgccctgg        360 ttccctcgga caatccagga gctggataga tttgccaacc agatcctgtc ttacggagca       420
gagctggacg cagatcaccc tggcttcaag gacccagtgt atcgggcccg agaaaagcag       480
tttgccgata tcgcctacaa ttataggcac ggacagccaa tccctcgcgt ggagtatatg       540
gaggaggaga agaagacctg gggcacagtg ttcaagaccc tgaagagcct gtacaagaca       600
cacgcctgct acgagtataa ccacatcttc cccctgctgg agaagtattg tggcttcac        660 gaggacaata tccctcagct ggaggacgtg agccagttcc tgcagacctg cacaggctt        720 aggctgagc cagtggcagg actgctgagc tcccgggact tcctgggagg actggccttc       780 agagtgttc actgcaccca gtacatcagg cacggctca agccaatgta taccaccagag      840 cccgacatct gtcacgagct gctgggccac gtgccctgt ttagcgatag atccttcgcc       900
cagttttccc aggagatcgg actggcatct ctggagcac ctgacgagta catcgagaag       960
ctggccacca tctattggtt cacagtggag tttggcctgt gcaagcagg cgatagcatc       1020 aaggcctacg gagcaggact gctgtctagc ttcggcgagc tgcagtattg tctgtccgag       1080
aagccaaagc tgctgccct ggagctggag aagaccgcca tccagaacta caccgtgaca       1140
gagttccagc ccctgtacta tgtggccgag tcttttaacg atgccaagga aaggtgaga      1200
```

```
aatttcgccg ccacaatccc taggcccttc agcgtgcggt acgacccttt a tacccagagg    1260 atcgaggtgc tggataatac acagcagctg aagatcctgg ctgactcaat caatagcgaa    1320
atcggaatcc tgtgctccgc cctgcagaaa atcaaatga                            1359

<210> SEQ ID NO 26
<211> LENGTH: 106
<212> TYPE: DNA
<213> ORGANISM: Artificial Sequence
<220> FEATURE:
<223> OTHER INFORMATION: truncated AAV2 5'ITR

<400> SEQUENCE: 26
ctgcgcgctc gctcgctcac tgaggccgcc cgggcaaagc ccgggcgtcg ggcgaccttt      60
ggtcgcccgg cctcagtgag cgagcgagcg cgcagagagg gagtgg                   106

<210> SEQ ID NO 27
<211> LENGTH: 143
<212> TYPE: DNA
<213> ORGANISM: Artificial Sequence
<220> FEATURE:
<223> OTHER INFORMATION: modified AAV2 3'ITR

<400> SEQUENCE: 27
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc    120
gagcgcgcag agagggagtg gcc                                            143

<210> SEQ ID NO 28
<211> LENGTH: 1873
<212> TYPE: DNA
<213> ORGANISM: Artificial Sequence
<220> FEATURE:
<223> OTHER INFORMATION: CAG promoter

<400> SEQUENCE: 28
gatcttcaat attggccatt agccatatta ttcattggtt atatagcata aatcaatatt      60
ggctattggc cattgcatac gttgtatcta tatcataata tgtacattta tattggctca    120
tgtccaatat gaccgccatg ttggcattga ttattgacta gttattaata gtaatcaatt    180
acggggtcat tagttcatag cccatatatg gagttccgcg ttacataact tacggtaaat    240
ggcccgcctg gctgaccgcc caacgacccc cgcccattga cgtcaataat gacgtatgtt    300
cccatagtaa cgccaatagg gactttccat tgacgtcaat gggtggagta tttacggtaa    360
actgcccact tggcagtaca tcaagtgtat catatgccaa gtccgcccccc tattgacgtc    420 aatgacggta aatggcccgc ctggcattat gcccagtaca tgaccttacg ggactttcct    480
acttggcagt acatctacgt attagtcatc gctattacca tggtcgaggt gagccccacg    540
ttctgcttca ctctccccat ctccccccc tccccacccc caattttgta tttatttatt    600
ttttaattat tttgtgcagc gatgggggcg gggggggggg ggggcgcgc gccaggcggg    660 gcggggcggg gcgaggggcg gggcggggcg aggcggagag gtgcggcggc agccaatcag    720
agcggcgcgc tccgaaagtt tccttttatg gcgaggcggc ggcggcggcg gccctataaa    780
aagcgaagcg cgcggcgggc gggagtcgct gcgacgctgc cttcgccccg tgccccgctc    840
cgccgccgcc tcgcgccgcc cgccccggct ctgactgacc gcgttactcc cacaggtgag    900
cgggcgggac ggcccttctc ctccgggctg taattagcgc ttggtttaat gacggcttgt    960
```

| | |
|---|---|
| ttcttttctg tggctgcgtg aaagccttga ggggctccgg agggcccctt tgtgcggggg | 1020 |
| ggagcggctc gggggggtgcg tgcgtgtgtg tgtgcgtggg gagcgccgcg tgcggcccgc | 1080 |
| gctgcccggc ggctgtgagc gctgcgggcg cggcgcgggg ctttgtgcgc tccgcagtgt | 1140 |
| gcgcgagggg agcgcggccg ggggcggtgc cccgcggtgc gggggggggct gcaggggaa | 1200 |
| caaaggctgc gtgcggggtg tgtgcgtggg ggggtgagca ggggtgtgg gcgcggcggt | 1260 |
| cgggctgtaa ccccccctg caccccctc cccgagttgc tgagcacggc ccggcttcgg | 1320 |
| gtgcggggct ccgtacgggg cgtggcgcgg ggctcgccgt gccgggcggg gggtggcggg | 1380 |
| aggtgggggt gccgggcggg gcggggccgc ctcgggccgg ggagggctcg ggggagggc | 1440 |
| gcggcggccc ccggagcgcc ggcggctgtc gaggcgcggc gagccgcagc cattgccttt | 1500 |
| tatggtaatc gtgcgagagg gcgcaggac ttcctttgtc ccaaatctgt gcggagccga | 1560 |
| aatctgggag gcgccgccgc accccctcta gcggcgcgcg ggcgaagcgg tgcggcgccg | 1620 |
| gcaggaagga aatgggcggg gagggccttc gtgcgtcgcc gcgccgccgt cccttctcc | 1680 |
| ctctccagcc tcggggctgt ccgcgggggg acggctgcct tcggggggga cggggcaggg | 1740 |
| cggggttcgg cttctggcgt gtgaccggcg gctctagagc ctctgctaac catgttcatg | 1800 |
| ccttcttctt tttcctacag ctcctgggca acgtgctggt tattgtgctg tctcatcatt | 1860 |
| ttggcaaaga att | 1873 |

<210> SEQ ID NO 29
<211> LENGTH: 192
<212> TYPE: DNA
<213> ORGANISM: Homo sapiens

<400> SEQUENCE: 29

| | |
|---|---|
| ccctaaaatg ggcaaacatt gcaagcagca aacagcaaac acacagccct ccctgcctgc | 60 |
| tgaccttgga gctggggcag aggtcagaga cctctctggg cccatgccac ctccaacatc | 120 |
| cactcgaccc cttggaattt cggtggagag gagcagaggt tgtcctggcg tggtttaggt | 180 |
| agtgtgagag gg | 192 |

<210> SEQ ID NO 30
<211> LENGTH: 205
<212> TYPE: DNA
<213> ORGANISM: Homo sapiens

<400> SEQUENCE: 30

| | |
|---|---|
| aatgactcct ttcggtaagt gcagtggaag ctgtacactg cccaggcaaa gcgtccgggc | 60 |
| agcgtaggcg ggcgactcag atcccagcca gtggacttag cccctgtttg ctcctccgat | 120 |
| aactggggtg accttggtta atattcacca gcagcctccc ccgttgcccc tctggatcca | 180 |
| ctgcttaaat acggacgagg acagg | 205 |

<210> SEQ ID NO 31
<211> LENGTH: 93
<212> TYPE: DNA
<213> ORGANISM: Simian virus 40

<400> SEQUENCE: 31

| | |
|---|---|
| ctctaaggta aatataaaat ttttaagtgt ataatgtgtt aaactactga ttctaattgt | 60 |
| ttctctcttt tagattccaa cctttggaac tga | 93 |

<210> SEQ ID NO 32
<211> LENGTH: 398

```
<212> TYPE: DNA
<213> ORGANISM: Artificial Sequence
<220> FEATURE:
<223> OTHER INFORMATION: pHMI-hPAH-TC-025 transcriptional regulatory
      region

<400> SEQUENCE: 32
ccctaaaatg ggcaaacatt gcaagcagca aacagcaaac acacagccct ccctgcctgc    60
tgaccttgga gctggggcag aggtcagaga cctctctggg cccatgccac ctccaacatc   120
cactcgaccc cttggaattt cggtggagag gagcagaggt tgtcctggcg tggtttaggt   180
agtgtgagag gggaatgact cctttcggta agtgcagtgg aagctgtaca ctgcccaggc   240
aaagcgtccg ggcagcgtag gcgggcgact cagatcccag ccagtggact tagcccctgt   300
ttgctcctcc gataactggg gtgaccttgg ttaatattca ccagcagcct ccccgttgc    360 ccctctggat ccactgctta aatacggacg aggacagg                           398

<210> SEQ ID NO 33
<211> LENGTH: 72
<212> TYPE: DNA
<213> ORGANISM: Homo sapiens

<400> SEQUENCE: 33
gggggaggct gctggtgaat attaaccaag gtcaccccag ttatcggagg agcaaacagg    60
ggctaagtcc ac                                                        72

<210> SEQ ID NO 34
<211> LENGTH: 170
<212> TYPE: DNA
<213> ORGANISM: Homo sapiens

<400> SEQUENCE: 34
cgatgctcta atctctctag acaaggttca tatttgtatg ggttacttat tctctctttg    60
ttgactaagt caataatcag aatcagcagg tttgcagtca gattggcagg ataagcagc   120 ctagctcagg agaagtgagt ataaaagccc caggctggga gcagccatca               170

<210> SEQ ID NO 35
<211> LENGTH: 92
<212> TYPE: DNA
<213> ORGANISM: Artificial Sequence
<220> FEATURE:
<223> OTHER INFORMATION: modified MVM intron

<400> SEQUENCE: 35
aagaggtaag ggtttaaggg atggttggtt ggtgggtat taatgtttaa ttacctggag     60
cacctgcctg aaatcacttt ttttcaggtt gg                                  92

<210> SEQ ID NO 36
<211> LENGTH: 254
<212> TYPE: DNA
<213> ORGANISM: Artificial Sequence
<220> FEATURE:
<223> OTHER INFORMATION: pHMI-hPAH-TC-010 transcriptional regulatory
      region

<400> SEQUENCE: 36
gggggaggct gctggtgaat attaaccaag gtcaccccag ttatcggagg agcaaacagg    60
ggctaagtcc acctcgagcc atggcgatgc tctaatctct ctagacaagg ttcatatttg   120
tatgggttac ttattctctc tttgttgact aagtcaataa tcagaatcag caggtttgca   180
```

```
gtcagattgg cagggataag cagcctagct caggagaagt gagtataaaa gccccaggct    240
gggagcagcc atca                                                      254

<210> SEQ ID NO 37
<211> LENGTH: 592
<212> TYPE: DNA
<213> ORGANISM: Homo sapiens

<400> SEQUENCE: 37
gtaaatttta tggaatgtga atcataattc aatttttcaa catgcgttag gagggacatt     60
tcaaactctt ttttacccta gactttccta ccatcaccca gagtatccag ccaggagggg    120
aggggctaga gacaccagaa gtttagcagg gaggagggcg tagggattcg gggaatgaag    180
ggatgggatt cagactaggg ccaggaccca gggatggaga gaaagagatg gagtggttt     240 gggggcttgg tgacttagag aacagagctg caggctcaga ggcacacagg agtttctggg    300
ctcaccctgc ccccttccaa cccctcagtt cccatcctcc agcagctgtt tgtgtgctgc    360
ctctgaagtc cacactgaac aaacttcagc ctactcatgt ccctaaaatg gcaaacatt     420 gcaagcagca aacagcaaac acacagccct ccctgcctgc tgaccttgga gctggggcag    480
aggtcagaga cctctctggg cccatgccac tccaacatc cactcgaccc cttggaattt    540
cggtggagag gagcagaggt tgtcctggcg tggtttaggt agtgtgagag gg           592

<210> SEQ ID NO 38
<211> LENGTH: 423
<212> TYPE: DNA
<213> ORGANISM: Homo sapiens

<400> SEQUENCE: 38
gctctaaccc actctgatct cccagggcgg cagtaagtct tcagcatcag gcattttggg     60
gtgactcagt aaatggtaga tcttgctacc agtggaacag ccactaagga ttctgcagtg    120
agagcagagg gccagctaag tggtactctc ccagagactg tctgactcac gccaccccct    180
ccaccttgga cacaggacgc tgtggtttct gagccaggta caatgactcc tttcggtaag    240
tgcagtggaa gctgtacact gcccaggcaa agcgtccggg cagcgtaggc gggcgactca    300
gatcccagcc agtggactta gcccctgttt gctcctccga taactggggt gaccttggtt    360
aatattcacc agcagcctcc cccgttgccc ctctggatcc actgcttaaa tacggacgag    420
gac                                                                 423

<210> SEQ ID NO 39
<211> LENGTH: 1021
<212> TYPE: DNA
<213> ORGANISM: Artificial Sequence
<220> FEATURE:
<223> OTHER INFORMATION: pHMI-hPAH-TC-011 transcriptional regulatory
      region

<400> SEQUENCE: 39
gtaaatttta tggaatgtga atcataattc aatttttcaa catgcgttag gagggacatt     60
tcaaactctt ttttacccta gactttccta ccatcaccca gagtatccag ccaggagggg    120
aggggctaga gacaccagaa gtttagcagg gaggagggcg tagggattcg gggaatgaag    180
ggatgggatt cagactaggg ccaggaccca gggatggaga gaaagagatg gagtggttt     240 gggggcttgg tgacttagag aacagagctg caggctcaga ggcacacagg agtttctggg    300
ctcaccctgc ccccttccaa cccctcagtt cccatcctcc agcagctgtt tgtgtgctgc    360
```

```
ctctgaagtc cacactgaac aaacttcagc ctactcatgt ccctaaaatg ggcaaacatt      420
gcaagcagca aacagcaaac acacagccct ccctgcctgc tgaccttgga gctggggcag      480
aggtcagaga cctctctggg cccatgccac ctccaacatc cactcgaccc cttggaattt      540
cggtggagag gagcagaggt tgtcctggcg tggtttaggt agtgtgagag ggcttaaggc      600
tctaacccac tctgatctcc cagggcggca gtaagtcttc agcatcaggc attttggggt      660
gactcagtaa atggtagatc ttgctaccag tggaacagcc actaaggatt ctgcagtgag      720
agcagagggc cagctaagtg gtactctccc agagactgtc tgactcacgc cacccctcc       780 accttggaca caggacgctg tggtttctga gccaggtaca atgactcctt tcggtaagtg      840
cagtggaagc tgtacactgc ccaggcaaag cgtccgggca gcgtaggcgg gcgactcaga      900
tcccagccag tggacttagc ccctgtttgc tcctccgata actggggtga ccttggttaa      960
tattcaccag cagcctcccc cgttgcccct ctggatccac tgcttaaata cggacgagga     1020
c                                                                    1021

<210> SEQ ID NO 40
<211> LENGTH: 1168
<212> TYPE: DNA
<213> ORGANISM: Artificial Sequence
<220> FEATURE:
<223> OTHER INFORMATION: modified human EF-1alpha promoter

<400> SEQUENCE: 40
cgtgaggctc cggtgcccgt cagtgggcag agcgcacatc gcccacagtc cccgagaagt       60
tggggggagg ggtcggcaat tgaaccggtg cctagaaaag gtggcgcggg gtaaactggg      120
aaagtgatgt cgtgtactgg ctccgccttt ttcccgaggg tggggagaa ccgtatataa       180 gtgcagtagt cgccgtgaac gttcttttc gcaacgggtt tgccgccaga acacaggtaa      240
gtgccgtgtg tggttcccgc gggcctggcc tctttacggg ttatggccct tgcgtgcctt      300
gaattacttc cacctggctc cagtacgtga ttcttgatcc cgagctggag ccaggggcgg      360
gccttgcgct ttaggagccc cttcgcctcg tgcttgagtt gaggcctggc ctgggcgctg      420
gggccgccgc gtgcgaatct ggtggcacct tcgcgcctgt ctcgctgctt tcgataagtc      480
tctagccatt taaaattttt gatgacctgc tgcgacgctt tttttctggc aagatagtct      540
tgtaaatgcg ggccaggatc tgcacactgg tatttcggtt tttggggccg cgggcggcga      600
cggggcccgt gcgtcccagc gcacatgttc ggcgaggcgg ggcctgcgag cgcggccacc      660
gagaatcgga cggggggtagt ctcaagctgg ccggcctgct ctggtgcctg gcctcgcgcc      720
gccgtgtatc gccccgccct gggcggcaag gctggcccgg tcggcaccag ttgcgtgagc      780
ggaaagatgg ccgcttcccg gccctgctcc aggggggctca aaatgaagga cgcggcgctc      840
gggagagcgg gcgggtgagt cacccacaca aaggaaaggg gcctttccgt cctcagccgt      900
cgcttcatgt gactccacgg agtaccgggc gccgtccagg cacctcgatt agttctggag      960
cttttggagt acgtcgtctt taggttgggg ggagggttt tatgcgatgg agtttcccca     1020
cactgagtgg gtggagactg aagttaggcc agcttggcac ttgatgtaat tctccttgga     1080
atttgccctt tttgagtttg gatcttggtt cattctcaag cctcagacag tggttcaaag     1140
tttttttctt ccatttcagg tgtcgtga                                       1168

<210> SEQ ID NO 41
<211> LENGTH: 1766
<212> TYPE: DNA
<213> ORGANISM: Artificial Sequence
```

<220> FEATURE:
<223> OTHER INFORMATION: pHMI-hPAH-TC-012 transcriptional regulatory
      region

<400> SEQUENCE: 41

```
gtaaatttta tggaatgtga atcataattc aattttttcaa catgcgttag gagggacatt      60
tcaaactctt ttttacccta gactttccta ccatcaccca gagtatccag ccaggagggg     120
aggggctaga gacaccagaa gtttagcagg gaggagggcg tagggattcg gggaatgaag     180
ggatgggatt cagactaggg ccaggaccca gggatggaga gaaagagatg agagtggttt     240
gggggcttgg tgacttagag aacagagctg caggctcaga ggcacacagg agtttctggg     300
ctcaccctgc ccccttccaa cccctcagtt cccatcctcc agcagctgtt tgtgtgctgc     360
ctctgaagtc cacactgaac aaacttcagc ctactcatgt ccctaaaatg ggcaaacatt     420
gcaagcagca aacagcaaac acacagccct ccctgcctgc tgaccttgga gctggggcag     480
aggtcagaga cctctctggg cccatgccac ctccaacatc cactcgaccc cttggaattt     540
cggtggagag gagcagaggt tgtcctggcg tggtttaggt agtgtgagag ggcttaagcg     600
tgaggctccg gtgcccgtca gtgggcagag cgcacatcgc ccacagtccc cgagaagttg     660
ggggagggg tcggcaattg aaccggtgcc tagagaaggt ggcgcggggt aaactgggaa     720
agtgatgtcg tgtactggct ccgccttttt cccgagggtg ggggagaacc gtatataagt     780
gcagtagtcg ccgtgaacgt tcttttttcgc aacgggtttg ccgccagaac acaggtaagt     840
gccgtgtgtg gttcccgcgg gcctggcctc tttacgggtt atggcccttg cgtgccttga     900
attacttcca cctggctcca gtacgtgatt cttgatcccg agctggagcc aggggcgggc     960
cttgcgcttt aggagcccct tcgcctcgtg cttgagttga ggcctggcct gggcgctggg    1020
gccgccgcgt gcgaatctgg tggcaccttc gcgcctgtct cgctgctttc gataagtctc    1080
tagccattta aaattttttga tgacctgctg cgacgctttt tttctggcaa gatagtcttg    1140
taaatgcggg ccaggatctg cacactggta tttcggtttt tggggccgcg ggcggcgacg    1200
gggcccgtgc gtcccagcgc acatgttcgg cgaggcgggg cctgcgagcg cggccaccga    1260
gaatcggacg ggggtagtct caagctggcc ggcctgctct ggtgcctggc ctcgcgccgc    1320
cgtgtatcgc cccgccctgg gcggcaaggc tggcccggtc ggcaccagtt gcgtgagcgg    1380
aaagatggcc gcttcccggc cctgctccag ggggctcaaa atggaggacg cggcgctcgg    1440
gagagcgggc gggtgagtca cccacacaaa ggaaaggggc ctttccgtcc tcagccgtcg    1500
cttcatgtga ctccacggag taccgggcgc cgtccaggca cctcgattag ttctggagct    1560
tttggagtac gtcgtcttta ggttgggggg aggggtttta tgcgatggag tttccccaca    1620
ctgagtgggt ggagactgaa gttaggccag cttggcactt gatgtaattc tccttggaat    1680
ttgccctttt tgagtttgga tcttggttca ttctcaagcc tcagacagtg gttcaaagtt    1740
tttttcttcc atttcaggtg tcgtga                                         1766
```

<210> SEQ ID NO 42
<211> LENGTH: 122
<212> TYPE: DNA
<213> ORGANISM: Simian virus 40

<400> SEQUENCE: 42

```
aacttgttta ttgcagctta taatggttac aaataaagca atagcatcac aaatttcaca      60
aataaagcat ttttttcact gcattctagt tgtggtttgt ccaaactcat caatgtatct     120
ta                                                                   122
```

<210> SEQ ID NO 43
<211> LENGTH: 133
<212> TYPE: DNA
<213> ORGANISM: Simian virus 40

<400> SEQUENCE: 43

```
tgctttattt gtgaaatttg tgatgctatt gctttatttg taaccattat aagctgcaat      60
aaacaagtta acaacaacaa ttgcattcat tttatgtttc aggttcaggg ggaggtgtgg     120
gaggtttttt aaa                                                        133
```

<210> SEQ ID NO 44

<400> SEQUENCE: 44

000

<210> SEQ ID NO 45
<211> LENGTH: 198
<212> TYPE: DNA
<213> ORGANISM: Simian virus 40

<400> SEQUENCE: 45

```
gatccagaca tgataagata cattgatgag tttggacaaa ccacaactag aatgcagtga      60
aaaaaatgct ttatttgtga aatttgtgat gctattgctt tatttgtaac cattataagc     120
tgcaataaac aagttaacaa caacaattgc attcatttta tgtttcaggt tcagggggag     180
gtgtgggagg ttttttaa                                                   198
```

<210> SEQ ID NO 46
<211> LENGTH: 3392
<212> TYPE: DNA
<213> ORGANISM: Artificial Sequence
<220> FEATURE:
<223> OTHER INFORMATION: pHMI-hPAH-TC-004 transfer genome

<400> SEQUENCE: 46

```
gatcttcaat attggccatt agccatatta ttcattggtt atatagcata atcaatatt       60 ggctattggc cattgcatac gttgtatcta tatcataata tgtacattta tattggctca    120
tgtccaatat gaccgccatg ttggcattga ttattgacta gttattaata gtaatcaatt    180
acggggtcat tagttcatag cccatatatg gagttccgcg ttacataact acggtaaat     240 ggcccgcctg gctgaccgcc caacgacccc cgcccattga cgtcaataat gacgtatgtt    300
cccatagtaa cgccaatagg gactttccat tgacgtcaat gggtggagta tttacggtaa    360
actgcccact tggcagtaca tcaagtgtat catatgccaa gtccgccccc tattgacgtc    420
aatgacggta aatggcccgc ctggcattat gcccagtaca tgaccttacg gactttcct     480 acttggcagt acatctacgt attagtcatc gctattacca tggtcgaggt gagccccacg    540
ttctgcttca ctctccccat ctcccccccc tccccacccc caattttgta tttatttatt    600
ttttaattat tttgtgcagc gatggggggcg ggggggggg ggggcgcgc gccaggcggg    660 gcggggcggg gcgaggggcg gggcgggcg aggcggagag gtgcggcggc agccaatcag    720
agcggcgcgc tccgaaagtt ccttttatg gcgaggcggc ggcggcggcg ccctataaa      780 aagcgaagcg cgcggcgggc gggagtcgct gcgacgctgc cttcgccccg tgccccgctc    840
cgccgccgcc tcgcgccgcc cgccccggct ctgactgacc gcgttactcc cacaggtgag    900
cgggcgggac ggcccttctc ctccgggctg taattagcgc ttggtttaat gacggcttgt    960
```

```
ttcttttctg tggctgcgtg aaagccttga ggggctccgg gagggccctt tgtgcggggg    1020
ggagcggctc gggggtgcg tgcgtgtgtg tgtgcgtggg gagcgccgcg tgcggcccgc    1080
gctgcccggc ggctgtgagc gctgcgggcg cggcgcgggg ctttgtgcgc tccgcagtgt    1140
gcgcgagggg agcgcggccg ggggcggtgc cccgcggtgc gggggggggct gcaggggaa    1200 caaaggctgc gtgcggggtg tgtgcgtggg ggggtgagca gggggtgtgg gcgcggcggt    1260
cgggctgtaa ccccccctg cacccccctc cccgagttgc tgagcacggc ccggcttcgg    1320
gtgcggggct ccgtacgggg cgtggcgcgg ggctcgccgt gccgggcggg gggtggcggc    1380
aggtgggggt gccgggcggg gcggggccgc ctcgggccgg ggagggctcg ggggagggc    1440 gcggcggccc ccggagcgcc ggcggctgtc gaggcgcggc gagccgcagc cattgccttt    1500
tatggtaatc gtgcgagagg gcgcagggac ttcctttgtc ccaaatctgt gcggagccga    1560
aatctgggag gcgccgccgc accccctcta gcgggcgcgg ggcgaagcgg tgcggcgccg    1620
gcaggaagga aatgggcggg gagggccttc gtgcgtcgcc gcgccgccgt cccttctcc    1680 ctctccagcc tcgggctgt ccgcggggg acggctgcct tcgggggga cggggcaggg    1740 cggggttcgg cttctggcgt gtgaccgcg gctctagagc ctctgctaac catgttcatg    1800
ccttcttctt tttcctacag ctcctgggca acgtgctggt tattgtgctg tctcatcatt    1860
ttggcaaaga attccgccac catgtccacc gctgtgctgg agaaccctgg gctggggagg    1920
aaactgtcag acttcgggca ggagacttca tacattgagg ataactgtaa ccagaatggc    1980
gccatctctc tgatcttcag cctgaaggag aagtgggcg ccctggcaaa ggtgctcgc    2040 ctgtttgagg agaacgacgt gaatctgacc cacatcgagt cccggccttc tagactgaag    2100
aaggacgagt acgagttctt tacccacctg gataagcggt ccctgccagc cctgacaaac    2160
atcatcaaga tcctgaggca cgacatcgga gcaaccgtgc acgagctgtc tcgggacaag    2220
aagaaggata ccgtgccctg gttccctcgg acaatccagg agctggatag atttgccaac    2280
cagatcctgt cttacggagc agagctggac gcagatcacc ctggcttcaa ggacccagtg    2340
tatcgggccc ggagaaagca gtttgccgat atcgcctaca attataggca cggacagcca    2400
atccctcgcg tggagtatat ggaggaggag aagaagacct ggggcacagt gttcaagacc    2460
ctgaagagcc tgtacaagac acacgcctgc tacgagtata accacatctt cccctgctg    2520 gagaagtatt gtggctttca cgaggacaat atccctcagc tggaggacgt gagccagttc    2580
ctgcagacct gcacaggctt taggctgagg ccagtggcag gactgctgag ctcccgggac    2640
ttcctgggag gactggcctt cagagtgttt cactgcaccc agtacatcag gcacggctcc    2700
aagccaatgt ataccacaga gcccgacatc tgtcacgagc tgctgggcca cgtgcccctg    2760
tttagcgata gatccttcgc ccagttttcc caggagatcg gactggcatc tctgggagca    2820
cctgacgagt acatcgagaa gctggccacc atctattggt tcacagtgga gtttggcctg    2880
tgcaagcagg gcgatagcat caaggcctac ggagcaggac tgctgtctag cttcggcgag    2940
ctgcagtatt gtctgtccga aagccaaag ctgctgcccc tggagctgga aagaccgcc    3000 atccagaact acaccgtgac agagttccag ccctgtact atgtggccga gtcttttaac    3060
gatgccaagg agaaggtgag aaatttcgcc gccacaatcc ctaggccctt cagcgtgcgg    3120
tacgacccct atcccagag gatcgaggtg ctggataata cacagcagct gaagatcctg    3180
gctgactcaa tcaatagcga aatcggaatc ctgtgctccg ccctgcagaa aatcaaatga    3240
atcgattcta gagtcgagcc gcggactagt aacttgttta ttgcagctta taatggttac    3300
```

| | |
|---|---:|
| aaataaagca atagcatcac aaatttcaca aataaagcat ttttttcact gcattctagt | 3360 |
| tgtggtttgt ccaaactcat caatgtatct ta | 3392 |

<210> SEQ ID NO 47
<211> LENGTH: 2042
<212> TYPE: DNA
<213> ORGANISM: Artificial Sequence
<220> FEATURE:
<223> OTHER INFORMATION: pHMI-hPAH-TC-025 transfer genome

<400> SEQUENCE: 47

| | |
|---|---:|
| ccctaaaatg gcaaacatt gcaagcagca aacagcaaac acacagccct ccctgcctgc | 60 |
| tgaccttgga gctggggcag aggtcagaga cctctctggg cccatgccac ctccaacatc | 120 |
| cactcgaccc cttggaattt cggtggagag gagcagaggt tgtcctggcg tggtttaggt | 180 |
| agtgtgagag gggaatgact cctttcggta agtgcagtgg aagctgtaca ctgcccaggc | 240 |
| aaagcgtccg ggcagcgtag gcgggcgact cagatcccag ccagtggact tagcccctgt | 300 |
| ttgctcctcc gataactggg gtgaccttgg ttaatattca ccagcagcct ccccgttgc | 360 |
| ccctctggat ccactgctta aatacgacg aggacagggc cctgtctcct cagcttcagg | 420 |
| caccaccact gacctgggac agtgaatcct ctaaggtaaa tataaaattt ttaagtgtat | 480 |
| aatgtgttaa actactgatt ctaattgttt ctctctttta gattccaacc tttggaactg | 540 |
| accgccacca tgtccaccgc tgtgctggag aaccctgggc tggggaggaa actgtcagac | 600 |
| ttcgggcagg agacttcata cattgaggat aactgtaacc agaatggcgc catctctctg | 660 |
| atcttcagcc tgaaggagga agtgggcgcc ctggcaaagg tgctgcgcct gtttgaggag | 720 |
| aacgacgtga atctgaccca catcgagtcc cggccttcta gactgaagaa ggacgagtac | 780 |
| gagttctttta cccacctgga taagcggtcc ctgccagccc tgacaaacat catcaagatc | 840 |
| ctgaggcacg acatcggagc aaccgtgcac gagctgtctc gggacaagaa gaaggatacc | 900 |
| gtgccctggt tccctcggac aatccaggag ctggatagat tgccaaccca gatcctgtct | 960 |
| tacggagcag agctggacgc agatcaccct ggcttcaagg acccagtgta tcgggcccgg | 1020 |
| agaaagcagt ttgccgatat cgcctacaat tataggcacg acagccaat ccctcgcgtg | 1080 |
| gagtatatgg aggaggagaa aaagacctgg ggcacagtgt tcaagaccct gaagagcctg | 1140 |
| tacaagacac acgcctgcta cgagtataac cacatcttcc ccctgctgga aagtatttgt | 1200 |
| ggctttcacg aggacaatat ccctcagctg gaggacgtga gccagttcct gcagacctgc | 1260 |
| acaggcttta ggctgaggcc agtggcagga ctgctgagct cccgggactt cctgggagga | 1320 |
| ctggccttca gagtgttca ctgcacccag tacatcaggc acggctccaa gccaatgtat | 1380 |
| acaccagagc ccgacatctg tcacgagctg ctgggccacg tgcccctgtt tagcgataga | 1440 |
| tccttcgccc agttttccca ggagatcgga ctggcatctc tgggagcacc tgacgagtac | 1500 |
| atcgagaagc tggccaccat ctattggttc acagtggagt ttggcctgtg caagcagggc | 1560 |
| gatagcatca aggcctacgg agcaggactg ctgtctagct tcggcgagct gcagtattgt | 1620 |
| ctgtccgaga agccaaagct gctgcccctg gagctggaga agaccgccat ccagaactac | 1680 |
| accgtgacag agttccagcc cctgtactat gtggccgagt cttttaacga tgccaaggag | 1740 |
| aaggtgagaa atttcgccgc cacaatccct aggcccttca gcgtgcggta cgacccttat | 1800 |
| acccagagga tcgaggtgct ggataataca cagcagctga agatcctggc tgactcaatc | 1860 |
| aatagcgaaa tcggaatcct gtgctccgcc ctgcagaaaa tcaaatgaat gctttatttg | 1920 |
| tgaaatttgt gatgctattg ctttatttgt aaccattata agctgcaata aacaagttaa | 1980 |

```
caacaacaat tgcattcatt ttatgtttca ggttcagggg gaggtgtggg aggttttta    2040 aa                                                                  2042

<210> SEQ ID NO 48
<211> LENGTH: 1927
<212> TYPE: DNA
<213> ORGANISM: Artificial Sequence
<220> FEATURE:
<223> OTHER INFORMATION: pHMI-hPAH-TC-010 transfer genome

<400> SEQUENCE: 48
gggggaggct gctggtgaat attaaccaag gtcaccccag ttatcggagg agcaaacagg     60
ggctaagtcc acctcgagcc atggcgatgc tctaatctct ctagacaagg ttcatatttg    120
tatgggttac ttattctctc tttgttgact aagtcaataa tcagaatcag caggtttgca    180
gtcagattgg cagggataag cagcctagct caggagaagt gagtataaaa gccccaggct    240
gggagcagcc atcagctagc gccggcaaga ggtaagggtt taagggatgg ttggttggtg    300
gggtattaat gtttaattac ctggagcacc tgcctgaaat cactttttt caggttgggc     360 caccatgtcc accgctgtgc tggagaaccc tgggctgggg aggaaactgt cagacttcgg    420
gcaggagact tcatacattg aggataactg taaccagaat ggcgccatct ctctgatctt    480
cagcctgaag gaggaagtgg gcgccctggc aaaggtgctg cgcctgtttg aggagaacga    540
cgtgaatctg acccacatcg agtcccggcc ttctagactg aagaaggacg agtacgagtt    600 ctttaccca ctggataagc ggtccctgcc agccctgaca acatcatca agatcctgag      660 gcacgacatc ggagcaaccg tgcacagct gtctcgggac aagaagaagg ataccgtgcc     720
ctggttccct cggacaatcc aggagctgga tagatttgcc aaccagatcc tgtcttacgg    780
agcagagctg gacgcagatc accctggctt caaggaccca gtgtatcggg cccggagaaa    840
gcagtttgcc gatatcgcct acaattatag gcacggacag ccaatccctc gcgtggagta    900
tatggaggag gagaagaaga cctggggcac agtgttcaag accctgaaga gcctgtacaa    960
gacacacgcc tgctacgagt ataaccacat cttcccctg ctggagaagt attgtggctt    1020
tcacgaggac aatatccctc agctggagga cgtgagccaa ttcctgcaga cctgcacagg   1080
ctttaggctg aggccagtgg caggactgct gagctcccgg gacttcctgg aggactggc    1140 cttcagagtg tttcactgca cccagtacat caggcacggc tccaagccaa tgtatacacc   1200
agagcccgac atctgtcacg agctgctggg ccacgtgccc ctgtttagcg atagatcctt   1260
cgcccagttt tcccaggaga tcggactggc atctctggga gcacctgacg agtacatcga   1320
gaagctggcc accatctatt ggttcacagt ggagtttggc ctgtgcaagc agggcgatag   1380
catcaaggcc tacggagcag gactgctgtc tagcttcggc gagctgcagt attgtctgtc   1440
cgagaagcca agctgctgc cctggagct ggagaagacc gccatccaga actacaccgt    1500
gacagagttc cagcccctgt actatgtggc cgagtctttt aacgatgcca aggagaaggt   1560
gagaaatttc gccgccacaa tccctaggcc cttcagcgtg cggtacgacc ttatacccca   1620
gaggatcgag gtgctggata tacacagca gctgaagatc ctggctgact caatcaatag    1680
cgaaatcgga atcctgtgct ccgccctgca gaaaatcaaa tgaatcgtag atccagacat   1740
gataagatac attgatgagt ttggacaaac cacaactaga atgcagtgaa aaaatgctt    1800 tatttgtgaa atttgtgatg ctattgcttt atttgtaacc attataagct gcaataaaca   1860
agttaacaac aacaattgca ttcattttat gtttcaggtt caggggggagg tgtgggaggt   1920
``` ttttaa                                                                1927

<210> SEQ ID NO 49
<211> LENGTH: 2694
<212> TYPE: DNA
<213> ORGANISM: Artificial Sequence
<220> FEATURE:
<223> OTHER INFORMATION: pHMI-hPAH-TC-011

<400> SEQUENCE: 49

```
gtaaatttta tggaatgtga atcataattc aattttttcaa catgcgttag gagggacatt    60
tcaaactctt ttttacccta gactttccta ccatcaccca gagtatccag ccaggagggg   120
aggggctaga gacaccagaa gtttagcagg gaggagggcg tagggattcg gggaatgaag   180
ggatgggatt cagactaggg ccaggaccca gggatggaga gaaagagatg agagtggttt   240
gggggcttgg tgacttagag aacagagctg caggctcaga ggcacacagg agtttctggg   300
ctcaccctgc ccccttccaa cccctcagtt cccatcctcc agcagctgtt tgtgtgctgc   360
ctctgaagtc cacactgaac aaacttcagc ctactcatgt ccctaaaatg ggcaaacatt   420
gcaagcagca aacagcaaac acacagcct cctgcctgc tgaccttgga gctggggcag   480
aggtcagaga cctctctggg cccatgccac ctccaacatc cactcgaccc cttggaattt   540
cggtggagag gagcagaggt tgtcctggcg tggtttaggt agtgtgagag ggcttaaggc   600
tctaacccac tctgatctcc cagggcggca gtaagtcttc agcatcaggc attttggggt   660
gactcagtaa atggtagatc ttgctaccag tggaacagcc actaaggatt ctgcagtgag   720
agcagagggc cagctaagtg gtactctccc agagactgtc tgactcacgc cacccctcc   780
accttggaca caggacgctg tggtttctga gccaggtaca atgactcctt tcggtaagtg   840
cagtggaagc tgtacactgc ccaggcaaag cgtccgggca gcgtaggcgg gcgactcaga   900
tcccagccag tggacttagc ccctgtttgc tcctccgata actggggtga ccttggttaa   960
tattcaccag cagcctcccc cgttgcccct ctggatccac tgcttaaata cggacgagga  1020
cgctagcgcc ggcaagaggt aagggtttaa gggatggttg gttggtgggg tattaatgtt  1080
taattacctg gagcacctgc ctgaaatcac ttttttttcag gttgggccac catgtccacc  1140
gctgtgctgg agaaccctgg gctggggagg aaactgtcag acttcgggca ggagacttca  1200
tacattgagg ataactgtaa ccagaatggc gccatctctc tgatcttcag cctgaaggag  1260
gaagtgggcg ccctggcaaa ggtgctgcgc ctgtttgagg agaacgacgt gaatctgacc  1320
cacatcgagt cccggccttc tagactgaag aaggacgagt acgagttctt tacccacctg  1380
gataagcggt ccctgccagc cctgacaaac atcatcaaga tcctgaggca cgacatcgga  1440
gcaaccgtgc acgagctgtc tcgggacaag aagaaggata ccgtgccctg gttccctcgg  1500
acaatccagg agctggatag atttgccaac cagatcctgt cttacggagc agagctggac  1560
gcagatcacc ctggcttcaa ggacccagtg tatcggcc ggagaaagca gtttgccgat  1620
atcgcctaca attataggca cggacagcca atccctcgcg tggagtatat ggaggaggag  1680
aagaagacct ggggcacagt gttcaagacc ctgaagagcc tgtacaagac acacgcctgc  1740
tacgagtata accacatctt ccccctgctg gagaagtatt gtggctttca cgaggacaat  1800
atccctcagc tggaggacgt gagccagttc ctgcagacct gcacaggctt taggctgagg  1860
ccagtggcag gactgctgag ctcccgggac ttcctgggag actggccttc agagtgtttt  1920
cactgcaccc agtacatcag gcacggctcc aagccaatgt atacaccaga gcccgacatc  1980
tgtcacgagc tgctgggcca cgtgccctg tttagcgata gatccttcgc ccagttttcc  2040
```

```
caggagatcg gactggcatc tctgggagca cctgacgagt acatcgagaa gctggccacc    2100
atctattggt tcacagtgga gtttggcctg tgcaagcagg gcgatagcat caaggcctac    2160
ggagcaggac tgctgtctag cttcggcgag ctgcagtatt gtctgtccga gaagccaaag    2220
ctgctgcccc tggagctgga gaagaccgcc atccagaact acaccgtgac agagttccag    2280
cccctgtact atgtggccga gtcttttaac gatgccaagg agaaggtgag aaatttcgcc    2340
gccacaatcc ctaggccctt cagcgtgcgg tacgaccctt atacccagag gatcgaggtg    2400
ctggataata cacagcagct gaagatcctg gctgactcaa tcaatagcga aatcggaatc    2460
ctgtgctccg ccctgcagaa aatcaaatga atcgtagatc cagacatgat aagatacatt    2520
gatgagtttg acaaaccac aactagaatg cagtgaaaaa aatgctttat ttgtgaaatt    2580
tgtgatgcta ttgctttatt tgtaaccatt ataagctgca ataaacaagt taacaacaac    2640
aattgcattc attttatgtt tcaggttcag ggggaggtgt gggaggtttt ttaa          2694
```

```
<210> SEQ ID NO 50
<211> LENGTH: 3335
<212> TYPE: DNA
<213> ORGANISM: Artificial Sequence
<220> FEATURE:
<223> OTHER INFORMATION: pHMI-hPAH-TC-012

<400> SEQUENCE: 50
```

```
gtaaatttta tggaatgtga atcataattc aattttttcaa catgcgttag gagggacatt    60
tcaaactctt ttttacccta gactttccta ccatcaccca gagtatccag ccaggagggg    120
aggggctaga gacaccagaa gtttagcagg gaggagggcg tagggattcg gggaatgaag    180
ggatgggatt cagactaggg ccaggaccca gggatggaga gaaagagatg agagtggttt    240
gggggcttgg tgacttagag aacagagctg caggctcaga ggcacacagg agtttctggg    300
ctcaccctgc ccccttccaa cccctcagtt cccatcctcc agcagctgtt tgtgtgctgc    360
ctctgaagtc cacactgaac aaacttcagc ctactcatgt ccctaaaatg ggcaaacatt    420
gcaagcagca aacagcaaac acacagccct ccctgcctgc tgaccttgga gctggggcag    480
aggtcagaga cctctctggg cccatgccac ctccaacatc cactcgaccc cttggaattt    540
cggtggagag gagcagaggt tgtcctggcg tggtttaggt agtgtgagag ggcttaagcg    600
tgaggctccg gtgcccgtca gtgggcagag cgcacatcgc ccacagtccc cgagaagttg    660
gggggagggg tcggcaattg aaccggtgcc tagagaaggt ggcgcggggt aaactgggaa    720
agtgatgtcg tgtactggct ccgccttttt cccgagggtg ggggagaacc gtatataagt    780
gcagtagtcg ccgtgaacgt tctttttcgc aacgggtttg ccgccagaac acaggtaagt    840
gccgtgtgtg gttcccgcgg gcctggcctc tttacgggt atggcccttg cgtgccttga    900
attacttcca cctggctcca gtacgtgatt cttgatcccg agctggagcc aggggcgggc    960
cttgcgcttt aggagcccct tcgcctcgtg cttgagttga ggcctggcct gggcgctggg    1020
gccgccgcgt gcgaatctgg tggcaccttc gcgcctgtct cgctgctttc gataagtctc    1080
tagccattta aaatttttga tgacctgctg cgacgctttt tttctggcaa gatagtcttg    1140
taaatgcggg ccaggatctg cacactggta tttcggtttt tggggccgcg gcggcgacg    1200 gggcccgtgc gtcccagcgc acatgttcgg cgaggcgggg cctgcgagcg cggccaccga    1260
gaatcggacg ggggtagtct caagctgccc ggcctgctct ggtgcctggc ctcgcgccgc    1320
cgtgtatcgc cccgccctgg gcggcaaggc tggcccggtc ggcaccagtt gcgtgagcgg    1380
```

```
aaagatggcc gcttcccggc cctgctccag ggggctcaaa atggaggacg cggcgctcgg   1440
gagagcgggc gggtgagtca cccacacaaa ggaaagggc cttccgtcc tcagccgtcg     1500
cttcatgtga ctccacggag taccgggcgc cgtccaggca cctcgattag ttctggagct   1560
tttggagtac gtcgtcttta ggttgggggg aggggtttta tgcgatggag tttccccaca   1620
ctgagtgggt ggagactgaa gttaggccag cttggcactt gatgtaattc tccttggaat   1680
ttgccctttt tgagtttgga tcttggttca ttctcaagcc tcagacagtg gttcaaagtt   1740
tttttcttcc atttcaggtg tcgtgagcca ccatgtccac cgctgtgctg agaaccctg    1800
ggctggggag gaaactgtca gacttcgggc aggagacttc atacattgag gataactgta   1860
accagaatgg cgccatctct ctgatcttca gcctgaagga ggaagtgggc gccctggcaa   1920
aggtgctgcg cctgtttgag gagaacgacg tgaatctgac ccacatcgag tcccggcctt   1980
ctagactgaa gaaggacgag tacgagttct ttacccacct ggataagcgg tccctgccag   2040
ccctgacaaa catcatcaag atcctgaggc acgacatcgg agcaaccgtg cacgagctgt   2100
ctcgggacaa gaagaaggat accgtgccct ggttccctcg acaatccag gagctggata    2160
gatttgccaa ccagatcctg tcttacggag cagagctgga cgcagatcac cctggcttca   2220
aggacccagt gtatcgggcc cggagaaagc agtttgccga tatcgcctac aattataggc   2280
acggacagcc aatccctcgc gtggagtata tggaggagga agaagaagacc tggggcacag  2340
tgttcaagac cctgaagagc ctgtacaaga cacacgcctg ctacgagtat aaccacatct   2400
tccccctgct ggagaagtat tgtggctttc acgaggacaa tatccctcag ctggaggacg   2460
tgagccagtt cctgcagacc tgcacaggct ttaggctgag gccagtggca ggactgctga   2520
gctcccggga cttcctggga ggactggcct tcagagtgtt tcactgcacc cagtacatca   2580
ggcacggctc caagccaatg tataccaccag agcccgacac tgtcacgag ctgctgggcc   2640
acgtgccct gtttagcgat agatccttcg cccagttttc ccaggagatc ggactggcat   2700
ctctgggagc acctgacgag tacatcgaga gctggccac catctattgg ttcacagtgg   2760
agtttggcct gtgcaagcag ggcgatagca tcaaggccta cggagcagga ctgctgtcta   2820
gcttcggcga gctgcagtat tgtctgtccg agaagccaaa gctgctgccc ctggagctgg   2880
agaagaccgc catccagaac tacaccgtga cagagttcca gccctgtac tatgtggccg    2940
agtcttttaa cgatgccaag gagaaggtga gaaatttcgc cgccacaatc cctaggccct   3000
tcagcgtgcg gtacgaccct tatacccaga ggatcgaggt gctggataat acacagcagc   3060
tgaagatcct ggctgactca atcaatagcg aaatcggaat cctgtgctcc gccctgcaga   3120
aaatcaaatg aatcgtagat ccagacatga taagatacat tgatgagttt ggacaaacca   3180
caactagaat gcagtgaaaa aaatgcttta tttgtgaaat ttgtgatgct attgcttat   3240
ttgtaaccat tataagctgc aataaacaag ttaacaacaa caattgcatt cattttatgt   3300
ttcaggttca gggggaggtg tgggaggttt tttaa                             3335
```

<210> SEQ ID NO 51
<211> LENGTH: 3783
<212> TYPE: DNA
<213> ORGANISM: Artificial Sequence
<220> FEATURE:
<223> OTHER INFORMATION: pHMI-hPAH-TC-004 transfer genome (from 5' ITR to 3' ITR)

<400> SEQUENCE: 51

```
ttggccactc cctctctgcg cgctcgctcg ctcactgagg ccgggcgacc aaaggtcgcc    60
```

```
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgcaga tcttcaatat tggccattag ccatattatt cattggttat    240
atagcataaa tcaatattgg ctattggcca ttgcatacgt tgtatctata tcataatatg    300
tacatttata ttggctcatg tccaatatga ccgccatgtt ggcattgatt attgactagt    360
tattaatagt aatcaattac ggggtcatta gttcatagcc catatatgga gttccgcgtt    420
acataactta cggtaaatgg cccgcctggc tgaccgccca acgaccccg cccattgacg    480 tcaataatga cgtatgttcc catagtaacg ccaatagga cttcccattg acgtcaatgg    540
gtggagtatt tacggtaaac tgcccacttg gcagtacatc aagtgtatca tatgccaagt    600
ccgcccccta ttgacgtcaa tgacggtaaa tggcccgcct ggcattatgc ccagtacatg    660
accttacggg actttcctac ttggcagtac atctacgtat tagtcatcgc tattaccatg    720
gtcgaggtga gccccacgtt ctgcttcact ctccccatct ccccccctc cccacccca    780 attttgtatt tatttatttt ttaattattt tgtgcagcga tggggcggg ggggggggg    840 gggcgcgcgc caggcggggc ggggcggggc gaggggcggg gcggggcgag gcggagaggt    900
gcggcggcag ccaatcagag cggcgcgctc cgaaagtttc cttttatggc gaggcggcgg    960
cggcggcggc cctataaaaa gcgaagcgcg cggcgggcgg gagtcgctgc gacgctgcct   1020
tcgccccgtg ccccgctccg ccgccgcctc gcgccgcccg ccccggctct gactgaccgc   1080
gttactccca caggtgagcg ggcgggacgg cccttctcct ccgggctgta attagcgctt   1140
ggtttaatga cggcttgttt cttttctgtg gctgcgtgaa agccttgagg ggctccggga   1200
gggccctttg tgcgggggg agcggctcgg ggggtgcgtg cgtgtgtgtg tgcgtgggga   1260
gcgccgcgtg cggcccgcgc tgcccggcgg ctgtgagcgc tgcgggcgcg gcgcggggct   1320
ttgtgcgctc cgcagtgtgc gcgaggggag cgcggccggg ggcggtgccc cgcggtgcgg   1380
ggggggctgc gaggggaaca aaggctgcgt gcggggtgtg tgcgtggggg ggtgagcagg   1440
gggtgtgggc gcggcggtcg ggctgtaacc cccccctgca ccccccctccc cgagttgctg   1500 agcacggccc ggcttcgggt gcgggctcc gtacggggcg tggcgcgggg ctcgccgtgc   1560
cgggcggggg gtggcggcag gtggggtgc cgggcggggc ggggccgcct cgggccgggg   1620
agggctcggg ggaggggcgc ggcggccccc ggagcgccgg cggctgtcga ggcgcggcga   1680
gccgcagcca ttgccttta tggtaatcgt gcgagagggc gcagggactt cctttgtccc   1740
aaatctgtgc ggagccgaaa tctgggaggc gccgccgcac cccctctagc gggcgcgggg   1800
cgaagcggtg cggcgccggc aggaaggaaa tgggcgggga gggccttcgt gcgtcgccgc   1860
gccgccgtcc ccttctcccct ctccagcctc ggggctgtcc gcgggggac ggctgccttc   1920 gggggggacg gggcagggcg gggttcggct tctggcgtgt gaccggcggc tctagagcct   1980
ctgctaacca tgttcatgcc ttcttctttt tcctacagct cctgggcaac gtgctggtta   2040
ttgtgctgtc tcatcatttt ggcaaagaat tccgccacca tgtccaccgc tgtgctggag   2100
aaccctgggc tggggaggaa actgtcagac ttcgggcagg agacttcata cattgaggat   2160
aactgtaacc agaatggcgc catctctctg atcttcagcc tgaaggagga agtgggcgcc   2220
ctggcaaagg tgctgcgcct gtttgaggag aacgacgtga atctgaccca catcgagtcc   2280
cggccttcta gactgaagaa ggacgagtac gagttcttta cccacctgga taagcggtcc   2340
ctgccagccc tgacaaacat catcaagatc ctgaggcacg acatcggagc aaccgtgcac   2400
gagctgtctc gggacaagaa gaaggatacc gtgccctggt tccctcggac aatccaggag   2460
```

```
ctggatagat tgccaacca gatcctgtct tacggagcag agctggacgc agatcaccct    2520
ggcttcaagg acccagtgta tcgggcccgg agaaagcagt tgccgatat cgcctacaat    2580 tataggcacg acagccaat ccctcgcgtg gagtatatgg aggaggagaa gaagacctgg    2640
ggcacagtgt tcaagaccct gaagagcctg tacaagacac acgcctgcta cgagtataac    2700
cacatcttcc ccctgctgga gaagtattgt ggctttcacg aggacaatat ccctcagctg    2760
gaggacgtga gccagttcct gcagacctgc acaggcttta ggctgaggcc agtggcagga    2820
ctgctgagct cccgggactt cctgggagga ctggccttca gagtgtttca ctgcacccag    2880
tacatcaggc acggctccaa gccaatgtat acaccagagc ccgacatctg tcacgagctg    2940
ctgggccacg tgcccctgtt tagcgataga tccttcgccc agttttccca ggagatcgga    3000
ctggcatctc tgggagcacc tgacgagtac atcgagaagc tggccaccat ctattggttc    3060
acagtggagt ttggcctgtg caagcagggc gatagcatca aggcctacgg agcaggactg    3120
ctgtctagct tcggcgagct gcagtattgt ctgtccgaga gccaaagct gctgcccctg    3180 gagctggaga agaccgccat ccagaactac accgtgacag agttccagcc cctgtactat    3240
gtggccgagt ctttttaacga tgccaaggag aaggtgagaa atttcgccgc acaatccct    3300 aggccccttca gcgtgcggta cgacccttat acccagagga tcgaggtgct ggataataca    3360
cagcagctga agatcctggc tgactcaatc aatagcgaaa tcggaatcct gtgctccgcc    3420
ctgcagaaaa tcaaatgaat cgattctaga gtcgagccgc ggactagtaa cttgtttatt    3480
gcagcttata atggttacaa ataaagcaat agcatcacaa atttcacaaa taaagcattt    3540
ttttcactgc attctagttg tggtttgtcc aaactcatca atgtatctta ggtctagata    3600
cgtagataag tagcatggcg ggttaatcat taactacaag gaaccctag tgatggagtt    3660 ggccactccc tctctgcgcg ctcgctcgct cactgaggcc gggcgaccaa aggtcgcccg    3720
acgcccgggc tttgcccggg cggcctcagt gagcgagcga gcgcgcagag agggagtggc    3780
caa                                                                3783
```

<210> SEQ ID NO 52
<211> LENGTH: 2356
<212> TYPE: DNA
<213> ORGANISM: Artificial Sequence
<220> FEATURE:
<223> OTHER INFORMATION: pHMI-hPAH-TC-025 transfer genome (from 5' ITR to 3' ITR)

<400> SEQUENCE: 52

```
ctgcgcgctc gctcgctcac tgaggccgcc cgggcaaagc ccgggcgtcg gcgacctttt     60
ggtcgcccgg cctcagtgag cgagcgagcg cgcagagagg gagtggaatt cacgcgtgga    120
tctgaattca attcacgcgt ggtacctccc taaaatgggc aaacattgca agcagcaaac    180
agcaaacaca cagccctccc tgcctgctga ccttggagct ggggcagagg tcagagacct    240
ctctgggccc atgccaccc caacatccac tcgacccctt ggaatttcgg tggagaggag    300
cagaggttgt cctggcgtgg tttaggtagt gtgagagggg aatgactcct ttcggtaagt    360
gcagtggaag ctgtacactg cccaggcaaa gcgtccgggc agcgtaggcg ggcgactcag    420
atcccagcca gtggacttag cccctgtttg ctcctccgat aactggggtg accttggtta    480
atattcacca gcagcctccc ccgttgcccc tctggatcca ctgcttaaat acggacgagg    540
acagggcccc gtcctctcag cttcaggcac caccactgac ctgggacagt gaatcctcta    600
aggtaaatat aaaattttta agtgtataat gtgttaaact actgattcta attgtttctc    660
```

```
tcttttagat tccaacccttt ggaactgacc gccaccatgt ccaccgctgt gctggagaac      720
cctgggctgg ggaggaaact gtcagacttc gggcaggaga cttcatacat tgaggataac      780
tgtaaccaga atggcgccat ctctctgatc ttcagcctga aggaggaagt gggcgccctg      840
gcaaaggtgc tgcgcctgtt tgaggagaac gacgtgaatc tgacccacat cgagtcccgg      900
ccttctagac tgaagaagga cgagtacgag ttctttaccc acctggataa gcggtccctg      960
ccagccctga caaacatcat caagatcctg aggcacgaca tcggagcaac cgtgcacgag     1020
ctgtctcggg acaagaagaa ggataccgtg ccctggttcc ctcggacaat ccaggagctg     1080
gatagatttg ccaaccagat cctgtcttac ggagcagagc tggacgcaga tcaccctggc     1140
ttcaaggacc cagtgtatcg ggcccggaga aagcagtttg ccgatatcgc ctacaattat     1200
aggcacggac agccaatccc tcgcgtggag tatatggagg aggagaagaa gacctggggc     1260
acagtgttca agaccctgaa gagcctgtac aagacacacg cctgctacga gtataaccac     1320
atcttccccc tgctggagaa gtattgtggc tttcacgagg acaatatccc tcagctggag     1380
gacgtgagcc agttcctgca gacctgcaca ggctttaggc tgaggccagt ggcaggactg     1440
ctgagctccc gggacttcct gggaggactg gccttcagag tgtttcactg cacccagtac     1500
atcaggcacg gctccaagcc aatgtataca ccagagcccg acatctgtca cgagctgctg     1560
ggccacgtgc cctgtttag cgatagatcc ttcgcccagt tttcccagga gatcggactg     1620
gcatctctgg agcacctgac cgagtacatc gagaagctgg ccaccatcta ttggttcaca     1680
gtggagtttg gcctgtgcaa gcagggcgat agcatcaagg cctacggagc aggactgctg     1740
tctagcttcg gcgagctgca gtattgtctg tccgagaagc caaagctgct gccccctggag     1800 ctggagaaga ccgccatcca gaactacacc gtgacagagt ccagcccct gtactatgtg     1860 gccgagtctt ttaacgatgc caaggagaag gtgagaaatt cgccgccac aatccctagg     1920 cccttcagcg tgcggtacga ccccttatacc cagaggatcg aggtgctgga taatacacag     1980
cagctgaaga tcctggctga ctcaatcaat agcgaaatcg gaatcctgtg ctccgccctg     2040
cagaaaatca aatgaatgct ttatttgtga aatttgtgat gctattgctt tatttgtaac     2100
cattataagc tgcaataaac aagttaacaa caacaattgc attcattta tgtttcaggt     2160 tcaggggag gtgtgggagg tttttttaag catgctgggg agagatcgat ctgaggaacc     2220
cctagtgatg gagttggcca ctccctctct gcgcgctcgc tcgctcactg aggccgggcg     2280
accaaaggtc gcccgacgcc cgggctttgc ccgggcggcc tcagtgagcg agcgagcgcg     2340
cagagaggga gtggcc                                                      2356

<210> SEQ ID NO 53
<211> LENGTH: 2323
<212> TYPE: DNA
<213> ORGANISM: Artificial Sequence
<220> FEATURE:
<223> OTHER INFORMATION: pHMI-hPAH-TC-010 transfer genome (from 5' ITR
      to 3' ITR)

<400> SEQUENCE: 53
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctggagg ggtggagtcg tgacgtgaat tacgtcatag      180
ggttagggag gtcctgcagg ggaggctgct ggtgaatat taaccaaggt caccccagtt      240
atcggaggag caaacagggg ctaagtccac ctcgagccat ggcgatgctc taatctctct      300
```

```
agacaaggtt catatttgta tgggttactt attctctctt tgttgactaa gtcaataatc      360
agaatcagca ggtttgcagt cagattggca gggataagca gcctagctca ggagaagtga      420
gtataaaagc cccaggctgg gagcagccat cagctagcgc cggcaagagg taagggttta      480
agggatggtt ggttggtggg gtattaatgt ttaattacct ggagcacctg cctgaaatca      540
ctttttttca ggttgggcca ccatgtccac cgctgtgctg gagaaccctg gctggggag       600
gaaactgtca gacttcgggc aggagacttc atacattgag gataactgta accagaatgg      660
cgccatctct ctgatcttca gcctgaagga ggaagtgggc gccctggcaa aggtgctgcg      720
cctgtttgag gagaacgacg tgaatctgac ccacatcgag tcccggcctt ctagactgaa      780
gaaggacgag tacgagttct ttacccacct ggataagcgg tccctgccag ccctgacaaa      840
catcatcaag atcctgaggc acgacatcgg agcaaccgtg cacgagctgt ctcgggacaa      900
gaagaaggat accgtgccct ggttccctcg acaatccag gagctggata gatttgccaa       960
ccagatcctg tcttacggag cagagctgga cgcagatcac cctggcttca aggacccagt     1020
gtatcgggcc cggagaaagc agtttgccga tatcgcctac aattataggc acggacagcc     1080
aatccctcgc gtggagtata tggaggagga agaagaaacc tggggcacag tgttcaagac     1140
cctgaagagc ctgtacaaga cacacgcctg ctacgagtat aaccacatct tccccctgct     1200
ggagaagtat tgtggctttc acgaggacaa tatccctcag ctggaggacg tgagccagtt     1260
cctgcagacc tgcacaggct ttaggctgag gccagtggca ggactgctga gctcccggga     1320
cttcctggga ggactggcct tcagagtgtt tcactgcacc cagtacatca ggcacggctc     1380
caagccaatg tatacaccag agcccgacat ctgtcacgag ctgctgggcc acgtgcccct     1440
gtttagcgat agatccttcg cccagttttc ccaggagatc ggactggcat ctctgggagc     1500
acctgacgag tacatcgaga agctggccac catctatgg ttcacagtgg agtttggcct      1560
gtgcaagcag ggcgatagca tcaaggccta cggagcagga ctgctgtcta gcttcggcga     1620
gctgcagtat tgtctgtccg agaagccaaa gctgctgccc ctggagctgg agaagaccgc     1680
catccagaac tacaccgtga cagagttcca gccctgtac tatgtggccg agtctttaa       1740
cgatgccaag gagaaggtga aaatttcgc cgccacaatc cctaggccct tcagcgtgcg      1800
gtacgaccct tatcccaga ggatcgaggt gctggataat acacagcagc tgaagatcct      1860
ggctgactca atcaatagcg aaatcggaat cctgtgctcc gccctgcaga aaatcaaatg     1920
aatcgtagat ccagacatga taagatacat tgatgagttt ggacaaacca caactagaat     1980
gcagtgaaaa aaatgcttta tttgtgaaat ttgtgatgct attgctttat ttgtaaccat     2040
tataagctgc aataaacaag ttaacaacaa caattgcatt cattttatgt ttcaggttca     2100
gggggaggtg tgggaggttt tttaagcttg tttaaacgta cgtagataag tagcatggcg     2160
ggttaatcat taactacaag gaaccctag tgatggagtt ggccactccc tctctgcgcg     2220
ctcgctcgct cactgaggcc gggcgaccaa aggtcgcccg acgcccgggc tttgcccggg     2280
cggcctcagt gagcgagcga gcgcgcagag agggagtggc caa                       2323
```

<210> SEQ ID NO 54
<211> LENGTH: 3090
<212> TYPE: DNA
<213> ORGANISM: Artificial Sequence
<220> FEATURE:
<223> OTHER INFORMATION: pHMI-hPAH-TC-011 transfer genome (from 5' ITR to 3' ITR)

<400> SEQUENCE: 54

| | |
|---|---:|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgcagt aaattttatg gaatgtgaat cataattcaa ttttttcaaca | 240 |
| tgcgttagga gggacatttc aaactctttt ttaccctaga ctttcctacc atcacccaga | 300 |
| gtatccagcc aggaggggag gggctagaga caccagaagt ttagcaggga ggagggcgta | 360 |
| gggattcggg gaatgaaggg atgggattca gactagggcc aggacccagg gatggagaga | 420 |
| aagagatgag agtggtttgg gggcttggtg acttagagaa cagagctgca ggctcagagg | 480 |
| cacacaggag tttctgggct caccctgccc ccttccaacc cctcagttcc catcctccag | 540 |
| cagctgtttg tgtgctgcct ctgaagtcca cactgaacaa acttcagcct actcatgtcc | 600 |
| ctaaaatggg caaacattgc aagcagcaaa cagcaaacac acagccctcc ctgcctgctg | 660 |
| accttggagc tggggcagag gtcagagacc tctctgggcc catgccacct ccaacatcca | 720 |
| ctcgacccct tggaatttcg gtggagagga gcagaggttg tcctggcgtg gtttaggtag | 780 |
| tgtgagaggg cttaaggctc taacccactc tgatctccca gggcggcagt aagtcttcag | 840 |
| catcaggcat tttggggtga ctcagtaaat ggtagatctt gctaccagtg gaacagccac | 900 |
| taaggattct gcagtgagag cagagggcca gctaagtggt actctcccag agactgtctg | 960 |
| actcacgcca ccccctccac cttggacaca ggacgctgtg gtttctgagc caggtacaat | 1020 |
| gactcctttc ggtaagtgca gtggaagctg tacactgccc aggcaaagcg tccgggcagc | 1080 |
| gtaggcgggc gactcagatc ccagccagtg gacttagccc ctgtttgctc ctccgataac | 1140 |
| tggggtgacc ttggttaata ttcaccagca gcctcccccg ttgcccctct ggatccactg | 1200 |
| cttaaatacg gacgaggacg ctagcgccgg caagaggtaa gggtttaagg gatggttggt | 1260 |
| tggtggggta ttaatgttta attacctgga gcacctgcct gaaatcactt ttttttcaggt | 1320 |
| tgggccacca tgtccaccgc tgtgctggag acccctgggc tggggaggaa actgtcagac | 1380 |
| ttcgggcagg agacttcata cattgaggat aactgtaacc agaatggcgc catctctctg | 1440 |
| atcttcagcc tgaaggagga agtgggcgcc ctggcaaagg tgctgcgcct gttgaggag | 1500 |
| aacgacgtga atctgaccca catcgagtcc cggccttcta gactgaagaa ggacgagtac | 1560 |
| gagttctttta cccacctgga taagcggtcc ctgccagccc tgacaaacat catcaagatc | 1620 |
| ctgaggcacg acatcggagc aaccgtgcac gagctgtctc gggacaagaa gaaggatacc | 1680 |
| gtgccctggt tccctcggac aatccaggag ctggatagat tgccaaccag atcctgtct | 1740 |
| tacggagcag agctggacgc agatcaccct ggcttcaagg acccagtgta tcgggcccgg | 1800 |
| agaaagcagt ttgccgatat cgcctacaat tataggcacg acagccaat ccctcgcgtg | 1860 |
| gagtatatgg aggaggagaa aagaccctgg ggcacagtgt tcaagaccct gaagagcctg | 1920 |
| tacaagacac acgcctgcta cgagtataac cacatcttcc ccctgctgga aagtattgt | 1980 |
| ggctttcacg aggacaatat ccctcagctg gaggacgtga gccagttcct gcagacctgc | 2040 |
| acaggcttta ggctgaggcc agtggcagga ctgctgagct cccgggactt cctgggagga | 2100 |
| ctggccttca gagtgtttca ctgcacccag tacatcaggc acggctccaa gccaatgtat | 2160 |
| acaccagagc ccgacatctg tcacgagctg ctgggccacg tgcccctgtt tagcgataga | 2220 |
| tccttcgccc agttttccca ggagatcgga ctggcatctc tgggagcacc tgacgagtac | 2280 |
| atcgagaagc tggccaccat ctattggttc acagtggagt ttggcctgtg caagcagggc | 2340 |

| gatagcatca | aggcctacgg | agcaggactg | ctgtctagct | tcggcgagct | gcagtattgt | 2400 |
| ctgtccgaga | agccaaagct | gctgcccctg | gagctggaga | agaccgccat | ccagaactac | 2460 |
| accgtgacag | agttccagcc | cctgtactat | gtggccgagt | cttttaacga | tgccaaggag | 2520 |
| aaggtgagaa | atttcgccgc | cacaatccct | aggcccttca | gcgtgcggta | cgacccttat | 2580 |
| acccagagga | tcgaggtgct | ggataataca | cagcagctga | agatcctggc | tgactcaatc | 2640 |
| aatagcgaaa | tcggaatcct | gtgctccgcc | ctgcagaaaa | tcaaatgaat | cgtagatcca | 2700 |
| gacatgataa | gatacattga | tgagtttgga | caaaccacaa | ctagaatgca | gtgaaaaaaa | 2760 |
| tgctttattt | gtgaaatttg | tgatgctatt | gctttatttg | taaccattat | aagctgcaat | 2820 |
| aaacaagtta | acaacaacaa | ttgcattcat | tttatgtttc | aggttcaggg | ggaggtgtgg | 2880 |
| gaggtttttt | aagcttgttt | aaacgtacgt | agataagtag | catggcgggt | taatcattaa | 2940 |
| ctacaaggaa | cccctagtga | tggagttggc | cactccctct | ctgcgcgctc | gctcgctcac | 3000 |
| tgaggccggg | cgaccaaagg | tcgcccgacg | cccgggcttt | gcccgggcgg | cctcagtgag | 3060 |
| cgagcgagcg | cgcagagagg | gagtggccaa | | | | 3090 |

<210> SEQ ID NO 55
<211> LENGTH: 3731
<212> TYPE: DNA
<213> ORGANISM: Artificial Sequence
<220> FEATURE:
<223> OTHER INFORMATION: pHMI-hPAH-TC-012 transfer genome (from 5' ITR to 3' ITR)

<400> SEQUENCE: 55

| ttggccactc | cctctctgcg | cgctcgctcg | ctcactgagg | ccgggcgacc | aaaggtcgcc | 60 |
| cgacgcccgg | gctttgcccg | gcggcctca | gtgagcgagc | gagcgcgcag | agagggagtg | 120 |
| gccaactcca | tcactagggg | ttcctggagg | ggtggagtcg | tgacgtgaat | tacgtcatag | 180 |
| ggttagggag | gtcctgcagt | aaattttatg | gaatgtgaat | cataattcaa | ttttcaaca | 240 |
| tgcgttagga | gggacatttc | aaactctttt | ttaccctaga | ctttcctacc | atcacccaga | 300 |
| gtatccagcc | aggaggggag | gggctagaga | caccagaagt | ttagcaggga | ggagggcgta | 360 |
| gggattcggg | gaatgaaggg | atgggattca | gactagggcc | aggacccagg | gatggagaga | 420 |
| aagagatgag | agtggtttgg | gggcttggtg | acttagagaa | cagagctgca | ggctcagagg | 480 |
| cacacaggag | tttctgggct | cacctgcc | ccttccaacc | cctcagttcc | catcctccag | 540 |
| cagctgtttg | tgtgctgcct | ctgaagtcca | cactgaacaa | acttcagcct | actcatgtcc | 600 |
| ctaaaatggg | caaacattgc | aagcagcaaa | cagcaaacac | acagccctcc | ctgcctgctg | 660 |
| accttggagc | tggggcagag | gtcagagacc | tctctgggcc | catgccacct | ccaacatcca | 720 |
| ctcgacccct | tggaatttcg | gtggagagga | gcagaggttg | tcctggcgtg | gtttaggtag | 780 |
| tgtgagaggg | cttaagcgtg | aggctccggt | gcccgtcagt | gggcagagcg | cacatcgccc | 840 |
| acagtccccg | agaagttggg | gggaggggtc | ggcaattgaa | ccggtgccta | gagaaggtgg | 900 |
| cgcggggtaa | actgggaaag | tgatgtcgtg | tactggctcc | gcctttttcc | cgagggtggg | 960 |
| ggagaaccgt | atataagtgc | agtagtcgcc | gtgaacgttc | tttttcgcaa | cgggtttgcc | 1020 |
| gccagaacac | aggtaagtgc | cgtgtgtggt | tcccgcgggc | ctggcctctt | tacgggttat | 1080 |
| ggcccttgcg | tgccttgaat | tacttccacc | tggctccagt | acgtgattct | tgatcccgag | 1140 |
| ctggagccag | gggcgggcct | tgcgctttag | gagccccttc | gcctcgtgct | tgagttgagg | 1200 |
| cctggcctgg | gcgctggggc | cgccgcgtgc | gaatctggtg | gcaccttcgc | gcctgtctcg | 1260 |

```
ctgctttcga taagtctcta gccatttaaa attttttgatg acctgctgcg acgcttttt     1320 tctggcaaga tagtcttgta aatgcgggcc aggatctgca cactggtatt tcggttttg     1380 gggccgcggg cggcgacggg gcccgtgcgt cccagcgcac atgttcggcg aggcggggcc    1440
tgcgagcgcg gccaccgaga atcggacggg ggtagtctca agctggccgg cctgctctgg    1500
tgcctggcct cgcgccgccg tgtatcgccc cgccctgggc ggcaaggctg gcccggtcgg    1560
caccagttgc gtgagcggaa agatggccgc ttcccggccc tgctccaggg ggctcaaaat    1620
ggaggacgcg gcgctcggga gagcgggcgg gtgagtcacc cacacaaagg aaaggggcct    1680
ttccgtcctc agccgtcgct tcatgtgact ccacggagta ccgggcgccg tccaggcacc    1740
tcgattagtt ctggagcttt tggagtacgt cgtctttagg ttgggggggag gggttttatg    1800 cgatggagtt tccccacact gagtgggtgg agactgaagt taggccagct tggcacttga    1860
tgtaattctc cttggaattt gcccttttg agtttggatc ttggttcatt ctcaagcctc      1920
agacagtggt tcaaagtttt tttcttccat ttcaggtgtc gtgagccacc atgtccaccg    1980
ctgtgctgga gaaccctggg ctggggagga aactgtcaga cttcgggcag gagacttcat    2040
acattgagga taactgtaac cagaatggcg ccatctctct gatcttcagc ctgaaggagg    2100
aagtgggcgc cctggcaaag gtgctgcgcc tgtttgagga gaacgacgtg aatctgaccc    2160
acatcgagtc ccggccttct agactgaaga aggacgagta cgagttcttt acccacctgg    2220
ataagcggtc cctgccagcc ctgacaaaca tcatcaagat cctgaggcac gacatcggag    2280
caaccgtgca cgagctgtct cgggacaaga agaaggatac cgtgccctgg ttccctcgga    2340
caatccagga gctggataga tttgccaacc agatcctgtc ttacggagca gagctggacg    2400
cagatcaccc tggcttcaag gacccagtgt atcgggcccg gagaaagcag tttgccgata    2460
tcgcctacaa ttataggcac ggacagccaa tccctcgcgt ggagtatatg gaggaggaga    2520
agaagacctg ggcacagtg ttcaagaccc tgaagagcct gtacaagaca cacgcctgct     2580
acgagtataa ccacatcttc cccctgctgg agaagtattg tggctttcac gaggacaata    2640
tccctcagct ggaggacgtg agccagttcc tgcagacctg cacaggcttt aggctgaggc    2700
cagtggcagg actgctgagc tcccgggact tcctgggagg actggccttc agagtgtttc    2760
actgcaccca gtacatcagg cacggctcca agccaatgta taccccagag cccgacatct    2820
gtcacgagct gctgggccac gtgcccctgt ttagcgatag atccttcgcc cagttttccc    2880
aggagatcgg actggcatct ctgggagcac ctgacgagta catcgagaag ctggccacca    2940
tctattggtt cacagtggag tttgcctgt gcaagcaggg cgatagcatc aaggcctacg     3000
gagcaggact gctgtctagc ttcggcgagc tgcagtattg tctgtccgag aagccaaagc    3060
tgctgcccct ggagctggag aagaccgcca tccagaacta caccgtgaca gagttccagc    3120
ccctgtacta tgtggccgag tcttttaacg atgccaagga gaaggtgaga aatttcgccg    3180
ccacaatccc taggcccttc agcgtgcggt acgacccctt acccagagg atcgaggtgc     3240 tggataatac acagcagctg aagatcctgg ctgactcaat caatagcgaa tcggaatcc     3300 tgtgctccgc cctgcagaaa atcaaatgaa tcgtagatcc agacatgata agatacattg    3360
atgagtttgg acaaaccaca actagaatgc agtgaaaaaa atgctttatt tgtgaaattt    3420
gtgatgctat tgctttattt gtaaccatta taagctgcaa taaacaagtt aacaacaaca    3480
attgcattca ttttatgttt caggttcagg gggaggtgtg ggaggttttt taagcttgtt    3540
taaacgtacg tagataagta gcatggcggg ttaatcatta actacaagga acccctagtg    3600
atggagttgg ccactccctc tctgcgcgct cgctcgctca ctgaggccgg gcgaccaaag    3660
```

```
gtcgcccgac gcccgggctt tgcccgggcg gcctcagtga gcgagcgagc gcgcagagag      3720
ggagtggcca a                                                            3731

<210> SEQ ID NO 56
<211> LENGTH: 37
<212> TYPE: DNA
<213> ORGANISM: Artificial Sequence
<220> FEATURE:
<223> OTHER INFORMATION: 37 bp additional 3' ITR sequence from wtAAV2

<400> SEQUENCE: 56
gtagataagt agcatggcgg gttaatcatt aactaca                                  37

<210> SEQ ID NO 57
<211> LENGTH: 180
<212> TYPE: DNA
<213> ORGANISM: Artificial Sequence
<220> FEATURE:
<223> OTHER INFORMATION: 3'ITR with additional 37 bp sequence

<400> SEQUENCE: 57
gtagataagt agcatggcgg gttaatcatt aactacaagg aaccccctagt gatggagttg        60 gccactccct ctctgcgcgc tcgctcgctc actgaggccg ggcgaccaaa ggtcgcccga       120
cgcccgggct tgcccgggc ggcctcagtg agcgagcgag cgcgcagaga gggagtggcc       180

<210> SEQ ID NO 58
<211> LENGTH: 380
<212> TYPE: DNA
<213> ORGANISM: Artificial Sequence
<220> FEATURE:
<223> OTHER INFORMATION: CMV enhancer

<400> SEQUENCE: 58
ggcattgatt attgactagt tattaatagt aatcaattac ggggtcatta gttcatagcc        60
catatatgga gttccgcgtt acataactta cggtaaatgg cccgcctggc tgaccgccca       120
acgacccccg cccattgacg tcaataatga cgtatgttcc catagtaacg ccaatagggga      180 ctttccattg acgtcaatgg gtggagtatt tacggtaaac tgcccacttg gcagtacatc      240
aagtgtatca tatgccaagt ccgcccccta ttgacgtcaa tgacggtaaa tggcccgcct      300
ggcattatgc ccagtacatg accttacggg actttcctac ttggcagtac atctacgtat      360
tagtcatcgc tattaccatg                                                   380

<210> SEQ ID NO 59
<211> LENGTH: 1246
<212> TYPE: DNA
<213> ORGANISM: Artificial Sequence
<220> FEATURE:
<223> OTHER INFORMATION: CBA promoter

<400> SEQUENCE: 59
tcgaggtgag ccccacgttc tgcttcactc tccccatctc ccccccctcc ccaccccccaa       60 ttttgtattt atttattttt taattatttt gtgcagcgat ggggggcgggg ggggggggg      120 ggcgcgcgcc aggcggggcg gggcggggcg agggggcggg cggggcgagg cggagaggtg      180
cggcggcagc caatcagagc ggcgcgctcc gaaagtttcc ttttatggcg aggcggcggc      240
ggcggcggcc ctataaaaag cgaagcgcgc ggcgggcggg agtcgctgcg cgctgccttc      300
gccccgtgcc ccgctccgcc gccgcctcgc gccgcccgcc ccggctctga ctgaccgcgt      360
```

| | |
|---|---|
| tactcccaca ggtgagcggg cgggacggcc cttctcctcc gggctgtaat tagcgcttgg | 420 |
| tttaatgacg gcttgtttct tttctgtggc tgcgtgaaag ccttgagggg ctccgggagg | 480 |
| gcccttgtg cgggggagc ggctcggggg gtgcgtgcgt gtgtgtgtgc gtggggagcg | 540 |
| ccgcgtgcgg ctccgcgctg cccggcggct gtgagcgctg cgggcgcggc gcgggggctt | 600 |
| gtgcgctccg cagtgtgcgc gaggggagcg cggccggggg cggtgccccg cggtgcgggg | 660 |
| ggggctgcga ggggaacaaa ggctgcgtgc ggggtgtgtg cgtggggggg tgagcagggg | 720 |
| gtgtgggcgc gtcggtcggg ctgcaacccc ccctgcaccc ccctccccga gttgctgagc | 780 |
| acggccggc ttcgggtgcg gggctccgta cggggcgtgg cgcggggctc gccgtgccgg | 840 |
| gcgggggtg gcggcaggtg ggggtgccgg gcggggcggg gccgcctcgg gccggggagg | 900 |
| gctcggggga ggggcgcggc ggccccgga gcgccggcgg ctgtcgaggc gcggcgagcc | 960 |
| gcagccattg cctttatgg taatcgtgcg agagggcgca gggacttcct ttgtcccaaa | 1020 |
| tctgtgcgga gccgaaatct gggaggcgcc gccgcacccc ctctagcggg cgcggggcga | 1080 |
| agcggtgcgg cgccggcagg aaggaaatgg gcggggaggg ccttcgtgcg tcgccgcgcc | 1140 |
| gccgtcccct tctccctctc cagcctcggg gctgtccgcg ggggacggc tgccttcggg | 1200 |
| ggggacgggg cagggcgggg ttcggcttct ggcgtgtgac cggcgg | 1246 |

<210> SEQ ID NO 60
<211> LENGTH: 95
<212> TYPE: DNA
<213> ORGANISM: Artificial Sequence
<220> FEATURE:
<223> OTHER INFORMATION: rabbit beta-globin element

<400> SEQUENCE: 60

| | |
|---|---|
| cctctgctaa ccatgttcat gccttcttct ttttcctaca gctcctgggc aacgtgctgg | 60 |
| ttattgtgct gtctcatcat tttggcaaag aattc | 95 |

<210> SEQ ID NO 61
<211> LENGTH: 3301
<212> TYPE: DNA
<213> ORGANISM: Artificial Sequence
<220> FEATURE:
<223> OTHER INFORMATION: pHMI-hPAH-TC-009 transfer genome

<400> SEQUENCE: 61

| | |
|---|---|
| tggcattgat tattgactag ttattaatag taatcaatta cggggtcatt agttcatagc | 60 |
| ccatatatgg agttccgcgt tacataactt acggtaaatg gcccgcctgg ctgaccgccc | 120 |
| aacgaccccc gcccattgac gtcaataatg acgtatgttc ccatagtaac gccaataggg | 180 |
| actttccatt gacgtcaatg ggtggagtat ttacggtaaa ctgcccactt ggcagtacat | 240 |
| caagtgtatc atatgccaag tccgccccct attgacgtca atgacggtaa atggcccgcc | 300 |
| tggcattatg cccagtacat gaccttacgg gactttccta cttggcagta catctacgta | 360 |
| ttagtcatcg ctattaccat ggtcgaggtg agccccacgt tctgcttcac tctccccatc | 420 |
| tccccccct cccaccccc aattttgtat ttatttattt tttaattatt ttgtgcagcg | 480 |
| atggggcgg gggggggg ggggcgcgcg ccaggcgggg cggggcgggg cgaggggcgg | 540 |
| ggcggggcga ggcggagagg tgcggcggca gccaatcaga gcggcgcgct ccgaaagttt | 600 |
| ccttttatgg cgaggcggcg gcggcggcgg ccctataaaa agcgaagcgc gcggcgggcg | 660 |
| ggagtcgctg cgcgctgcct tcgccccgtg ccccgctccg ccgccgcctc gcgccgcccg | 720 |
| ccccggctct gactgaccgc gttactccca caggtgagcg gcgggacgg cccttctcct | 780 |

-continued

```
ccgggctgta attagcgctt ggtttaatga cggcttgttt cttttctgtg gctgcgtgaa    840
agccttgagg ggctccggga gggccctttg tgcggggggga gcggctcggg gggtgcgtgc    900
gtgtgtgtgt gcgtggggag cgccgcgtgc ggctccgcgc tgcccggcgg ctgtgagcgc    960
tgcgggcgcg gcgcggggct tgtgcgctc cgcagtgtgc gcgaggggag cgcggccggg   1020
ggcggtgccc cgcggtgcgg ggggggctgc gaggggaaca aaggctgcgt gcggggtgtg   1080
tgcgtggggg ggtgagcagg gggtgtgggc gcgtcggtcg ggctgcaacc cccctgcac   1140
ccccctcccc gagttgctga gcacggcccg gcttcgggtg cggggctccg tacggggcgt   1200
ggcgcggggc tcgccgtgcc gggcgggggg tggcggcagg tgggggtgcc gggcggggcg   1260
gggccgcctc gggccgggga gggctcgggg aggggcgcg gcggccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcgggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg gggggacgg ggcagggcgg ggttcggctt ctggcgtgtg   1620
accggcggct ctagagcctc tgctaaccat gttcatgcct tcttctttt cctacagctc   1680
ctgggcaacg tgctggttat tgtgctgtct catcattttg gcaaagaatt ccgccaccat   1740
gtccaccgct gtgctggaga accctgggct ggggaggaaa ctgtcagact cgggcagga   1800
gacttcatac attgaggata actgtaacca gaatggcgcc atctctctga tcttcagcct   1860
gaaggaggaa gtgggcgccc tggcaaaggt gctgcgcctg tttgaggaga cgacgtgaa   1920
tctgacccac atcgagtccc ggccttctag actgaagaag gacgagtacg agttctttac   1980
ccacctggat aagcggtccc tgccagccct gacaaacatc atcaagatcc tgaggcacga   2040
catcggagca accgtgcacg agctgtctcg ggacaagaag aaggataccg tgccctggtt   2100
ccctcggaca atccaggagc tggatagatt tgccaaccag atcctgtctt acggagcaga   2160
gctggacgca gatcaccctg gcttcaagga cccagtgtat cgggcccgga gaaagcagtt   2220
tgccgatatc gcctacaatt ataggcacgg acagccaatc cctcgcgtgg agtatatgga   2280
ggaggagaag aagacctggg gcacagtgtt caagaccctg aagagcctgt acaagacaca   2340
cgcctgctac gagtataacc acatcttccc cctgctggag aagtattgtg ctttcacga   2400
ggacaatatc cctcagctgg aggacgtgag ccagttcctg cagacctgca caggctttag   2460
gctgaggcca gtgcaggac tgctgagctc ccgggacttc ctgggaggac tggccttcag   2520
agtgtttcac tgcacccagt acatcaggca cggctccaag ccaatgtata caccagagcc   2580
cgacatctgt cacgagctgc tgggccacgt gcccctgttt agcgatagat ccttcgccca   2640
gttttcccag gagatcggac tggcatctct gggagcacct gacgagtaca tcgagaagct   2700
ggccaccatc tattggttca cagtggagtt tggcctgtgc aagcagggcg atagcatcaa   2760
ggcctacgga gcaggactgc tgtctagctt cggcgagctg cagtattgtc tgtccgagaa   2820
gccaaagctg ctgcccctgg agctggaaaa gaccgccatc cagaactaca ccgtgacaga   2880
gttccagccc ctgtactatg tggccgagtc ttttaacgat gccaaggaga aggtgagaaa   2940
tttcgccgcc acaatcccta ggcccttcag cgtgcggtac gaccctttata cccagaggat   3000
cgaggtgctg gataatacac agcagctgaa gatcctggct gactcaatca atagcgaaat   3060
cggaatcctg tgctccgccc tgcagaaaat caaatgaatc gtagatccag acatgataag   3120
```

| | |
|---|---|
| atacattgat gagtttggac aaaccacaac tagaatgcag tgaaaaaat gctttatttg | 3180 |
| tgaaatttgt gatgctattg ctttatttgt aaccattata agctgcaata aacaagttaa | 3240 |
| caacaacaat tgcattcatt ttatgtttca ggttcagggg gaggtgtggg aggttttta | 3300 |
| a | 3301 |

<210> SEQ ID NO 62
<211> LENGTH: 3701
<212> TYPE: DNA
<213> ORGANISM: Artificial Sequence
<220> FEATURE:
<223> OTHER INFORMATION: pHMI-hPAH-TC-009 transfer genome

<400> SEQUENCE: 62

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat acgtcatag | 180 |
| ggttagggag gtcctgcaga tctggcattg attattgact agttattaat agtaatcaat | 240 |
| tacggggtca ttagttcata gcccatatat ggagttccgc gttacataac ttacggtaaa | 300 |
| tggcccgcct ggctgaccgc ccaacgaccc ccgcccattg acgtcaataa tgacgtatgt | 360 |
| tcccatagta acgccaatag ggactttcca ttgacgtcaa tgggtggagt atttacggta | 420 |
| aactgcccac ttggcagtac atcaagtgta tcatatgcca agtccgcccc ctattgacgt | 480 |
| caatgacggt aaatggcccg cctggcatta tgcccagtac atgaccttac gggactttcc | 540 |
| tacttggcag tacatctacg tattagtcat cgctattacc atggtcgagg tgagccccac | 600 |
| gttctgcttc actctcccca tctccccccc ctccccaccc caatttttgt atttatttat | 660 |
| tttttaatta ttttgtgcag cgatgggggc ggggggggg gggggcgcg cgccaggcgg | 720 |
| ggcggggcgg ggcgaggggc ggggcgggc gaggcggaga ggtgcggcgg cagccaatca | 780 |
| gagcggcgcg ctccgaaagt ttccttttat ggcgaggcgg cggcggcggc ggccctataa | 840 |
| aaagcgaagc gcgcggcggg cggagtcgc tgcgcgctgc cttcgccccg tgccccgctc | 900 |
| cgccgccgcc tcgcgccgcc cgccccggct ctgactgacc gcgttactcc cacaggtgag | 960 |
| cgggcgggac ggcccttctc ctccgggctg taattagcgc ttggtttaat gacggcttgt | 1020 |
| ttcttttctg tggctgcgtg aaagccttga ggggctccgg gagggccctt tgtgcggggg | 1080 |
| gagcggctcg gggggtgcgt gcgtgtgtgt gtgcgtgggg agccgcgcgt gcggctccgc | 1140 |
| gctgcccggc ggctgtgagc gctgcgggcg cggcgcgggg cttgtgcgc tccgcagtgt | 1200 |
| gcgcgagggg agcgcggccg ggggcggtgc cccgcggtgc ggggggggct gcgaggggaa | 1260 |
| caaaggctgc gtgcgggtg tgtgcgtggg gggtgagca ggggtgtgg gcgcgtcggt | 1320 |
| cgggctgcaa cccccctgc acccccctcc ccgagttgct gagcacggcc cggcttcggg | 1380 |
| tgcggggctc cgtacggggc gtggcgcggg gctcgccgtg ccgggcgggg ggtggcggca | 1440 |
| ggtgggggtg ccggcggg cggggccgcc tcggccgggg gagggctcgg ggagggggcg | 1500 |
| cggcggcccc cggagcgccg gcggctgtcg aggcgcggcg agccgcagcc attgccttt | 1560 |
| atggtaatcg tgcgagaggg cgcagggact tcctttgtcc caaatctgtg cggagccgaa | 1620 |
| atctgggagg cgccgccgca cccctctag cgggcgcggg gcgaagcggt gcggcgccgg | 1680 |
| caggaaggaa atgggcgggg agggccttcg tgcgtcgccg cgccgccgtc cccttctccc | 1740 |
| tctccagcct cggggctgtc cgcggggga cggctgcctt cggggggac ggggcagggc | 1800 |
| ggggttcggc ttctggcgtg tgaccggcgg ctctagagcc tctgctaacc atgttcatgc | 1860 |

```
cttcttcttt ttcctacagc tcctgggcaa cgtgctggtt attgtgctgt ctcatcattt   1920
tggcaaagaa ttccgccacc atgtccaccg ctgtgctgga gaaccctggg ctggggagga   1980
aactgtcaga cttcgggcag gagacttcat acattgagga taactgtaac cagaatggcg   2040
ccatctctct gatcttcagc ctgaaggagg aagtgggcgc cctggcaaag gtgctgcgcc   2100
tgtttgagga gaacgacgtg aatctgaccc acatcgagtc ccggccttct agactgaaga   2160
aggacgagta cgagttcttt acccacctgg ataagcggtc cctgccagcc ctgacaaaca   2220
tcatcaagat cctgaggcac gacatcggag caaccgtgca cgagctgtct cgggacaaga   2280
agaaggatac cgtgccctgg ttccctcgga caatccagga gctggataga tttgccaacc   2340
agatcctgtc ttacggagca gagctggacg cagatcaccc tggcttcaag gacccagtgt   2400
atcgggcccg gagaaagcag tttgccgata tcgcctacaa ttataggcac ggacagccaa   2460
tccctcgcgt ggagtatatg gaggaggaga agaagacctg ggcacagtg ttcaagaccc   2520 tgaagagcct gtacaagaca cacgcctgct acgagtataa ccacatcttc ccctgctgg   2580 agaagtattg tggcttcac gaggacaata tccctcagct ggaggacgtg agccagttcc   2640
tgcagacctg cacaggcttt aggctgaggc cagtggcagg actgctgagc tcccgggact   2700
tcctgggagg actggccttc agagtgtttc actgcaccca gtacatcagg cacggctcca   2760
agccaatgta tacccagag cccgacatct gtcacgagct gctgggccac gtgcccctgt   2820
ttagcgatag atccttcgcc cagttttccc aggagatcgg actggcatct ctgggagcac   2880
ctgacgagta catcgagaag ctggccacca tctattggtt cacagtggag tttggcctgt   2940
gcaagcaggg cgatagcatc aaggcctacg gagcaggact gctgtctagc ttcggcgagc   3000
tgcagtattg tctgtccgag aagccaaagc tgctgcccct ggagctggag aagaccgcca   3060
tccagaacta caccgtgaca gagttccagc ccctgtacta tgtggccgag tcttttaacg   3120
atgccaagga gaaggtgaga atttcgccg ccacaatccc taggcccttc agcgtgcggt   3180
acgaccctta tacccagagg atcgaggtgc tggataatac acagcagctg aagatcctgg   3240
ctgactcaat caatagcgaa atcggaatcc tgtgctccgc cctgcagaaa atcaaatgaa   3300
tcgtagatcc agacatgata agatacattg atgagtttgg acaaaccaca actagaatgc   3360
agtgaaaaaa atgctttatt tgtgaaattt gtgatgctat tgctttattt gtaaccatta   3420
taagctgcaa taaacaagtt aacaacaaca attgcattca ttttatgttt caggttcagg   3480
gggaggtgtg ggaggttttt taagcttgtt taaacgtacg tagataagta gcatggcggg   3540
ttaatcatta actacaagga acccctagtg atggagttgg ccactccctc tctgcgcgct   3600
cgctcgctca ctgaggccgg gcgaccaaag gtcgcccgac gcccgggctt tgcccgggcg   3660
gcctcagtga gcgagcgagc gcgcagagag ggagtggcca a                       3701
```

<210> SEQ ID NO 63
<211> LENGTH: 1061
<212> TYPE: DNA
<213> ORGANISM: Artificial Sequence
<220> FEATURE:
<223> OTHER INFORMATION: CASI promoter region

<400> SEQUENCE: 63

```
tagggaggtc ctgcacgtta cataacttac ggtaaatggc ccgcctggct gaccgcccaa     60 cgaccccgc ccattgacgt caataatgac gtatgttccc atagtaacgc caatagggac    120
tttccattga cgtcaatggg tggagtattt acggtaaact gcccacttgg cagtacatca    180
```

| | |
|---|---|
| agtgtatcat atgccaagta cgccccctat tgacgtcaat gacggtaaat ggcccgcctg | 240 |
| gcattatgcc cagtacatga ccttatggga ctttcctact tggcagtaca tctacgtatt | 300 |
| agtcatcgct attaccatgg tcgaggtgag ccccacgttc tgcttcactc tccccatctc | 360 |
| ccccccctcc caccccccaa ttttgtattt atttattttt taattatttt gtgcagcgat | 420 |
| ggggggcgggg ggggggggggg gcgcgcgcca ggcggggcgg ggcggggcga ggggcggggc | 480 |
| ggggcgaggc ggagaggtgc ggcggcagcc aatcagagcg gcgcgctccg aaagtttcct | 540 |
| tttatggcga ggcggcggcg gcggcggccc tataaaaagc gaagcgcgcg gcgggcggga | 600 |
| gtcgctgcgc gctgccttcg ccccgtgccc cgctccgccg ccgcctcgcg ccgcccgccc | 660 |
| cggctctgac tgaccgcgtt actaaaacag gtaagtccgg cctccgcgcc gggttttggc | 720 |
| gcctcccgcg ggcgcccccc tcctcacggc gagcgctgcc acgtcagacg aagggcgcag | 780 |
| cgagcgtcct gatccttccg cccggacgct caggacagcg gcccgctgct cataagactc | 840 |
| ggccttagaa ccccagtatc agcagaagga cattttagga cgggacttgg gtgactctag | 900 |
| ggcactggtt ttctttccag agagcggaac aggcgaggaa aagtagtccc ttctcggcga | 960 |
| ttctgcggag ggatctccgt ggggcggtga acgccgatga tgcctctact aaccatgttc | 1020 |
| atgttttctt ttttttttcta caggtcctgg gtgacgaaca g | 1061 |

<210> SEQ ID NO 64
<211> LENGTH: 2630
<212> TYPE: DNA
<213> ORGANISM: Artificial Sequence
<220> FEATURE:
<223> OTHER INFORMATION: pHMI-hPAH-TC-013 transfer genome

<400> SEQUENCE: 64

| | |
|---|---|
| tagggaggtc ctgcacgtta cataacttac ggtaaatggc ccgcctggct gaccgcccaa | 60 |
| cgaccccgc ccattgacgt caataatgac gtatgttccc atagtaacgc caatagggac | 120 |
| tttccattga cgtcaatggg tggagtattt acgtaaact gcccacttgg cagtacatca | 180 |
| agtgtatcat atgccaagta cgccccctat tgacgtcaat gacggtaaat ggcccgcctg | 240 |
| gcattatgcc cagtacatga ccttatggga ctttcctact tggcagtaca tctacgtatt | 300 |
| agtcatcgct attaccatgg tcgaggtgag ccccacgttc tgcttcactc tccccatctc | 360 |
| ccccccctcc caccccccaa ttttgtattt atttattttt taattatttt gtgcagcgat | 420 |
| ggggggcgggg ggggggggggg gcgcgcgcca ggcggggcgg ggcggggcga ggggcggggc | 480 |
| ggggcgaggc ggagaggtgc ggcggcagcc aatcagagcg gcgcgctccg aaagtttcct | 540 |
| tttatggcga ggcggcggcg gcggcggccc tataaaaagc gaagcgcgcg gcgggcggga | 600 |
| gtcgctgcgc gctgccttcg ccccgtgccc cgctccgccg ccgcctcgcg ccgcccgccc | 660 |
| cggctctgac tgaccgcgtt actaaaacag gtaagtccgg cctccgcgcc gggttttggc | 720 |
| gcctcccgcg ggcgcccccc tcctcacggc gagcgctgcc acgtcagacg aagggcgcag | 780 |
| cgagcgtcct gatccttccg cccggacgct caggacagcg gcccgctgct cataagactc | 840 |
| ggccttagaa ccccagtatc agcagaagga cattttagga cgggacttgg gtgactctag | 900 |
| ggcactggtt ttctttccag agagcggaac aggcgaggaa aagtagtccc ttctcggcga | 960 |
| ttctgcggag ggatctccgt ggggcggtga acgccgatga tgcctctact aaccatgttc | 1020 |
| atgttttctt ttttttttcta caggtcctgg gtgacgaaca ggccaccatg tccaccgctg | 1080 |
| tgctggagaa ccctggcctg gggaggaaac tgtcagactt cggcaggag acttcataca | 1140 |
| ttgaggataa ctgtaaccag aatggcgcca tctctctgat cttcagcctg aaggaggaag | 1200 |

```
tgggcgccct ggcaaaggtg ctgcgcctgt ttgaggagaa cgacgtgaat ctgacccaca    1260
tcgagtcccg gccttctaga ctgaagaagg acgagtacga gttctttacc cacctggata    1320
agcggtccct gccagccctg acaaacatca tcaagatcct gaggcacgac atcggagcaa    1380
ccgtgcacga gctgtctcgg gacaagaaga aggataccgt gccctggttc cctcggacaa    1440
tccaggagct ggatagattt gccaaccaga tcctgtctta cggagcagag ctggacgcag    1500
atcaccctgg cttcaaggac ccagtgtatc gggcccggag aaagcagttt gccgatatcg    1560
cctacaatta taggcacgga cagccaatcc ctcgcgtgga gtatatggag gaggagaaga    1620
agacctgggg cacagtgttc aagaccctga agagcctgta caagacacac gcctgctacg    1680
agtataacca catcttcccc ctgctggaga agtattgtgg ctttcacgag acaatatcc     1740 ctcagctgga ggacgtgagc cagttcctgc agacctgcac aggctttagg ctgaggccag    1800
tggcaggact gctgagctcc cgggacttcc tgggaggact ggccttcaga gtgtttcact    1860
gcacccagta catcaggcac ggctccaagc caatgtatac accagagccc gacatctgtc    1920
acgagctgct gggccacgtg cccctgttta gcgatagatc cttcgcccag ttttcccagg    1980
agatcggact ggcatctctg ggagcacctg acgagtacat cgagaagctg gccaccatct    2040
attggttcac agtggagttt ggcctgtgca agcagggcga tagcatcaag gcctacggag    2100
caggactgct gtctagcttc ggcgagctgc agtattgtct gtccgagaag ccaaagctgc    2160
tgcccctgga gctggagaag accgccatcc agaactacac cgtgacagag ttccagcccc    2220
tgtactatgt ggccgagtct tttaacgatg ccaaggagaa ggtgagaaat ttcgccgcca    2280
caatccctag gcccttcagc gtgcggtacg acccttatac ccagaggatc gaggtgctgg    2340
ataatacaca gcagctgaag atcctggctg actcaatcaa tagcgaaatc ggaatcctgt    2400
gctccgccct gcagaaaatc aaatgaatcg tagatccaga catgataaga tacattgatg    2460
agtttggaca aaccacaact agaatgcagt gaaaaaaatg cttttatttgt gaaatttgtg    2520 atgctattgc tttatttgta accattataa gctgcaataa acaagttaac aacaacaatt    2580
gcattcattt tatgtttcag gttcagggg aggtgtggga ggttttttaa                2630
```

<210> SEQ ID NO 65
<211> LENGTH: 3011
<212> TYPE: DNA
<213> ORGANISM: Artificial Sequence
<220> FEATURE:
<223> OTHER INFORMATION: pHMI-hPAH-TC-013 transfer genome

<400> SEQUENCE: 65

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctggagg ggtggagtcg tgacgtgaat tacgtcatag      180
ggttagggag gtcctgcacg ttacataact tacggtaaat ggcccgcctg gctgaccgcc      240
caacgacccc cgcccattga cgtcaataat gacgtatgtt cccatagtaa cgccaatagg      300
gactttccat tgacgtcaat gggtggagta tttacggtaa actgcccact tggcagtaca      360
tcaagtgtat catatgccaa gtacgccccc tattgacgtc aatgacggta aatggcccgc      420
ctggcattat gcccagtaca tgaccttatg ggactttcct acttggcagt acatctacgt      480
attagtcatc gctattacca tggtcgaggt gagccccacg ttctgcttca ctctccccat      540 ctccccccc tccccacccc caattttgta tttatttatt ttttaattat tttgtgcagc      600
```

```
gatggggcg gggggggggg ggggcgcgcg ccaggcgggg cggggcgggg cgagggggcgg    660
ggcggggcga ggcggagagg tgcgcggca gccaatcaga gcggcgcgct ccgaaagttt    720
ccttttatgg cgaggcggcg gcggcggcgg ccctataaaa agcgaagcgc gcggcgggcg    780
ggagtcgctg cgcgctgcct tcgcccgtg ccccgctccg ccgccgcctc gcgccgcccg    840
ccccggctct gactgaccgc gttactaaaa caggtaagtc cggcctccgc gccgggtttt    900
ggcgcctccc gcgggcgccc ccctcctcac ggcgagcgct gccacgtcag acgaagggcg    960
cagcgagcgt cctgatcctt ccgcccggac gctcaggaca gcggcccgct gctcataaga   1020
ctcggcctta gaaccccagt atcagcagaa ggacattta ggacgggact tgggtgactc   1080
tagggcactg gttttctttc cagagagcgg aacaggcgag gaaaagtagt cccttctcgg   1140
cgattctgcg gagggatctc cgtgggcgg tgaacgccga tgatgcctct actaaccatg   1200
ttcatgtttt ctttttttt ctacaggtcc tgggtgacga acaggccacc atgtccaccg   1260
ctgtgctgga gaaccctggg ctgggagga aactgtcaga cttcgggcag gagacttcat   1320
acattgagga taactgtaac cagaatggcg ccatctctct gatcttcagc ctgaaggagg   1380
aagtgggcgc cctggcaaag gtgctgcgcc tgtttgagga aacgacgtg aatctgaccc   1440
acatcgagtc ccgccttct agactgaaga aggacgagta cgagttcttt acccacctgg   1500
ataagcggtc cctgccagcc ctgacaaaca tcatcaagat cctgaggcac gacatcggag   1560
caaccgtgca cgagctgtct cgggacaaga agaaggatac cgtgccctgg ttccctcgga   1620
caatccagga gctggataga tttgccaacc agatcctgtc ttacggagca gagctggacg   1680
cagatcaccc tggcttcaag gacccagtgt atcgggcccg gagaaagcag tttgccgata   1740
tcgcctacaa ttataggcac ggacagccaa tccctcgcgt ggagtatatg gaggaggaga   1800
agaagacctg gggcacagtg ttcaagaccc tgaagagcct gtacaagaca cacgcctgct   1860
acgagtataa ccacatcttc cccctgctgg agaagtattg tggctttcac gaggacaata   1920
tccctcagct ggaggacgtg agccagttcc tgcagacctg cacaggcttt aggctgaggc   1980
cagtggcagg actgctgagc tcccgggact tcctgggagg actggccttc agagtgtttc   2040
actgcaccca gtacatcagg cacggctcca gccaatgta tacaccagag cccgacatct   2100
gtcacgagct gctgggccac gtgcccctgt ttagcgatag atccttcgcc cagttttccc   2160
aggagatcgg actggcatct ctgggagcac ctgacgagta catcgagaag ctggccacca   2220
tctattggtt cacagtggag tttggcctgt gcaagcaggg cgatagcatc aaggcctacg   2280
gagcaggact gctgtctagc ttcggcgagc tgcagtattg tctgtccgag aagccaaagc   2340
tgctgcccct ggagctggag aagaccgcca tccagaacta caccgtgaca gagttccagc   2400
ccctgtacta tgtggccgag tcttttaacg atgccaagga aaggtgaga atttcgccg   2460
ccacaatccc taggcccttc agcgtgcggt acgacccta tacccagagg atcgaggtgc   2520
tggataatac acagcagctg aagatcctgg ctgactcaat caatagcgaa atcggaatcc   2580
tgtgctccgc cctgcagaaa atcaaatgaa tcgtagatcc agacatgata agatacattg   2640
atgagtttgg acaaaccaca actagaatgc agtgaaaaaa atgctttatt tgtgaaattt   2700
gtgatgctat tgctttattt gtaaccatta taagctgcaa taaacaagtt aacaacaaca   2760
attgcattca ttttatgttt caggttcagg gggaggtgtg ggaggttttt taagcttgtt   2820
taaacgtacg tagataagta gcatggcggg ttaatcatta actacaagga accctagtg   2880
atggagttgg ccactccctc tctgcgcgct cgctcgctca ctgaggccgg gcgaccaaag   2940
gtcgcccgac gcccgggctt tgcccgggcg gcctcagtga gcgagcgagc gcgcagagag   3000
```

-continued

| | |
|---|---|
| ggagtggcca a | 3011 |

<210> SEQ ID NO 66
<211> LENGTH: 913
<212> TYPE: DNA
<213> ORGANISM: Artificial Sequence
<220> FEATURE:
<223> OTHER INFORMATION: hAAT promoter region

<400> SEQUENCE: 66

| | |
|---|---|
| tagggaggtc ctgcacagaa ggggaggagg gggcagcagc tgtctgacca ctgttggtct | 60 |
| tgcaacttgt gtccccaggt taattttaa aaagcagtca aaagtccaag tggcccttgg | 120 |
| cagcatttac tctctctgtt tgctctggtt aataatctca ggagcacaaa cattcctgga | 180 |
| ggcaggagaa gaaatcaaca tcctggactt atcctctggg cctctcccca cccccaggat | 240 |
| tgtaactgaa atgcttcact ggtgctcctt ttgttttaag gcattggatc ttcatagcta | 300 |
| ctgatcgtgc ccaagcacac agtatctgca gcaaccactt aggcctccag gaatgtggtg | 360 |
| accattgacc ctaattcatt ccccttcatg gatcctatgt aaccatcctc caaaaagagc | 420 |
| tttcgcaaac tcaaataaac acaggaaagg aagaccttct tatctttgag agtatatgtt | 480 |
| tagccctata gctctaaccc actctgatct cccagggcgg cagtaagtct tcagcatcag | 540 |
| gcattttggg gtgactcagt aaatggtaga tcttgctacc agtggaacag ccactaagga | 600 |
| ttctgcagtg agagcagagg gccagctaag tggtactctc ccagagactg tctgactcac | 660 |
| gccacccct ccaccttgga cacaggacgc tgtggtttct gagccaggta caatgactcc | 720 |
| tttcggtaag tgcagtggaa gctgtacact gcccaggcaa agcgtccggg cagcgtaggc | 780 |
| gggcgactca gatcccagcc agtggactta gcccctgttt gctcctccga taactggggt | 840 |
| gaccttggtt aatattcacc agcagcctcc cccgttgccc ctctggatcc actgcttaaa | 900 |
| tacggacgag gac | 913 |

<210> SEQ ID NO 67
<211> LENGTH: 2600
<212> TYPE: DNA
<213> ORGANISM: Artificial Sequence
<220> FEATURE:
<223> OTHER INFORMATION: pHMI-hPAH-TC-017 transfer genome

<400> SEQUENCE: 67

| | |
|---|---|
| tagggaggtc ctgcacagaa ggggaggagg gggcagcagc tgtctgacca ctgttggtct | 60 |
| tgcaacttgt gtccccaggt taattttaa aaagcagtca aaagtccaag tggcccttgg | 120 |
| cagcatttac tctctctgtt tgctctggtt aataatctca ggagcacaaa cattcctgga | 180 |
| ggcaggagaa gaaatcaaca tcctggactt atcctctggg cctctcccca cccccaggat | 240 |
| tgtaactgaa atgcttcact ggtgctcctt ttgttttaag gcattggatc ttcatagcta | 300 |
| ctgatcgtgc ccaagcacac agtatctgca gcaaccactt aggcctccag gaatgtggtg | 360 |
| accattgacc ctaattcatt ccccttcatg gatcctatgt aaccatcctc caaaaagagc | 420 |
| tttcgcaaac tcaaataaac acaggaaagg aagaccttct tatctttgag agtatatgtt | 480 |
| tagccctata gctctaaccc actctgatct cccagggcgg cagtaagtct tcagcatcag | 540 |
| gcattttggg gtgactcagt aaatggtaga tcttgctacc agtggaacag ccactaagga | 600 |
| ttctgcagtg agagcagagg gccagctaag tggtactctc ccagagactg tctgactcac | 660 |
| gccacccct ccaccttgga cacaggacgc tgtggtttct gagccaggta caatgactcc | 720 |

| | |
|---|---:|
| tttcggtaag tgcagtggaa gctgtacact gcccaggcaa agcgtccggg cagcgtaggc | 780 |
| gggcgactca gatcccagcc agtggactta gcccctgttt gctcctccga taactggggt | 840 |
| gaccttggtt aatattcacc agcagcctcc cccgttgccc ctctggatcc actgcttaaa | 900 |
| tacgacgag gacgctagcg ccggcaagag gtaagggttt aagggatggt tggttggtgg | 960 |
| ggtattaatg tttaattacc tggagcacct gcctgaaatc acttttttc aggttggtta | 1020 |
| attaaggatc cgccaccatg tccaccgctg tgctggagaa ccctgggctg gggaggaaac | 1080 |
| tgtcagactt cgggcaggag acttcataca ttgaggataa ctgtaaccag aatggcgcca | 1140 |
| tctctctgat cttcagcctg aaggaggaag tgggcgccct ggcaaaggtg ctgcgcctgt | 1200 |
| ttgaggagaa cgacgtgaat ctgacccaca tcgagtcccg gccttctaga ctgaagaagg | 1260 |
| acgagtacga gttctttacc cacctggata agcggtccct gccagccctg acaaacatca | 1320 |
| tcaagatcct gaggcacgac atcggagcaa ccgtgcacga gctgtctcgg gacaagaaga | 1380 |
| aggataccgt gccctggttc cctcggacaa tccaggagct ggatagattt gccaaccaga | 1440 |
| tcctgtctta cggagcagag ctggacgcag atcaccctgg cttcaaggac ccagtgtatc | 1500 |
| gggcccggag aaagcagttt gccgatatcg cctacaatta taggcacgga cagccaatcc | 1560 |
| ctcgcgtgga gtatatggag gaggagaaga agacctgggg cacagtgttc aagaccctga | 1620 |
| agagcctgta caagacacac gcctgctacg agtataacca catcttcccc ctgctggaga | 1680 |
| agtattgtgg ctttcacgag gacaatatcc ctcagctgga ggacgtgagc cagttcctgc | 1740 |
| agacctgcac aggctttagg ctgaggccag tggcaggact gctgagctcc cgggacttcc | 1800 |
| tgggaggact ggccttcaga gtgtttcact gcacccagta catcaggcac ggctccaagc | 1860 |
| caatgtatac accagagccc gacatctgtc acgagctgct gggccacgtg cccctgttta | 1920 |
| gcgatagatc cttcgcccag ttttcccagg agatcggact ggcatctctg ggagcacctg | 1980 |
| acgagtacat cgagaagctg gccaccatct attggttcac agtggagttt ggcctgtgca | 2040 |
| agcagggcga tagcatcaag gcctacggag caggactgct gtctagcttc ggcgagctgc | 2100 |
| agtattgtct gtccgagaag ccaaagctgc tgccctgga gctggagaag accgccatcc | 2160 |
| agaactacac cgtgacagag ttccagcccc tgtactatgt ggccgagtct tttaacgatg | 2220 |
| ccaaggagaa ggtgagaaat ttcgccgcca caatccctag gcccttcagc gtgcggtacg | 2280 |
| acccttatac ccagaggatc gaggtgctgg ataatacaca gcagctgaag atcctggctg | 2340 |
| actcaatcaa tagcgaaatc ggaatcctgt gctccgccct gcagaaaatc aaatgaatcg | 2400 |
| tagatccaga catgataaga tacattgatg agtttggaca aaccacaact agaatgcagt | 2460 |
| gaaaaaaatg ctttatttgt gaaatttgtg atgctattgc tttatttgta accattataa | 2520 |
| gctgcaataa acaagttaac aacaacaatt gcattcattt tatgtttcag gttcagggg | 2580 |
| aggtgtggga ggttttttaa | 2600 |

<210> SEQ ID NO 68
<211> LENGTH: 2981
<212> TYPE: DNA
<213> ORGANISM: Artificial Sequence
<220> FEATURE:
<223> OTHER INFORMATION: pHMI-hPAH-TC-017 transfer genome

<400> SEQUENCE: 68

| | |
|---|---:|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |

```
ggttagggag gtcctgcaca gaaggggagg aggggggcagc agctgtctga ccactgttgg   240
tcttgcaact tgtgtcccca ggttaatttt taaaaagcag tcaaaagtcc aagtggccct   300
tggcagcatt tactctctct gtttgctctg gttaataatc tcaggagcac aaacattcct   360
ggaggcagga gaagaaatca acatcctgga cttatcctct gggcctctcc ccaccccag    420 gattgtaact gaaatgcttc actggtgctc cttttgtttt aaggcattgg atcttcatag   480
ctactgatcg tgcccaagca cacagtatct gcagcaacca cttaggcctc caggaatgtg   540
gtgaccattg accctaattc attccccttc atggatccta tgtaaccatc ctccaaaaag   600
agctttcgca aactcaaata aacacaggaa aggaagacct tcttatcttt gagagtatat   660
gtttagccct atagctctaa cccactctga tctcccaggg cggcagtaag tcttcagcat   720
caggcatttt ggggtgactc agtaaatggt agatcttgct accagtggaa cagccactaa   780
ggattctgca gtgagagcag agggccagct aagtggtact ctcccagaga ctgtctgact   840
cacgccaccc cctccacctt ggacacagga cgctgtggtt tctgagccag gtacaatgac   900
tcctttcggt aagtgcagtg gaagctgtac actgcccagg caaagcgtcc gggcagcgta   960
ggcgggcgac tcagatccca gccagtggac ttagcccctg tttgctcctc cgataactgg  1020
ggtgaccttg gttaatattc accagcagcc tcccccgttg cccctctgga tccactgctt  1080
aaatacggac gaggacgcta cgccggcaa gaggtaaggg tttaagggat ggttggttgg   1140
tggggtatta atgtttaatt acctggagca cctgcctgaa atcacttttt ttcaggttgg   1200
ttaattaagg atccgccacc atgtccaccg ctgtgctgga aaccctggg ctggggagga   1260 aactgtcaga cttcgggcag gagacttcat acattgagga taactgtaac cagaatggcg   1320
ccatctctct gatcttcagc ctgaaggagg aagtgggcgc cctggcaaag gtgctgcgcc   1380
tgtttgagga gaacgacgtg aatctgaccc acatcgagtc ccggccttct agactgaaga   1440
aggacgagta cgagttcttt acccacctgg ataagcggtc cctgccagcc ctgacaaaca   1500
tcatcaagat cctgaggcac gacatcggag caaccgtgca cgagctgtct cgggacaaga   1560
agaaggatac cgtgccctgg ttccctcgga caatccagga gctggataga tttgccaacc   1620
agatcctgtc ttacggagca gagctggacg cagatcaccc tggcttcaag gacccagtgt   1680
atcgggcccg gagaaagcag tttgccgata tcgcctacaa ttataggcac ggacagccaa   1740
tccctcgcgt ggagtatatg gaggaggaga agaagacctg gggcacagtg ttcaagaccc   1800
tgaagagcct gtacaagaca cacgcctgct acgagtataa ccacatcttc ccctgctgg    1860 agaagtattg tggctttcac gaggacaata tccctcagct ggaggacgtg agccagttcc   1920
tgcagacctg cacaggcttt aggctgaggc cagtggcagg actgctgagc tcccgggact   1980
tcctgggagg actggccttc agagtgtttc actgcaccca gtacatcagg cacggctcca   2040
agccaatgta taccagag cccgacatct gtcacgagct gctgggccac gtgcccctgt    2100
ttagcgatag atccttcgcc cagttttccc aggagatcgg actggcatct ctgggagcac   2160
ctgacgagta catcgagaag ctggccacca tctattggtt cacagtggag tttggcctgt   2220
gcaagcaggg cgatagcatc aaggcctacg gagcaggact gctgtctagc ttcggcgagc   2280
tgcagtattg tctgtccgag aagccaaagc tgctgccct ggagctggag aagaccgcca    2340
tccagaacta caccgtgaca gagttccagc ccctgtacta tgtggccgag tcttttaacg   2400
atgccaagga aggtgagaa aatttcgccg ccacaatccc taggcccttc agcgtgcggt     2460 acgacccta tacccagagg atcgaggtgc tggataatac acagcagctg aagatcctgg    2520
```

| | | | |
|---|---|---|---|
| ctgactcaat | caatagcgaa | atcggaatcc tgtgctccgc cctgcagaaa atcaaatgaa | 2580 |
| tcgtagatcc | agacatgata | agatacattg atgagtttgg acaaaccaca actagaatgc | 2640 |
| agtgaaaaaa | atgctttatt | tgtgaaattt gtgatgctat tgctttattt gtaaccatta | 2700 |
| taagctgcaa | taaacaagtt | aacaacaaca attgcattca ttttatgttt caggttcagg | 2760 |
| gggaggtgtg | ggaggttttt | taagcttgtt taaacgtacg tagataagta gcatggcggg | 2820 |
| ttaatcatta | actacaagga | acccctagtg atggagttgg ccactccctc tctgcgcgct | 2880 |
| cgctcgctca | ctgaggccgg | gcgaccaaag gtcgcccgac gcccgggctt tgcccgggcg | 2940 |
| gcctcagtga | gcgagcgagc | gcgcagagag ggagtggcca a | 2981 |

<210> SEQ ID NO 69
<211> LENGTH: 1359
<212> TYPE: DNA
<213> ORGANISM: Artificial Sequence
<220> FEATURE:
<223> OTHER INFORMATION: pHMI-hPAH-TC-018 PAH sequence

<400> SEQUENCE: 69

| | | | |
|---|---|---|---|
| atgtccactg | ctgtgctgga | gaacccaggc ctgggcagga agttgagtga ctttgggcag | 60 |
| gagacctcct | acatagaaga | caattgcaat cagaatgggg ccatctctct gatcttcagc | 120 |
| cttaaagagg | aggtgggtgc | tctggcaaaa gtgctcagac tctttgagga gaatgatgtg | 180 |
| aatctcaccc | acattgaatc | caggcccagc agactcaaaa aggatgaata tgaattcttc | 240 |
| acccacttgg | acaaaaggtc | cttacctgcc cttacaaata tcatcaaaat tttgagacat | 300 |
| gacatagggg | caactgtaca | tgaactgagt agagataaaa aaaagacac agtcccctgg | 360 |
| ttccccagga | ccatccagga | attggacagg tttgcaaacc agatactgag ctatggtgct | 420 |
| gagttggatg | ctgatcaccc | aggcttcaag gaccctgtgt acagagcaag agaaaagcag | 480 |
| tttgctgaca | ttgcctacaa | ttacaggcac ggccaaccca ttcctagagt cgagtacatg | 540 |
| gaagaagaga | agaaaacctg | ggcactgtc ttcaagaccc tgaagtcact gtacaagaca | 600 |
| catgcctgct | atgaatacaa | ccacatattt ccactcctag agaaatactg tggattccat | 660 |
| gaggacaata | taccccaatt | ggaggatgtc tcacagtttc tgcagacttg tacaggtttt | 720 |
| aggctgaggc | cagtggctgg | gcttctcagc agcagggact tcctgggtgg actggccttc | 780 |
| agggtgtttc | actgtacaca | atacatcaga catggtagca aaccaatgta tactcctgaa | 840 |
| ccagacatct | gccatgagct | gcttgggcat gtgcctctgt tttcagacag gtcctttgct | 900 |
| cagttctcac | aagagattgg | gctagcttca ctggagctc cagatgagta tattgaaaaa | 960 |
| ctggcaacaa | tttactggtt | tacagtggag tttggacttt gtaagcaggg agactccatc | 1020 |
| aaggcctatg | gtgcaggatt | gttgtcttcc tttgggaac tgcaatattg tctctctgaa | 1080 |
| aagcctaagt | tgctaccact | ggagcttgag aagactgcca ttcagaacta cacagtgact | 1140 |
| gaattccagc | cctctacta | tgttgcagag tctttcaatg atgccaagga aaaggttagg | 1200 |
| aactttgctg | caacaatccc | cagacctttc agtgtgaggt atgaccccta cactcagaga | 1260 |
| attgaagttc | tggataacac | ccagcagctg aaaattctgg cagatagtat caactctgag | 1320 |
| attggaatcc | tgtgttctgc | cctgcagaag atcaagtga | 1359 |

<210> SEQ ID NO 70
<211> LENGTH: 1359
<212> TYPE: DNA
<213> ORGANISM: Artificial Sequence
<220> FEATURE:
<223> OTHER INFORMATION: pHMI-hPAH-TC-019 PAH sequence

<400> SEQUENCE: 70

```
atgtccactg ctgtgctgga gaacccaggc ctgggcagga agttgagtga ctttgggcag      60
gagacctcct acatagaaga caattgcaat cagaatgggg ccatctctct gatcttcagc     120
cttaaagagg aggtgggtgc tctggcaaaa gtgctcagac tgtttgagga gaatgatgtg     180
aatctcaccc acattgaatc caggcccagc agactcaaaa aggatgaata tgaattcttc     240
acccacttgg acaaaaggtc cttacctgcc cttacaaata tcatcaaaat tttgagacat     300
gacatagggg caactgtaca tgaactgagt agagataaaa aaaagacac agtcccctgg     360
ttccccagga ccatccagga attggacagg tttgcaaacc agatactgag ctatggtgct     420
gagttggatg ctgatcaccc aggcttcaag accctgtgt acagagcaag gagaaagcag     480
tttgctgaca ttgcctacaa ttacaggcac ggccaaccca ttcctagagt cgagtacatg     540
gaagaagaga agaaaacctg gggcactgtc ttcaagaccc tgaagtcact gtacaagaca     600
catgcctgct atgaatacaa ccacatattt ccactcctag agaaatactg tggattccat     660
gaggacaata taccccaatt ggaggatgtc tcacagtttc tgcagacttg tacaggtttt     720
aggctgaggc cagtggctgg gctcctcagc agcagggact tcctgggtgg actggccttt     780
cgagttttcc actgtactca gtatatcaga catggctcca agcctatgta taccccagaa     840
cctgacatct gccatgaact gcttgggcat gtgcctctct tttcagaccg ttcctttgcc     900
cagtttctc aggagattgg actagccagc ctaggtgcac cagatgagta cattgagaag     960
ttagcaacca tttactggtt cacagtggag ttcggtctct gcaagcaagg ggactcaata    1020
aaggcctatg gagcaggcct cctgtcaagt tttggagaac tccaatactg cctatctgag    1080
aagcctaaat tattacccct tggaactaga aaaactgcaa tacagaacta cacagtgact    1140
gagtttcagc cactctacta tgtggcagag tcctttaatg atgccaaaga aaaggtccga    1200
aattttgctg caacaattcc caggcccttc tctgttcgct atgatccata cacccaaaga    1260
attgaagtcc tagataacac ccagcagctg aaaatcctgg cagacagtat caactctgaa    1320
attggaatcc tctgttctgc cctgcagaag atcaagtga                            1359
```

<210> SEQ ID NO 71
<211> LENGTH: 1359
<212> TYPE: DNA
<213> ORGANISM: Artificial Sequence
<220> FEATURE:
<223> OTHER INFORMATION: pHMI-hPAH-TC-020 PAH sequence

<400> SEQUENCE: 71

```
atgtccactg ctgtgctgga gaacccaggc ctgggcagga agttgagtga ctttgggcag      60
gagacctcct acatagaaga caattgcaat cagaatgggg ccatctctct gatcttcagc     120
cttaaagagg aggtgggtgc tctggcaaaa gtgctcagac tctttgagga gaatgatgtg     180
aatctcaccc acattgaatc caggcccagc agactcaaaa aggatgaata tgaattcttc     240
acccacttgg acaaaaggtc cttacctgcc cttacaaata tcatcaaaat tttgagacat     300
gacatagggg caactgtaca tgaactgagt agagataaaa aaaagacac agtcccctgg     360
ttccccagga ccatccagga attggacagg tttgcaaacc agatactgag ctatggtgct     420
gagttggatg ctgatcaccc aggcttcaag accctgtgt acagagcaag gagaaagcag     480
tttgctgaca ttgcctacaa ttacaggcac ggccaaccca ttcctagagt cgagtacatg     540
gaagaagaga agaaaacctg gggcactgtc ttcaagaccc tgaagtcact gtacaagaca     600
```

| | |
|---|---|
| catgcctgct atgaatacaa ccacatattt ccactcctag agaaatactg tggattccat | 660 |
| gaggacaata tacccccaatt ggaggatgtc tcacagtttc tgcagacttg tacaggtttt | 720 |
| aggctgaggc cagtggctgg gcttctcagc agcagggact tcctgggtgg actggccttc | 780 |
| agggtgtttc actgtacaca atacatcaga catggtagca aaccaatgta tactcctgaa | 840 |
| ccagacatct gccatgagct gcttgggcat gtgcctctgt tcagcgacag aagctttgct | 900 |
| cagtttagcc aggagattgg gctggccagc ctgggcgccc tgatgagta tatcgagaaa | 960 |
| ctggccacaa tctactggtt cacagtggag ttcggcctgt gcaagcaggg cgactcaatc | 1020 |
| aaggcctatg cgccggcct gctgagcagc ttcggcgaac tgcagtactg cctgagcgag | 1080 |
| aagcccaagc tgctgccact ggagctggag aaaaccgcca tccagaacta cacagtgaca | 1140 |
| gagttccagc ctctgtacta tgtggccgag agcttcaacg atgccaagga gaaggtgagg | 1200 |
| aattttgccg ccactatccc caggcctttc tccgtgagat atgaccccta cacccagcga | 1260 |
| atcgaggtgc tggacaatac ccagcagctg aagatcctgg ccgattccat caactctgag | 1320 |
| atcggcattc tgtgtagcgc cctgcagaag attaagtga | 1359 |

<210> SEQ ID NO 72
<211> LENGTH: 1359
<212> TYPE: DNA
<213> ORGANISM: Artificial Sequence
<220> FEATURE:
<223> OTHER INFORMATION: pHMI-hPAH-TC-021 PAH sequence

<400> SEQUENCE: 72

| | |
|---|---|
| atgtccactg ctgtgctgga gaacccaggc ctgggaagga agctgagtga ctttggccag | 60 |
| gagacctcct acatagagga caactgcaat cagaacgggg ccatcagcct gatcttcagc | 120 |
| cttaaagagg aggtaggcgc tctggcaaaa gtgctcagac tctttgagga gaatgatgtg | 180 |
| aatctcaccc acattgaatc caggcccagc agactcaaaa aggatgaata tgaattttc | 240 |
| acccacttgg acaaaaggtc cttacctgcc cttacaaata tcatcaaaat tttgagacat | 300 |
| gacatagggg caactgtaca tgaactgagt agagataaaa aaaagacac agtcccctgg | 360 |
| ttccccagga ccatacagga attggacagg tttgcaaacc agatactgag ctatggtgct | 420 |
| gaattggatg ctgatcaccc aggcttcaag gaccctgtgt acagagcacg aagaaagcag | 480 |
| tttgctgaca ttgcctacaa ttacaggcac ggccaaccca ttcctagagt cgagtacatg | 540 |
| gaagaagaaa agaaaacctg ggcactgtgt tcaagaccc tgaagtcact gtacaagaca | 600 |
| catgcctgct atgaatacaa ccacatattt ccactcctag agaaatactg tggattccat | 660 |
| gaggacaaca tacccccaatt ggaggatgtg tcacagtttc tgcagacttg tacaggtttt | 720 |
| aggctgaggc cagtggcagg gcttctcagc agcagggact tcctgggtgg actggccttc | 780 |
| agggtgtttc actgtacaca gtacatcaga catggtagca aaccaatgta tactcctgaa | 840 |
| ccagacatct gccatgagct gcttgggcat gtgcctctgt tttcagacag gtcctttgct | 900 |
| caattctcac aggagattgg actagccagc ctaggtgcac cagatgagta cattgagaag | 960 |
| ttagcaacca tttactggtt cacagtggag ttcggccttt gcaagcaagg ggactcaata | 1020 |
| aaggcctatg agcaggcct cctgtcaagt tttggagaac tacaatactg cctatctgag | 1080 |
| aagcctaaat tattacccctt ggaactagag aaaactgcaa tacagaacta cacagtgact | 1140 |
| gagtttcagc cactctacta tgtggccgag tccttcaatg atgccaaaga aaaggtccga | 1200 |
| aattttgctg caacaattcc caggcctttc tctgttcgct atgatcctta cacccaaaga | 1260 |
| attgaagtcc tagataacac ccagcagctg aagatcctgg ctgatagcat aaacagcgaa | 1320 |

```
attggaatcc tctgttctgc cctgcagaag atcaagtga                              1359
```

<210> SEQ ID NO 73
<211> LENGTH: 1359
<212> TYPE: DNA
<213> ORGANISM: Artificial Sequence
<220> FEATURE:
<223> OTHER INFORMATION: pHMI-hPAH-TC-022 PAH sequence

<400> SEQUENCE: 73

```
atgtccactg ctgtgctgga gaacccaggc ctgggcagga agttgagtga ctttgggcag        60
gagacctcct acatagaaga caattgcaat cagaatgggg ccatctctct gatcttcagc       120
cttaaagagg aggtgggtgc tctggcaaaa gtgctcagac tctttgagga gaatgatgtg       180
aatctcaccc acattgaatc caggcccagc agactcaaaa aggatgaata tgaattcttc       240
acccacttgg acaaaaggtc cttacctgcc cttacaaata tcatcaaaat tttgagacat       300
gacataggggc aactgtaca tgaactgagt agagataaaa aaaaagacac agtcccctgg       360
ttccccagga ccatccagga attggacagg tttgcaaacc agatactgag ctatggtgct       420
gagttggatg ctgatcaccc aggcttcaag gaccctgtgt acagagcaag agaaaagcag       480
tttgctgaca ttgcctacaa ttacaggcac ggccaaccca ttcctagagt cgagtacatg       540
gaagaagaga gaaaacctg gggcactgtc ttcaagaccc tgaagtcact gtacaagaca       600
catgcctgct atgaatacaa ccacatattt ccactcctag agaaatactg tggattccat       660
gaggacaata tacccaatt ggaggatgtc tcacagtttc tgcagacttg tacaggtttt       720
aggctgaggc cagtggctgg gcttctcagc agcagggact tcctgggtgg actggccttt       780
cgagttttcc actgtactca gtatatcaga catggctcca agcccatgta cacccccagaa       840
cctgacatct gccatgaact gcttgggcat gtgcctctgt tttcagaccg ttccttgcc       900
cagttttctc aggagattgg actagccagc ctaggtgcac cagatgagta cattgagaag       960
ttagcaacca tttactggtt cacagtggag ttcggccttt gcaagcaagg ggactcaata      1020
aaggcctatg gagcaggcct cctgtcaagt tttggagaac tacaatactg cctatctgag      1080
aagcctaaat tattacccctt ggaactagaa aaaactgcaa tacagaacta cacagtgact      1140
gagtttcagc cactctacta tgtggcagag tcctttaatg atgccaaaga aaaggtccga      1200
aattttgctg caacaattcc caggcctttc tctgttcgct atgatccata cacccaaaga      1260
attgaagtcc tagataacac ccagcagctg aaaatcctgg cagacagcat caactctgaa      1320
attggaatcc tctgttctgc cctgcagaag atcaagtga                             1359
```

<210> SEQ ID NO 74
<211> LENGTH: 2111
<212> TYPE: DNA
<213> ORGANISM: Artificial Sequence
<220> FEATURE:
<223> OTHER INFORMATION: pHMI-hPAH-TC-018 transfer genome

<400> SEQUENCE: 74

```
ccctaaaatg ggcaaacatt gcaagcagca acagcaaaac acacagccct ccctgcctgc        60
tgaccttgga gctggggcag aggtcagaga cctctctggg cccatgccac ctccaacatc       120
cactcgaccc cttggaattt cggtggagag gagcagaggt tgtcctggcg tggtttaggt       180
agtgtgagag gggaatgact cctttcggta agtgcagtgg aagctgtaca ctgcccaggc       240
aaagcgtccg ggcagcgtag gcgggcgact cagatcccag ccagtggact tagcccctgt       300
```

```
ttgctcctcc gataactggg gtgaccttgg ttaatattca ccagcagcct ccccgttgc      360
ccctctggat ccactgctta aatacggacg aggacagggc cctgtctcct cagcttcagg    420
caccaccact gacctgggac agtgaatcct ctaaggtaaa tataaaattt ttaagtgtat    480
aatgtgttaa actactgatt ctaattgttt ctctctttta gattccaacc tttggaactg   540
accgccacca tgtccactgc tgtgctggag aacccaggcc tgggcaggaa gttgagtgac   600
tttgggcagg agacctccta catagaagac aattgcaatc agaatggggc catctctctg   660
atcttcagcc ttaaagagga ggtgggtgct ctggcaaaag tgctcagact cttttgaggag  720
aatgatgtga atctcaccca cattgaatcc aggcccagca gactcaaaaa ggatgaatat   780
gaattcttca cccacttgga caaaaggtcc ttacctgccc ttacaaatat catcaaaatt   840
ttgagacatg atagggggc aactgtacat gaactgagta gagataaaaa aaaagacaca    900
gtcccctggt tccccaggac catccaggaa ttggacaggt ttgcaaacca gatactgagc   960
tatggtgctg agttggatgc tgatcaccca ggcttcaagg accctgtgta cagagcaagg  1020
agaaagcagt ttgctgacat tgcctacaat tacaggcacg ccaacccat tcctagagtc    1080
gagtacatgg aagaagagaa gaaaacctgg ggcactgtct tcaagaccct gaagtcactg   1140
tacaagacac atgcctgcta tgaatacaac cacatatttc cactcctaga gaaatactgt   1200
ggattccatg aggacaatat accccaattg gaggatgtct cacagtttct gcagacttgt   1260
acaggttta ggctgaggcc agtggctggg cttctcagca gcaggacttcc ctgggtgga    1320
ctggccttca gggtgtttca ctgtacacaa tacatcagac atggtagcaa accaatgtat  1380
actcctgaac cagacatctg ccatgagctg cttgggcatg tgcctctgtt ttcagacagg   1440
tcctttgctc agttctcaca agagattggg ctagcttcac tgggagctcc agatgagtat   1500
attgaaaaac tggcaacaat ttactggttt acagtggagt ttggactttg taagcaggga  1560
gactccatca aggcctatgg tgcaggattg ttgtcttcct ttggggaact gcaatattgt   1620
ctctctgaaa agcctaagtt gctaccactg gagcttgaga agactgccat tcagaactac  1680
acagtgactg aattccagcc cctctactat gttgcagagt cttcaatga tgccaaggag   1740
aaggttagga acttttgctgc aacaatcccc agacctttca gtgtgaggta tgaccctac   1800
actcagagaa ttgaagttct ggataacacc cagcagctga aaattctggc agatagtatc  1860
aactctgaga ttggaatcct gtgttctgcc ctgcagaaga tcaagtgact cgagatccag  1920
acatgataag atacattgat gagtttggac aaaccacaac tagaatgcag tgaaaaaaat  1980
gctttatttg tgaaatttgt gatgctattg ctttattttgt aaccattata agctgcaata  2040
aacaagttaa caacaacaat tgcattcatt ttatgtttca ggttcagggg gaggtgtggg  2100
aggtttttta a                                                        2111
```

<210> SEQ ID NO 75
<211> LENGTH: 2426
<212> TYPE: DNA
<213> ORGANISM: Artificial Sequence
<220> FEATURE:
<223> OTHER INFORMATION: pHMI-hPAH-TC-018 transfer genome

<400> SEQUENCE: 75

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggaatt cacgcgtgga  120
tctgaattca attcacgcgt ggtacctccc taaaatgggc aaacattgca agcagcaaac  180
agcaaacaca cagccctccc tgcctgctga ccttggagct ggggcagagg tcagagacct  240
```

```
ctctgggccc atgccacctc aacatccac tcgacccctt ggaatttcgg tggagaggag     300
cagaggttgt cctggcgtgg tttaggtagt gtgagagggg aatgactcct ttcggtaagt     360
gcagtggaag ctgtacactg cccaggcaaa gcgtccgggc agcgtaggcg ggcgactcag     420
atcccagcca gtgacttag ccctgtttg ctcctccgat aactggggtg accttggtta     480
atattcacca gcagcctccc ccgttgcccc tctggatcca ctgcttaaat acggacgagg     540
acagggccct gtctcctcag cttcaggcac accactgac ctgggacagt gaatcctcta     600
aggtaaatat aaaatttta agtgtataat gtgttaaact actgattcta attgtttctc     660
tcttttagat tccaaccttt ggaactgacc gccaccatgt ccactgctgt gctggagaac     720
ccaggcctgg gcaggaagtt gagtgacttt gggcaggaga cctcctacat agaagacaat     780
tgcaatcaga atgggccat ctctctgatc ttcagcctta agaggaggt gggtgctctg     840
gcaaaagtgc tcagactctt tgaggagaat gatgtgaatc tcacccacat gaatccagg     900
cccagcagac tcaaaagga tgaatatgaa ttcttcaccc acttggacaa aaggtcctta     960
cctgcccta caaatatcat caaaattttg agacatgaca taggggcaac tgtacatgaa    1020
ctgagtagag ataaaaaaaa agacacagtc ccctggttcc ccaggaccat ccaggaattg    1080
gacaggtttg caaaccagat actgagctat ggtgctgagt tggatgctga tcacccaggc    1140
ttcaaggacc ctgtgtacag agcaaggaga aagcagtttg ctgacattgc ctacaattac    1200
aggcacggcc aacccattcc tagagtcgag tacatggaag aagagaagaa aacctggggc    1260
actgtcttca agaccctgaa gtcactgtac aagacacatg cctgctatga atacaaccac    1320
atatttccac tcctagagaa atactgtgga ttccatgagg acaatatacc ccaattggag    1380
gatgtctcac agtttctgca gacttgtaca ggttttaggc tgaggccagt ggctgggctt    1440
ctcagcagca gggacttcct gggtggactg gccttcaggg tgtttcactg tacacaatac    1500
atcagacatg gtagcaaacc aatgtatact cctgaaccag acatctgcca tgagctgctt    1560
gggcatgtgc ctctgttttc agacaggtcc tttgctcagt tctcacaaga gattgggcta    1620
gcttcactgg gagctccaga tgagtatatt gaaaaactgg caacaattta ctggtttaca    1680
gtggagtttg gactttgtaa gcaggagac tccatcaagg cctatggtgc aggattgttg    1740
tcttcctttg gggaactgca atattgtctc tctgaaaagc ctaagttgct accactggag    1800
cttgagaaga ctgccattca gaactacaca gtgactgaat tccagcccct ctactatgtt    1860
gcagagtctt tcaatgatgc caaggagaag gttaggaact tgctgcaac aatccccaga    1920
cctttcagtg tgaggtatga ccctacact cagagaattg aagttctgga taacacccag    1980
cagctgaaaa ttctggcaga tagtatcaac tctgagattg gaatcctgtg ttctgccctg    2040
cagaagatca agtgactcga gatccagaca tgataagata cattgatgag tttgacaaa    2100
ccacaactag aatgcagtga aaaaatgct ttatttgtga aatttgtgat gctattgctt    2160
tatttgtaac cattataagc tgcaataaac aagttaacaa caacaattgc attcatttta    2220
tgtttcaggt tcaggggagg gtgtgggagg tttttttaaag catgctgggg agagatcgat    2280
ctgaggaacc cctagtgatg gagttggcca ctccctctct gcgcgctcgc tcgctcactg    2340
aggccgggcg accaaaggtc gcccgacgcc cgggctttgc ccgggcggcc tcagtgagcg    2400
agcgagcgcg cagagaggga gtggcc                                         2426
```

<210> SEQ ID NO 76
<211> LENGTH: 2111
<212> TYPE: DNA

<213> ORGANISM: Artificial Sequence
<220> FEATURE:
<223> OTHER INFORMATION: pHMI-hPAH-TC-019 transfer genome

<400> SEQUENCE: 76

```
ccctaaaatg ggcaaacatt gcaagcagca aacagcaaac acacagccct ccctgcctgc      60
tgaccttgga gctggggcag aggtcagaga cctctctggg cccatgccac ctccaacatc     120
cactcgaccc cttggaattt cggtggagag gagcagaggt tgtcctggcg tggtttaggt     180
agtgtgagag gggaatgact cctttcggta agtgcagtgg aagctgtaca ctgcccaggc     240
aaagcgtccg ggcagcgtag gcgggcgact cagatcccag ccagtggact tagcccctgt     300
ttgctcctcc gataactggg gtgaccttgg ttaatattca ccagcagcct ccccgttgc      360
ccctctggat ccactgctta aatacggacg aggacagggc cctgtctcct cagcttcagg     420
caccaccact gacctgggac agtgaatcct ctaaggtaaa tataaaattt ttaagtgtat     480
aatgtgttaa actactgatt ctaattgttt ctctctttta gattccaacc tttggaactg     540
accgccacca tgtccactgc tgtgctggag aacccaggcc tgggcaggaa gttgagtgac     600
tttgggcagg agacctccta catagaagac aattgcaatc agaatggggc catctctctg     660
atcttcagcc ttaaagagga ggtgggtgct ctggcaaaag tgctcagact gtttgaggag     720
aatgatgtga atctcaccca cattgaatcc aggcccagca gactcaaaaa ggatgaatat     780
gaattcttca cccacttgga caaaaggtcc ttacctgccc ttacaaatat catcaaaatt     840
ttgagacatg acatagggc aactgtacat gaactgagta gagataaaaa aaaagacaca     900
gtcccctggt tccccaggac catccaggaa ttggacaggt tgcaaaacca gatactgagc     960
tatggtgctg agttggatgc tgatcaccca ggcttcaagg accctgtgta cagagcaagg    1020
agaaagcagt ttgctgacat tgcctacaat tacaggcacg ccaacccat tcctagagtc     1080
gagtacatgg aagaagagaa gaaaacctgg ggcactgtct tcaagaccct gaagtcactg    1140
tacaagacac atgcctgcta tgaatacaac cacatatttc cactcctaga gaaatactgt    1200
ggattccatg aggacaatat accccaattg gaggatgtct cacagtttct gcagacttgt    1260
acaggtttta ggctgaggcc agtggctggg ctcctcagca gcagggactt cctgggtgga    1320
ctggccttc gagttttcca ctgtactcag tatatcagac atggctccaa gcctatgtat    1380
accccagaac ctgacatctg ccatgaactg cttgggcatg tgcctctctt ttcagaccgt    1440
tcctttgccc agtttctca ggagattgga ctagccagcc taggtgcacc agatgagtac     1500
attgagaagt tagcaaccat ttactggttc acagtggagt tcggtctctg caagcaaggg    1560
gactcaataa aggcctatgg agcaggcctc ctgtcaagtt ttggagaact ccaatactgc    1620
ctatctgaga agcctaaatt attacccttg gaactagaaa aaactgcaat acagaactac    1680
acagtgactg agtttcagcc actctactat gtggcagagt cctttaatga tgccaaagaa    1740
aaggtccgaa atttttgctgc aacaattccc aggccttct ctgttcgcta tgatccatac     1800
acccaaagaa ttgaagtcct agataacacc cagcagctga aatcctggc agacagtatc     1860
aactctgaaa ttggaatcct ctgttctgcc ctgcagaaga tcaagtgact cgagatccag    1920
acatgataag atacattgat gagtttggac aaaccacaac tagaatgcag tgaaaaaaat    1980
gctttatttg tgaaatttgt gatgctattg ctttatttgt aaccattata agctgcaata    2040
aacaagttaa caacaacaat tgcattcatt ttatgtttca ggttcagggg gaggtgtggg    2100
aggttttta a                                                          2111
```

-continued

```
<210> SEQ ID NO 77
<211> LENGTH: 2426
<212> TYPE: DNA
<213> ORGANISM: Artificial Sequence
<220> FEATURE:
<223> OTHER INFORMATION: pHMI-hPAH-TC-019 transfer genome

<400> SEQUENCE: 77
ctgcgcgctc gctcgctcac tgaggccgcc cgggcaaagc ccgggcgtcg ggcgaccttt      60
ggtcgcccgg cctcagtgag cgagcgagcg cgcagagagg gagtggaatt cacgcgtgga    120
tctgaattca attcacgcgt ggtaccctcc taaaatgggc aaacattgca agcagcaaac    180
agcaaacaca cagccctccc tgcctgctga ccttggagct ggggcagagg tcagagacct    240
ctctgggccc atgccacctc aacatccac tcgaccccttt ggaatttcgg tggagaggag    300
cagaggttgt cctggcgtgg tttaggtagt gtgagagggg aatgactcct ttcggtaagt    360
gcagtggaag ctgtacactg cccaggcaaa gcgtccgggc agcgtaggcg ggcgactcag    420
atcccagcca gtggacttag cccctgtttg ctcctccgat aactggggtg accttggtta    480
atattcacca gcagcctccc ccgttgcccc tctggatcca ctgcttaaat acggacgagg    540
acagggccct gtctcctcag cttcaggcac caccactgac ctgggacagt gaatcctcta    600
aggtaaatat aaaattttta agtgtataat gtgttaaact actgattcta attgtttctc    660
tcttttagat tccaaccttt ggaactgacc gccaccatgt ccactgctgt gctggagaac    720
ccaggcctgg gcaggaagtt gagtgacttt gggcaggaga cctcctacat agaagacaat    780
tgcaatcaga atggggccat ctctctgatc ttcagcctta agaggaggt gggtgctctg    840
gcaaaagtgc tcagactgtt tgaggagaat gatgtgaatc tcacccacat tgaatccagg    900
cccagcagac tcaaaaagga tgaatatgaa ttcttcaccc acttggacaa aaggtcctta    960
cctgccctta caaatatcat caaaattttg agacatgaca taggggcaac tgtacatgaa   1020
ctgagtagag ataaaaaaaa agacacagtc ccctggttcc ccaggaccat ccaggaattg   1080
gacaggttg caaaccagat actgagctat ggtgctgagt tggatgctga tcacccaggc   1140
ttcaaggacc ctgtgtacag agcaaggaga aagcagtttg ctgacattgc ctacaattac   1200
aggcacggcc aacccattcc tagagtcgag tacatggaag aagagaagaa acctgggc    1260
actgtcttca agaccctgaa gtcactgtac aagacacatg cctgctatga atacaaccac   1320
atatttccac tcctagagaa atactgtgga ttccatgagg acaatatacc ccaattggag   1380
gatgtctcac agtttctgca gacttgtaca ggttttaggc tgaggccagt ggctgggctc   1440
ctcagcagca gggacttcct gggtggactg gccttcagag ttttccactg tactcagtat   1500
atcagacatg gctccaagcc tatgtatacc ccagaacctg acatctgcca tgaactgctt   1560
gggcatgtgc ctctctttc agaccgttcc tttgcccagt tttctcagga gattggacta   1620
gccagcctag gtgcaccaga tgagtacatt gagaagttag caaccattta ctggttcaca   1680
gtggagttcg gtctctgcaa gcaaggggac tcaataaagg cctatggagc aggcctcctg   1740
tcaagttttg gagaactcca atactgccta tctgagaagc taaattatt accccttggaa   1800
ctagaaaaaa ctgcaataca gaactacaca gtgactgagt ttcagccact ctactatgtg   1860
gcagagtcct ttaatgatgc caagaaaag gtccgaaatt ttgctgcaac aattcccagg   1920
cccttctctg ttcgctatga tccatacacc caaagaattg aagtcctaga taacacccag   1980
cagctgaaaa tcctggcaga cagtatcaac tctgaaattg gaatcctctg ttctgccctg   2040
cagaagatca agtgactcga gatccagaca tgataagata cattgatgag tttggacaaa   2100
```

```
ccacaactag aatgcagtga aaaaaatgct ttatttgtga aatttgtgat gctattgctt   2160
tatttgtaac cattataagc tgcaataaac aagttaacaa caacaattgc attcatttta   2220
tgtttcaggt tcagggggag gtgtgggagg ttttttaaag catgctgggg agagatcgat   2280
ctgaggaacc cctagtgatg gagttggcca ctccctctct gcgcgctcgc tcgctcactg   2340
aggccgggcg accaaaggtc gcccgacgcc cgggctttgc ccgggcggcc tcagtgagcg   2400
agcgagcgcg cagagaggga gtggcc                                       2426

<210> SEQ ID NO 78
<211> LENGTH: 2111
<212> TYPE: DNA
<213> ORGANISM: Artificial Sequence
<220> FEATURE:
<223> OTHER INFORMATION: pHMI-hPAH-TC-020 transfer genome

<400> SEQUENCE: 78
ccctaaaatg ggcaaacatt gcaagcagca aacagcaaac acacagccct ccctgcctgc     60
tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg ggcagcgtag gcgggcgact cagatcccag ccagtggact tagcccctgt    300
ttgctcctcc gataactggg gtgaccttgg ttaatattca ccagcagcct cccccgttgc    360
ccctctggat ccactgctta aatacggacg aggacagggc cctgtctcct cagcttcagg    420
caccaccact gacctgggac agtgaatcct ctaaggtaaa tataaaattt ttaagtgtat    480
aatgtgttaa actactgatt ctaattgttt ctctcttttta gattccaacc tttggaactg    540
accgccacca tgtccactgc tgtgctggag aacccaggcc tgggcaggaa gttgagtgac    600
tttgggcagg agacctccta catagaagac aattgcaatc agaatggggc catctctctg    660
atcttcagcc ttaaagagga ggtgggtgct ctggcaaaag tgctcagact cttttgagga g    720 aatgatgtga atctcaccca cattgaatcc aggcccagca gactcaaaaa ggatgaatat    780
gaattcttca cccacttgga caaaggtcc ttacctgccc ttacaaatat catcaaaatt     840
ttgagacatg acataggggc aactgtacat gaactgagta gagataaaaa aaaagacaca    900
gtcccctggt tccccaggac catccaggaa ttggacaggt ttgcaaacca gatactgagc    960
tatggtgctg agttggatgc tgatcaccca ggcttcaagg accctgtgta cagagcaagg   1020
agaaagcagt ttgctgacat tgcctacaat tacaggcacg ccaacccat tcctagagtc    1080 gagtacatgg aagaagagaa gaaaacctgg ggcactgtct tcaagaccct gaagtcactg   1140
tacaagacac atgcctgcta tgaatacaac cacatatttc cactcctaga aaatactgt    1200 ggattccatg aggacaatat accccaattg gaggatgtct cacagtttct gcagacttgt   1260
acaggtttta ggctgaggcc agtggctggg cttctcagca gcagggactt cctgggtgga   1320
ctggccttca gggtgtttca ctgtacacaa tacatcagac atggtagcaa accaatgtat   1380
actcctgaac cagacatctg ccatgagctg cttgggcatg tgcctctgtt cagcgacaga   1440
agctttgctc agtttagcca ggagattggg ctggccagcc tgggcgcccc tgatgagtat   1500
atcgagaaac tggccacaat ctactggttc acagtggagt tcggcctgtg caagcagggc   1560
gactcaatca aggcctatgg cgccggcctg ctgagcagct tcggcgaact gcagtactgc   1620
ctgagcgaga gcccaagct gctgccactg gagctggaga aaaccgccat ccagaactac   1680
acagtgacag agttccagcc tctgtactat gtggccgaga gcttcaacga tgccaaggag   1740
```

```
aaggtgagga attttgccgc cactatcccc aggcctttct ccgtgagata tgaccoctac    1800 acccagcgaa tcgaggtgct ggacaatacc cagcagctga agatcctggc cgattccatc    1860
aactctgaga tcggcattct gtgtagcgcc ctgcagaaga ttaagtgact cgagatccag    1920
acatgataag atacattgat gagtttggac aaaccacaac tagaatgcag tgaaaaaaat    1980
gctttatttg tgaaatttgt gatgctattg ctttatttgt aaccattata agctgcaata    2040
aacaagttaa caacaacaat tgcattcatt ttatgtttca ggttcagggg gaggtgtggg    2100
aggtttttta a                                                         2111

<210> SEQ ID NO 79
<211> LENGTH: 2426
<212> TYPE: DNA
<213> ORGANISM: Artificial Sequence
<220> FEATURE:
<223> OTHER INFORMATION: pHMI-hPAH-TC-020 transfer genome

<400> SEQUENCE: 79
ctgcgcgctc gctcgctcac tgaggccgcc cgggcaaagc ccgggcgtcg ggcgaccttt      60
ggtcgcccgg cctcagtgag cgagcgagcg cgcagagagg gagtggaatt cacgcgtgga    120
tctgaattca attcacgcgt ggtacctccc taaaatgggc aaacattgca agcagcaaac    180
agcaaacaca cagccctccc tgcctgctga ccttggagct ggggcagagg tcagagacct    240
ctctgggccc atgccacctc caacatccac tcgaccccct tggaatttcgg tggagaggag    300 cagaggttgt cctggcgtgg tttaggtagt gtgagagggg aatgactcct ttcggtaagt    360
gcagtggaag ctgtacactg cccaggcaaa gcgtccgggc agcgtaggcg ggcgactcag    420
atcccagcca gtggacttag cccctgtttg ctcctccgat aactgggtg  accttggtta    480 atattcacca gcagcctccc ccgttgcccc tctggatcca ctgcttaaat acggacgagg    540
acagggccct gtctcctcag cttcaggcac caccactgac ctgggacagt gaatcctcta    600
aggtaaatat aaaatttta agtgtataat gtgttaaact actgattcta attgtttctc    660
tcttttagat tccaaccttt ggaactgacc gccaccatgt ccactgctgt gctggagaac    720
ccaggcctgg gcaggaagtt gagtgacttt ggcaggagaa cctcctacat agaagacaat    780
tgcaatcaga atgggccat ctctctgatc ttcagcctta agaggaggt gggtgctctg    840 gcaaaagtgc tcagactctt tgaggagaat gatgtgaatc tcacccacat tgaatccagg    900
cccagcagac tcaaaaagga tgaatatgaa ttcttcaccc acttggacaa aggtcctta    960 cctgccctta caaatatcat caaaattttg agacatgaca tagggcaac tgtacatgaa    1020 ctgagtagag ataaaaaaaa agacacagtc ccctggttcc ccaggaccat ccaggaattg    1080
gacaggtttg caaaccagat actgagctat ggtgctgagt tggatgctga tcacccaggc    1140
ttcaaggacc ctgtgtacag agcaaggaga aagcagtttg ctgacattgc ctacaattac    1200
aggcacggcc aacccattcc tagagtcgag tacatggaag aagagaagaa acctgggc     1260 actgtcttca gaccctgaa gtcactgtac aagacacatg cctgctatga atacaaccac    1320
atatttccac tcctagagaa atactgtgga ttccatgagg acaatatacc ccaattggag    1380
gatgtctcac agtttctgca gacttgtaca gttttaggc tgaggccagt ggctgggctt    1440
ctcagcagca gggacttcct gggtggactg gccttcaggg tgtttcactg tacacaatac    1500
atcagacatg gtagcaaacc aatgtatact cctgaaccag acatctgcca tgagctgctt    1560
gggcatgtgc ctctgttcag cgacagaagc tttgctcagt ttagccagga gattgggctg    1620
```

```
gccagcctgg gcgcccctga tgagtatatc gagaaactgg ccacaatcta ctggttcaca    1680
gtggagttcg gcctgtgcaa gcagggcgac tcaatcaagg cctatggcgc cggcctgctg    1740
agcagcttcg gcgaactgca gtactgcctg agcgagaagc ccaagctgct gccactggag    1800
ctggagaaaa ccgccatcca gaactacaca gtgacagagt ccagcctct gtactatgtg    1860 gccgagagct tcaacgatgc caaggagaag gtgaggaatt ttgccgccac tatccccagg    1920
cctttctccg tgagatatga cccctacacc cagcgaatcg aggtgctgga caatacccag    1980
cagctgaaga tcctggccga ttccatcaac tctgagatcg gcattctgtg tagcgccctg    2040
cagaagatta agtgactcga gatccagaca tgataagata cattgatgag tttggacaaa    2100
ccacaactag aatgcagtga aaaaaatgct ttatttgtga aatttgtgat gctattgctt    2160
tatttgtaac cattataagc tgcaataaac aagttaacaa caacaattgc attcatttta    2220
tgtttcaggt tcagggggag gtgtgggagg ttttttaaag catgctgggg agagatcgat    2280
ctgaggaacc cctagtgatg gagttggcca ctccctctct gcgcgctcgc tcgctcactg    2340
aggccgggcg accaaaggtc gcccgacgcc cgggctttgc ccgggcggcc tcagtgagcg    2400
agcgagcgcg cagagaggga gtggcc                                         2426
```

<210> SEQ ID NO 80
<211> LENGTH: 2111
<212> TYPE: DNA
<213> ORGANISM: Artificial Sequence
<220> FEATURE:
<223> OTHER INFORMATION: pHMI-hPAH-TC-021 transfer genome

<400> SEQUENCE: 80

```
ccctaaaatg gcaaacatt gcaagcagca acagcaaac acacagccct cctgcctgc        60 tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg ggcagcgtag gcgggcgact cagatcccag ccagtggact tagcccctgt    300
ttgctcctcc gataactggg gtgaccttgg ttaatattca ccagcagcct cccccgttgc    360
ccctctggat ccactgctta aatacggacg aggacagggc cctgtctcct cagcttcagg    420
caccaccact gacctgggac agtgaatcct ctaaggtaaa tataaaattt ttaagtgtat    480
aatgtgttaa actactgatt ctaattgttt ctctctttta gattccaacc tttggaactg    540
accgccacca tgtccactgc tgtgctggag aacccaggcc tgggaaggaa gctgagtgac    600
tttggccagg agacctccta catagaggac aactgcaatc agaacgggc catcagcctg    660 atcttcagcc ttaaagagga ggtaggcgct ctggcaaaag tgctcagact ctttgaggag    720
aatgatgtga atctcaccca cattgaatcc aggcccagca gactcaaaaa ggatgaatat    780 gaattttttca cccacttgga caaaaggtcc ttacctgccc ttacaaatat catcaaaatt    840
ttgagacatg acatagggc aactgtacat gaactgagta gagataaaaa aaaagacaca    900
gtcccctggt tccccaggac catacaggaa ttggacaggt ttgcaaacca gatactgagc    960
tatggtgctg aattggatgc tgatcaccca ggcttcaagg accctgtgta cagagcacga   1020
agaaagcagt ttgctgacat tgcctacaat tacaggcacg ccaaccccat tcctagagtc   1080
gagtacatgg aagaagaaaa gaaaacctgg ggcactgtgt tcaagaccct gaagtcactg   1140
tacaagacac atgcctgcta tgaatacaac cacatatttc cactcctaga gaatactgt   1200 ggattccatg aggacaacat accccaattg gaggatgtgt cacagtttct gcagacttgt   1260
```

```
acaggttttta ggctgaggcc agtggcaggg cttctcagca gcagggactt cctgggtgga    1320
ctggccttca gggtgtttca ctgtacacag tacatcagac atggtagcaa accaatgtat    1380
actcctgaac cagacatctg ccatgagctg cttgggcatg tgcctctgtt ttcagacagg    1440
tcctttgctc aattctcaca ggagattgga ctagccagcc taggtgcacc agatgagtac    1500
attgagaagt tagcaaccat ttactggttc acagtggagt tcggcctttg caagcaaggg    1560
gactcaataa aggcctatgg agcaggcctc ctgtcaagtt tggagaact acaatactgc     1620 ctatctgaga agcctaaatt attacccttg gaactagaga aaactgcaat acagaactac    1680
acagtgactg agtttcagcc actctactat gtggccgagt ccttcaatga tgccaaagaa    1740
aaggtccgaa attttgctgc aacaattccc aggcctttct ctgttcgcta tgatccttac    1800
acccaaagaa ttgaagtcct agataacacc cagcagctga agatcctggc tgatagcata    1860
aacagcgaaa ttggaatcct ctgttctgcc ctgcagaaga tcaagtgact cgagatccag    1920
acatgataag atacattgat gagtttggac aaaccacaac tagaatgcag tgaaaaaaat    1980
gctttatttg tgaaatttgt gatgctattg ctttatttgt aaccattata agctgcaata    2040
aacaagttaa caacaacaat tgcattcatt ttatgtttca ggttcagggg gaggtgtggg    2100
aggtttttta a                                                         2111
```

<210> SEQ ID NO 81
<211> LENGTH: 2426
<212> TYPE: DNA
<213> ORGANISM: Artificial Sequence
<220> FEATURE:
<223> OTHER INFORMATION: pHMI-hPAH-TC-021 transfer genome

<400> SEQUENCE: 81

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggaatt cacgcgtgga   120
tctgaattca attcacgcgt ggtacctccc taaaatgggc aaacattgca agcagcaaac   180
agcaaacaca cagccctccc tgcctgctga ccttggagct ggggcagagg tcagagacct   240
ctctgggccc atgccacctc caacatccac tcgacccctt ggaatttcgg tggagaggag   300
cagaggttgt cctggcgtgg tttaggtagt gtgagagggg aatgactcct ttcggtaagt   360
gcagtggaag ctgtacactg cccaggcaaa gcgtccgggc agcgtaggcg ggcgactcag   420
atcccagcca gtggacttag cccctgtttg ctcctccgat aactggggtg accttggtta   480
atattcacca gcagcctccc ccgttgcccc tctggatcca ctgcttaaat acggacgagg   540
acagggccct gtctcctcag cttcaggcac caccactgac ctgggacagt gaatcctcta   600
aggtaaatat aaaattttta agtgtataat gtgttaaact actgattcta attgtttctc   660
tcttttagat tccaaccttt ggaactgacc gccaccatgt ccactgctgt gctggagaac   720
ccaggcctgg gaaggaagct gagtgacttt ggccaggaga cctcctacat agaggacaac   780
tgcaatcaga acgggccat cagcctgatc ttcagcctta agaggaggt aggcgctctg    840 gcaaagtgc tcagactctt tgaggagaat gatgtgaatc tcacccacat tgaatccagg    900
cccagcagac tcaaaaagga tgaatatgaa tttttcaccc acttggacaa aagtccttta    960 cctgcccctta caaatatcat caaaattttg agacatgaca tggggcaac tgtacatgaa   1020 ctgagtagag ataaaaaaaa agacacagtc cctggttcc ccaggaccat acaggaattg    1080
gacaggtttg caaaccagat actgagctat ggtgctgaat tggatgctga tcacccaggc   1140
```

| | | |
|---|---|---|
| ttcaaggacc ctgtgtacag agcacgaaga aagcagtttg ctgacattgc ctacaattac | 1200 |
| aggcacggcc aacccattcc tagagtcgag tacatggaag aagaaaagaa aacctggggc | 1260 |
| actgtgttca agaccctgaa gtcactgtac aagacacatg cctgctatga atacaaccac | 1320 |
| atatttccac tcctagagaa atactgtgga ttccatgagg acaacatacc ccaattggag | 1380 |
| gatgtgtcac agtttctgca gacttgtaca ggttttaggc tgaggccagt ggcagggctt | 1440 |
| ctcagcagca gggacttcct gggtggactg gccttcaggg tgtttcactg tacacagtac | 1500 |
| atcagacatg gtagcaaacc aatgtatact cctgaaccag acatctgcca tgagctgctt | 1560 |
| gggcatgtgc ctctgttttc agacaggtcc tttgctcaat tctcacagga gattggacta | 1620 |
| gccagcctag gtgcaccaga tgagtacatt gagaagttag caaccattta ctggttcaca | 1680 |
| gtggagttcg gcctttgcaa gcaaggggac tcaataaagg cctatggagc aggcctcctg | 1740 |
| tcaagttttg gagaactaca atactgccta tctgagaagc taaattatt accccttggaa | 1800 |
| ctagagaaaa ctgcaataca gaactacaca gtgactgagt ttcagccact ctactatgtg | 1860 |
| gccgagtcct tcaatgatgc caaagaaaag gtccgaaatt ttgctgcaac aattcccagg | 1920 |
| cctttctctg ttcgctatga tccttacacc caaagaattg aagtcctaga taacacccag | 1980 |
| cagctgaaga tcctggctga tagcataaac agcgaaattg gaatcctctg ttctgccctg | 2040 |
| cagaagatca agtgactcga gatccagaca tgataagata cattgatgag tttggacaaa | 2100 |
| ccacaactag aatgcagtga aaaaaatgct ttatttgtga aatttgtgat gctattgctt | 2160 |
| tatttgtaac cattataagc tgcaataaac aagttaacaa caacaattgc attcatttta | 2220 |
| tgtttcaggt tcaggggag gtgtgggagg ttttttaaag catgctgggg agagatcgat | 2280 |
| ctgaggaacc cctagtgatg gagttggcca ctccctctct gcgcgctcgc tcgctcactg | 2340 |
| aggccgggcg accaaaggtc gcccgacgcc cgggctttgc ccgggcggcc tcagtgagcg | 2400 |
| agcgagcgcg cagagaggga gtggcc | 2426 |

<210> SEQ ID NO 82
<211> LENGTH: 2111
<212> TYPE: DNA
<213> ORGANISM: Artificial Sequence
<220> FEATURE:
<223> OTHER INFORMATION: pHMI-hPAH-TC-022 transfer genome

<400> SEQUENCE: 82

| | | |
|---|---|---|
| ccctaaaatg ggcaaacatt gcaagcagca acagcaaac acacagccct ccctgcctgc | 60 |
| tgaccttgga gctggggcag aggtcagaga cctctctggg cccatgccac ctccaacatc | 120 |
| cactcgaccc cttggaattt cggtggagag gagcagaggt tgtcctggcg tggtttaggt | 180 |
| agtgtgagag gggaatgact cctttcggta agtgcagtgg aagctgtaca ctgcccaggc | 240 |
| aaagcgtccg ggcagcgtag gcgggcgact cagatcccag ccagtggact tagcccctgt | 300 |
| ttgctcctcc gataactggg gtgaccttgg ttaatattca ccagcagcct ccccgttgc | 360 |
| ccctctggat ccactgctta aatacggacg aggacagggc cctgtctcct cagcttcagg | 420 |
| caccaccact gacctgggac agtgaatcct ctaaggtaaa tataaaattt ttaagtgtat | 480 |
| aatgtgttaa actactgatt ctaattgttt ctctctttta gattccaacc tttgaactg | 540 |
| accgccacca tgtccactgc tgtgctggag aacccaggcc tgggcaggaa gttgagtgac | 600 |
| tttgggcagg agacctccta catagaagac aattgcaatc agaatgggc catctctctg | 660 |
| atcttcagcc ttaaagagga ggtgggtgct ctggcaaaag tgctcagact ctttgaggag | 720 |
| aatgatgtga atctcaccca cattgaatcc aggcccagca gactcaaaaa ggatgaatat | 780 |

```
gaattcttca cccacttgga caaaaggtcc ttacctgccc ttacaaatat catcaaaatt      840
ttgagacatg acatagggc aactgtacat gaactgagta gagataaaaa aaaagacaca       900
gtcccctggt tccccaggac catccaggaa ttggacaggt ttgcaaacca gatactgagc      960
tatggtgctg agttggatgc tgatcaccca ggcttcaagg accctgtgta cagagcaagg     1020
agaaagcagt ttgctgacat tgcctacaat tacaggcacg gccaacccat tcctagagtc    1080
gagtacatgg aagaagagaa gaaaacctgg ggcactgtct tcaagaccct gaagtcactg    1140
tacaagacac atgcctgcta tgaatacaac acatatttc cactcctaga gaaatactgt     1200
ggattccatg aggacaatat accccaattg gaggatgtct cacagtttct gcagacttgt    1260 acaggttta ggctgaggcc agtggctggg cttctcagca gcagggactt cctgggtgga    1320
ctggcctttc gagttttcca ctgtactcag tatatcagac atggctccaa gcccatgtat    1380 acccagaac ctgacatctg ccatgaactg cttgggcatg tgcctctgtt ttcagaccgt    1440
tcctttgccc agttttctca ggagattgga ctagccagcc taggtgcacc agatgagtac    1500
attgagaagt tagcaaccat ttactggttc acagtggagt tcggcctttg caagcaaggg    1560
gactcaataa aggcctatgg agcaggcctc tgtcaagtt ttggagaact acaatactgc    1620
ctatctgaga agcctaaatt attacccttg gaactagaaa aaactgcaat acagaactac    1680
acagtgactg agtttcagcc actctactat gtggcagagt cctttaatga tgccaaagaa    1740
aaggtccgaa attttgctgc aacaattccc aggccttct ctgttcgcta tgatccatac     1800
acccaaagaa ttgaagtcct agataacacc cagcagctga aaatcctggc agacagcatc    1860
aactctgaaa ttggaatcct ctgttctgcc ctgcagaaga tcaagtgact cgagatccag    1920
acatgataag atacattgat gagtttggac aaaccacaac tagaatgcag tgaaaaaat    1980 gctttatttg tgaaatttgt gatgctattg ctttatttgt aaccattata agctgcaata    2040
aacaagttaa caacaacaat tgcattcatt ttatgtttca ggttcagggg gaggtgtggg    2100 aggttttta a                                                           2111
```

<210> SEQ ID NO 83
<211> LENGTH: 2426
<212> TYPE: DNA
<213> ORGANISM: Artificial Sequence
<220> FEATURE:
<223> OTHER INFORMATION: pHMI-hPAH-TC-022 transfer genome

<400> SEQUENCE: 83

```
ctgcgcgctc gctcgctcac tgaggccgcc cgggcaaagc ccgggcgtcg ggcgaccttt       60
ggtcgcccgg cctcagtgag cgagcgagcg cgcagagagg gagtggaatt cacgcgtgga     120
tctgaattca attcacgcgt ggtacctccc taaaatgggc aaacattgca agcagcaaac     180
agcaaacaca cagccctccc tgcctgctga ccttggagct ggggcagagg tcagagacct    240
ctctgggccc atgccacctc caacatccac tcgacccctt ggaatttcgg tggagaggag    300
cagaggttgt cctggcgtgg tttaggtagt gtgagagggg aatgactcct ttcggtaagt    360
gcagtggaag ctgtacactg cccaggcaaa gcgtccgggc agcgtaggcg ggcgactcag    420
atcccagcca gtgacttag cccctgtttg ctcctccgat aactgggtg accttggtta     480 atattcacca gcagcctccc ccgttgcccc tctggatcca ctgcttaaat acggacgagg   540
acagggccct gtctcctcag cttcaggcac caccactgac ctgggacagt gaatcctcta    600
aggtaaatat aaaattttta agtgtataat gtgttaaact actgattcta attgtttctc    660
```

| | |
|---|---:|
| tcttttagat tccaaccttt ggaactgacc gccaccatgt ccactgctgt gctggagaac | 720 |
| ccaggcctgg gcaggaagtt gagtgacttt gggcaggaga cctcctacat agaagacaat | 780 |
| tgcaatcaga atggggccat ctctctgatc ttcagcctta agaggaggt gggtgctctg | 840 |
| gcaaaagtgc tcagactctt tgaggagaat gatgtgaatc tcacccacat gaatccagg | 900 |
| cccagcagac tcaaaaagga tgaatatgaa ttcttcaccc acttggacaa aaggtcctta | 960 |
| cctgccctta caaatatcat caaaattttg agacatgaca tagggcaac tgtacatgaa | 1020 |
| ctgagtagag ataaaaaaaa agacacagtc ccctggttcc ccaggaccat ccaggaattg | 1080 |
| gacaggtttg caaccagat actgagctat ggtgctgagt tggatgctga tcacccaggc | 1140 |
| ttcaaggacc ctgtgtacag agcaaggaga aagcagtttg ctgacattgc ctacaattac | 1200 |
| aggcacggcc aacccattcc tagagtcgag tacatggaag aagagaagaa acctggggc | 1260 |
| actgtcttca agaccctgaa gtcactgtac aagacacatg cctgctatga atacaaccac | 1320 |
| atatttccac tcctagagaa atactgtgga ttccatgagg acaatatacc ccaattggag | 1380 |
| gatgtctcac agtttctgca gacttgtaca ggttttaggc tgaggccagt ggctgggctt | 1440 |
| ctcagcagca gggacttcct gggtggactg gcctttcgag ttttccactg tactcagtat | 1500 |
| atcagacatg gctccaagcc catgtatacc ccagaacctg acatctgcca tgaactgctt | 1560 |
| gggcatgtgc tctgttttc agaccgttcc tttgcccagt tttctcagga gattggacta | 1620 |
| gccagcctag gtgcaccaga tgagtacatt gagaagttag caaccattta ctggttcaca | 1680 |
| gtggagttcg gcctttgcaa gcaagggac tcaataaagg cctatggagc aggcctcctg | 1740 |
| tcaagttttg gagaactaca atactgccta tctgagaagc ctaaattatt accttggaa | 1800 |
| ctagaaaaaa ctgcaataca gaactacaca gtgactgagt ttcagccact ctactatgtg | 1860 |
| gcagagtcct ttaatgatgc caaagaaaag gtccgaaatt ttgctgcaac aattcccagg | 1920 |
| cctttctctg ttcgctatga tccatacacc caaagaattg aagtcctaga taacacccag | 1980 |
| cagctgaaaa tcctggcaga cagcatcaac tctgaaattg gaatcctctg ttctgccctg | 2040 |
| cagaagatca agtgactcga gatccagaca tgataagata cattgatgag tttggacaaa | 2100 |
| ccacaactag aatgcagtga aaaaaatgct ttatttgtga aatttgtgat gctattgctt | 2160 |
| tatttgtaac cattataagc tgcaataaac aagttaacaa caacaattgc attcatttta | 2220 |
| tgtttcaggt tcagggggag gtgtgggagg ttttttaaag catgctgggg agagatcgat | 2280 |
| ctgaggaacc cctagtgatg gagttggcca ctccctctct gcgcgctcgc tcgctcactg | 2340 |
| aggccgggcg accaaaggtc gcccgacgcc cgggctttgc ccgggcggcc tcagtgagcg | 2400 |
| agcgagcgcg cagagaggga gtggcc | 2426 |

<210> SEQ ID NO 84
<211> LENGTH: 2111
<212> TYPE: DNA
<213> ORGANISM: Artificial Sequence
<220> FEATURE:
<223> OTHER INFORMATION: pHMI-hPAH-TC-023 transfer genome

<400> SEQUENCE: 84

| | |
|---|---:|
| ccctaaaatg gcaaacatt gcaagcagca aacagcaaac acacagccct ccctgcctgc | 60 |
| tgaccttgga gctggggcag aggtcagaga cctctctggg cccatgccac ctccaacatc | 120 |
| cactcgaccc cttggaattt cggtggagag gagcagaggt tgtcctggcg tggtttaggt | 180 |
| agtgtgagag gggaatgact ccttcggta agtgcagtgg aagctgtaca ctgcccaggc | 240 |
| aaagcgtccg ggcagcgtag gcgggcgact cagatcccag ccagtggact tagcccctgt | 300 |

```
ttgctcctcc gataactggg gtgaccttgg ttaatattca ccagcagcct cccccgttgc    360
ccctctggat ccactgctta aatacggacg aggacagggc cctgtctcct cagcttcagg    420
caccaccact gacctgggac agtgaatcct ctaaggtaaa tataaaattt ttaagtgtat    480
aatgtgttaa actactgatt ctaattgttt ctctctttta gattccaacc tttggaactg    540
accgccacca tgtccactgc ggtcctggaa acccaggct tgggcaggaa actctctgac     600
tttggacagg aaacaagcta tattgaagac aactgcaatc aaaatggtgc catatcactg    660
atcttctcac tcaaagaaga agttggtgca ttggccaaag tattgcgctt atttgaggag    720
aatgatgtaa acctgaccca cattgaatct agaccttctc gtttaaagaa agatgagtat    780 gaattttca cccatttgga taaacgtagc ctgcctgctc tgacaaacat catcaagatc     840
ttgaggcatg acattggtgc cactgtccat gagctttcac gagataagaa gaaagacaca    900
gtgccctggt tcccaagaac cattcaagag ctggacagat tgccaatca gattctcagc     960 tatggagcgg aactggatgc tgaccaccct ggttttaaag atcctgtgta ccgtgcaaga   1020
cggaagcagt ttgctgacat tgcctacaac taccgccatg ggcagcccat ccctcgagtg   1080
gaatacatgg aggaagaaaa gaaaacatgg ggcacagtgt tcaagactct gaagtccttg   1140 tataaaccc atgcttgcta tgagtacaat cacatttttc cacttcttga aaagtactgt    1200
ggcttccatg aagataacat tccccagctg gaagacgttt ctcaattcct gcagacttgc   1260 actggttttcc gcctccgacc tgtggctggc ctgctttcct ctcgggattt cttgggtggc   1320
ctggccttcc gagtcttcca ctgcacacag tacatcagac atggatccaa gcccatgtat   1380
acccccgaac ctgacatctg ccatgagctg ttgggacatg tgcccttgtt ttcagatcgc   1440
agctttgccc agttttccca ggaaattggc cttgcctctc tgggtgcacc tgatgaatac   1500
attgaaaagc tcgccacaat ttactggttt actgtggagt ttgggctctg caaacaagga   1560
gactccataa aggcatatgg tgctgggctc ctgtcatcct ttggtgaatt acagtactgc   1620
ttatcagaga agccaaagct tctcccctg gagctggaga agacagccat ccaaaattac    1680
actgtcacgg agttccagcc cctgtattac gtggcagaga gttttaatga tgccaaggag   1740
aaagtaagga actttgctgc cacaatacct cggcccttct cagttcgcta cgacccatac   1800
acccaaagga ttgaggtctt ggacaatacc cagcagctta agattttggc tgattccatt   1860
aacagtgaaa ttgaatcct ttgcagtgcc ctccagaaaa taagtaact cgagatccag    1920 acatgataag atacattgat gagtttggac aaaccacaac tagaatgcag tgaaaaaaat   1980
gctttatttg tgaaatttgt gatgctattg ctttatttgt aaccattata agctgcaata   2040
aacaagttaa caacaacaat tgcattcatt ttatgtttca ggttcagggg gaggtgtggg   2100 aggttttta a                                                         2111
```

<210> SEQ ID NO 85
<211> LENGTH: 2426
<212> TYPE: DNA
<213> ORGANISM: Artificial Sequence
<220> FEATURE:
<223> OTHER INFORMATION: pHMI-hPAH-TC-023 transfer genome

<400> SEQUENCE: 85

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggaatt cacgcgtgga   120
tctgaattca attcacgcgt ggtacctccc taaaatgggc aaacattgca agcagcaaac   180
```

```
agcaaacaca cagccctccc tgcctgctga ccttggagct ggggcagagg tcagagacct    240
ctctgggccc atgccacctc caacatccac tcgaccccctt ggaatttcgg tggagaggag    300
cagaggttgt cctggcgtgg tttaggtagt gtgagagggg aatgactcct ttcggtaagt    360
gcagtggaag ctgtacactg cccaggcaaa gcgtccgggc agcgtaggcg ggcgactcag    420
atcccagcca gtggacttag cccctgtttg ctcctccgat aactggggtg accttggtta    480
atattcacca gcagcctccc ccgttgcccc tctggatcca ctgcttaaat acggacgagg    540
acagggccct gtctcctcag cttcaggcac caccactgac ctgggacagt gaatcctcta    600
aggtaaatat aaaattttta agtgtataat gtgttaaact actgattcta attgtttctc    660
tcttttagat tccaacccttt ggaactgacc gccaccatgt ccactgcggt cctggaaaac    720
ccaggcttgg gcaggaaact ctctgacttt ggacaggaaa caagctatat tgaagacaac    780
tgcaatcaaa atggtgccat atcactgatc ttctcactca aagaagaagt tggtgcattg    840
gccaaagtat tgcgcttatt tgaggagaat gatgtaaacc tgacccacat tgaatctaga    900
ccttctcgtt taagaaaga tgagtatgaa ttttcaccc atttggataa acgtagcctg    960
cctgctctga caaacatcat caagatcttg aggcatgaca ttggtgccac tgtccatgag    1020 cttttcacgag ataagaagaa agacacagtg ccctggttcc caagaaccat tcaagagctg    1080
gacagatttg ccaatcagat tctcagctat ggagcggaac tggatgctga ccaccctggt    1140
tttaaagatc ctgtgtaccg tgcaagacgg aagcagtttg ctgacattgc ctacaactac    1200
cgccatgggc agcccatccc tcgagtggaa tacatggagg aagaaaagaa aacatggggc    1260
acagtgttca agactctgaa gtccttgtat aaaacccatg cttgctatga gtacaatcac    1320
atttttccac ttcttgaaaa gtactgtggc ttccatgaag ataacattcc ccagctggaa    1380
gacgtttctc aattcctgca gacttgcact ggtttccgcc tccgacctgt ggctggcctg    1440 cttttcctctc gggatttctt gggtggcctg ccttccgag tcttccactg cacacagtac    1500
atcagacatg gatccaagcc catgtatacc cccgaacctg acatctgcca tgagctgttg    1560
ggacatgtgc ccttgttttc agatcgcagc tttgcccagt ttcccagga aattggcctt    1620 gcctctctgg gtgcacctga tgaatacatt gaaaagctcg ccacaattta ctggtttact    1680
gtggagtttg gctctgcaa acaaggagac tccataaagg catatggtgc tgggctcctg    1740
tcatcctttg gtgaattaca gtactgctta tcagagaagc caaagcttct cccccctggag    1800 ctggagaaga cagccatcca aaattacact gtcacggagt tccagcccct gtattacgtg    1860
gcagagagtt ttaatgatgc caaggagaaa gtaaggaact ttgctgccac aatacctcgg    1920
cccttctcag ttcgctacga cccatacacc caaaggattg aggtcttgga caatacccag    1980
cagcttaaga ttttggctga ttccattaac agtgaaattg gaatcctttg cagtgccctc    2040
cagaaaataa agtaactcga gatccagaca tgataagata cattgatgag tttggacaaa    2100
ccacaactag aatgcagtga aaaaaatgct ttatttgtga aatttgtgat gctattgctt    2160
tatttgtaac cattataagc tgcaataaac aagttaacaa caacaattgc attcattta    2220 tgtttcaggt tcagggggag gtgtgggagg ttttttaaag catgctgggg agagatcgat    2280
ctgaggaacc cctagtgatg gagttggcca ctccctctct gcgcgctcgc tcgctcactg    2340
aggccgggcg accaaaggtc gcccgacgcc cgggctttgc ccgggcggcc tcagtgagcg    2400
agcgagcgcg cagagaggga gtggcc                                         2426
```

<210> SEQ ID NO 86
<211> LENGTH: 2042

<212> TYPE: DNA
<213> ORGANISM: Artificial Sequence
<220> FEATURE:
<223> OTHER INFORMATION: pHMI-01004 transfer genome

<400> SEQUENCE: 86

```
ccctaaaatg ggcaaacatt gcaagcagca acagcaaac acacagccct ccctgcctgc    60
tgaccttgga gctggggcag aggtcagaga cctctctggg cccatgccac ctccaacatc   120
cactcgaccc cttggaattt cggtggagag agcagaggt tgtcctggcg tggtttaggt   180
agtgtgagag gggaatgact cctttcggta agtgcagtgg aagctgtaca ctgcccaggc   240
aaagcgtccg ggcagcgtag gcgggcgact cagatcccag ccagtggact tagcccctgt   300
ttgctcctcc gataactggg gtgaccttgg ttaatattca ccagcagcct ccccgttgc    360
ccctctggat ccactgctta aatacggacg aggacagggc cctgtctcct cagcttcagg   420
caccaccact gacctgggac agtgaatcct ctaaggtaaa tataaaattt ttaagtgtat   480
aatgtgttaa actactgatt ctaattgttt ctctctttta gattccaacc tttggaactg   540
accgccacca tgtccaccgc tgtgctggag aaccctgggc tggggaggaa actgtcagac   600
ttcgggcagg agacttcata cattgaggat aactgtaacc agaatggcgc catctctctg   660
atcttcagcc tgaaggagga agtgggcgcc ctggcaaagg tgctgcgcct gtttgaggag   720
aacgacgtga atctgaccca catcgagtcc cggccttcta gactgaagaa ggacgagtac   780
gagttcttta cccacctgga taagcggtcc ctgccagccc tgacaaacat catcaagatc   840
ctgaggcacg acatcggagc aaccgtgcac gagctgtctc gggacaagaa gaaggatacc   900
gtgccctggt tccctcggac aatccaggag ctggatagat ttgccaacca gatcctgtct   960
tacggagcag agctggacgc agatcaccct ggcttcaagg acccagtgta tcgggcccgg  1020
agaaagcagt ttgccgatat cgcctacaat tataggcacg acagccaat ccctcgcgtg   1080
gagtatatgg aggaggagaa gaagacctgg ggcacagtgt tcaagaccct gaagagcctg  1140
tacaagacac acgcctgcta cgagtataac cacatcttcc ccctgctgga agtgtattgt  1200
ggctttcacg aggacaatat ccctcagctg gaggacgtga gccagttcct gcagacctgc  1260
acaggctta ggctgaggcc agtggcagga ctgctgagct cccgggactt cctgggagga  1320
ctggccttca gagtgtttca ctgcacccag tacatcaggc acggctccaa gccaatgtat  1380
acaccagagc ccgacatctg tcacgagctg ctggccacg tgcccctgtt tagcgataga  1440
tccttcgccc agttttccca ggagatcgga ctggcatctc tgggagcacc tgacgagtac  1500
atcgagaagc tggccaccat ctattggttc acagtggagt ttggcctgtg caagcagggc  1560
gatagcatca aggcctacgg agcaggactg ctgtctagct tcggcgagct gcagtattgt  1620
ctgtccgaga agcaaaagct gctgcccctg gagctggaga gaccgccat ccagaactac  1680
accgtgacag agttccagcc cctgtactat gtggccgagt ctttaacga tgccaaggag  1740
aaggtgagaa atttcgccgc cacaatccct aggcccttca gcgtgcggta cgacccttat  1800
acccagagga tcgaggtgct ggataataca cagcagctga gatcctggc tgactcaatc  1860
aatagcgaaa tcggaatcct gtgctccgcc ctgcagaaaa tcaaatgaat gctttatttg  1920
tgaaatttgt gatgctattg ctttatttgt aaccattata agctgcaata aacaagttaa  1980
caacaacaat tgcattcatt ttatgtttca ggttcagggg gaggtgtggg aggtttttta  2040
aa                                                                 2042
```

<210> SEQ ID NO 87

<211> LENGTH: 2356
<212> TYPE: DNA
<213> ORGANISM: Artificial Sequence
<220> FEATURE:
<223> OTHER INFORMATION: pHMI-01004 transfer genome

<400> SEQUENCE: 87

| | | | | | | |
|---|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggaatt | cacgcgtgga | 120 |
| tctgaattca | attcacgcgt | ggtacctccc | taaaatgggc | aaacattgca | agcagcaaac | 180 |
| agcaaacaca | cagccctccc | tgcctgctga | ccttggagct | ggggcagagg | tcagagacct | 240 |
| ctctgggccc | atgccacctc | caacatccac | tcgacccctt | ggaatttcgg | tggagaggag | 300 |
| cagaggttgt | cctggcgtgg | tttaggtagt | gtgagagggg | aatgactcct | ttcggtaagt | 360 |
| gcagtggaag | ctgtacactg | cccaggcaaa | gcgtccgggc | agcgtaggcg | ggcgactcag | 420 |
| atcccagcca | gtggacttag | cccctgtttg | ctcctccgat | aactgggtg | accttggtta | 480 |
| atattcacca | gcagcctccc | ccgttgcccc | tctggatcca | ctgcttaaat | acggacgagg | 540 |
| acagggccct | gtctcctcag | cttcaggcac | caccactgac | ctgggacagt | gaatcctcta | 600 |
| aggtaaatat | aaaattttta | agtgtataat | gtgttaaact | actgattcta | attgtttctc | 660 |
| tcttttagat | tccaaccttt | ggaactgacc | gccaccatgt | ccaccgctgt | gctggagaac | 720 |
| cctgggctgg | ggaggaaact | gtcagacttc | ggcaggaga | cttcatacat | tgaggataac | 780 |
| tgtaaccaga | atggcgccat | ctctctgatc | ttcagcctga | aggaggaagt | gggcgccctg | 840 |
| gcaaaggtgc | tgcgcctgtt | tgaggagaac | gacgtgaatc | tgacccacat | cgagtcccgg | 900 |
| ccttctagac | tgaagaagga | cgagtacgag | ttctttaccc | acctggataa | gcggtccctg | 960 |
| ccagccctga | caaacatcat | caagatcctg | aggcacgaca | tcggagcaac | cgtgcacgag | 1020 |
| ctgtctcggg | acaagaagaa | ggataccgtg | ccctggttcc | ctcggacaat | ccaggagctg | 1080 |
| gatagatttg | ccaaccagat | cctgtcttac | ggagcagagc | tggacgcaga | tcaccctggc | 1140 |
| ttcaaggacc | cagtgtatcg | ggcccggaga | aagcagtttg | ccgatatcgc | ctacaattat | 1200 |
| aggcacggac | agccaatccc | tcgcgtggag | tatatggagg | aggagaagaa | gacctggggc | 1260 |
| acagtgttca | agaccctgaa | gagcctgtac | aagacacacg | cctgctacga | gtataaccac | 1320 |
| atcttccccc | tgctggagaa | gtattgtggc | tttcacgagg | acaatatccc | tcagctggag | 1380 |
| gacgtgagcc | agttcctgca | gacctgcaca | ggctttaggc | tgaggccagt | ggcaggactg | 1440 |
| ctgagctccc | gggacttcct | gggaggactg | gccttcagag | tgtttcactg | cacccagtac | 1500 |
| atcaggcacg | gctccaagcc | aatgtataca | ccagagcccg | acatctgtca | cgagctgctg | 1560 |
| ggccacgtgc | cctgtttag | cgatagatcc | ttcgcccagt | tttcccagga | gatcggactg | 1620 |
| gcatctctgg | agcacctga | cgagtacatc | gagaagctgg | ccaccatcta | ttggttcaca | 1680 |
| gtggagtttg | gcctgtgcaa | gcagggcgat | agcatcaagg | cctacggagc | aggactgctg | 1740 |
| tctagcttcg | gcgagctgca | gtattgtctg | tccgagaagc | aaagctgct | gccctggag | 1800 |
| ctggagaaga | ccgccatcca | gaactacacc | gtgacagagt | tccagccct | gtactatgtg | 1860 |
| gccgagtctt | ttaacgatgc | caaggagaag | gtgagaaatt | tcgccgccac | aatccctagg | 1920 |
| cccttcagcg | tgcggtacga | cccttatacc | cagaggatcg | aggtgctgga | taatacacag | 1980 |
| cagctgaaga | tcctggctga | ctcaatcaat | agcgaaatcg | gaatcctgtg | ctccgccctg | 2040 |
| cagaaaatca | aatgaatgct | ttatttgtga | aatttgtgat | gctattgctt | tatttgtaac | 2100 |
| cattataagc | tgcaataaac | aagttaacaa | caacaattgc | attcatttta | tgtttcaggt | 2160 |

```
tcaggggag   gtgtgggagg   ttttttaaag   catgctgggg   agagatcgat   ctgaggaacc      2220
cctagtgatg   gagttggcca   ctccctctct   gcgcgctcgc   tcgctcactg   aggccgggcg      2280
accaaaggtc   gcccgacgcc   cgggctttgc   ccgggcggcc   tcagtgagcg   agcgagcgcg      2340
cagagaggga   gtggcc                                                             2356

<210> SEQ ID NO 88
<211> LENGTH: 5041
<212> TYPE: DNA
<213> ORGANISM: Artificial Sequence
<220> FEATURE:
<223> OTHER INFORMATION: pHMI-01004 full sequence

<400> SEQUENCE: 88
agaaaaactc   atcgagcatc   aaatgaaatt   gcaatttatt   catatcagga   ttatcaatac        60 catattttg    aaaaagccgt   ttctgtaatg   aaggagaaaa   ctcaccgagg   cagttccata       120
ggatggcaag   atcctggtat   cggtctgcga   ttccgactcg   tccaacatca   atacaaccta       180
ttaatttccc   ctcgtcaaaa   ataaggttat   caagtgagaa   atcaccatga   gtgacgactg       240
aatccggtga   gaatggcaaa   agtttatgca   tttctttcca   gacttgttca   acaggccagc       300
cattacgctc   gtcatcaaaa   tcactcgcat   caaccaaacc   gttattcatt   cgtgattgcg       360
cctgagcgag   gcgaaatacg   cgatcgctgt   taaaaggaca   attacaaaca   ggaatcgagt       420
gcaaccggcg   caggaacact   gccagcgcat   caacaatatt   ttcacctgaa   tcaggatatt       480
cttctaatac   ctggaacgct   gtttttccgg   ggatcgcagt   ggtgagtaac   catgcatcat       540
caggagtacg   gataaaatgc   ttgatggtcg   gaagtggcat   aaattccgtc   agccagttta       600
gtctgaccat   ctcatctgta   acatcattgg   caacgctacc   tttgccatgt   ttcagaaaca       660
actctggcgc   atcgggcttc   ccatacaagc   gatagattgt   cgcacctgat   tgcccgacat       720
tatcgcgagc   ccatttatac   ccatataaat   cagcatccat   gttggaattt   aatcgcggcc       780
tcgacgtttc   ccgttgaata   tggctcatat   tcttcctttt   tcaatattat   tgaagcattt       840
atcagggtta   ttgtctcatg   agcggataca   tatttgaatg   tatttagaaa   aataaacaaa       900
taggggtcag   tgttacaacc   aattaaccaa   ttctgaacat   tatcgcgagc   ccatttatac       960
ctgaatatgg   ctcataacac   cccttgtttg   cctggcggca   gtagcgcggt   ggtcccacct      1020
gacccccatg   cgaactcaga   agtgaaacgc   cgtagcgccg   atggtagtgt   ggggactccc      1080
catgcgagag   tagggaactg   ccaggcatca   aataaaacga   aggctcagt    cgaaagactg      1140 ggcctttcgc   ccaaaccata   tgattgacat   gctagtttta   cgattaccgt   tcatcgccct      1200
gcgcgctcgc   tcgctcactg   aggccgcccg   ggcaaagccc   gggcgtcggg   cgacctttgg      1260
tcgcccggcc   tcagtgagcg   agcgagcgcg   cagagaggga   gtggaattca   cgcgtggatc      1320
tgaattcaat   tcacgcgtgg   tacctcccta   aaatgggcaa   acattgcaag   cagcaaacag      1380
caaacacaca   gccctccctg   cctgctgacc   ttggagctgg   gcagaggtc    agagacctct      1440 ctgggcccat   gccacctcca   acatccactc   gaccccttgg   aatttcggtg   gagaggagca      1500
gaggttgtcc   tggcgtggtt   taggtagtgt   gagaggggaa   tgactccttt   cggtaagtgc      1560
agtggaagct   gtacactgcc   caggcaaagc   gtccgggcag   cgtaggcggg   cgactcgat      1620 cccagccagt   ggacttagcc   cctgtttgct   cctccgataa   ctgggggtgac  cttggttaat      1680 attccaccagc  agcctccccc   gttgcccctc   tggatccact   gcttaaatac   ggacgaggac      1740
agggccctgt   ctcctcagct   tcaggcacca   ccactgacct   gggacagtga   atcctctaag      1800
```

```
gtaaatataa aattttttaag tgtataatgt gttaaactac tgattctaat tgtttctctc    1860
ttttagattc caacctttgg aactgaccgc caccatgtcc accgctgtgc tggagaaccc    1920
tgggctgggg aggaaactgt cagacttcgg gcaggagact tcatacattg aggataactg    1980
taaccagaat ggcgccatct ctctgatctt cagcctgaag gaggaagtgg gcgccctggc    2040
aaaggtgctg cgcctgtttg aggagaacga cgtgaatctg acccacatcg agtcccggcc    2100
ttctagactg aagaaggacg agtacgagtt ctttacccac ctggataagc ggtccctgcc    2160
agccctgaca aacatcatca agatcctgag gcacgacatc ggagcaaccg tgcacgagct    2220
gtctcgggac aagaagaagg ataccgtgcc ctggttccct cggacaatcc aggagctgga    2280
tagatttgcc aaccagatcc tgtcttacgg agcagagctg gacgcagatc accctggctt    2340
caaggaccca gtgtatcggg cccggagaaa gcagtttgcc gatatcgcct acaattatag    2400
gcacggacag ccaatccctc gcgtggagta tatggaggag gagaagaaga cctggggcac    2460
agtgttcaag accctgaaga gcctgtacaa gacacacgcc tgctacgagt ataaccacat    2520
cttccccctg ctggagaagt attgtggctt tcacgaggac aatatccctc agctggagga    2580
cgtgagccag ttcctgcaga cctgcacagg ctttaggctg aggccagtgg caggactgct    2640
gagctcccgg gacttcctgg gaggactggc cttcagagtt tttcactgca cccagtacat    2700
caggcacggc tccaagccaa tgtatacacc agagcccgac atctgtcacg agctgctggg    2760
ccacgtgccc ctgtttagcg atagatcctt cgcccagttt ccccaggaga tcggactggc    2820
atctctggga gcacctgacg agtacatcga gaagctggcc accatctatt ggttcacagt    2880
ggagtttggc ctgtgcaagc agggcgatag catcaaggcc tacggagcag gactgctgtc    2940
tagcttcggc gagctgcagt attgtctgtc cgagaagcca aagctgctgc ccctggagct    3000
ggagaagacc gccatccaga actacaccgt gacagagttc cagcccctgt actatgtggc    3060
cgagtctttt aacgatgcca aggagaaggt gagaaatttc gccgccacaa tccctaggcc    3120
cttcagcgtg cggtacgacc cttataccca gaggatcgag gtgctggata atacacagca    3180
gctgaagatc ctggctgact caatcaatag cgaaatcgga atcctgtgct ccgccctgca    3240
gaaaatcaaa tgaatgcttt atttgtgaaa tttgtgatgc tattgcttta tttgtaacca    3300
ttataagctg caataaacaa gttaacaaca acaattgcat tcattttatg tttcaggttc    3360
agggggaggt gtgggaggtt ttttaaagca tgctggggag agatcgatct gaggaacccc    3420
tagtgatgga gttggccact ccctctctgc gcgctcgctc gctcactgag gccgggcgac    3480
caaaggtcgc ccgacgcccg ggctttgccc gggcggcctc agtgagcgag cgagcgcgca    3540
gagagggagt ggcccatatg cggtaccaga attcgggtct agacgtcaaa agggcgacac    3600
aaaatttatt ctaaatgcat aataaatact gataacatct tatagtttgt attatatttt    3660
gtattatcgt tgacatgtat aattttgata tcaaaaactg attttccctt tattattttc    3720
gagatttatt tcttaattc tctttaacaa actagaaata ttgtatatac aaaaaatcat    3780
aaataataga tgaatagttt aattataggt gttcatcaat cgaaaaagca acgtatctta    3840
tttaaagtgc gttgcttttt tctcatttat aaggttaaat aattctcata tatcaagcaa    3900
agtgacaggc gcccttaaat attctgacaa atgctctttc cctaaactcc ccccataaaa    3960
aaacccgccg aagcgggttt ttacgttatt tgcggattaa cgattactcg ttatcagaac    4020
cgcccagggg gcccgagctt aagactggcc gtcgttttac aacacagaaa gagtttgtag    4080
aaacgcaaaa aggccatccg tcaggggcct tctgcttagt ttgatgcctg gcagttccct    4140
actctcgcct tccgcttcct cgctcactga ctcgctgcgc tcggtcgttc ggctgcggcg    4200
```

```
agcggtatca gctcactcaa aggcggtaat acggttatcc acagaatcag gggataacgc    4260
aggaaagaac atgtgagcaa aaggccagca aaaggccagg aaccgtaaaa aggccgcgtt    4320
gctggcgttt ttccataggc tccgcccccc tgacgagcat cacaaaaatc gacgctcaag    4380
tcagaggtgg cgaaacccga caggactata aagataccag gcgtttcccc ctggaagctc    4440
cctcgtgcgc tctcctgttc cgaccctgcc gcttaccgga tacctgtccg cctttctccc    4500
ttcgggaagc gtggcgcttt ctcatagctc acgctgtagg tatctcagtt cggtgtaggt    4560
cgttcgctcc aagctgggct gtgtgcacga accccccgtt cagcccgacc gctgcgcctt    4620
atccggtaac tatcgtcttg agtccaaccc ggtaagacac gacttatcgc cactggcagc    4680
agccactggt aacaggatta gcagagcgag gtatgtaggc ggtgctacag agttcttgaa    4740
gtggtgggct aactacggct acactagaag aacagtattt ggtatctgcg ctctgctgaa    4800
gccagttacc ttcggaaaaa gagttggtag ctcttgatcc ggcaaacaaa ccaccgctgg    4860
tagcggtggt ttttttgttt gcaagcagca gattacgcgc agaaaaaaag gatctcaaga    4920
agatcctttg atcttttcta cggggtctga cgctcagtgg aacgacgcgc gcgtaactca    4980
cgttaaggga ttttggtcat gagcttgcgc cgtcccgtca gtcagcgta atgctctgct     5040 t                                                                   5041
```

<210> SEQ ID NO 89
<211> LENGTH: 2042
<212> TYPE: DNA
<213> ORGANISM: Artificial Sequence
<220> FEATURE:
<223> OTHER INFORMATION: pHMI-01008 transfer genome

<400> SEQUENCE: 89

```
ccctaaaatg ggcaaacatt gcaagcagca acagcaaac acacagccct ccctgcctgc      60
tgaccttgga gctggggcag aggtcagaga ccctctctggg cccatgccac ctccaacatc   120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg ggcagcgtag gcgggcgact cagatcccag ccagtggact tagcccctgt    300
ttgctcctcc gataactggg gtgaccttgg ttaatattca ccagcagcct ccccccgttgc   360 ccctctggat ccactgctta aatacggacg aggacagggc cctgtctcct cagcttcagg    420
caccaccact gacctgggac agtgaatcct ctaaggtaaa tataaaattt ttaagtgtat    480
aatgtgttaa actactgatt ctaattgttt ctctcttta gattccaacc tttgaactg     540 accgccacca tgtccaccgc tgtgctggag aaccctgggc tggggaggaa actgtcagac    600
ttcgggcagg agacttcata cattgaggat aactgtaacc agaatggcgc catctctctg    660
atcttcagcc tgaaggagga agtgggcgcc ctggcaaagg tgctgcgcct gtttgaggag    720
aacgacgtga atctgaccca catcgagtcc cggccttcta gactgaagaa ggacgagtac    780
gagttcttta cccacctgga taagcggtcc ctgccagccc tgacaaacat catcaagatc    840
ctgaggcacg acatcggagc aaccgtgcac gagctgtctc gggacaagaa gaaggatacc    900 gtgcctggt tccctcggac aatccaggag ctggatagat tgccaaccag atcctgtct     960 tacggagcag agctggacgc agatcaccct ggcttcaagg acccagtgta tcgggcccgg   1020
agaaagcagt ttgccgatat cgcctacaat tataggcacg acagccaat ccctcgcgtg   1080 gagtatatgg aggaggagaa gaagacctgg ggcacagtgt tcaagaccct gaagagcctg    1140
```

| | |
|---|---|
| tacaagacac acgcctgcta cgagtataac cacatcttcc ccctgctgga gaagtattgt | 1200 |
| ggctttcacg aggacaatat ccctcagctg gaggacgtga gccagttcct gcagacctgc | 1260 |
| acaggcttta ggctgaggcc agtggcagga ctgctgagct cccgggactt cctgggagga | 1320 |
| ctggccttca gagtgtttca ctgcacccag tacatcaggc acggctccaa gccaatgtat | 1380 |
| acaccagagc ccgacatctg tcacgagctg ctgggccacg tgcccctgtt tagcgataga | 1440 |
| tccttcgccc agttttccca ggagatcgga ctggcatctc tgggagcacc tgacgagtac | 1500 |
| atcgagaagc tggccaccat ctattggttc acagtggagt ttggcctgtg caagcagggc | 1560 |
| gatagcatca aggcctacgg agcaggactg ctgtctagct cggcgagct gcagtattgt | 1620 |
| ctgtccgaga agccaaagct gctgcccctg agctggaga agaccgccat ccagaactac | 1680 |
| accgtgacag agttccagcc cctgtactat gtggccgagt cttttaacga tgccaaggag | 1740 |
| aaggtgagaa atttcgccgc cacaatccct aggcccttca gcgtgcggta cgacccttat | 1800 |
| acccagagga tcgaggtgct ggataataca cagcagctga agatcctggc tgactcaatc | 1860 |
| aatagcgaaa tcggaatcct gtgctccgcc ctgcagaaaa tcaaatgaat gctttatttg | 1920 |
| tgaaatttgt gatgctattg ctttatttgt aaccattata agctgcaata aacaagttaa | 1980 |
| caacaacaat tgcattcatt ttatgtttca ggttcagggg gaggtgtggg aggttttta | 2040 |
| aa | 2042 |

<210> SEQ ID NO 90
<211> LENGTH: 2393
<212> TYPE: DNA
<213> ORGANISM: Artificial Sequence
<220> FEATURE:
<223> OTHER INFORMATION: pHMI-01008 transfer genome

<400> SEQUENCE: 90

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggaatt cacgcgtgga | 120 |
| tctgaattca attcacgcgt ggtacctccc taaaatgggc aaacattgca agcagcaaac | 180 |
| agcaaacaca cagccctccc tgcctgctga ccttggagct ggggcagagg tcagagacct | 240 |
| ctctgggccc atgccacctc caacatccac tcgacccctt ggaatttcgg tggagaggag | 300 |
| cagaggttgt cctggcgtgg tttaggtagt gtgagagggg aatgactcct ttcggtaagt | 360 |
| gcagtggaag ctgtacactg cccaggcaaa gcgtccgggc agcgtaggcg ggcgactcag | 420 |
| atcccagcca gtggacttag cccctgtttg ctcctccgat aactgggtg accttggtta | 480 |
| atattcacca gcagcctccc ccgttgcccc tctggatcca ctgcttaaat acggacgagg | 540 |
| acagggccct gtctcctcag cttcaggcac caccactgac ctgggacagt gaatcctcta | 600 |
| aggtaaatat aaaattttta agtgtataat gtgttaaact actgattcta attgtttctc | 660 |
| tcttttagat ccaacctttt ggaactgacc gccaccatgt ccaccgctgt gctggagaac | 720 |
| cctgggctgg ggaggaaact gtcagacttc ggcaggaga cttcatacat tgaggataac | 780 |
| tgtaaccaga atggcgccat ctctctgatc ttcagcctga aggaggaagt gggcgccctg | 840 |
| gcaaaggtgc tgcgcctgtt tgaggagaac gacgtgaatc tgacccacat cgagtcccgg | 900 |
| ccttctagac tgaagaagga cgagtacgag ttctttaccc acctggataa gcggtccctg | 960 |
| ccagccctga caaacatcat caagatcctg aggcacgaca tcggagcaac cgtgcacgag | 1020 |
| ctgtctcggg acaagaagaa ggataccgtg ccctggttcc ctcggacaat ccaggagctg | 1080 |
| gatagatttg ccaaccagat cctgtcttac ggagcagagc tggacgcaga tcaccctggc | 1140 |

| | | | |
|---|---|---|---|
| ttcaaggacc | cagtgtatcg | ggcccggaga | aagcagtttg | ccgatatcgc | ctacaattat | 1200 |
| aggcacggac | agccaatccc | tcgcgtggag | tatatggagg | aggagaagaa | gacctggggc | 1260 |
| acagtgttca | agaccctgaa | gagcctgtac | aagacacacg | cctgctacga | gtataaccac | 1320 |
| atcttccccc | tgctggagaa | gtattgtggc | tttcacgagg | acaatatccc | tcagctggag | 1380 |
| gacgtgagcc | agttcctgca | gacctgcaca | ggctttaggc | tgaggccagt | ggcaggactg | 1440 |
| ctgagctccc | gggacttcct | gggaggactg | gccttcagag | tgtttcactg | cacccagtac | 1500 |
| atcaggcacg | gctccaagcc | aatgtataca | ccagagcccg | acatctgtca | cgagctgctg | 1560 |
| ggccacgtgc | ccctgtttag | cgatagatcc | ttcgcccagt | tttcccagga | gatcggactg | 1620 |
| gcatctctgg | gagcacctga | cgagtacatc | gagaagctgg | ccaccatcta | ttggttcaca | 1680 |
| gtggagtttg | gcctgtgcaa | gcagggcgat | agcatcaagg | cctacggagc | aggactgctg | 1740 |
| tctagcttcg | gcgagctgca | gtattgtctg | tccgagaagc | aaagctgct | gcccctggag | 1800 |
| ctggagaaga | ccgccatcca | gaactacacc | gtgacagagt | tccagcccct | gtactatgtg | 1860 |
| gccgagtctt | ttaacgatgc | caaggagaag | gtgagaaatt | tcgccgccac | aatccctagg | 1920 |
| cccttcagcg | tgcggtacga | cccttatacc | cagaggatcg | aggtgctgga | taatacacag | 1980 |
| cagctgaaga | tcctggctga | ctcaatcaat | agcgaaatcg | aatcctgtg | ctccgccctg | 2040 |
| cagaaaatca | aatgaatgct | ttatttgtga | aatttgtgat | gctattgctt | tatttgtaac | 2100 |
| cattataagc | tgcaataaac | aagttaacaa | caacaattgc | attcatttta | tgtttcaggt | 2160 |
| tcagggggag | gtgtgggagg | ttttttaaag | catgctgggg | agagatcgat | ctggtagata | 2220 |
| agtagcatgg | cgggttaatc | attaactaca | aggaacccct | agtgatggag | ttggccactc | 2280 |
| cctctctgcg | cgctcgctcg | ctcactgagg | ccgggcgacc | aaaggtcgcc | cgacgcccgg | 2340 |
| gctttgcccg | ggcggcctca | gtgagcgagc | gagcgcgcag | agagggagtg | gcc | 2393 |

<210> SEQ ID NO 91
<211> LENGTH: 5078
<212> TYPE: DNA
<213> ORGANISM: Artificial Sequence
<220> FEATURE:
<223> OTHER INFORMATION: pHMI-01008 full sequence

<400> SEQUENCE: 91

| | | | |
|---|---|---|---|
| agaaaaactc | atcgagcatc | aaatgaaatt | gcaatttatt | catatcagga | ttatcaatac | 60 |
| catatttttg | aaaaagccgt | ttctgtaatg | aaggagaaaa | ctcaccgagg | cagttccata | 120 |
| ggatggcaag | atcctggtat | cggtctgcga | ttccgactcg | tccaacatca | atacaaccta | 180 |
| ttaatttccc | ctcgtcaaaa | ataaggttat | caagtgagaa | atcaccatga | gtgacgactg | 240 |
| aatccggtga | gaatggcaaa | agtttatgca | tttctttcca | gacttgttca | acaggccagc | 300 |
| cattacgctc | gtcatcaaaa | tcactcgcat | caaccaaacc | gttattcatt | cgtgattgcg | 360 |
| cctgagcgag | gcgaaatacg | cgatcgctgt | taaaaggaca | attacaaaca | ggaatcgagt | 420 |
| gcaaccggcg | caggaacact | gccagcgcat | caacaatatt | ttcacctgaa | tcaggatatt | 480 |
| cttctaatac | ctggaacgct | gtttttccgg | ggatcgcagt | ggtgagtaac | catgcatcat | 540 |
| caggagtacg | gataaaatgc | ttgatggtcg | gaagtggcat | aaattccgtc | agccagttta | 600 |
| gtctgaccat | ctcatctgta | acatcattgg | caacgctacc | tttgccatgt | ttcagaaaca | 660 |
| actctggcgc | atcgggcttc | ccatacaagc | gatagattgt | cgcacctgat | tgcccgacat | 720 |
| tatcgcgagc | ccatttatac | ccatataaat | cagcatccat | gttggaattt | aatcgcggcc | 780 |

```
tcgacgtttc ccgttgaata tggctcatat tcttccttt tcaatattat tgaagcattt      840
atcagggtta ttgtctcatg agcggataca tatttgaatg tatttagaaa aataaacaaa     900
tagggtcag tgttacaacc aattaaccaa ttctgaacat tatcgcgagc ccatttatac     960
ctgaatatgg ctcataacac cccttgtttg cctggcggca gtagcgcggt ggtcccacct    1020
gaccccatgc cgaactcaga agtgaaacgc cgtagcgccg atggtagtgt ggggactccc    1080
catgcgagag tagggaactg ccaggcatca aataaaacga aaggctcagt cgaaagactg    1140
ggcctttcgc ccaaaccata tgattgacat gctagtttta cgattaccgt tcatcgccct    1200
gcgcgctcgc tcgctcactg aggccgcccg ggcaaagccc gggcgtcggg cgacctttgg    1260
tcgcccggcc tcagtgagcg agcgagcgcg cagagaggga gtggaattca cgcgtggatc    1320
tgaattcaat tcacgcgtgg tacctcccta aatgggcaa acattgcaag cagcaaacag    1380
caaacacaca gccctccctg cctgctgacc ttggagctgg ggcagaggtc agagacctct    1440
ctgggcccat gccacctcca acatccactc gaccccttgg aatttcggtg agaggagca    1500
gaggttgtcc tggcgtggtt taggtagtgt gagagggaa tgactccttt cggtaagtgc    1560
agtggaagct gtacactgcc caggcaaagc gtccgggcag cgtaggcggg cgactcagat    1620
cccagccagt ggacttagcc cctgtttgct cctccgataa ctggggtgac cttggttaat    1680
attcaccagc agcctccccc gttgcccctc tggatccact gcttaaatac ggacgaggac    1740
agggccctgt ctcctcagct tcaggcacca ccactgacct gggacagtga atcctctaag    1800
gtaaatataa aattttttaag tgtataatgt gttaaactac tgattctaat tgtttctctc    1860
ttttagattc caacctttgg aactgaccgc caccatgtcc accgctgtgc tggagaaccc    1920
tgggctgggg aggaaactgt cagacttcgg gcaggagact tcatacattg aggataactg    1980
taaccagaat ggcgccatct ctctgatctt cagcctgaag gaggaagtgg gcgccctggc    2040
aaaggtgctg cgcctgtttg aggagaacga cgtgaatctg acccacatcg agtcccggcc    2100
ttctagactc aagaaggacg agtacgagtt ctttacccac ctggataagc ggtccctgcc    2160
agccctgaca aacatcatca gatcctgagg cacgacatc ggagcaaccg tgcacgagct    2220
gtctcgggac aagaagaagg ataccgtgcc ctggttccct cggacaatcc aggagctgga    2280
tagatttgcc aaccagatcc tgtcttacgg agcagagctg gacgcagatc accctggctt    2340
caaggaccca gtgtatcggg cccggagaaa gcagtttgcc gatatcgcct acaattatag    2400
gcacggacag ccaatccctc gcgtggagta tatggaggag gagaagaaga cctggggcac    2460
agtgttcaag accctgaaga gcctgtacaa gacacacgcc tgctacgagt ataaccacat    2520
cttccccctg ctggagaagt attgtggctt tcacgaggac aatatccctc agctggagga    2580
cgtgagccaa ttcctgcaga cctgcacagg cttttaggctg aggccagtgg caggactgct    2640
gagctcccgg gacttcctgg aggactggc cttcagagtg tttcactgca cccagtacat    2700
caggcacggc tccaagccaa tgtatacacc agagcccgac atctgtcacg agctgctggg    2760
ccacgtgccc ctgtttagcg atagatcctt cgcccagttt ccccaggaga tcggactggc    2820
atctctggga gcacctgacg agtacatcga gaagctggcc accatctatt ggttcacagt    2880
ggagtttggc ctgtgcaagc agggcgatag catcaaggcc tacggagcag gactgctgtc    2940
tagcttcggc gagctgcagt attgtctgtc cgagaagcca aagctgctgc ccctggagct    3000
ggagaagacc gccatccaga actacaccgt gacagagttc cagcccctgt actatgtggc    3060
cgagtctttt aacgatgcca aggagaaggt gagaaatttc gccgccacaa tccctaggcc    3120
cttcagcgtg cggtacgacc cttatacccca gaggatcgag gtgctggata atacacagca    3180
```

| | |
|---|---|
| gctgaagatc ctggctgact caatcaatag cgaaatcgga atcctgtgct ccgccctgca | 3240 |
| gaaaatcaaa tgaatgcttt atttgtgaaa tttgtgatgc tattgcttta tttgtaacca | 3300 |
| ttataagctg caataaacaa gttaacaaca acaattgcat tcattttatg tttcaggttc | 3360 |
| agggggaggt gtgggaggtt ttttaaagca tgctggggag agatcgatct ggtagataag | 3420 |
| tagcatggcg ggttaatcat taactacaag gaaccCctag tgatggagtt ggccactccc | 3480 |
| tctctgcgcg ctcgctcgct cactgaggcc gggcgaccaa aggtcgcccg acgcccgggc | 3540 |
| tttgcccggg cggcctcagt gagcgagcga gcgcgcagag agggagtggc ccatatgcgg | 3600 |
| taccagaatt cgggtctaga cgtcaaaagg gcgacacaaa atttattcta aatgcataat | 3660 |
| aaatactgat aacatcttat agtttgtatt atattttgta ttatcgttga catgtataat | 3720 |
| tttgatatca aaaactgatt ttcccttat tatttcgag atttattttc ttaattctct | 3780 |
| ttaacaaact agaaatattg tatatacaaa aaatcataaa taatagatga atagtttaat | 3840 |
| tataggtgtt catcaatcga aaagcaacg tatcttattt aaagtgcgtt gcttttttct | 3900 |
| catttataag gttaaataat tctcatatat caagcaaagt gacaggcgcc cttaaatatt | 3960 |
| ctgacaaatg ctcttttccct aaactccccc cataaaaaaa cccgccgaag cgggttttta | 4020 |
| cgttatttgc ggattaacga ttactcgtta tcagaaccgc ccaggggggcc cgagcttaag | 4080 |
| actggccgtc gttttacaac acagaaagag tttgtagaaa cgcaaaaagg ccatccgtca | 4140 |
| ggggccttct gcttagtttg atgcctggca gttccctact ctcgccttcc gcttcctcgc | 4200 |
| tcactgactc gctgcgctcg tcgttcggc tgcggcgagc ggtatcagct cactcaaagg | 4260 |
| cggtaatacg gttatccaca gaatcagggg ataacgcagg aaagaacatg tgagcaaaag | 4320 |
| gccagcaaaa ggccaggaac cgtaaaaagg ccgcgttgct ggcgttttc cataggctcc | 4380 |
| gcccccctga cgagcatcac aaaaatcgac gctcaagtca gaggtggcga aacccgacag | 4440 |
| gactataaag ataccaggcg tttccccctg gaagctccct cgtgcgctct cctgttccga | 4500 |
| ccctgccgct taccggatac ctgtccgcct ttctcccttc gggaagcgtg cgctttctc | 4560 |
| atagctcacg ctgtaggtat ctcagttcgg tgtaggtcgt tcgctccaag ctgggctgtg | 4620 |
| tgcacgaacc ccccgttcag cccgaccgct gcgccttatc cggtaactat cgtcttgagt | 4680 |
| ccaacccggt aagacacgac ttatcgccac tggcagcagc cactggtaac aggattagca | 4740 |
| gagcgaggta tgtaggcggt gctacagagt tcttgaagtg gtgggctaac tacggctaca | 4800 |
| ctagaagaac agtatttggt atctgcgctc tgctgaagcc agttaccttc ggaaaaagag | 4860 |
| ttggtagctc ttgatccggc aaacaaacca ccgctggtag cggtggtttt tttgtttgca | 4920 |
| agcagcagat tacgcgcaga aaaaaggat ctcaagaaga tcctttgatc ttttctacgg | 4980 |
| ggtctgacgc tcagtggaac gacgcgcgcg taactcacgt taagggattt tggtcatgag | 5040 |
| cttgcgccgt cccgtcaagt cagcgtaatg ctctgctt | 5078 |

```
<210> SEQ ID NO 92
<211> LENGTH: 6020
<212> TYPE: DNA
<213> ORGANISM: Artificial Sequence
<220> FEATURE:
<223> OTHER INFORMATION: pHMI-hPAH-TC-025 full sequence

<400> SEQUENCE: 92
```

| | |
|---|---|
| aacgccagca acgcggcctt tttacggttc ctggcctttt gctggccttt tgctcacatg | 60 |
| ttctttcctg cgttatcccc tgattctgtg gataaccgta ttaccgcctt tgagtgagct | 120 |

-continued

| | | |
|---|---|---|
| gataccgctc gccgcagccg aacgaccgag cgcagcgagt cagtgagcga ggaagcggaa | 180 |
| gagcgcccaa tacgcaaacc gcctctcccc gcgcgttggc cgattcatta atgcagcagc | 240 |
| tggcgtaata gcgaagaggc ccgcaccgat cgcccttccc aacagttgcg cagcctgaat | 300 |
| ggcgaatgga attccagacg attgagcgtc aaaatgtagg tatttccatg agcgtttttc | 360 |
| ctgttgcaat ggctggcggt aatattgttc tggatattac cagcaaggcc gatagtttga | 420 |
| gttcttctac tcaggcaagt gatgttatta ctaatcaaag aagtattgcg caacggtta | 480 |
| atttgcgtga tggacagact cttttactcg gtggcctcac tgattataaa aacacttctc | 540 |
| aggattctgg cgtaccgttc ctgtctaaaa tccctttaat cggcctcctg tttagctccc | 600 |
| gctctgattc taacgaggaa agcacgttat acgtgctcgt caaagcaacc atagtacgcg | 660 |
| ccctgtagcg cgcattaag cgcggcgggt gtggtggtta cgcgcagcgt gaccgctaca | 720 |
| cttgccagcg ccctagcgcc cgctcctttc gctttcttcc cttcctttct cgccacgttc | 780 |
| gccggctttc cccgtcaagc tctaaatcgg gggctccctt tagggttccg atttagtgct | 840 |
| ttacggcacc tcgaccccaa aaaacttgat tagggtgatg gttcacgtag tgggccatcg | 900 |
| ccctgataga cggttttcg ccctttgacg ttggagtcca cgttctttaa tagtggactc | 960 |
| ttgttccaaa ctggaacaac actcaaccct atctcggtct attctttga tttataaggg | 1020 |
| attttgccga tttcggccta ttggttaaaa aatgagctga tttaacaaaa atttaacgcg | 1080 |
| aattttaaca aaatattaac gcttacaatt taaatatttg cttatacaat cttcctgttt | 1140 |
| ttggggcttt tctgattatc aaccggggta catatgattg acatgctagt tttacgatta | 1200 |
| ccgttcatcg ccctgcgcgc tcgctcgctc actgaggccg cccgggcaaa gcccgggcgt | 1260 |
| cgggcgacct ttggtcgccc ggcctcagtg agcgagcgag cgcgcagaga gggagtggaa | 1320 |
| ttcacgcgtg gatctgaatt caattcacgc gtggtacctc cctaaaatgg gcaaacattg | 1380 |
| caagcagcaa acagcaaaca cacagccctc cctgcctgct gaccttggag ctgggcaga | 1440 |
| ggtcagagac ctctctgggc ccatgccacc tccaacatcc actcgacccc ttggaatttc | 1500 |
| ggtggagagg agcagaggtt gtcctggcgt ggtttaggta gtgtgagagg ggaatgactc | 1560 |
| ctttcggtaa gtgcagtgga agctgtacac tgcccaggca aagcgtccgg gcagcgtagg | 1620 |
| cgggcgactc agatcccagc cagtggactt agcccctgtt tgctcctccg ataactgggg | 1680 |
| tgaccttggt taatattcac cagcagcctc ccccgttgcc cctctggatc cactgcttaa | 1740 |
| atacggacga ggacagggcc ctgtctcctc agcttcaggc accaccactg acctgggaca | 1800 |
| gtgaatcctc taaggtaaat ataaaatttt taagtgtata atgtgttaaa ctactgattc | 1860 |
| taattgtttc tctcttttag attccaacct ttggaactga ccgccaccat gtccaccgct | 1920 |
| gtgctggaga accctgggct ggggaggaaa ctgtcagact tcgggcagga gacttcatac | 1980 |
| attgaggata actgtaacca gaatggcgcc atctctctga tcttcagcct gaaggaggaa | 2040 |
| gtgggcgccc tggcaaaggt gctgcgcctg tttgaggaga cgacgtgaa tctgacccac | 2100 |
| atcgagtccc ggccttctag actgaagaag gacgagtacg agttctttac ccacctggat | 2160 |
| aagcggtccc tgccagccct gacaaacatc atcaagatcc tgaggcacga catcggagca | 2220 |
| accgtgcacg agctgtctcg ggacaagaag aaggataccg tgcccggtt ccctcggaca | 2280 |
| atccaggagc tggatagatt tgccaaccag atcctgtctt acggagcaga gctggacgca | 2340 |
| gatcaccctg gcttcaagga cccagtgtat cgggcccgga aaagcagtt tgccgatatc | 2400 |
| gcctacaatt ataggcacgg acagccaatc cctcgcgtgg agtatatgga ggaggagaag | 2460 |
| aagacctggg gcacagtgtt caagaccctg aagagcctgt acaagacaca cgcctgctac | 2520 |

```
gagtataacc acatcttccc cctgctggag aagtattgtg gctttcacga ggacaatatc    2580
cctcagctgg aggacgtgag ccagttcctg cagacctgca caggctttag gctgaggcca    2640
gtggcaggac tgctgagctc ccgggacttc ctgggaggac tggccttcag agtgtttcac    2700
tgcacccagt acatcaggca cggctccaag ccaatgtata caccagagcc cgacatctgt    2760
cacgagctgc tgggccacgt gccctgttt agcgatagat ccttcgccca gttttcccag     2820
gagatcggac tggcatctct gggagcacct gacgagtaca tcgagaagct ggccaccatc    2880
tattggttca cagtggagtt tggcctgtgc aagcagggcg atagcatcaa ggcctacgga    2940
gcaggactgc tgtctagctt cggcgagctg cagtattgtc tgtccgagaa gccaaagctg    3000
ctgcccctgg agctggagaa gaccgccatc agaactaca ccgtgacaga gttccagccc      3060
ctgtactatg tggccgagtc ttttaacgat gccaaggaga aggtgagaaa tttcgccgcc    3120
acaatcccta ggcccttcag cgtgcggtac gaccccttata cccagaggat cgaggtgctg    3180
gataatacac agcagctgaa gatcctggct gactcaatca atagcgaaat cggaatcctg    3240
tgctccgccc tgcagaaaat caaatgaatg ctttatttgt gaaatttgtg atgctattgc    3300
tttatttgta accattataa gctgcaataa acaagttaac aacaacaatt gcattcattt    3360
tatgtttcag gttcagggg aggtgtggga ggttttttaa agcatgctgg ggagagatcg    3420
atctgaggaa cccctagtga tggagttggc cactccctct ctgcgcgctc gctcgctcac    3480
tgaggccggg cgaccaaagg tcgcccgacg cccgggcttt gcccgggcgg cctcagtgag    3540
cgagcgagcg cgcagagagg gagtggcccc cccccccccc cccccggcg attctcttgt    3600 ttgctccaga ctctcaggca atgacctgat agcctttgta gagacctctc aaaaatagct    3660
accctctccg gcatgaattt atcagctaga acggttgaat atcatattga tggtgatttg    3720
actgtctccg gccttttctca cccgtttgaa tctttaccta cacattactc aggcattgca    3780
tttaaaatat atgagggttc taaaaatttt tatccttgcg ttgaaataaa gcttctccc    3840 gcaaaagtat tacagggtca taatgttttt ggtacaaccg atttagcttt atgctctgag    3900
gctttattgc ttaattttgc taattctttg ccttgcctgt atgatttatt ggatgttgga    3960
atcgcctgat gcggtatttt ctccttacgc atctgtgcgg tatttcacac cgcatatggt    4020
gcactctcag tacaatctgc tctgatgccg catagttaag ccagccccga cacccgccaa    4080
cacccgctga cgcgccctga cgggcttgtc tgctcccggc atccgcttac agacaagctg    4140
tgaccgtctc cgggagctgc atgtgtcaga ggttttcacc gtcatcaccg aaacgcgcga    4200
gacgaaaggg cctcgtgata cgcctatttt tataggttaa tgtcatgata ataatggttt    4260
cttagacgtc aggtggcact tttcgggaa atgtgcgcgg aaccctatt tgtttatttt      4320 tctaaataca ttcaaatatg tatccgctca tgagacaata accctgataa atgcttcaat    4380
aatattgaaa aaggaagagt atgagtattc aacatttccg tgtcgccctt attccctttt    4440
ttgcggcatt ttgccttcct gttttgctc acccagaaac gctggtgaaa gtaaaagatg    4500
ctgaagatca gttgggtgca cgagtgggtt acatcgaact ggatctcaac agcggtaaga    4560
tccttgagag ttttcgcccc gaagaacgtt ttccaatgat gagcactttt aaagttctgc    4620
tatgtggcgc ggtattatcc cgtattgacg ccgggcaaga gcaactcggt cgccgcatac    4680
actattctca gaatgacttg gttgagtact caccagtcac agaaaagcat cttacggatg    4740
gcatgacagt aagagaatta tgcagtgctg ccataaccat gagtgataac actgcggcca    4800
acttacttct gacaacgatc ggaggaccga aggagctaac cgcttttttg cacaacatgg    4860
```

-continued

```
gggatcatgt aactcgcctt gatcgttggg aaccggagct gaatgaagcc ataccaaacg    4920
acgagcgtga caccacgatg cctgtagcaa tggcaacaac gttgcgcaaa ctattaactg    4980
gcgaactact tactctagct tcccggcaac aattaataga ctggatggag gcggataaag    5040
ttgcaggacc acttctgcgc tcggcccttc cggctggctg gtttattgct gataaatctg    5100
gagccggtga gcgtgggtct cgcggtatca ttgcagcact ggggccagat ggtaagccct    5160
cccgtatcgt agttatctac acgacgggga gtcaggcaac tatggatgaa cgaaatagac    5220
agatcgctga gataggtgcc tcactgatta agcattggta actgtcagac caagtttact    5280
catatatact ttagattgat ttaaaacttc atttttaatt taaaaggatc taggtgaaga    5340
tcctttttga taatctcatg accaaaatcc cttaacgtga gttttcgttc cactgagcgt    5400 cagacccccgt agaaaagatc aaaggatctt cttgagatcc ttttttttctg cgcgtaatct    5460 gctgcttgca aacaaaaaaa ccaccgctac cagcggtggt ttgtttgccg gatcaagagc    5520
taccaactct ttttccgaag gtaactggct tcagcagagc gcagatacca aatactgtcc    5580
ttctagtgta gccgtagtta ggccaccact tcaagaactc tgtagcaccg cctacatacc    5640
tcgctctgct aatcctgtta ccagtggctg ctgccagtgg cgataagtcg tgtcttaccg    5700
ggttggactc aagacgatag ttaccggata aggcgcagcg gtcgggctga acgggggggtt    5760 cgtgcacaca gcccagcttg gagcgaacga cctacaccga actgagatac ctacagcgtg    5820
agctatgaga aagcgccacg cttcccgaag ggagaaaggc ggacaggtat ccggtaagcg    5880
gcagggtcgg aacaggagag cgcacgaggg agcttccagg gggaaacgcc tggtatcttt    5940
atagtcctgt cgggtttcgc cacctctgac ttgagcgtcg attttgtga tgctcgtcag    6000 gggggcggag cctatggaaa                                                6020
```